US012522812B2

(12) United States Patent
Cheng et al.

(10) Patent No.: US 12,522,812 B2
(45) Date of Patent: Jan. 13, 2026

(54) CRISPR-ASSOCIATED SYSTEMS AND COMPONENTS

(71) Applicant: ARBOR BIOTECHNOLOGIES, INC., Cambridge, MA (US)

(72) Inventors: David R. Cheng, Boston, MA (US); David A. Scott, Somerville, MA (US); Winston X. Yan, Brookline, MA (US)

(73) Assignee: Arbor Biotechnologies, Inc., Cambridge, MA (US)

( * ) Notice: Subject to any disclaimer, the term of this patent is extended or adjusted under 35 U.S.C. 154(b) by 1421 days.

(21) Appl. No.: 17/055,719

(22) PCT Filed: May 16, 2019

(86) PCT No.: PCT/US2019/032750

§ 371 (c)(1),
(2) Date: Nov. 16, 2020

(87) PCT Pub. No.: WO2019/222555

PCT Pub. Date: Nov. 21, 2019

(65) Prior Publication Data

US 2021/0198664 A1 Jul. 1, 2021

Related U.S. Application Data

(60) Provisional application No. 62/672,489, filed on May 16, 2018.

(51) Int. Cl.

| | |
|---|---|
| *C12N 9/22* | (2006.01) |
| *A61K 31/7088* | (2006.01) |
| *A61K 38/46* | (2006.01) |
| *C12N 9/96* | (2006.01) |
| *C12N 15/11* | (2006.01) |
| *C12N 15/113* | (2010.01) |
| *C12N 15/90* | (2006.01) |
| *C12Q 1/6832* | (2018.01) |

(52) U.S. Cl.
CPC ............ *C12N 9/22* (2013.01); *A61K 31/7088* (2013.01); *A61K 38/465* (2013.01); *C12N 9/96* (2013.01); *C12N 15/11* (2013.01); *C12N 15/113* (2013.01); *C12N 15/907* (2013.01); *C12Q 1/6832* (2013.01); *C07K 2319/80* (2013.01); *C12N 2310/20* (2017.05); *C12N 2310/531* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 5,580,859 | A | 12/1996 | Felgner et al. |
| 5,589,466 | A | 12/1996 | Felgner et al. |
| 5,593,972 | A | 1/1997 | Weiner et al. |
| 8,454,972 | B2 | 6/2013 | Nabel et al. |
| 8,795,965 | B2 | 8/2014 | Zhang |
| 8,871,445 | B2 | 10/2014 | Cong et al. |
| 10,808,245 | B2 | 10/2020 | Chong et al. |
| 11,667,904 | B2 | 6/2023 | Cheng et al. |
| 2017/0211142 | A1 | 7/2017 | Smargon et al. |
| 2018/0371487 | A1 | 12/2018 | Yang |
| 2023/0407281 | A1 | 12/2023 | Cheng et al. |

FOREIGN PATENT DOCUMENTS

| | | | |
|---|---|---|---|
| CN | 111690720 | A | 9/2020 |
| CN | 112195164 | A | 1/2021 |
| EP | 3009511 | A2 | 4/2016 |
| WO | 2012164565 | A1 | 12/2012 |
| WO | 2014/093622 | A2 | 6/2014 |
| WO | 2015/070083 | A1 | 5/2015 |
| WO | 2016094872 | A1 | 6/2016 |
| WO | 2016094874 | A1 | 6/2016 |
| WO | 2016106236 | A1 | 6/2016 |
| WO | 2016205764 | A1 | 12/2016 |
| WO | 2017070605 | A1 | 4/2017 |
| WO | 2017091630 | A1 | 6/2017 |
| WO | 2017127807 | A1 | 7/2017 |
| WO | 2017219027 | A1 | 12/2017 |
| WO | 2018035250 | A1 | 2/2018 |
| WO | 2018035388 | A1 | 2/2018 |
| WO | 2019178427 | A1 | 9/2019 |
| WO | 2019178428 | A1 | 9/2019 |
| WO | 2019201331 | A1 | 10/2019 |
| WO | 2019/217944 | A1 | 11/2019 |
| WO | 2020028823 | A1 | 2/2020 |
| WO | 2020088450 | A1 | 5/2020 |

(Continued)

OTHER PUBLICATIONS

GenBank OGR07204. MAG: hypothetical protein A2511_12455 [Deltaproteobacteria bacterium RIFOXYD12_FULL_50_9], Deposited Oct. 20, 2016. 2 pages (Year: 2016).*
Speth et al., Draft Genome Sequence of Anammox Bacterium "Candidatus Scalindua brodae," Obtained Using Differential Coverage Binning of Sequencing Data from Two Reactor Enrichments. Genome Announc 3 (1) (2015) (Year: 2015).*
GenBank: KHE91659.1. MAG: RAMP superfamily protein [Candidatus Scalindua brodae. Submitted (Oct. 15, 2014) (Year: 2014).*
Makarova et al. Evolutionary classification of CRISPR-Cas systems: a burst of class 2 and derived variants (Nat Rev Microbio, 2020,18:67-83) (Year: 2020).*

(Continued)

*Primary Examiner* — Arthur S Leonard
(74) *Attorney, Agent, or Firm* — K&L Gates LLP

(57) ABSTRACT

The disclosure describes novel systems, methods, and compositions for the manipulation of nucleic acids in a targeted fashion. The disclosure describes non-naturally occurring, engineered CRISPR systems, components, and methods for targeted modification of DNA, RNA, and protein substrates. Each system includes one or more protein components and one or more nucleic acid components that together target DNA, RNA, or protein substrates.

18 Claims, 14 Drawing Sheets

Specification includes a Sequence Listing.

(56) References Cited

FOREIGN PATENT DOCUMENTS

| | | | |
|---|---|---|---|
| WO | 2020/168051 | A1 | 8/2020 |
| WO | 2020/168075 | A1 | 8/2020 |
| WO | 2020/168088 | A1 | 8/2020 |
| WO | 2020/168122 | A1 | 8/2020 |
| WO | 2020/168132 | A1 | 8/2020 |
| WO | 2020181101 | A1 | 9/2020 |
| WO | 2020/236936 | A1 | 11/2020 |

OTHER PUBLICATIONS

Abudayyeh et al. "C2c2 is a single-component programmable RNA-guided RNA-targeting CRISPR effector" Science (2016) vol. 353, No. 6299, pp aaf5573-1-aaf5573-9.

Allerson et al. "Fully 2'-modified oligonucleotide duplexes with improved in vitro potency and stability compared to unmodified small interfering RNA," J. Med. Chem., 48.4 (2005): 901-904.

Al-Shayeb et al., "Clades of huge phages from across Earth's ecosystems," Nature (2020) vol. 578, pp. 425-431 and Methods pages.

Aravind et al "Classification of the caspase-hemoglobinase fold: detection of new families and implications for the origin of the eukaryotic separins" (2002) Proteins 46(4): 355-67.

Baba et al. "Construction of *Escherichia coli* K-12 in-frame, single-gene knockout mutants: the Keio collection" (2006) Mol. Syst. Biol. 2: 2006.0008.

Bell et al., "A high-throughput screening strategy for detecting CRISPR-Cas9 induced mutations using next-generation sequencing," BMC Genomics (2014) vol. 15, No. 1002, pp. 1-7.

Bisaria et al., "Lessons from Enzyme Kinetics Reveal Specificity Principles for RNA-Guided Nucleases in RNA Interference and CRISPR-Based Genome Editing," Cell Systems 4(1): 21-9 (Jan. 2017).

Boyle et al., "Quantification of Cas9 binding and cleavage across diverse guide sequences maps landscapes of target engagement," Science Advances 7(8): eabe5496 (Feb. 2021).

Bramsen et al., "Development of therapeutic-grade small interfering RNAs by chemical engineering," Front. Genet., Aug. 20, 2012; 3:154.

Canver et al., "BCL11A enhancer dissection by Cas9-mediated in situ saturating mutagenesis," Nature, Nov. 12, 2015; 527(7577):192-7.

Chen et al., "CRISPR-Cas12a target binding unleashes indiscriminate single-stranded DNase activity, Science 360 (6387)" 436-9 (Feb. 2018).

Chen et al., "Enhanced proofreading governs CRISPR-Cas9 targeting accuracy," Nature 550(7676)407-10 (Sep. 2017).

Chen et al., "Spatially resolved, highly multiplexed RNA profiling in single cells," Science, Apr. 24, 2015; 348(6233): aaa6090.

Chou-Zheng et al "A type III-A CRISPR-Cas system employs degradosome nucleases to ensure robust immunity" (2019) eLife 8:e45393.

Cooper et al., "RNA and disease," Cell, 136.4 (2009): 777-793.

Databse EMBL Online—Speth D.R. et al. "Candidatus Scalindua brodae CHAT domain protein," retrieved from UNIPARC accession No. UPI0005442945, database Accession No. KHE91663, dated Dec. 14, 2014.

Datlinger et al., "Pooled CRISPR screening with single-cell transcriptome read-out," Nat. Methods., Mar. 2017; 14 (3):297-3.

Dong et al., "The crystal structure of Cpf1 in complex with CRISPR RNA," Nature 532(7600): 522-6 (Apr. 2016).

Eckstein et al "Phosphorothioates, essential components of therapeutic oligonucleotides," Nucl. Acid Ther., 24 (2014), pp. 374-387.

Epstein et al "Engineering a Self-Inactivating CRISPR System for AAV Vectors," Mol. Ther., 24 (2016): S50.

Estrella et al., "RNA-activated DNA cleavage by the Type III-B CRISPR-Cas effector complex" (2019) Genes & Dev 30:460-470.

Garrett et al., "CRISPR-based immune systems of the Sulfolobales: complexity and diversity," Biochem Soc Trans (2011) vol. 39, pp. 51-57.

Gaudelli et al., "Programmable base editing of A.T to G.C in genomic DNA without DNA cleavage," Nature 551 (7681): 464-71 (Oct. 2017).

Gerdes et al. "Experimental determination and system level analysis of essential genes in *Escherichia coli* MG1655" (2003) J. Bacteriol. 185(19): 5673-84.

Goldfless et al. "Direct and specific chemical control of eukaryotic translation with a synthetic RNA-protein interaction," Nucl. Acids Res., 40.9 (2012): e64-e64.

Gootenberg et al. "Nucleic acid detection with CRISPR-Cas13a/C2c2," Science, Apr. 28, 2017; 356(6336):438-442.

Hallbrink et al., "Prediction of cell-penetrating peptides," Methods Mol. Biol., 2015; 1324:39-58.

Hammond et al., "A CRISPR-Cas9 gene drive system targeting female reproduction in the malaria mosquito vector Anopheles gambiae," Nat. Biotechnol., Jan. 2016; 34(1):78-83.

Hirosawa et al. "Cell-type-specific genome editing with a microRNA-responsive CRISPR-Cas9 switch," Nucl. Acids Res., Jul. 27, 2017; 45(13): e118.

Hlavova et al., "Improving microalgae for biotechnology-from genetics to synthetic biology," Biotechnol. Adv., Nov. 1, 2015; 33:1194-203.

Huang et al., "Structural basis for two metal-ion catalysis of DNA cleavage by Cas12i2," Nature Communications 11 (1): 5241 (Oct. 2020).

International Search Report and Written Opinion for International Application No. PCT/US2019/022376 dated Jun. 17, 2019.

International Search Report for International Application No. PCT/US2019/022375, mailed Jun. 13, 2019 (6 pages).

International Search Report for PCT/US2019/032750, mailed Sep. 25, 2019.

Jones et al., "Massively parallel kinetic profiling of natural and engineered CRISPR nucleases," Nature Biotechnology 39(1): 84-93 (Jan. 2021).

Kelley et al., "Versatility of chemically synthesized guide RNAs for CRISPR-Cas9 genome editing," J. Biotechnol. Sep. 10, 2016; 233:74-83.

Kim et al., "Efficient Transcriptional Gene Repression by Type V-A CRISPR-Cpf1 from Eubacterium eligens," ACS Synthetic Biology 6(7): 1273-82 (Apr. 2017).

Klein et al., "Hybridization Kinetics Explains CRISPR-Cas Off-Targeting Rules," Cell Reports 22(6): 1413-23 (Feb. 2018).

Kleinstiver et al., "Engineered CRISPR-Cas12a variants with increased activities and improved targeting ranges for gene, epigenetic and base editing," Nature Biotechnology 37(3): 276-82 (Feb. 2019).

Kleinstiver et al., "High-fidelity CRISPR-Cas9 nucleases with no detectable genome-wide off-target effects," Nature 529(7587): 490-5 (Jan. 2016).

Konermann et al. "Optical control of mammalian endogenous transcription and epigenetic states," Nature, 500.7463 (2013): 472.

Koonin et al., "Diversity, classification and evolution of CRISPR-Cas systems," Current Opinion in Microbiology 37: 67-78 (Jun. 2017).

Liu et al., "C2c1-sgRNA Complex Structure Reveals RNA-Guided DNA Cleavage Mechanism," Mol Cell. 65(2):310-22 (Dec. 2016).

Makarova et al., "An updated evolutionary classification of CRISPR-Cas systems," Nat. Rev. Microbiol. 13 (11):722-36 (Sep. 2015).

Makarova et al., "Annotation and Classification of CRISPR-Cas Systems," Methods Mol Biol (2015) vol. 1311, pp. 47-75.

Makarova et al., "Classification and Nomenclature of CRISPR-Cas Systems: Where from Here?" CRISPR J. 1 (5):325-36 (Oct. 2018).

Makarova et al., "Unification of Cas protein families and a simple scenario for the origin and evolution of CRISPR-Cas systems," Biology Direct (2011) vol. 6, Article 38, 27 pages.

Murugan et al., "The Revolution Continues: Newly Discovered Systems Expand the CRISPR-Cas Toolkit," Molecular Cell 68(1): 15-25 (Oct. 2017).

Nicolaou et al., "Molecular diagnosis of peanut and legume allergy," Curr. Opin. Allergy Clin. Immunol., Jun. 2011; 11(3):222-8.

(56) References Cited

OTHER PUBLICATIONS

Nowak et al., "Guide RNA engineering for versatile Cas9 functionality," Nucl. Acid. Res., Nov. 16, 2016; 44 (20):9555-9564.
O'Connell et al. "Programmable RNA recognition and cleavage by CRISPR/Cas9" Nature (2014) vol. 516, No. 7530, pp. 263-266.
Osborne et al., "Transcriptional and post-transcriptional impact of toxic RNA in myotonic dystrophy," Hum. Mol. Genet., Apr. 15, 2009; 18(8):1471-81.
Pausch et al., "CRISPR-Cas-Phi from huge phages is a hypercompact genome editor," Science (2020) vol. 369, pp. 333-337.
Ramakrishna et al., "Gene disruption by cell-penetrating peptide-mediated delivery of Cas9 protein and guide RNA," Genome Res., Jun. 2014;24(6):1020-7.
Ran et al., "Double nicking by RNA-guided CRISPR Cas9 for enhanced genome editing specificity," Cell 154 (6):1380-9 (Aug. 2013).
Sequence Alignment of SEQ ID No. 5 with BHT45754, Search conducted on Apr. 26, 2021, 4 pages. (Year: 2021).
Sequence Alignment of SEQ ID No. 5 with BIV42102, Search conducted on Apr. 26, 2021, 3 pages. (Year: 2021).
Sequence Alignment of SEQ ID No. 5 with BGX25975, Search conducted on Jun. 5, 2020, 4 pages. (Year: 2020).
Sequence Alignment of SEQ ID No. 5 with BGX25978, Search conducted on Jun. 11, 2020, 7 pages. (Year: 2020).
Sequence Alignment of SEQ ID No. 5 with BGX25997, Search conducted on Jun. 11, 2020, 7 pages. (Year: 2020).
Shmakov et al., "Discovery and Functional Characterization of Diverse Class 2 CRISPR-Cas Systems," Molecular Cell 60(3): 385-97 (Oct. 2015).
Slaymaker et al., "Rationally engineered Cas9 nucleases with improved specificity," Science 351(6268): 84-8 (Jan. 2016).
Smargon et al. "Cas13b Is a Type VI-B CRISPR-Associated RNA-Guided RNase Differentially Regulated by Accessory Proteins Csx27 and Csx28" Molecular Cell (2017) vol. 65, No. 4, pp. 618-630.
Stella et al., "Class 2 CRISPR-Cas RNA-guided endonucleases: Swiss Army knives of genome editing," Nature Structural & Molecular Biology 24(11): 882-92 (Oct. 2017).
Strecker et al., "Engineering of CRISPR-Cas12b for human genome editing," Nature Communications 10(1): 212 (Jan. 2019).
Strohkendl et al., "Kinetic basis for DNA target specificity of CRISPR-Cas12a," Molecular Cell 71(5): 816-24 (Sep. 2018).
Strutt et al. "RNA-dependent RNA targeting by CRISPR-Cas9" eLIFE (2018) vol. 7, e 32724, pp. 1-17.
Tamulaitis et al., "Type III CRISPR-Cas Immunity: Major Differences Brushed Aside," Trends Microbiol (2017) vol. 25, No. 1, pp. 49-61.
Verwaal et al., "CRISPR/Cpf1 enables fast and simple genome editing of *Saccharomyces cerevisiae*," Yeast, Sep. 8, 2017. doi: 10.1002/yea.3278.
Wright et al. "Rational design of a split-Cas9 enzyme complex," Proc. Nat'l. Acad. Sci., 112.10 (2015): 2984-2989.
Written Opinion of the International Searching Authority for International Application No. PCT/US2019/022375 (7 pages).
Wu et al., "Structural basis of stringent PAM recognition by CRISPR-C2c1 in complex with sgRNA," Cell Res. 27 (5):705-8 (Apr. 2017).
Yamano et al., "Crystal Structure of Cpf1 in Complex with Guide RNA and Target DNA," Cell 165(4):949-62 (Apr. 2016).
Yan et al., "Cas13d Is a Compact RNA-Targeting Type VI CRISPR Effector Positively Modulated by a WYL-Domain-Containing Accessory Protein," Mol. Cell 70(2)327-39.e5 (Mar. 2018).
Yan et al., "Functionally diverse type V CRISPR-Cas systems," Science 363(6422):88-91 (Dec. 2018).
Yang et al., "PAM-Dependent Target DNA Recognition and Cleavage by C2c1 CRISPR-Cas Endonuclease," Cell 167 (7):1814-28 (Dec. 2016).
Zetsche et al., "A split-Cas9 architecture for inducible genome editing and transcription modulation," Nature Biotech., 33.2 (2015): 139-142.
Zetsche et al., "Cpf1 is a single RNA-guided endonuclease of a class 2 CRISPR-Cas system," Cell 163(3), 759-71 (Sep. 2015).
Zhang et al., "Mechanisms for target recognition and cleavage by the Cas12i RNA-guided endonuclease," Nature Structural & Molecular Biology 27:1069-76 (Sep. 2020).
Carabias, A. et al. "Structure of the mini-RNA-guided endonuclease CRISPR-Cas12j3." Nature Communications vol. 12,1 4476. (2021): 1-12.
Chylinski, K. et al. "Classification and evolution of type II CRISPR-Cas systems." Nucleic Acids Research vol. 42,10 (2014): 6091-105.
Guo, H. H. et al. "Protein tolerance to random amino acid change." Proceedings of the National Academy of Sciences of the United States of America vol. 101,25 (2004): 9205-10.

* cited by examiner

Type III-E | Direct Repeat

Alignment

Type III-E | Effector A - Functional Domains

```
Query:       CLUST.019911  [M=796]
Scores for complete sequences (score includes all domains):
   --- full sequence ---   --- best 1 domain ---    -#dom-
    E-value  score  bias    E-value  score  bias    exp  N  Sequence                    Description
    ------- ------ -----    ------- ------ -----   ---- --  --------                    -----------
    5 3e-89  309 6   0.0    5 8e-89  309 5   0.0    1.0  1  A0A0B0EKL4_9BACT/474-681     A0A0B0EKL4.1 PF12770.6;CHA
    6.4e-76  266.4   0.1    7.5e-76  266.1   0.1    1.0  1  I3IJ32_9BACT/506-720         I3IJ32.1 PF12770.6;CHAT;
    2.7e-59  211.4   0.0      3e-59  211.2   0.0    1.0  1  A0A0M2UUX8_9BACT/510-766     A0A0M2UUX8.1 PF12770.6;CHA
    6.4e-57  203.5   0.2    7.4e-57  203.3   0.2    1.0  1  A0A0M9E5G0_9DELT/841-1101    A0A0M9E5G0.1 PF12770.6;CHA
    7 1e-24   94 3   0 7    8.9e-24   93 9   0 7    1.0  1  K9ZFL8_ANACC/786-1097        K9ZFL8 1 PF12770.6;CHAT;
    1.4e-20   83.4   0.1    1.7e-20   83.0   0.1    1.0  1  A7BQU5_9GAMM/952-1233        A7BQU5.1 PF12770.6;CHAT;
```

FIG. 5

Type III-E | JRYO01000185 crRNA Depletion Values by DR orientation

SEQUENCE LISTING

```
<160> NUMBER OF SEQ ID NOS: 315

<210> SEQ ID NO 1
<211> LENGTH: 716
<212> TYPE: PRT
<213> ORGANISM: Candidatus Scalindua brodae

<400> SEQUENCE: 1

Met Asn Asn Thr Glu Glu Asn Ile Asp Arg Ile Gln Glu Pro Thr Arg
1               5                   10                  15

Glu Asp Ile Asp Arg Lys Glu Ala Glu Arg Leu Leu Asp Glu Ala Phe
            20                  25                  30

Asn Pro Arg Thr Lys Pro Val Asp Arg Lys Lys Ile Ile Asn Ser Ala
        35                  40                  45

Leu Lys Ile Leu Ile Gly Leu Tyr Lys Glu Lys Lys Asp Asp Leu Thr
    50                  55                  60

Ser Ala Ser Phe Ile Ser Ile Ala Arg Ala Tyr Tyr Leu Val Ser Ile
65                  70                  75                  80

Thr Ile Leu Pro Lys Gly Thr Thr Ile Pro Glu Lys Lys Lys Glu Ala
                85                  90                  95

Leu Arg Lys Gly Ile Glu Phe Ile Asp Arg Ala Ile Asn Lys Phe Asn
            100                 105                 110

Gly Ser Ile Leu Asp Ser Gln Arg Ala Phe Arg Ile Lys Ser Val Leu
        115                 120                 125

Ser Ile Glu Phe Asn Arg Ile Asp Arg Glu Lys Cys Asp Asn Ile Lys
    130                 135                 140

Leu Lys Asn Leu Leu Asn Glu Ala Val Asp Lys Gly Cys Thr Asp Phe
145                 150                 155                 160

Asp Thr Tyr Glu Trp Asp Ile Gln Ile Ala Ile Arg Leu Cys Glu Leu
                165                 170                 175

Gly Val Asp Met Glu Gly His Phe Asp Asn Leu Ile Lys Ser Asn Lys
            180                 185                 190

Ala Asn Asp Leu Gln Lys Ala Lys Ala Tyr Tyr Phe Ile Lys Lys Asp
        195                 200                 205

Asp His Lys Ala Lys Glu His Met Asp Lys Cys Thr Ala Ser Leu Lys
    210                 215                 220

Tyr Thr Pro Cys Ser His Arg Leu Trp Asp Glu Thr Val Gly Phe Ile
225                 230                 235                 240

Glu Arg Leu Lys Gly Asp Ser Ser Thr Leu Trp Arg Asp Phe Ala Ile
                245                 250                 255
```

```
Lys Thr Tyr Arg Ser Cys Arg Val Gln Glu Lys Glu Thr Gly Thr Leu
            260                 265                 270

Arg Leu Arg Trp Tyr Trp Ser Arg His Arg Val Leu Tyr Asp Met Ala
        275                 280                 285

Phe Leu Ala Val Lys Glu Gln Ala Asp Asp Glu Glu Pro Asp Val Asn
    290                 295                 300

Val Lys Gln Ala Lys Ile Lys Lys Leu Ala Glu Ile Ser Asp Ser Leu
305                 310                 315                 320

Lys Ser Arg Phe Ser Leu Arg Leu Ser Asp Met Glu Lys Met Pro Lys
                325                 330                 335

Ser Asp Asp Glu Ser Asn His Glu Phe Lys Lys Phe Leu Asp Lys Cys
            340                 345                 350

Val Thr Ala Tyr Gln Asp Gly Tyr Val Ile Asn Arg Ser Glu Asp Lys
        355                 360                 365

Glu Gly Gln Gly Glu Asn Lys Ser Thr Thr Ser Lys Gln Pro Glu Pro
    370                 375                 380

Arg Pro Gln Ala Lys Leu Leu Glu Leu Thr Gln Val Pro Glu Gly Trp
385                 390                 395                 400

Val Val Val His Phe Tyr Leu Asn Lys Leu Glu Gly Met Gly Asn Ala
                405                 410                 415

Ile Val Phe Asp Lys Cys Ala Asn Ser Trp Gln Tyr Lys Glu Phe Gln
            420                 425                 430

Tyr Lys Glu Leu Phe Glu Val Phe Leu Thr Trp Gln Ala Asn Tyr Asn
        435                 440                 445

Leu Tyr Lys Glu Asn Ala Ala Glu His Leu Val Thr Leu Cys Lys Lys
    450                 455                 460

Ile Gly Glu Thr Met Pro Phe Leu Phe Cys Asp Asn Phe Ile Pro Asn
465                 470                 475                 480

Gly Lys Asp Val Leu Phe Val Pro His Asp Phe Leu His Arg Leu Pro
                485                 490                 495

Leu His Gly Ser Ile Glu Asn Lys Thr Asn Gly Lys Leu Phe Leu Glu
            500                 505                 510

Asn His Ser Cys Cys Tyr Leu Pro Ala Trp Ser Phe Ala Ser Glu Lys
        515                 520                 525

Glu Ala Ser Thr Ser Asp Glu Tyr Val Leu Leu Lys Asn Phe Asp Gln
    530                 535                 540

Gly His Phe Glu Thr Leu Gln Asn Asn Gln Ile Trp Gly Thr Gln Ser
545                 550                 555                 560

Val Lys Asp Gly Ala Ser Ser Asp Asp Leu Glu Asn Ile Arg Asn Asn
                565                 570                 575

Pro Arg Leu Leu Thr Ile Leu Cys His Gly Glu Ala Asn Met Ser Asn
            580                 585                 590

Pro Phe Arg Ser Met Leu Lys Leu Ala Asn Gly Gly Ile Thr Tyr Leu
        595                 600                 605

Glu Ile Leu Asn Ser Val Lys Gly Leu Lys Gly Ser Gln Val Ile Leu
    610                 615                 620

Gly Ala Cys Glu Thr Asp Leu Val Pro Pro Leu Ser Asp Val Met Asp
625                 630                 635                 640

Glu His Tyr Ser Val Ala Thr Ala Leu Leu Leu Ile Gly Ala Ala Gly
                645                 650                 655

Val Val Gly Thr Met Trp Lys Val Arg Ser Asn Lys Thr Lys Ser Leu
            660                 665                 670

Ile Glu Trp Lys Leu Glu Asn Ile Glu Tyr Lys Leu Asn Glu Trp Gln
```

```
        675                 680                 685

Lys Glu Thr Gly Gly Ala Ala Tyr Lys Asp His Pro Pro Thr Phe Tyr
    690                 695                 700

Arg Ser Ile Ala Phe Arg Ser Ile Gly Phe Pro Leu
705                 710                 715


<210> SEQ ID NO 2
<211> LENGTH: 849
<212> TYPE: PRT
<213> ORGANISM: Deltaproteobacteria bacterium

<400> SEQUENCE: 2

Met Asn Gln Asn Ile Asp Arg Ala Val Gly Ala Ile Leu Ala Ile Glu
1               5                   10                  15

Thr Ala Thr Pro Leu Thr Glu Ser Ser Thr Leu Ala Gln Arg Glu Arg
            20                  25                  30

His Gln Lys Leu Leu His Asp Glu Thr Lys Lys Ile Glu Gln Ala Phe
        35                  40                  45

Ile Ala Leu Ala Gln Pro Pro Gln Cys Arg Ala Val Glu Ile Ala Ala
    50                  55                  60

Leu Ser Arg Phe Leu Gln Met Thr Pro Leu Ala Val Gly Pro Leu Arg
65                  70                  75                  80

Lys Arg Val Ile Cys Arg Ala Glu Pro Leu Lys Asp Asp Ala His Glu
                85                  90                  95

Gln Glu Ile Ala Ser His Phe Asn Gly Leu Leu Leu Arg Leu Ala Lys
            100                 105                 110

Gly Leu Leu Ala Ser Ala Leu Asn Pro Ala Gly Ile Pro Trp Arg Arg
        115                 120                 125

Arg Val Leu Trp Leu Glu Lys Ala Ala His Ile Ala His Arg Phe Asp
    130                 135                 140

Lys Glu Pro Leu Ala Asp Asp Lys Glu Arg Thr Glu Ala Ala Gly Val
145                 150                 155                 160

Leu Ala Arg Cys Cys Leu His Leu Ala Leu Ala His Leu Pro Lys Gly
                165                 170                 175

Lys Asp Lys Ser Ala Met Ala Glu Arg Gln Glu Asp Leu Leu Gln Ser
            180                 185                 190

Leu Met Trp Ala Gln Lys Ala Ile Val Leu Ala Gly Gln Asp Lys Leu
        195                 200                 205

Ser Gly Glu Glu Tyr Lys Leu Leu Lys Ala Leu Val Leu Ile Glu Leu
    210                 215                 220

Asp Asn Leu Ser Pro Gly Arg Phe Gln Gln Gln Leu Asn Tyr Val Leu
225                 230                 235                 240

Tyr Asp Leu Ala Val Ile Trp Leu Glu Arg Asp Thr Ala Thr Lys Pro
                245                 250                 255

Phe His Pro Gln Glu Leu Phe Val Leu Trp Arg Tyr Leu Ala Thr Asp
            260                 265                 270

Phe Glu Pro Asp Leu Asn Met Leu Leu Phe Lys Gly Ser Asn Thr Ser
        275                 280                 285

Glu Arg Thr Ala Ala Val Gln Gln Ala Ser Pro Glu Ala Glu Arg Phe
    290                 295                 300

Arg Pro Leu Leu Pro Leu Ile His Ala Trp Ser Ala Trp Lys Leu Asp
305                 310                 315                 320

Pro Pro Asn Asn Lys Ile Ala Glu Val Ile Leu Gln Ala Val Asn Asn
                325                 330                 335
```

```
Leu Asp Glu His Gln Val Tyr Glu Gln Val Trp Lys Trp Thr Val Asp
            340                 345                 350

Phe Leu Gln Glu Leu Arg Asn Thr Gly Ala Val Asp Trp Gln Leu Pro
        355                 360                 365

Ala Ile Ala Ala Trp Glu Leu Cys Asn Lys Lys Glu Lys Glu Leu Pro
    370                 375                 380

Phe Gly Phe Gln Ile Arg Gln Tyr Trp Ser Arg Leu Asp Ser Leu Tyr
385                 390                 395                 400

Arg Leu Ala Phe Asp Gly Ala Leu Glu Leu Lys Asp Cys Met Thr Ala
                405                 410                 415

Ala Arg Ile Val Asp Ser Leu Lys Ser Arg Thr Pro Leu Thr Trp Arg
            420                 425                 430

Asp Met Asp Thr Leu Phe Ala Lys Leu Pro Lys Glu Lys Ala Asp Gln
        435                 440                 445

Leu Arg Glu Ala Phe Tyr Ser Met Glu Val Gln Ala Arg Met Gly Phe
    450                 455                 460

Tyr Ala Glu Ala Lys Glu Asp Ala Asn Lys Leu Lys Lys Leu Leu Ala
465                 470                 475                 480

Ala Gln Val Arg Lys Ile Arg Asp Ile Glu Ser Val Pro Ala Gly Trp
                485                 490                 495

Thr Val Val His Phe His Leu Arg Glu Asp Gln Asp Leu Gly Tyr Ala
            500                 505                 510

Leu Ala Cys Arg Leu Thr Ala Asp Gly Met Ser Tyr Trp Thr Asn His
        515                 520                 525

Ile Phe Pro Val Ala Gly Ile Arg Arg Ala Tyr Asp Cys Trp Leu Glu
    530                 535                 540

Ala Tyr His Gly Met Glu Pro Gly Ala Arg Glu Lys Ser Gly Tyr Gln
545                 550                 555                 560

Leu Val Glu Leu Ser Glu Ile Met Gly Lys Asp Leu Asp Phe Leu Phe
                565                 570                 575

Glu Leu Ala Gly Glu Asp Gly Ala Arg Gly Leu Leu Phe Val Pro His
            580                 585                 590

Gly Phe Ser His Leu Leu Pro Leu His Ala Ala Lys Lys Asp Gly Ser
        595                 600                 605

Tyr Leu Phe Glu Lys Ile Pro Ser Leu Thr Leu Pro Ala Trp Glu Phe
    610                 615                 620

Ala Pro Asp Val Asp Gln Ile Pro Val Ser Asp Gly Gln Asp Phe Cys
625                 630                 635                 640

Phe Ile Ser Gln Arg Ala Asn Glu Gln Asp Leu Val Gly Asn Ile Glu
                645                 650                 655

Arg Ser His Thr Trp Asn Gly Val Cys Asn Lys Asn Ala Ala Trp Thr
            660                 665                 670

Asn Val Leu Asn Thr Asn Lys Glu Trp Ser Lys Ala Pro Pro Arg Trp
        675                 680                 685

Leu Val Phe Trp Cys His Gly Gln Ala Asp Pro His Val Ala Phe Arg
    690                 695                 700

Ser Lys Leu Leu Leu Gly Thr Leu Gly Val Ser Leu Phe Glu Ile Gln
705                 710                 715                 720

Glu Ala Ala Leu Ser Leu Thr Gly Thr Lys Val Val Leu Ala Val Cys
                725                 730                 735

Glu Ser Asp Leu Ala Pro Pro Glu Glu Tyr Glu Lys Thr Asp Asp His
            740                 745                 750

Leu Ser Leu Ala Ala Pro Phe Leu Leu Lys Gly Ala Arg Gln Val Leu
```

755 760 765

Ala Ala Ile Trp Glu Gly Ala Gln Leu Asp Leu Leu Lys Ala Met Lys
770 775 780

Glu Met Leu Ser Asn Gln Asp Lys His Ser Trp Glu Ile Leu Arg Glu
785 790 795 800

Leu Gln Ser Cys Trp Met Arg Gln Pro Gly Ala Ile Phe Asn Asp Glu
805 810 815

Tyr Ile Arg Leu Tyr Tyr Ala Ala Ser Phe Arg Ile Leu Gly Phe Pro
820 825 830

Glu Val Ala Thr Thr Asn Met Ala Thr Ala Thr Ala Gln Glu Glu Ile
835 840 845

Ala

<210> SEQ ID NO 3
<211> LENGTH: 751
<212> TYPE: PRT
<213> ORGANISM: Desulfonema ishimotonii

<400> SEQUENCE: 3

Met Ser Asn Pro Ile Arg Asp Ile Gln Asp Arg Leu Lys Thr Ala Lys
1 5 10 15

Phe Asp Asn Lys Asp Asp Met Met Asn Leu Ala Ser Ser Leu Tyr Lys
20 25 30

Tyr Glu Lys Gln Leu Met Asp Ser Ser Glu Ala Thr Leu Cys Gln Gln
35 40 45

Gly Leu Ser Asn Arg Pro Asn Ser Phe Ser Gln Leu Ser Gln Phe Arg
50 55 60

Asp Ser Asp Ile Gln Ser Lys Ala Gly Gly Gln Thr Gly Lys Phe Trp
65 70 75 80

Gln Asn Glu Tyr Glu Ala Cys Lys Asn Phe Gln Thr His Lys Glu Arg
85 90 95

Arg Glu Thr Leu Glu Gln Ile Ile Arg Phe Leu Gln Asn Gly Ala Glu
100 105 110

Glu Lys Asp Ala Asp Asp Leu Leu Leu Lys Thr Leu Ala Arg Ala Tyr
115 120 125

Phe His Arg Gly Leu Leu Tyr Arg Pro Lys Gly Phe Ser Val Pro Ala
130 135 140

Arg Lys Val Glu Ala Met Lys Lys Ala Ile Ala Tyr Cys Glu Ile Ile
145 150 155 160

Leu Asp Lys Asn Glu Glu Glu Ser Glu Ala Leu Arg Ile Trp Leu Tyr
165 170 175

Ala Ala Met Glu Leu Arg Arg Cys Gly Glu Glu Tyr Pro Glu Asn Phe
180 185 190

Ala Glu Lys Leu Phe Tyr Leu Ala Asn Asp Gly Phe Ile Ser Glu Leu
195 200 205

Tyr Asp Ile Arg Leu Phe Leu Glu Tyr Thr Glu Arg Glu Glu Asp Asn
210 215 220

Asn Phe Leu Asp Met Ile Leu Gln Glu Asn Gln Asp Arg Glu Arg Leu
225 230 235 240

Phe Glu Leu Cys Leu Tyr Lys Ala Arg Ala Cys Phe His Leu Asn Gln
245 250 255

Leu Asn Asp Val Arg Ile Tyr Gly Glu Ser Ala Ile Asp Asn Ala Pro
260 265 270

Gly Ala Phe Ala Asp Pro Phe Trp Asp Glu Leu Val Glu Phe Ile Arg

```
        275                 280                 285

Met Leu Arg Asn Lys Lys Ser Glu Leu Trp Lys Glu Ile Ala Ile Lys
    290                 295                 300

Ala Trp Asp Lys Cys Arg Glu Lys Glu Met Lys Val Gly Asn Asn Ile
305                 310                 315                 320

Tyr Leu Ser Trp Tyr Trp Ala Arg Gln Arg Glu Leu Tyr Asp Leu Ala
                325                 330                 335

Phe Met Ala Gln Asp Gly Ile Glu Lys Lys Thr Arg Ile Ala Asp Ser
            340                 345                 350

Leu Lys Ser Arg Thr Thr Leu Arg Ile Gln Glu Leu Asn Glu Leu Arg
        355                 360                 365

Lys Asp Ala His Arg Lys Gln Asn Arg Arg Leu Glu Asp Lys Leu Asp
    370                 375                 380

Arg Ile Ile Glu Gln Glu Asn Glu Ala Arg Asp Gly Ala Tyr Leu Arg
385                 390                 395                 400

Arg Asn Pro Pro Cys Phe Thr Gly Gly Lys Arg Glu Glu Ile Pro Phe
                405                 410                 415

Ala Arg Leu Pro Gln Asn Trp Ile Ala Val His Phe Tyr Leu Asn Glu
            420                 425                 430

Leu Glu Ser His Glu Gly Gly Lys Gly Gly His Ala Leu Ile Tyr Asp
        435                 440                 445

Pro Gln Lys Ala Glu Lys Asp Gln Trp Gln Asp Lys Ser Phe Asp Tyr
    450                 455                 460

Lys Glu Leu His Arg Lys Phe Leu Glu Trp Gln Glu Asn Tyr Ile Leu
465                 470                 475                 480

Asn Glu Glu Gly Ser Ala Asp Phe Leu Val Thr Leu Cys Arg Glu Ile
                485                 490                 495

Glu Lys Ala Met Pro Phe Leu Phe Lys Ser Glu Val Ile Pro Glu Asp
            500                 505                 510

Arg Pro Val Leu Trp Ile Pro His Gly Phe Leu His Arg Leu Pro Leu
        515                 520                 525

His Ala Ala Met Lys Ser Gly Asn Asn Ser Asn Ile Glu Ile Phe Trp
    530                 535                 540

Glu Arg His Ala Ser Arg Tyr Leu Pro Ala Trp His Leu Phe Asp Pro
545                 550                 555                 560

Ala Pro Tyr Ser Arg Glu Glu Ser Ser Thr Leu Leu Lys Asn Phe Glu
                565                 570                 575

Glu Tyr Asp Phe Gln Asn Leu Glu Asn Gly Glu Ile Glu Val Tyr Ala
            580                 585                 590

Pro Ser Ser Pro Lys Lys Val Lys Glu Ala Ile Arg Glu Asn Pro Ala
        595                 600                 605

Ile Leu Leu Leu Leu Cys His Gly Glu Ala Asp Met Thr Asn Pro Phe
    610                 615                 620

Arg Ser Cys Leu Lys Leu Lys Asn Lys Asp Met Thr Ile Phe Asp Leu
625                 630                 635                 640

Leu Thr Val Glu Asp Val Arg Leu Ser Gly Ser Arg Ile Leu Leu Gly
                645                 650                 655

Ala Cys Glu Ser Asp Met Val Pro Pro Leu Glu Phe Ser Val Asp Glu
            660                 665                 670

His Leu Ser Val Ser Gly Ala Phe Leu Ser His Lys Ala Gly Glu Ile
        675                 680                 685

Val Ala Gly Leu Trp Thr Val Asp Ser Glu Lys Val Asp Glu Cys Tyr
    690                 695                 700
```

Ser Tyr Leu Val Glu Glu Lys Asp Phe Leu Arg Asn Leu Gln Glu Trp
705 710 715 720

Gln Met Ala Glu Thr Glu Asn Phe Arg Ser Glu Asn Asp Ser Ser Leu
725 730 735

Phe Tyr Lys Ile Ala Pro Phe Arg Ile Ile Gly Phe Pro Ala Glu
740 745 750

<210> SEQ ID NO 4
<211> LENGTH: 816
<212> TYPE: PRT
<213> ORGANISM: Unknown
<220> FEATURE:
<221> NAME/KEY: source
<223> OTHER INFORMATION: /note="Description of Unknown:
Soil metagenome sequence"

<400> SEQUENCE: 4

Met Glu His Lys Thr Met Thr Glu Pro Ala Gly Gln Asn Pro Ser Ala
1 5 10 15

Thr Asp Asn Asp Phe Glu Lys Phe Ile Ile Asp Thr Gly Cys Val Phe
20 25 30

Phe Ala Thr Pro Gln Glu Asp Pro Lys Tyr Gln Asn Asn Lys Val Glu
35 40 45

Trp His Gln Gly Leu Cys Arg Phe Ala Gln Asn Asp Ser Pro Pro Thr
50 55 60

Val Ile Gly Ser Ala Ile Phe Phe Leu Gln Lys Leu Gln Glu Pro Gly
65 70 75 80

Leu Phe Ser Gly Leu Pro Val Ser Pro Glu Leu Cys Ser Lys Ile Ser
85 90 95

Lys Asp Lys Asn Glu Ile Val Ala Tyr His Gln Gln Cys Ile Leu Arg
100 105 110

Leu Cys Glu Glu Leu Leu Val Lys Gly Arg Glu Ala Lys Glu His Arg
115 120 125

Glu Arg Arg Gln Ala Phe Asp Gln Ala Ile Lys Phe Leu Leu Val Leu
130 135 140

Lys Lys Gly Thr Ser Ser Asp Thr Pro Ser Pro Asn Gly His Ile His
145 150 155 160

Phe Gln Asp Gln Val Ser Ile Leu Leu Ala Glu Ala Tyr Tyr Leu Arg
165 170 175

Gly Lys Ile Ile Arg Pro Lys Gly Phe Ser Val Pro Ala Lys Lys Ile
180 185 190

Glu Thr Leu Glu Val Ala Glu Lys Ile Leu Val Asp Leu Val Ala Arg
195 200 205

Asp Thr Thr Gly Lys Ala Arg Arg Leu Arg Ala Met Val His Ile Asp
210 215 220

Leu Ala Ala Leu Arg Asp Pro Ala Asp Asp Ser Gly Asn Leu Gln Asp
225 230 235 240

Tyr Arg Gln Ala Leu Glu Gln Ala Val Ser Ser Ile Gly Asp Thr Lys
245 250 255

Thr Cys Gly Arg Asp Glu Ile Val Ile Ile Leu Ala Arg Ala Glu Asp
260 265 270

Asn Ala Gly Trp Thr Gly Ser Asp Gly Leu Ser Ala Arg Leu Glu Glu
275 280 285

Leu Val Asn Asn Gly Ala Ala Gly Pro Leu Asp Gln Ala Arg Ala Tyr
290 295 300

```
Leu Leu Leu Gly Gln Asn Asn Leu Ala Val Thr Gln Thr Glu Lys Ala
305                 310                 315                 320

Ile Thr Arg Met Ala Ala Thr Asp Asn Pro Thr Pro Phe Ser His Glu
                325                 330                 335

Asp Trp Arg Leu Leu Val Arg Leu Leu Arg Asp Leu Lys His Gln Asn
            340                 345                 350

Thr Ala Gly Ile Asp Lys Leu Ile Leu Asp Thr Trp Arg Lys Val His
        355                 360                 365

Gln Ile Glu Arg Gln Thr Lys Asn Gly Met His Val Arg Trp Tyr Trp
    370                 375                 380

Ser Arg Gln Arg Asp Leu Tyr Asp Leu Ala Phe His Ala Ala Gly Asn
385                 390                 395                 400

Asp Ala Arg Leu Lys Ala Gln Ile Ala Asp Ser Leu Lys Ala Arg Pro
                405                 410                 415

Ala Leu His Leu Gly Gln Ala Ala Asp Leu Gly Leu Ala Val Glu Gln
            420                 425                 430

Met Glu Ala Gly Leu Leu Asp Arg Tyr Met Pro Gly Lys Met Leu Glu
        435                 440                 445

Gln Thr Thr Asp Met Ala Ala Pro Ala Ala Pro Gly Ser Ala Gly Trp
    450                 455                 460

Pro Glu Leu Pro Arg Pro Trp Ile Ala Val His Phe Tyr Leu Ser Asn
465                 470                 475                 480

Gly Phe Gly His Pro Glu Gly Lys Gln Gln Gly His Ala Leu Ile Gln
                485                 490                 495

Asp Ser Ser Lys Gly Asp Gly Lys Asp Thr Trp Ser Glu Arg Thr Phe
            500                 505                 510

Asp Tyr Phe Pro Ile Trp Ala Ala Phe Met Thr Trp Gln Glu Asn Tyr
        515                 520                 525

Gln Arg Leu Lys Lys Glu Ala Ala Pro Asp Leu Glu Arg Leu Cys Gln
    530                 535                 540

Val Met Gly Arg Gln Met Pro Phe Leu Phe Ala Pro Glu Asp Leu Pro
545                 550                 555                 560

Leu Glu Arg Pro Val Val Phe Val Pro His Asp Phe Leu His Arg Leu
                565                 570                 575

Pro Leu His Ala Ala Leu Ile Asp Asn Gly Glu Glu Ser Gly Ile Pro
            580                 585                 590

Ala Gln Ser His Pro Ile Thr Tyr Leu Pro Gly Trp Trp Met Val Thr
        595                 600                 605

Ser Gln Ala Ala Asn Pro Asn Glu Thr Ala Ser Lys Asn Thr Pro Ser
    610                 615                 620

Pro Val Ala Pro Val Ala Leu Val His Trp Asp Asn Ser Glu Asp Ile
625                 630                 635                 640

His Asp Ile Ile Lys Gln Ala Asn Gly Thr Val Val Val Asn Ala Ser
                645                 650                 655

Arg Ser Asp Trp Leu Lys Leu Lys His Asn Ala Val Gly Leu Lys Val
            660                 665                 670

Leu Tyr Cys His Gly Gln Ala Gly Tyr Thr Asn Pro Phe Ala Ser Ser
        675                 680                 685

Leu Lys Leu Asp Gly Gly Gly Leu Tyr Leu Lys Asp Val Val Lys Gly
    690                 695                 700

Pro Pro Leu Val Gly Arg Phe Ile Leu Ala Ala Cys Glu Ser Asp Leu
705                 710                 715                 720

Val Leu Pro Ala Ser Thr Thr Leu Asp Glu Tyr Phe Ser Phe Ser Thr
```

```
                725                 730                 735

Gly Leu Leu Gln Lys Gly Ala Ala Glu Ile Leu Gly Thr Leu Trp Glu
            740                 745                 750

Val Asn Glu Thr Asp Ala Leu Ser Leu Ile Glu Thr Val Leu Arg Ala
        755                 760                 765

Pro Ala Ser Gly Asn Leu Ser Phe Val Leu Arg Asp Trp Leu Arg Asp
    770                 775                 780

Asn Leu Arg Ser Leu Thr Thr Glu Leu Phe Tyr Asp Ile Ala Ala Phe
785                 790                 795                 800

Arg Ala Leu Gly Gly Pro Tyr Pro Val Asp Thr Lys Glu Glu His Arg
                805                 810                 815


<210> SEQ ID NO 5
<211> LENGTH: 769
<212> TYPE: PRT
<213> ORGANISM: Unknown
<220> FEATURE:
<221> NAME/KEY: source
<223> OTHER INFORMATION: /note="Description of Unknown:
      Dolphin oral metagenome sequence"

<400> SEQUENCE: 5

Met Asn Thr Val Glu Leu Leu Gln Glu Glu Glu Arg Leu Thr Leu Asp
1               5                   10                  15

Leu Val Phe Leu Pro Pro Gly Ser Lys Asn Lys Glu Gln Lys Lys Asn
            20                  25                  30

Ala Leu Val Asp Leu Leu Leu Lys Ile Val Glu His Gly Glu Leu Thr
        35                  40                  45

Arg Lys Tyr Ser Ala Leu Leu Thr Leu Ser Arg Gly Ala Leu Arg Gly
    50                  55                  60

Glu Val His Phe Gly Glu Lys Leu Leu Pro Ser Pro Glu Ala Cys Ala
65                  70                  75                  80

Asn Leu Ala Lys Pro Glu Glu Ile Lys Lys Met Ile Arg Gln His Phe
                85                  90                  95

Gln Tyr Arg Leu Asp Leu Leu Glu Ala Ile Val Lys Lys Ala Ala Asp
            100                 105                 110

Asn Thr Tyr Ser His Ala Arg Arg Arg Lys Ala Leu Arg Ile Ala Ile
        115                 120                 125

Lys Glu Leu Glu Gln Ile Cys Glu Glu Ala Leu Asp Glu Leu Cys Phe
    130                 135                 140

Lys Ala Arg Leu Leu Leu Ala Glu Ala Leu Phe Glu Arg Gly Arg Ile
145                 150                 155                 160

Val Arg Pro Lys Gly Phe Ser Glu Pro Gly Lys Lys Lys Glu Leu Phe
                165                 170                 175

Gln Lys Ala Ile Asn Cys Ile Glu Gly Asn Cys Ser Glu Glu Ala Leu
            180                 185                 190

Arg Leu Arg Ala Arg Ile Tyr Leu Gln Trp Tyr Arg Phe Phe His Asp
        195                 200                 205

Glu Pro Pro Cys Asp Leu Asp Asp Ile Phe Thr Lys Ala Leu Ala Val
    210                 215                 220

Thr Asp Asp Lys Met Leu Lys Thr Glu Leu Leu Leu Leu Cys Gly Glu
225                 230                 235                 240

Arg Lys Glu Pro Asp Pro Tyr Thr Asp Asp Leu Arg Ala Leu Leu Asn
                245                 250                 255

Asp Gln Asn Val Ser Pro Leu Ser Arg Ala Arg Ala Ala Val Leu Leu
            260                 265                 270
```

```
Glu Asp Trp Glu Arg Cys Asn Val Glu Ile Tyr Glu Ala Ile Glu Asp
        275                 280                 285

Leu Gly Lys Thr Asp Phe Phe Gln Gln Asp Trp Glu Leu Val Val Thr
    290                 295                 300

Leu Leu Lys Lys Asn Tyr Asn Gln Phe His Gly Trp Ser Arg Ala Cys
305                 310                 315                 320

Thr Arg Leu Trp Glu Ile Thr Val Glu Lys Glu Ser Lys Asp Ala Gly
                325                 330                 335

His Gly Cys Val Leu Arg Trp Tyr Trp Ser Arg Gln Arg Asp Val Tyr
            340                 345                 350

Asn Leu Ala Phe Ala Ala Phe Glu Glu Cys Glu Asp Lys Ala Arg Val
        355                 360                 365

Val Asp Ser Leu Lys Asn Arg Pro Ala His His Phe Ser Gln Leu Glu
    370                 375                 380

Gln Leu Ala Gln Ser Ser Asp Ile Ile Lys Gln Trp Ile Glu Ser Glu
385                 390                 395                 400

Glu Ile Ile Asn Gln Asp Ser Phe Ala His Ser Leu Arg Arg His Glu
                405                 410                 415

Lys Gly Ala Lys Ser His Ser Gly Gly Ser Leu Arg Ile Phe Pro Cys
            420                 425                 430

Leu Pro Lys Gly Trp Ile Ala Val His Phe Phe Leu Ala Ser Trp Pro
        435                 440                 445

Glu Pro Lys Gly Tyr Ala Leu Ile His Asn Ala Asp Thr Asn Thr Trp
    450                 455                 460

Glu Gln Arg Asp Phe Lys Tyr Glu Gln Leu Trp Ala Thr Tyr Ile Ala
465                 470                 475                 480

Trp Gln Glu Val Ser Leu His Asn Lys Ile Arg Glu Ser Ala Leu Leu
                485                 490                 495

Leu Lys Ser Leu Cys Glu Thr Leu Gly Lys Glu Met Arg Trp Leu Phe
            500                 505                 510

Asp Glu Phe Leu Phe Pro Lys Glu Arg Arg Arg Val Leu Phe Val Pro
        515                 520                 525

His Asp Phe Leu His Arg Leu Pro Leu His Met Ala Ile Asp Ile Glu
    530                 535                 540

Ser Gln Thr Val Phe Ala Ala Lys Gln Pro Val Cys Tyr Leu Pro Ala
545                 550                 555                 560

Tyr His Leu Gln Asn Asn Ile Thr Glu Asn Lys Lys Thr Ser Ile Tyr
                565                 570                 575

Ala Leu Val Asn Leu Arg Glu Asn Lys Gln Gln Lys Lys Asp Glu Glu
            580                 585                 590

Ile Phe Ala Glu Lys Val Glu Lys Met Gly Ala Ile Val Arg Arg Pro
        595                 600                 605

Ala Leu Glu Ser Asp Leu Leu Asn Leu Asn Pro Val Pro Glu Lys Leu
    610                 615                 620

Val Leu Tyr Cys His Gly Ile Gly His Ser Ala Asn Pro Phe Ala Ser
625                 630                 635                 640

Lys Leu Cys Leu Gly Asp Thr Gly Val Ser Tyr Arg Asp Ile Leu Ala
                645                 650                 655

Leu Asn Arg Ser Leu Ala Gly Cys Arg Val Leu Leu Phe Ala Cys Glu
            660                 665                 670

Thr Asp Leu Val Pro Ala Gln Thr Ser Ser Ile Asp Glu His Leu Ser
        675                 680                 685
```

```
Ile Ser Asn Ala Leu Leu Gln Lys Gly Ala Phe Glu Val Leu Gly Ser
    690                 695                 700

Leu Trp Ala Leu Pro Gly Lys Thr Ile Tyr Gly Ile Thr Lys Thr Phe
705                 710                 715                 720

Ile Asp Asn Asp Asp Thr Ser Ala Val Leu His Ser Ser Leu Lys Arg
                725                 730                 735

Leu Phe Glu His Tyr Glu Lys Lys Asn Glu Lys Thr Arg Ala Gln Leu
            740                 745                 750

Leu Tyr Asn Trp Ala Ser Leu Arg Val Leu Ala Pro Ala Arg Glu Phe
        755                 760                 765

Ser


<210> SEQ ID NO 6
<211> LENGTH: 778
<212> TYPE: PRT
<213> ORGANISM: Unknown
<220> FEATURE:
<221> NAME/KEY: source
<223> OTHER INFORMATION: /note="Description of Unknown:
      Aquatic-marine-hydrothermal vent microbial mat sequence"

<400> SEQUENCE: 6

Met Arg Tyr Ser Ser Arg Thr Asn Cys Glu Ala Ile Asp Asn Leu Ala
1               5                   10                  15

Glu Ala Leu Gln Asp Gln Glu Asn Met Pro Glu Ile Ala Arg Arg Val
            20                  25                  30

Leu Glu Phe Glu Ala Glu Asn Ala Lys Pro Glu Asn Ala Leu Cys Gln
        35                  40                  45

His Gly Leu Pro His Thr Lys Lys Ala Ala Ser Gln Ile Ala Gly Val
    50                  55                  60

Arg Asp Lys His Ser Glu Phe Tyr Asp Asn Ala Leu Leu Asp Leu Val
65                  70                  75                  80

Glu Glu Trp Leu Lys Thr Tyr Glu Glu Ala Lys Lys Leu Thr His Arg
                85                  90                  95

Glu Arg Arg Gln Glu Met Glu Asp Lys Ile Arg Val Leu Gln Pro Val
            100                 105                 110

Leu Gln Ala Lys Gly Lys Asp Ala Asp Pro Arg Phe Leu Ser Leu Leu
        115                 120                 125

Ala Arg Ile Tyr Leu Tyr Arg Gly Met Leu Phe Arg Pro Lys Gly Phe
    130                 135                 140

Thr Thr Pro Ala Arg Lys Ile Glu Ala Leu Lys Lys Ala Val Gln Leu
145                 150                 155                 160

Ser Glu Lys Ala Val Glu Lys Glu Lys Asp Asn Pro Asn Phe Leu Arg
                165                 170                 175

Thr Trp Ala Gln Ala Ala Leu Glu Leu Glu Ala Ile Pro Glu Thr Ser
            180                 185                 190

Phe Lys Val Ser Ser Gly Leu Leu Lys Asp Ala Ala Val Cys Ile Asn
        195                 200                 205

Arg Asp Gly Ile His Ser Leu Asn Asp Leu Gln Val Ile Leu Glu Tyr
    210                 215                 220

Ala Glu Ser Glu Gly Lys Thr Ser Phe Leu Gln His Val Leu Val Glu
225                 230                 235                 240

Lys Arg Tyr Trp Lys Arg Pro Phe Asp Leu Phe Leu Leu Lys Ala Arg
                245                 250                 255

Ala Ala Phe Ala Leu Asn Arg Met Asp Asp Val Arg Tyr Phe Leu Lys
            260                 265                 270
```

```
Ser Ala Met Asp Lys Thr Pro Lys Ala Leu Ser Ser Pro Phe Trp Asp
        275                 280                 285

His Leu Val Asp Phe Leu Lys Lys Leu Arg Thr Lys Glu Gly Ser Asp
    290                 295                 300

Leu Trp Lys Glu Met Ala Val Ala Ala His Arg Leu Cys Arg Glu Lys
305                 310                 315                 320

Glu Val Lys Ile Ala Asn Asn Ile Tyr Leu Tyr Arg His Trp Ala Arg
                325                 330                 335

Gln Lys Ser Leu Tyr Asn Met Ala Phe Leu Ala Gln Asn Asp Leu Lys
            340                 345                 350

Glu Lys Ala Lys Ile Ala Asp Ser Leu Lys Ser Arg Pro Val Leu Arg
        355                 360                 365

Tyr Gln Ala Leu Arg Glu Met Lys Glu His Gln Asn Ile Ala Lys Leu
    370                 375                 380

Leu Glu Gln Asp Asp Gln Glu Arg Asp Gly Gly Tyr His Lys Gln Gln
385                 390                 395                 400

Val Glu Met Asp Glu Arg Thr Gly Lys Arg Leu Ser Glu Lys Met Glu
                405                 410                 415

Lys Ala Gly Val Ser Tyr Glu Asn Leu Pro Val Pro Trp Ile Ser Val
            420                 425                 430

His Phe Tyr Leu Asn Glu Ser Glu Asn Ser Glu Asp Glu Gly Ser Lys
        435                 440                 445

Gly Tyr Ala Leu Ile Phe Asp Ala Leu Thr Gln Ser Trp Lys Glu Arg
    450                 455                 460

Arg Phe Asp Tyr Ala Lys Leu His Arg Lys Phe Met Thr Trp Gln Glu
465                 470                 475                 480

Ala Tyr Ile Ser Ala Lys Lys Ser Ser Phe Ala Lys Asp Ser Leu Val
                485                 490                 495

Glu Leu Cys Arg Glu Ile Gly Asn Thr Met Pro Phe Leu Phe Asp Thr
            500                 505                 510

Ala Cys Ile Arg Asp Gly Ala Pro Val Leu Trp Ile Pro His Gly Phe
        515                 520                 525

Leu His Arg Leu Pro Leu His Ala Ala Ile Arg Asp Glu Ala Thr Asn
    530                 535                 540

Glu Ile Phe Leu Glu Asn His Ala Ser Arg Tyr Leu Pro Ala Trp Ser
545                 550                 555                 560

Ile Leu Asn Ser Ala Ser Ala Arg Arg Gly Lys Asp Ser Tyr Met Ile
                565                 570                 575

Lys Arg Phe Arg Ala Glu Asp Tyr Glu Lys Glu Pro Phe Ser Glu Leu
            580                 585                 590

Glu Asp Met Glu Trp Asp Asn Glu Glu His Glu Lys Leu Ala Thr Pro
        595                 600                 605

Asp Asp Leu Lys His Phe Met Ala Lys Asn Pro Gly Val Phe Ala Val
    610                 615                 620

Leu Cys His Gly His Gly Asp Ile Leu Asn Pro Leu Lys Ser Trp Leu
625                 630                 635                 640

Glu Leu Glu Gly Gly Gly Val Ser Val Leu Asp Ile Leu Arg Tyr Glu
                645                 650                 655

Lys Ala Asn Leu Ser Gly Thr Arg Val Leu Leu Gly Ala Cys Glu Ala
            660                 665                 670

Asp Met Ala Pro Pro Val Glu Tyr Ala Ile Asp Glu His Val Ser Leu
        675                 680                 685
```

Ser Ala Ala Phe Leu Ser His Lys Ala Gln Glu Val Ile Ala Gly Leu
    690                 695                 700

Trp Glu Ile Asn Ile Gly Glu Ala Asp Glu Cys Tyr Ala Glu Ile Leu
705                 710                 715                 720

Asp Cys Ser Asp Leu Ser Thr Glu Leu Lys Asp Trp Gln Cys Asp Trp
                725                 730                 735

Val Glu Lys Trp Arg Asp Asp Val Glu Ala Ser Gly Asp Asn Ser Thr
            740                 745                 750

Phe Tyr His Ile Thr Pro Phe Arg Ile Met Gly Phe Pro Leu Lys Leu
        755                 760                 765

Lys Glu Asn Asn Glu Ser Glu Ala Lys Gln
    770                 775

<210> SEQ ID NO 7
<211> LENGTH: 860
<212> TYPE: PRT
<213> ORGANISM: Unknown
<220> FEATURE:
<221> NAME/KEY: source
<223> OTHER INFORMATION: /note="Description of Unknown:
      Aquatic-marine-deep subsurface sequence"

<400> SEQUENCE: 7

Met Val Thr Pro Gln Ala Ser Lys Asn Pro Ala Val Asp Glu Ile Leu
1               5                   10                  15

Lys Gln Leu Thr Pro Tyr Asp Met Glu Thr Glu Asn Ala Lys Ala Ile
            20                  25                  30

Glu Thr Arg Lys Ser Cys Ile Glu Cys Leu Lys Gly Ile Cys Glu Arg
        35                  40                  45

Ala Gln Lys Gln Asn Asp Trp Val Ala Phe Gly Thr Ala Leu His Phe
    50                  55                  60

Leu His Glu Leu Ser Gly Thr Thr Ala Pro Val Phe Tyr Gly Ala Val
65                  70                  75                  80

Lys Gly Gln Ser Ala Cys Gly Gln Leu His Asn Met Gln Ala Ser Ile
                85                  90                  95

Lys Glu Ala Val Ala Arg Ile Thr Lys Ser Arg Ala Glu His Leu Arg
            100                 105                 110

Asp Lys Ala Leu Lys Pro Tyr Gly Ile Pro Tyr Leu Ser Arg His Arg
        115                 120                 125

Phe Leu Glu Lys Ala Ile Arg Met Val Trp Glu Leu Leu Gln Ser Asp
    130                 135                 140

Asn Gly Trp Pro Asp Ser Val Trp Leu His Arg Glu Ala Ser Gln Phe
145                 150                 155                 160

Ile Ala Arg Cys Phe Leu Asp Arg Gly Arg Leu Val Leu Pro Lys Gly
                165                 170                 175

Ser Ser Ile Pro Gln Lys Lys Ile Glu Ala Leu Lys Lys Ala Trp His
            180                 185                 190

Trp Ala Leu Lys Gly Ala Leu Lys Ala Lys Glu Asp Asp Ala Asp Ser
        195                 200                 205

Met Lys Leu Trp Leu Glu Phe Arg Glu Tyr Ile Leu Gln Thr Ala Lys
    210                 215                 220

Glu Asn Asp Ala Asp Ile Asp Ser Met Lys Leu Leu Ile Glu Ile Gly
225                 230                 235                 240

Leu Glu Leu Glu Leu Tyr Glu Lys Ser Phe Ser Pro Gln Val Asn Glu
                245                 250                 255

Leu Thr Arg Lys Ile Ala Ser Gly Lys Leu Leu Glu Asp Pro Lys Ser

```
            260                 265                 270

Ser Ala Asp Trp Pro Ile Ile Asp Arg Gly Arg Ser Ile Gly Cys Phe
        275                 280                 285

Asp Glu Lys Gln Asp Glu Ala Leu Phe Lys Leu Asp Leu Asn Lys Lys
    290                 295                 300

Glu Tyr Lys Glu Leu Pro Thr Leu Pro Leu Leu Arg Ala Lys Ala Gly
305                 310                 315                 320

His Arg Leu Lys Arg Asp Leu Ala Ser Ala Phe Asp Glu Ala Ser Phe
                325                 330                 335

Phe Arg Val Val Cys Asp Ala Val Arg Lys Leu Ala Asp Val Pro Phe
            340                 345                 350

Ser Ser Pro Ile Trp Val Glu Thr Ile Glu Phe Leu Ala Gln Leu Asp
        355                 360                 365

Pro Gly Ser Glu Ile Arg Asn Ala Ala Ser Val Ala Ala Trp Gln Ile
    370                 375                 380

Cys Lys Leu Lys Glu Glu Asp Leu Asp Leu Gly Leu Gln Val Arg Met
385                 390                 395                 400

Trp Trp Ser Arg His Lys Met Leu Tyr Asp Leu Ala Phe His Ala Ala
                405                 410                 415

Leu Ser Lys Asp Asp Trp Ala Leu Ala Ala Arg Ile Ala Asp Ser Pro
            420                 425                 430

Lys Ser Arg Pro Thr Ile Lys Ala Leu Ala Met Glu Ser Val Leu Asp
        435                 440                 445

Gly Asp Thr Leu Lys Gly Tyr Tyr Glu Leu Glu Ala Arg Gly Val Ala
    450                 455                 460

Arg Gly Tyr Asp Ser Thr Tyr His Arg Lys Lys Lys Ser Leu Glu Lys
465                 470                 475                 480

Ala Glu Ala Lys Lys Lys Arg Ala Ser Lys Asp Thr Gln Gly Leu Arg
                485                 490                 495

Pro Leu Asp Phe Glu Glu Asp Ile Pro Ala Gly Trp Ala Ala Ile His
            500                 505                 510

Leu Tyr Leu Asp Gln Asp Lys Lys Gly His Ala Leu Met Arg Ser Ala
        515                 520                 525

Gly Ser Thr Lys Asp Gly Trp Leu Tyr Lys Asp Phe Glu Ile Ser Asp
    530                 535                 540

Ile Trp Gln Lys Phe Gln Ala Trp Gln Ala Ala Asp Arg Tyr Asn Pro
545                 550                 555                 560

Lys Phe Gly Gly Ala Ala Thr Glu Leu His Ala Leu Cys Glu Ser Leu
                565                 570                 575

Gly Tyr Asp Asp Asp His Leu Gly Phe Leu Phe Asn Lys Asp Leu Pro
            580                 585                 590

Asp Asn Leu Ile Ile Ile Pro His Asp Ile Leu His Leu Val Pro Ile
        595                 600                 605

His Ser Val Met Lys Asn Gly Glu Ile Leu Leu Lys Gln Lys Lys Cys
    610                 615                 620

Ile Tyr Leu Pro Ala Trp Gly Leu Pro Arg Glu Thr Asp Ser Ala Ser
625                 630                 635                 640

Thr Pro Glu Gly Glu Gly Leu Phe Asp Asn Phe Glu Asp His Asp Pro
                645                 650                 655

Leu Arg Gln Tyr Leu Gln Pro Val Leu Gln Ala Trp Lys His Ser Ser
            660                 665                 670

Val Ser Ala Arg Asn Ile Lys Val Pro Asp Ala Thr Ala Asn Asp Val
        675                 680                 685
```

Arg Asn Tyr Leu Lys Asn Thr Thr Asn Pro Glu Trp Met Val Phe Leu
690 695 700

Cys His Gly Lys Ala Asp Pro Val Asn Pro Tyr Asn Ser Gly Leu Leu
705 710 715 720

Leu Arg Gly Ser His Leu Thr His Ala Ala Leu Val Glu Leu Pro Lys
725 730 735

Lys Met Ala Gly Thr Lys Val Phe Leu Gly Ala Cys Glu Thr Asp Met
740 745 750

Ser Pro Pro Lys Gln Lys Ser Val Asp Glu His Leu Ser Val Ser Thr
755 760 765

Ala Phe Phe Gln Lys Gly Ala Ser Glu Ile Ala Gly Gly Leu Trp Arg
770 775 780

Val His Ser Ala Ile Ala Lys Lys Met Val Glu His Ile Ser Glu Asn
785 790 795 800

Arg Lys Lys Pro Leu Val Asp Val Val Trp Glu Lys Gln Lys Asp Trp
805 810 815

Trp Asp Asn Gly Ile Gln Tyr Val Val Asp Gly Ile Thr Val Lys Val
820 825 830

Ser Asn Cys Phe Lys Lys Leu Tyr Tyr Leu Ser Ser Tyr Arg Val Val
835 840 845

Gly Phe Pro Arg Ala Ile Gly Glu Asn Thr Asp Glu
850 855 860

<210> SEQ ID NO 8
<211> LENGTH: 757
<212> TYPE: PRT
<213> ORGANISM: Unknown
<220> FEATURE:
<221> NAME/KEY: source
<223> OTHER INFORMATION: /note="Description of Unknown: Aquatic-freshwater-groundwater sequence"

<400> SEQUENCE: 8

Met Tyr Ser Asp Phe Pro Ala Leu Arg Leu Pro Glu Leu Ser Val Asp
1 5 10 15

Gln Lys Lys Leu Phe Lys Ile Ser Gly Thr Asn Pro Gln Leu Ile Tyr
20 25 30

Ile Leu Met Asn Glu Phe Asp Gly Glu Gly Asp Glu Pro Phe Phe Thr
35 40 45

Gly Leu Val Pro Asp Glu Thr Asp Leu Ser Glu Asn Lys Gln Ala Pro
50 55 60

Leu Leu Lys Glu Leu Ala Arg His Leu Leu Lys Glu Tyr Glu Asp Ile
65 70 75 80

Gly Arg Asn Arg Trp Lys His Ala Asp Gln Arg Arg Val Leu Glu Lys
85 90 95

Ala Ile Arg Leu Leu Asp Lys Ser His Gln Ala Glu Glu Asn Val Ser
100 105 110

Leu Glu Leu Gly Lys Ala Tyr Leu Tyr Arg Ala Arg Ile Ile Arg Pro
115 120 125

Lys Gly Phe Thr Val Pro Ala Lys Lys Ile Glu Ala Leu Asn Asn Ala
130 135 140

Leu His Phe Cys Glu Asp Ala Thr Asn His Gly Lys Ala Trp Ala Asp
145 150 155 160

His Phe Ala Gly Leu Val Ala Leu Glu Leu Tyr Arg Cys Gly Lys Thr
165 170 175

```
His Asp Asn Leu Ser Glu Leu Leu Asn Lys Ala Thr Ala Asp Ala Glu
            180                 185                 190

Leu Ser Glu Pro Asp Arg Arg Val Glu Phe Tyr Gln Met Arg Val Arg
        195                 200                 205

Leu Glu Glu Leu Arg Gln Asp Glu Gly Asn Gly Ser Pro Tyr Phe Ile
    210                 215                 220

Gln Asn Val Leu Thr Lys Ile Phe Glu Phe Gln Glu Pro Gly Met Glu
225                 230                 235                 240

Leu Glu Lys Leu Lys Val Ser Leu Gln Ser Pro Ser Ser Ser Lys Asp
                245                 250                 255

Lys Ile Ser Ser Ser Leu Glu Asp Leu Ile Leu Val Leu Lys Glu Tyr
            260                 265                 270

Pro Phe Ser His Pro Leu Trp Glu Asp Thr Val Arg Phe Ala Arg Arg
        275                 280                 285

Leu Tyr Phe Asn Arg Leu Glu Phe Trp Lys Glu Leu Ala Leu Arg Leu
    290                 295                 300

Trp Glu Ala Ala Glu Asp Glu Ser Arg Lys Ile Ser Ser Val His Leu
305                 310                 315                 320

Arg Trp Tyr Trp Ser Arg Gln Arg Asp Leu Tyr Asp Leu Ser Phe Leu
                325                 330                 335

Ala Ala Leu Lys Gln Gly Asn Pro Asn Leu Ala Ala Gln Val Thr Asp
            340                 345                 350

Ser Ala Lys Ser Arg Pro Ala Leu Ser Trp Gln Ala Ile Glu Arg Leu
        355                 360                 365

Lys His Gly Asn Glu Glu Leu Lys Asp Glu Ile Glu Asn Tyr Ala Gln
    370                 375                 380

Ala Leu Ser Gly Gly Tyr Ile Lys Gly Leu Leu Lys Pro Tyr Arg Lys
385                 390                 395                 400

Pro Glu Val Pro Asn Glu Glu Lys Pro Phe Phe Glu Gln His Leu Ile
                405                 410                 415

Asp Asn Asn Leu Ile Ala Ile Gln Phe Tyr Leu Val His Leu Glu Glu
            420                 425                 430

Phe Glu Lys Val Glu Arg Ser Arg Glu Arg Gly Tyr Ala Leu Ile Tyr
        435                 440                 445

Asp Gln Glu Ser Glu Lys Lys Trp Ser Phe Lys Thr Phe Asp Phe Ala
    450                 455                 460

Pro Ile Trp Glu Lys Tyr Val Ala Trp Gln Ser Val Tyr Phe Asp Leu
465                 470                 475                 480

Pro Pro Gln Gln Arg Asp Ala Ser Gly Thr Gln Leu Arg Tyr Leu Cys
                485                 490                 495

Glu Ala Leu Gly Lys Ala Leu Glu Phe Leu Phe Lys Ser Pro Glu Lys
            500                 505                 510

Gln Phe Ser Ser Asn Glu Lys Ser Lys Asp Ile Leu Phe Ile Pro His
        515                 520                 525

Asp Phe Leu His Arg Val Pro Leu His Gly Ala Met Leu Asp Asn Glu
    530                 535                 540

Asn Val Leu Leu Lys Thr Phe Asn Cys Phe Tyr Leu Pro Ala Ile Ser
545                 550                 555                 560

Tyr Ser Ala Lys Asn Gln Gly Pro Gln Gln Asn Lys Asn Ser Val Leu
                565                 570                 575

Leu Tyr Tyr Ser Gly Lys Ser Glu Glu Ser Asp Asp Pro Leu Phe Asn
            580                 585                 590

His Leu Lys Thr Lys Phe Asp Thr Pro Ile Asn Phe Ala Ser Ala Thr
```

```
        595                 600                 605

Asp Leu Leu Asp Ala Ala Gln Asn Pro Pro Ser Leu Leu Val Leu Tyr
    610                 615                 620

Cys His Gly Glu Ala Asp Ala Thr Asn Pro Tyr Leu Ser Arg Leu Lys
625                 630                 635                 640

Leu Lys Asp Asp Leu Met Leu Leu Asp Phe Ala Ser Ala Ala Gly Thr
                645                 650                 655

Phe Thr Gly Ser Lys Ile Phe Leu Gly Ala Cys Glu Thr Asp Leu Met
            660                 665                 670

Pro Pro Leu Asp Ala Pro Leu Asp Glu Gln Ile Ser Met Ala Thr Ile
        675                 680                 685

Phe Leu Ile Lys Arg Ser Glu Ser Val Ile Gly Ser Met Trp Glu Ala
    690                 695                 700

Lys Arg Met Lys Val Leu Asn Leu Leu Phe Met Lys Glu Gly Leu Phe
705                 710                 715                 720

Asp His Phe Phe Glu Gln Gln Arg Glu Trp Trp Lys Glu Glu Tyr Glu
                725                 730                 735

His Thr Asp Ser Asn Thr Ala Leu Tyr Asp Cys Leu Cys Phe Arg Met
            740                 745                 750

Tyr Arg Cys Tyr Phe
        755
```

```
<210> SEQ ID NO 9
<211> LENGTH: 822
<212> TYPE: PRT
<213> ORGANISM: Unknown
<220> FEATURE:
<221> NAME/KEY: source
<223> OTHER INFORMATION: /note="Description of Unknown:
      Bioremediation-terephthalate-wastewater bioreactor sequence"

<400> SEQUENCE: 9

Met Phe Gly Gly Val Glu Lys Asn Cys Leu Ala Leu Ser Leu Gly Arg
1               5                   10                  15

His Glu Lys Arg Gln Ile Tyr Lys Ser Ile Leu Ala Ala Gly Gly Leu
            20                  25                  30

Leu Leu Ala Gln Pro Ala Asp Glu Thr Phe Leu Pro Met Ile Thr Lys
        35                  40                  45

Tyr Tyr Arg Glu Ile Leu Ala Ala Glu Val Lys Leu Ala Phe Cys Leu
    50                  55                  60

Pro Asp Glu Ala His Asn Val Val Tyr Lys Arg Asp Glu Ala Cys Arg
65                  70                  75                  80

Glu Leu Val Gln Ala Cys Arg Asn Gln Ala Gly Gly Leu Thr Glu Gln
                85                  90                  95

Gly Tyr Gln Tyr Leu Gly Ser Ala Leu Leu Phe Leu Ser Gly Gly Leu
            100                 105                 110

Gly Glu Ala Pro Gly Leu Val Ala Leu Pro Val Leu Ser Gln Glu Leu
        115                 120                 125

Cys Glu Ala Leu Ala Ser Arg Glu Ala Asp Ile His Ala Phe His Ala
    130                 135                 140

Arg Gln Gly Leu Glu Val Ala Ala Ala Ile Ile Glu Arg Ala Arg Glu
145                 150                 155                 160

Pro Gln Trp Gln His Ala Gln Arg Arg Gln Ala Leu Glu Ala Val Ile
                165                 170                 175

Lys Asp Leu Gln Gln Arg Ser Ala Ile Cys Pro Pro Asp Leu Gln Asp
            180                 185                 190
```

```
Arg Leu Arg Leu Leu Leu Ala Gln Ala Tyr Leu Glu Arg Ser Arg Ile
        195                 200                 205

Ile Arg Pro Lys Gly Phe Thr Ile Ser Pro Lys Lys Lys Glu Ala Leu
    210                 215                 220

Asp Lys Ala Leu Glu Gln Leu Asp Gln Val Thr Asp Thr Gly Lys Thr
225                 230                 235                 240

Thr Leu Asp Tyr His Arg Phe Arg Gly Asp Ile Phe Leu Glu Leu Gly
                245                 250                 255

Arg Leu Glu Ala Arg Thr Gly Lys Glu Ile Glu Ala Cys Leu Ala Glu
            260                 265                 270

Ala Ile Leu Phe Leu Asp Pro Arg Thr Pro Ala Asn Leu Thr Pro Val
        275                 280                 285

Asp Cys Arg Leu Ile Val Ala Tyr Ala Arg Leu Ala Arg Asp Pro Ser
    290                 295                 300

Tyr Leu Pro Leu Val Leu Gly Ser Ser Lys Ala Thr Ala Leu Asp Arg
305                 310                 315                 320

Ala Trp Ala Ala Tyr Leu Ser Asn Asn Ala Ser Gly Ala Ala Lys Glu
                325                 330                 335

Ile Asn Thr Val Leu Gln Asp Leu Gln Arg Arg Trp Phe Ser His Pro
            340                 345                 350

Asp Trp Glu Gly Leu Val Asp Leu Leu Val Asp Trp Ala Arg Ser Ser
        355                 360                 365

Gln Lys Gly Trp Glu Asp Leu Ala Thr Ala Ala Trp Gln Val Cys Gln
    370                 375                 380

Lys Asn Glu Gln Glu Leu Arg Tyr Ser Gly Cys Gln Leu Arg Trp Tyr
385                 390                 395                 400

Trp Ser Arg His Gln Asp Leu Tyr Asp Leu Ala Phe Gln Ala Ala Pro
                405                 410                 415

Thr Leu Glu Glu Lys Ala Arg Val Ala Asp Ser Leu Lys Ser Arg Pro
            420                 425                 430

Leu Val Arg Leu Ala Leu Ala Glu Gln Leu Ala Gln Ala Gln Ala Lys
        435                 440                 445

Lys Lys Arg Gly Ala Asp Val Asp Phe Ala Gln Leu Ile Glu Gln Asp
    450                 455                 460

Ala Arg Ala Tyr Ala Asn Gln Tyr Ile Ala Gly Gly Leu Ala Ala Gly
465                 470                 475                 480

Ser Ala Ser Ala Pro Val Ala Pro Leu Ser Phe Thr Glu Leu Pro Asp
                485                 490                 495

Glu Gln Trp Leu Ala Val His Phe Tyr Leu Ser Ser Gly Ala Ala Ala
            500                 505                 510

Gly Leu Lys Lys Asn Met Ala Tyr Ala Leu Val Tyr Asp Ala Lys Asp
        515                 520                 525

Gln Lys Trp Ser Cys Glu Gly Pro Tyr Glu Thr Thr Asp Leu Trp Gln
    530                 535                 540

Ala Tyr Arg Arg Trp Gln Asp Asn Tyr Ala Ala Val Ser Gln Ala Ser
545                 550                 555                 560

Ala Pro Glu Leu Glu Ser Leu Cys Arg Gln Ile Gly Thr Thr Phe Pro
                565                 570                 575

Phe Leu Trp Ala Leu Pro Ser Glu Arg Pro Val Val Phe Ile Pro His
            580                 585                 590

Gly Phe Leu His Arg Leu Pro Leu His Met Ala Leu Arg Glu Asp Gly
        595                 600                 605
```

```
Ala Thr Leu Glu Val Trp Ala Ala Thr His Pro Ser Thr Tyr Leu Pro
    610                 615                 620

Ala Trp Ser Leu Arg Pro Arg Ala Asp Ala Gly Gly Ser Gln Asn Val
625                 630                 635                 640

Ala Ala Val Tyr Leu Pro Asp Glu Leu His Asp Ala Glu Asp Phe Gln
                645                 650                 655

Asn Ile Leu Ala Gly Gln Ser Phe Ala Ala Ala Ala Ser Trp Pro Val
            660                 665                 670

Phe Arg Lys Gln Ala Gly Gln Ala Arg Arg Leu Ala Leu Val Cys His
        675                 680                 685

Gly Leu Ala His Ala Val Asn Pro Phe Ala Ala Arg Leu Leu Leu Pro
    690                 695                 700

Glu Glu Pro Gln Leu Val Asp Phe Leu Thr Asp Leu Pro Ala Leu Pro
705                 710                 715                 720

Gly Ser Gln Val Phe Leu Ala Ala Cys Glu Ala Asp Met Ala Pro Ala
                725                 730                 735

Gln Glu Ala Pro Leu Asp Glu His Leu Ser Leu Ala Thr Ala Phe Leu
            740                 745                 750

Gln Lys Gly Ala Arg Glu Val Leu Gly Gly Val Phe Glu Val Asn Lys
        755                 760                 765

Tyr Leu Ala Asn Glu Leu Leu Ser Ser Phe Gly Ala Thr Ser Ala Ala
    770                 775                 780

Ala Cys Tyr Ser Leu Leu Trp Lys Trp Gln Gln Ala Arg Leu Asp Asn
785                 790                 795                 800

Phe Leu Asp Asn Pro Asp Pro Leu Asn Leu Tyr Trp Leu Ala Pro Trp
                805                 810                 815

Arg Val Leu Gly Leu Ser
            820


<210> SEQ ID NO 10
<211> LENGTH: 797
<212> TYPE: PRT
<213> ORGANISM: Unknown
<220> FEATURE:
<221> NAME/KEY: source
<223> OTHER INFORMATION: /note="Description of Unknown:
      Aquatic-freshwater-freshwater lake sediment sequence"

<400> SEQUENCE: 10

Met Thr Glu Thr Asn His Leu Ser Ser Asp Tyr Gln Lys Ala Ile Thr
1               5                   10                  15

Leu Glu Thr Lys Leu Ala Phe Leu Arg Pro Thr Gln Glu Gln Asp Thr
            20                  25                  30

Ile Glu Ser Thr Arg Arg Glu Leu Ala Glu Thr Leu Ser Arg Leu Val
        35                  40                  45

Asn Gln Lys Ile Ser Pro Glu Thr Leu Ser Ala Ile Thr Thr Leu His
    50                  55                  60

Gly Met Asp Leu Gln Gly Leu Gly Val Leu Ser Gly Ser Leu Pro Asn
65                  70                  75                  80

Lys Asp Arg Cys Ala Phe Ala Gly Asn Lys Lys Lys Phe Ser Ala Ala
                85                  90                  95

Trp Glu Phe His Trp Leu Gln Arg Ile Asp Leu Met Arg Lys Ile Ile
            100                 105                 110

Asp Lys Ala Ser Gly Gln Asp Asp Lys Leu Ser His Ala Ser Arg Arg
        115                 120                 125

Gln Ala Leu Gly Val Ala Ile Asn Ser Leu Glu Lys Ala Ile Ala Glu
```

```
    130                 135                 140

Ile Gly Asp Thr Gly Ile Leu Val Ser Lys Ala Arg Leu Asp Leu Ala
145                 150                 155                 160

Arg Ala Leu Phe His Arg Gly Arg Ile Val Arg Pro Lys Gly Phe Ser
                165                 170                 175

Val Pro Gly Lys Lys Lys Glu Leu Phe Leu Lys Ala Leu Asp Gln Ile
            180                 185                 190

Arg Ile Ala Thr Asn Asn Lys Asp Asp Asp Gln Thr Leu Phe Leu Lys
        195                 200                 205

Ala Glu Ile Tyr Leu Glu Trp Leu Arg Phe Phe Pro Met Glu Leu Pro
    210                 215                 220

Glu Asp Leu Asp Val Val Phe Lys Ala Ala Gln Gln Lys Ala Asp Glu
225                 230                 235                 240

Pro Leu Lys Thr Asn Leu Ile Leu Met Ile Gly Glu Arg Gly Ser Ala
                245                 250                 255

Lys Pro Ile Glu Leu Glu Ala Leu Gln Asn Ile Glu Val Asp Glu Lys
            260                 265                 270

Gln Glu Pro Leu Thr Arg Ala Arg Ala Ala Ala Ile Ser Gly Asn Trp
        275                 280                 285

Asp Ile Cys Ala Lys Tyr Leu Ser Glu Ala Ile Lys Lys Leu Glu Ile
    290                 295                 300

Lys Ser Phe Phe His Gln Asp Trp Glu Glu Ala Val Glu Leu Leu Lys
305                 310                 315                 320

Lys Gly Arg Thr Lys Ile Ser Asn Tyr Gln Trp Ala Thr Ile Cys Lys
                325                 330                 335

Ser Leu Trp Lys Leu Thr Val Gln Lys Glu Asn Arg Thr Ser Asn Gly
            340                 345                 350

Cys His Leu Arg Trp Tyr Trp Ser Arg Gln Arg Glu Val Tyr Asp Leu
        355                 360                 365

Ala Phe Glu Ala Ala Gly Asn Asp Tyr Ser Lys Lys Ala Lys Ile Thr
    370                 375                 380

Asp Ser Leu Lys Gly Arg Pro Ala Leu His Phe Ala Gln Met Glu Thr
385                 390                 395                 400

Ile Ala Glu Gly Glu Asp Glu Ile Lys Thr Trp Ile Glu His Gln Glu
                405                 410                 415

Ala Gly Phe Leu Asn Gln Tyr Ile Ser Ala Phe Glu Ser Ala Asp Gln
            420                 425                 430

Gly Lys Lys Pro Gly Asn Leu Ser Trp Pro Lys Leu Pro Lys Gly Trp
        435                 440                 445

Ile Ala Val His Phe Tyr Leu Gly Leu Gly Thr Cys Ser Gly Glu Lys
    450                 455                 460

Lys Gly Tyr Ala Leu Ile Gln Asn Gly Gln Asp Trp Tyr Gln Arg Thr
465                 470                 475                 480

Phe Asp Tyr Glu Val Leu Trp Val Ala Tyr Leu Ala Trp Gln Thr Met
                485                 490                 495

Tyr Gly Lys Cys Gly His Leu Asp Asp Ile Leu Lys Gln Gln Glu Val
            500                 505                 510

Leu Ser Pro Val Val Glu Ser Leu Cys Glu Gln Ile Gly Lys Glu Met
        515                 520                 525

Pro Trp Leu Phe Asp Pro Gly Leu Phe Pro Glu Gly Gln Ala Val Val
    530                 535                 540

Phe Ile Pro His Asp Phe Leu His Arg Leu Pro Leu His Met Ala Leu
545                 550                 555                 560
```

Asp Pro Lys Pro Asp Pro Gly Lys Ala Gln Leu Phe Leu Ser Leu His
565 570 575

Leu Val Leu Ser Leu Pro Ala Trp Trp Gln Ala Ser Glu Thr Asn Ser
580 585 590

Pro Pro Ala Pro Asp Thr Val Lys Ala Asn Glu Lys Ile Phe Leu Ala
595 600 605

Asn Phe Glu Asn Pro Ser Asp Ala Phe Gln Ser Leu Ile Asp Ala Ile
610 615 620

Pro Lys Ser Val Lys Val Glu Arg Val Ala Lys Lys Ser Asn Leu Leu
625 630 635 640

Glu Ala Asn Ser Pro Ser Leu Leu Val Val Tyr Cys Asn Gly Glu Ala
645 650 655

Gln Pro Gly Asn Pro Phe Ala Ser Arg Leu Leu Phe Ser Asp Ser Gly
660 665 670

Leu Pro Val Ser Gly Ile Leu Gly Ser Thr Ile Asn Leu Arg Arg Ser
675 680 685

Asn Ile Ile Leu Gly Ala Cys Glu Thr Asp Leu Met Leu Ala Leu Asn
690 695 700

Lys Thr Leu Asp Glu His Ile Thr Leu Ser Ser Ala Phe Ile Gln Lys
705 710 715 720

Gly Ala Glu Leu Val Ser Gly Thr Leu Trp Lys Ile His Glu Asn Asp
725 730 735

Glu Ile Asp Phe Ile Lys Leu Ala Leu Val Glu Asn Ser Ser Leu His
740 745 750

Glu Gln Trp Leu Lys Trp Tyr Asp Thr Asn Ile Lys Ala Tyr Glu Asn
755 760 765

Asp Pro Lys Asn Asn Pro Arg Val Phe Tyr Lys Ala Ala Ala Ile Arg
770 775 780

Ile Val Gly Lys Pro Trp Thr Ile Glu Asp Ile Gly Lys
785 790 795

<210> SEQ ID NO 11
<211> LENGTH: 789
<212> TYPE: PRT
<213> ORGANISM: Unknown
<220> FEATURE:
<221> NAME/KEY: source
<223> OTHER INFORMATION: /note="Description of Unknown:
Bioremediation-terephthalate-wastewater bioreactor sequence"

<400> SEQUENCE: 11

Met Ala Gln Pro Ala Asp Glu Thr Phe Leu Pro Met Ile Thr Lys Tyr
1 5 10 15

Tyr Arg Glu Ile Leu Ala Ala Glu Val Lys Leu Ala Phe Cys Leu Pro
20 25 30

Asp Glu Ala His Asn Val Val Tyr Lys Arg Asp Glu Ala Cys Arg Glu
35 40 45

Leu Val Gln Ala Cys Arg Asn Gln Ala Gly Gly Leu Thr Glu Gln Gly
50 55 60

Tyr Gln Tyr Leu Gly Ser Ala Leu Leu Phe Leu Ser Gly Gly Leu Gly
65 70 75 80

Glu Ala Pro Gly Leu Val Ala Leu Pro Val Leu Ser Gln Glu Leu Cys
85 90 95

Glu Ala Leu Ala Ser Arg Glu Ala Asp Ile His Ala Phe His Ala Arg
100 105 110

```
Gln Gly Leu Glu Val Ala Ala Ala Ile Ile Glu Arg Ala Arg Glu Pro
        115                 120                 125

Gln Trp Gln His Ala Gln Arg Arg Gln Ala Leu Glu Ala Val Ile Lys
    130                 135                 140

Asp Leu Gln Gln Arg Ser Ala Ile Cys Pro Pro Asp Leu Gln Asp Arg
145                 150                 155                 160

Leu Arg Leu Leu Leu Ala Gln Ala Tyr Leu Glu Arg Ser Arg Ile Ile
                165                 170                 175

Arg Pro Lys Gly Phe Thr Ile Ser Pro Lys Lys Lys Glu Ala Leu Asp
            180                 185                 190

Lys Ala Leu Glu Gln Leu Asp Gln Val Thr Asp Thr Gly Lys Thr Thr
        195                 200                 205

Leu Asp Tyr His Arg Phe Arg Gly Asp Ile Phe Leu Glu Leu Gly Arg
    210                 215                 220

Leu Glu Ala Arg Thr Gly Lys Glu Ile Glu Ala Cys Leu Ala Glu Ala
225                 230                 235                 240

Ile Leu Phe Leu Asp Pro Arg Thr Pro Ala Asn Leu Thr Pro Val Asp
                245                 250                 255

Cys Arg Leu Ile Val Ala Tyr Ala Arg Leu Ala Arg Asp Pro Ser Tyr
            260                 265                 270

Leu Pro Leu Val Leu Gly Ser Ser Lys Ala Thr Ala Leu Asp Arg Ala
        275                 280                 285

Trp Ala Ala Tyr Leu Ser Asn Asn Ala Ser Gly Ala Ala Lys Glu Ile
    290                 295                 300

Asn Thr Val Leu Gln Asp Leu Gln Arg Arg Trp Phe Ser His Pro Asp
305                 310                 315                 320

Trp Glu Gly Leu Val Asp Leu Leu Val Asp Trp Ala Arg Ser Ser Gln
                325                 330                 335

Lys Gly Trp Glu Asp Leu Ala Thr Ala Ala Trp Gln Val Cys Gln Lys
            340                 345                 350

Asn Glu Gln Glu Leu Arg Tyr Ser Gly Cys Gln Leu Arg Trp Tyr Trp
        355                 360                 365

Ser Arg His Gln Asp Leu Tyr Asp Leu Ala Phe Gln Ala Ala Pro Thr
    370                 375                 380

Leu Glu Glu Lys Ala Arg Val Ala Asp Ser Leu Lys Ser Arg Pro Leu
385                 390                 395                 400

Val Arg Leu Ala Leu Ala Glu Gln Leu Ala Gln Ala Gln Ala Lys Lys
                405                 410                 415

Lys Arg Gly Ala Asp Val Asp Phe Ala Gln Leu Ile Glu Gln Asp Ala
            420                 425                 430

Arg Ala Tyr Ala Asn Gln Tyr Ile Ala Gly Gly Leu Ala Ala Gly Ser
        435                 440                 445

Ala Ser Ala Pro Val Ala Pro Leu Ser Phe Thr Glu Leu Pro Asp Glu
    450                 455                 460

Gln Trp Leu Ala Val His Phe Tyr Leu Ser Ser Gly Ala Ala Ala Gly
465                 470                 475                 480

Leu Lys Lys Asn Met Ala Tyr Ala Leu Val Tyr Asp Ala Lys Asp Gln
                485                 490                 495

Lys Trp Ser Cys Glu Gly Pro Tyr Glu Thr Thr Asp Leu Trp Gln Ala
            500                 505                 510

Tyr Arg Arg Trp Gln Asp Asn Tyr Ala Ala Val Ser Gln Ala Ser Ala
        515                 520                 525

Pro Glu Leu Glu Ser Leu Cys Arg Gln Ile Gly Thr Thr Phe Pro Phe
```

```
    530                 535                 540

Leu Trp Ala Leu Pro Ser Glu Arg Pro Val Val Phe Ile Pro His Gly
545                 550                 555                 560

Phe Leu His Arg Leu Pro Leu His Met Ala Leu Arg Glu Asp Gly Ala
                565                 570                 575

Thr Leu Glu Val Trp Ala Ala Thr His Pro Ser Thr Tyr Leu Pro Ala
            580                 585                 590

Trp Ser Leu Arg Pro Arg Ala Asp Ala Gly Gly Ser Gln Asn Val Ala
        595                 600                 605

Ala Val Tyr Leu Pro Asp Glu Leu His Asp Ala Glu Asp Phe Gln Asn
    610                 615                 620

Ile Leu Ala Gly Gln Ser Phe Ala Ala Ala Ala Ser Trp Pro Val Phe
625                 630                 635                 640

Arg Lys Gln Ala Gly Gln Ala Arg Arg Leu Ala Leu Val Cys His Gly
                645                 650                 655

Leu Ala His Ala Val Asn Pro Phe Ala Ala Arg Leu Leu Leu Pro Glu
            660                 665                 670

Glu Pro Gln Leu Val Asp Phe Leu Thr Asp Leu Pro Ala Leu Pro Gly
        675                 680                 685

Ser Gln Val Phe Leu Ala Ala Cys Glu Ala Asp Met Ala Pro Ala Gln
    690                 695                 700

Glu Ala Pro Leu Asp Glu His Leu Ser Leu Ala Thr Ala Phe Leu Gln
705                 710                 715                 720

Lys Gly Ala Arg Glu Val Leu Gly Gly Val Phe Glu Val Asn Lys Tyr
                725                 730                 735

Leu Ala Asn Glu Leu Leu Ser Ser Phe Gly Ala Thr Ser Ala Ala Ala
            740                 745                 750

Cys Tyr Ser Leu Leu Trp Lys Trp Gln Gln Ala Arg Leu Asp Asn Phe
        755                 760                 765

Leu Asp Asn Pro Asp Pro Leu Asn Leu Tyr Trp Leu Ala Pro Trp Arg
    770                 775                 780

Val Leu Gly Leu Ser
785


<210> SEQ ID NO 12
<211> LENGTH: 809
<212> TYPE: PRT
<213> ORGANISM: Unknown
<220> FEATURE:
<221> NAME/KEY: source
<223> OTHER INFORMATION: /note="Description of Unknown:
      Aquatic-marine-marine sediment sequence"

<400> SEQUENCE: 12

Met Val Ser Met Gln Gln Ser Ala Cys Asn Glu Ile Lys Asn Leu Glu
1               5                   10                  15

Asn Ser Ile Asp Lys Asp Val Ser Glu Leu Ala Glu Ala Leu Ser His
            20                  25                  30

Phe Val Gln Ala Asn Leu Gln Pro Gln Thr Ala Leu Cys Gln Arg Gly
        35                  40                  45

Ile Pro Asp Lys Asn Asn Ala Val Leu Lys Ile His Lys Ala His Asn
    50                  55                  60

Thr Asp Ile Val Phe Ser Thr Leu Phe Asn Ile Leu Glu Lys Arg Leu
65                  70                  75                  80

Val Val Tyr Glu Ser Glu Val Tyr Asp Glu Ser Lys Ser Ser Lys Lys
                85                  90                  95
```

-continued

Asn Met Asn His Arg Gln Arg Arg Gln Met Leu Glu Asp Ile Ile Gln
100 105 110

Ala Leu Ile Pro Leu Lys Lys Lys Val Ser Asp Ser Glu Leu Lys Leu
115 120 125

Glu Lys Leu Glu Arg Lys Glu Ser Asp Ser Val Thr Lys Leu Lys Ser
130 135 140

Asp Ile Ala Gln Phe Asn Tyr Ile Tyr Ala Lys Val Tyr Phe Tyr Arg
145 150 155 160

Ser Leu Leu Phe Arg Pro Lys Gly Arg Ser Ile Pro Ala Arg Lys Ile
165 170 175

Glu Ala Ile Gln Glu Ala Tyr Ser Phe Ile Lys Lys Ser Leu Asn Leu
180 185 190

Ser Glu Thr Leu Ser Ser Trp Arg Leu Leu Gly Lys Ile Thr Leu Glu
195 200 205

Leu Leu Ser Leu Asn Glu Pro Tyr Leu Ser Asp Asp Ile Ile Ser Ser
210 215 220

Gly Leu His Ile Asp Glu Asn Phe Cys Leu Glu Asn Asn Ser Phe Ile
225 230 235 240

Leu Arg Asn Asp Ile Gln Thr Leu Leu Thr Phe Ser Glu Ile Thr Lys
245 250 255

Asp Val Ser Phe Val Glu Lys Ile Pro Thr Phe Glu Asn Ile Asn Ile
260 265 270

Lys Lys Lys Asp Lys Asp Tyr Leu Leu Leu Leu Ile Phe Ala Arg Ile
275 280 285

Ala Phe Leu Arg Asn Lys Ile Asn Glu Ser Asp Thr Leu Leu Thr Lys
290 295 300

Ala Ile Ser Asn Ala Pro Glu Ala Phe Ala Asn Pro Phe Trp Asp Asp
305 310 315 320

Leu Val Asp Phe Ile Thr Cys Leu Lys Arg Asn Asn Cys His Val Trp
325 330 335

Lys Lys Ala Ala Ile Asp Ala His Lys Ala Cys Tyr Lys Asn Glu Thr
340 345 350

Glu Ile Gly Asn Ile Tyr Leu Arg Trp Tyr Trp Ser Arg Gln Ser Asp
355 360 365

Leu Tyr Asp Leu Ala Phe Ile Ser Glu Asn Lys Leu Glu Glu Lys Ala
370 375 380

Arg Ile Ala Asp Ser Leu Lys Ser Arg Pro Ile Leu Gly Phe Gln Ala
385 390 395 400

Leu Asn Asn Met Lys Lys Asn Ile Asp Ile Leu Glu Gln Ile Leu Glu
405 410 415

Gln Glu Asn Glu Ala Arg Asp Asn Lys Tyr Leu Lys Lys Ile His Ser
420 425 430

Lys Ser Arg Lys Ile Phe Lys Lys Glu Lys Phe Ile Asp Phe Lys Leu
435 440 445

Leu Asp Asn His Trp Met Val Ile His Phe Tyr Leu Asn Glu Leu Glu
450 455 460

Gln Cys Gly Tyr Ala Leu Ile Phe Asp Cys Glu Thr Lys Asn Thr Asn
465 470 475 480

Ile Gln Thr Phe Arg Tyr Asn Glu Leu Phe Asn Thr Phe Leu Ser Trp
485 490 495

Gln Glu Thr Glu Leu His Glu Gln Lys Gln Lys Glu Asn Asn Glu Glu
500 505 510

Ile Phe Asn Lys Asp Leu Ile Gln Arg Gly Lys Ser Ile His Glu Leu
515 520 525

Cys Cys Glu Ile Gly Lys Thr Met Pro Phe Ile Phe Glu Leu Pro Glu
530 535 540

Asn Lys Ser Ile Leu Trp Val Pro His Gly Phe Ile His Arg Leu Pro
545 550 555 560

Leu His Ala Ala Ile Ser Ile Gln Thr Asn Ala Phe Leu Phe Glu Lys
565 570 575

His Glu Ser Arg Tyr Leu Ala Ala Trp His Gln Leu Asn Leu Lys Asn
580 585 590

Phe Gly Asn Gly Glu Gly Lys His Phe Leu Arg Ser Gly Gly Ser Lys
595 600 605

Phe Lys Thr Ile Thr Lys Lys Cys Lys Thr Asp Lys Trp Glu Met Val
610 615 620

Lys Arg Lys Ala Asn Gln Lys His Phe Phe Glu Ser Leu Asn Lys Asn
625 630 635 640

Leu Lys Thr Leu Val Ile Ile Cys His Gly Glu Cys Asp Ile Thr Asn
645 650 655

Ser Phe Gln Ser Cys Leu Glu Ile Ser Ala Ser Ser Val Gly Glu Ser
660 665 670

Asp Ser Asn Gly Leu Ile Asn Pro Leu Glu Lys Lys Ser Ile Thr Ile
675 680 685

Leu Asp Leu Leu Lys Ser Glu Asn Asn Ile Lys Gly Cys Arg Ile Phe
690 695 700

Leu Gly Ala Cys Glu Ser Asp Met Ala Ser Pro Ile Glu Phe Ile Val
705 710 715 720

Asp Glu His Leu Ser Leu Ser Ala Val Leu Leu Ser Leu Gly Ala Lys
725 730 735

Glu Val Ile Gly Gly Leu Trp Lys Leu Tyr Asp Ile Phe Val Glu Asp
740 745 750

Cys Tyr His Gln Leu Leu Asp Ser Asn Asn Leu Ser Gln Ser Leu Asn
755 760 765

Glu Trp Gln Leu Asn Met Ala Lys Glu Trp Lys Glu Asp Lys Thr Asp
770 775 780

Met Arg Tyr Leu Lys Leu Tyr Ser Phe Ala Ser Phe Arg Val Thr Gly
785 790 795 800

Phe Leu Pro Gln Lys Lys Gln Glu Pro
805

<210> SEQ ID NO 13
<211> LENGTH: 760
<212> TYPE: PRT
<213> ORGANISM: Unknown
<220> FEATURE:
<221> NAME/KEY: source
<223> OTHER INFORMATION: /note="Description of Unknown:
Anammox bioreactor sequence"

<400> SEQUENCE: 13

Met Lys Asn Arg Val Gln Ile Glu Ala Ile Ile Arg Asn Leu Gln Gly
1 5 10 15

Ala Ala Arg Asp Ser Lys Thr Asn Lys Leu Ser Glu Asn Ile Ile Ala
20 25 30

Tyr Asp Glu Tyr Arg Lys Ile His Lys Ser Ala Ser Leu Tyr Gln Phe
35 40 45

Gly Ile Ile Pro Ala Lys Glu Ser Ser Ser Val Leu Ala Glu Asn Glu

```
    50                  55                  60

Thr Asn His Val Ala Tyr Glu Asn Ala Ile Phe Glu Met Ala Glu Lys
65                  70                  75                  80

Asn Ile Glu Asn Phe Ser Ser Glu Asp Ile His Lys Lys Arg Lys Glu
                85                  90                  95

Met Ile Glu Ser Ala Leu Arg Leu Leu Met Gly Leu Tyr Lys Asp Arg
            100                 105                 110

His Glu Lys Leu Gln Pro Arg Thr Phe Val Leu Ile Ala Lys Ala Tyr
        115                 120                 125

Leu Leu Arg Ser Leu Ile Thr Arg Pro Lys Gly Ile Thr Ile Pro Glu
    130                 135                 140

Lys Lys Lys Glu Ala Leu Lys Lys Gly Ile Gly Phe Val Glu Ser Ala
145                 150                 155                 160

Ile Lys Lys Ile Gln Ser Ser Glu Asn Ile Leu Ser His Ser Ser Asp
                165                 170                 175

Ile Asp Leu Leu Glu Lys Ala Trp Arg Ile Lys Ser Gln Leu Tyr Leu
            180                 185                 190

Glu Tyr Tyr Arg Val Asn Lys Asp Glu Cys Asp Lys Asn Thr Leu Lys
        195                 200                 205

Glu Val Leu Glu Asn Ser Leu Ile Ser Gly Cys Asp Lys Phe Asp Lys
    210                 215                 220

Asn Ile Glu Asp Val Gln Ile Ala Ile Arg Tyr Cys Glu Leu Glu Ser
225                 230                 235                 240

Ser Arg Glu Tyr Leu Glu Gln Ile Ile Ser Ser His Leu Glu Gly Ile
                245                 250                 255

Glu Phe Glu Lys Ala Arg Ala Tyr Lys Leu Leu Glu Leu Glu Asn Glu
            260                 265                 270

Asn Glu Asp Glu Ile Arg Lys Ser Met Lys Val Val Ile Glu Glu Tyr
        275                 280                 285

Leu Ser Gly Phe Ser Asp Pro Leu Trp Glu Asp Ala Val Glu Phe Ile
    290                 295                 300

Asn Lys Leu Lys Ser Asp Asn Lys Asn Cys Trp Lys Glu Leu Ser Leu
305                 310                 315                 320

Asp Met Tyr Lys Val Cys Arg Glu Gln Glu Ala Glu Thr Ala Ser Leu
                325                 330                 335

His Leu Arg Trp Tyr Trp Ser Arg Gln Arg Arg Leu Tyr Asp Leu Ala
            340                 345                 350

Phe Ile Ala Ala Asp Lys Glu Glu Glu Lys Ala Lys Ile Ala Asp Ser
        355                 360                 365

Leu Lys Ser Arg Leu Ser Leu Arg Trp Ser Ala Leu Glu Glu Thr Gly
    370                 375                 380

Lys Lys Ser Lys Asn Lys Arg Glu Lys Glu Glu Ile Ser Arg Ile Leu
385                 390                 395                 400

Glu Ala Glu Ala Val Ala Met Leu Gly Gly Tyr Ile Lys Gly Ala Arg
                405                 410                 415

Lys Ile Leu Lys Lys Arg Arg Arg Pro Leu Pro Asp Glu Gln Arg Ser
            420                 425                 430

Ile Pro Lys Asp Trp Ile Val Ile His Phe Tyr Val Asn Gln Leu Glu
        435                 440                 445

Asn Lys Cys Tyr Ala Leu Ile Tyr Asn Lys Asp Glu Asn Thr Trp Lys
    450                 455                 460

Cys Glu Phe Val Lys Glu Tyr Gln Arg Leu Phe His Val Phe Leu Thr
465                 470                 475                 480
```

```
Trp Gln Thr Asn Tyr Asn Arg Cys Lys Glu Arg Ala Ala Asp Ser Leu
                485                 490                 495

Val Gln Leu Cys Lys Glu Ile Gly Asn Ala Met Pro Phe Leu Phe Asp
            500                 505                 510

Glu Cys Ile Ile Pro Gln Asp Lys Asn Val Leu Phe Ile Pro His Asp
        515                 520                 525

Phe Leu His Arg Leu Pro Leu His Gly Ala Ile His Glu Lys Asn Asn
    530                 535                 540

Gly Val Phe Leu Glu Asn His Pro Cys Cys Tyr Leu Pro Ala Trp Ser
545                 550                 555                 560

Phe Thr Ala Lys Glu Asn Asn Ala Val Val Gln Gly Ser Ile Leu Leu
                565                 570                 575

Lys Asn Phe Pro Glu Tyr Ser Tyr Glu Glu Leu Val Ser Asn Ser Thr
            580                 585                 590

Leu Trp Thr Ser Pro Val Lys Asp Pro Ala Ser Pro Asp Asp Leu Lys
        595                 600                 605

Thr Ile Ile Ala Ser Pro Glu Met Leu Val Ile Leu Cys His Gly Glu
    610                 615                 620

Ala Asp Ala Val Asn Pro Phe Asn Ala Arg Leu Lys Leu Thr Gly Asn
625                 630                 635                 640

Gly Ile Ser His Leu Glu Ile Leu Gln Ser Thr Lys Met Ile Leu Lys
                645                 650                 655

Gly Ser Lys Ile Ile Leu Gly Ala Cys Glu Thr Asp Leu Val Pro Pro
            660                 665                 670

Leu Ser Asp Ile Met Asp Glu His Leu Ser Ile Ala Thr Ala Phe Leu
        675                 680                 685

Thr Asn Gly Thr His Glu Ile Leu Gly Thr Met Trp Gln Ser Arg Pro
    690                 695                 700

Glu Asp Ile Glu Asp Ile Ile Arg Leu Leu Cys Asp Lys Lys Thr Ser
705                 710                 715                 720

Asp Thr Lys Ala Arg Gly Asp Leu Trp Asn Trp Gln Lys Glu Arg Ile
                725                 730                 735

Arg Asp Tyr Trp Ala Gly Glu Asp Ala Met Phe Tyr Arg Ser Val Ala
            740                 745                 750

Phe Arg Ile Ile Gly Leu Thr Ile
        755                 760


<210> SEQ ID NO 14
<211> LENGTH: 1722
<212> TYPE: PRT
<213> ORGANISM: Candidatus Scalindua brodae

<400> SEQUENCE: 14

Met Lys Ser Asn Asp Met Asn Ile Thr Val Glu Leu Thr Phe Phe Glu
1               5                   10                  15

Pro Tyr Arg Leu Val Glu Trp Phe Asp Trp Asp Ala Arg Lys Lys Ser
            20                  25                  30

His Ser Ala Met Arg Gly Gln Ala Phe Ala Gln Trp Thr Trp Lys Gly
        35                  40                  45

Lys Gly Arg Thr Ala Gly Lys Ser Phe Ile Thr Gly Thr Leu Val Arg
    50                  55                  60

Ser Ala Val Ile Lys Ala Val Glu Glu Leu Leu Ser Leu Asn Asn Gly
65                  70                  75                  80

Lys Trp Glu Gly Val Pro Cys Cys Asn Gly Ser Phe Gln Thr Asp Glu
```

-continued

```
                85                  90                  95

Ser Lys Gly Lys Lys Pro Ser Phe Leu Arg Lys Arg His Thr Leu Gln
            100                 105                 110

Trp Gln Ala Asn Asn Lys Asn Ile Cys Asp Lys Glu Glu Ala Cys Pro
        115                 120                 125

Phe Cys Ile Leu Leu Gly Arg Phe Asp Asn Ala Gly Lys Val His Glu
    130                 135                 140

Arg Asn Lys Asp Tyr Asp Ile His Phe Ser Asn Phe Asp Leu Asp His
145                 150                 155                 160

Lys Gln Glu Lys Asn Asp Leu Arg Leu Val Asp Ile Ala Ser Gly Arg
                165                 170                 175

Ile Leu Asn Arg Val Asp Phe Asp Thr Gly Lys Ala Lys Asp Tyr Phe
            180                 185                 190

Arg Thr Trp Glu Ala Asp Tyr Glu Thr Tyr Gly Thr Tyr Thr Gly Arg
        195                 200                 205

Ile Thr Leu Arg Asn Glu His Ala Lys Lys Leu Leu Leu Ala Ser Leu
    210                 215                 220

Gly Phe Val Asp Lys Leu Cys Gly Ala Leu Cys Arg Ile Glu Val Ile
225                 230                 235                 240

Lys Lys Ser Glu Ser Pro Leu Pro Ser Asp Thr Lys Glu Gln Ser Tyr
                245                 250                 255

Thr Lys Asp Asp Thr Val Glu Val Leu Ser Glu Asp His Asn Asp Glu
            260                 265                 270

Leu Arg Lys Gln Ala Glu Val Ile Val Glu Ala Phe Lys Gln Asn Asp
        275                 280                 285

Lys Leu Glu Lys Ile Arg Ile Leu Ala Asp Ala Ile Arg Thr Leu Arg
    290                 295                 300

Leu His Gly Glu Gly Val Ile Glu Lys Asp Glu Leu Pro Asp Gly Lys
305                 310                 315                 320

Glu Glu Arg Asp Lys Gly His His Leu Trp Asp Ile Lys Val Gln Gly
                325                 330                 335

Thr Ala Leu Arg Thr Lys Leu Lys Glu Leu Trp Gln Ser Asn Lys Asp
            340                 345                 350

Ile Gly Trp Arg Lys Phe Thr Glu Met Leu Gly Ser Asn Leu Tyr Leu
        355                 360                 365

Ile Tyr Lys Lys Glu Thr Gly Gly Val Ser Thr Arg Phe Arg Ile Leu
    370                 375                 380

Gly Asp Thr Glu Tyr Tyr Ser Lys Ala His Asp Ser Glu Gly Ser Asp
385                 390                 395                 400

Leu Phe Ile Pro Val Thr Pro Pro Glu Gly Ile Glu Thr Lys Glu Trp
                405                 410                 415

Ile Ile Val Gly Arg Leu Lys Ala Ala Thr Pro Phe Tyr Phe Gly Val
            420                 425                 430

Gln Gln Pro Ser Asp Ser Ile Pro Gly Lys Glu Lys Lys Ser Glu Asp
        435                 440                 445

Ser Leu Val Ile Asn Glu His Thr Ser Phe Asn Ile Leu Leu Asp Lys
    450                 455                 460

Glu Asn Arg Tyr Arg Ile Pro Arg Ser Ala Leu Arg Gly Ala Leu Arg
465                 470                 475                 480

Arg Asp Leu Arg Thr Ala Phe Gly Ser Gly Cys Asn Val Ser Leu Gly
                485                 490                 495

Gly Gln Ile Leu Cys Asn Cys Lys Val Cys Ile Glu Met Arg Arg Ile
            500                 505                 510
```

```
Thr Leu Lys Asp Ser Val Ser Asp Phe Ser Glu Pro Pro Glu Ile Arg
        515                 520                 525

Tyr Arg Ile Ala Lys Asn Pro Gly Thr Ala Thr Val Glu Asp Gly Ser
    530                 535                 540

Leu Phe Asp Ile Glu Val Gly Pro Glu Gly Leu Thr Phe Pro Phe Val
545                 550                 555                 560

Leu Arg Tyr Arg Gly His Lys Phe Pro Glu Gln Leu Ser Ser Val Ile
                565                 570                 575

Arg Tyr Trp Glu Glu Asn Asp Gly Lys Asn Gly Met Ala Trp Leu Gly
            580                 585                 590

Gly Leu Asp Ser Thr Gly Lys Gly Arg Phe Ala Leu Lys Asp Ile Lys
        595                 600                 605

Ile Phe Glu Trp Asp Leu Asn Gln Lys Ile Asn Glu Tyr Ile Lys Glu
    610                 615                 620

Arg Gly Met Arg Gly Lys Glu Lys Glu Leu Leu Glu Met Gly Glu Ser
625                 630                 635                 640

Ser Leu Pro Asp Gly Leu Ile Pro Tyr Lys Phe Phe Glu Glu Arg Glu
                645                 650                 655

Cys Leu Phe Pro Tyr Lys Glu Asn Leu Lys Pro Gln Trp Ser Glu Val
            660                 665                 670

Gln Tyr Thr Ile Glu Val Gly Ser Pro Leu Leu Thr Ala Asp Thr Ile
        675                 680                 685

Ser Ala Leu Thr Glu Pro Gly Asn Arg Asp Ala Ile Ala Tyr Lys Lys
    690                 695                 700

Arg Val Tyr Asn Asp Gly Asn Asn Ala Ile Glu Pro Glu Pro Arg Phe
705                 710                 715                 720

Ala Val Lys Ser Glu Thr His Arg Gly Ile Phe Arg Thr Ala Val Gly
                725                 730                 735

Arg Arg Thr Gly Asp Leu Gly Lys Glu Asp His Glu Asp Cys Thr Cys
            740                 745                 750

Asp Met Cys Ile Ile Phe Gly Asn Glu His Glu Ser Ser Lys Ile Arg
        755                 760                 765

Phe Glu Asp Leu Glu Leu Ile Asn Gly Asn Glu Phe Glu Lys Leu Glu
    770                 775                 780

Lys His Ile Asp His Val Ala Ile Asp Arg Phe Thr Gly Gly Ala Leu
785                 790                 795                 800

Asp Lys Ala Lys Phe Asp Thr Tyr Pro Leu Ala Gly Ser Pro Lys Lys
                805                 810                 815

Pro Leu Lys Leu Lys Gly Arg Phe Trp Ile Lys Lys Gly Phe Ser Gly
            820                 825                 830

Asp His Lys Leu Leu Ile Thr Thr Ala Leu Ser Asp Ile Arg Asp Gly
        835                 840                 845

Leu Tyr Pro Leu Gly Ser Lys Gly Gly Val Gly Tyr Gly Trp Val Ala
    850                 855                 860

Gly Ile Ser Ile Asp Asp Asn Val Pro Asp Asp Phe Lys Glu Met Ile
865                 870                 875                 880

Asn Lys Thr Glu Met Pro Leu Pro Glu Glu Val Glu Glu Ser Asn Asn
                885                 890                 895

Gly Pro Ile Asn Asn Asp Tyr Val His Pro Gly His Gln Ser Pro Lys
            900                 905                 910

Gln Asp His Lys Asn Lys Asn Ile Tyr Tyr Pro His Tyr Phe Leu Asp
        915                 920                 925
```

```
Ser Gly Ser Lys Val Tyr Arg Glu Lys Asp Ile Ile Thr His Glu Glu
    930                 935                 940

Phe Thr Glu Glu Leu Leu Ser Gly Lys Ile Asn Cys Lys Leu Glu Thr
945                 950                 955                 960

Leu Thr Pro Leu Ile Ile Pro Asp Thr Ser Asp Glu Asn Gly Leu Lys
                965                 970                 975

Leu Gln Gly Asn Lys Pro Gly His Lys Asn Tyr Lys Phe Phe Asn Ile
            980                 985                 990

Asn Gly Glu Leu Met Ile Pro Gly  Ser Glu Leu Arg Gly  Met Leu Arg
        995                 1000                1005

Thr His  Phe Glu Ala Leu Thr  Lys Ser Cys Phe Ala  Ile Phe Gly
    1010                1015                1020

Glu Asp  Ser Thr Leu Ser Trp  Arg Met Asn Ala Asp  Glu Lys Asp
    1025                1030                1035

Tyr Lys  Ile Asp Ser Asn Ser  Ile Arg Lys Met Glu  Ser Gln Arg
    1040                1045                1050

Asn Pro  Lys Tyr Arg Ile Pro  Asp Glu Leu Gln Lys  Glu Leu Arg
    1055                1060                1065

Asn Ser  Gly Asn Gly Leu Phe  Asn Arg Leu Tyr Thr  Ser Glu Arg
    1070                1075                1080

Arg Phe  Trp Ser Asp Val Ser  Asn Lys Phe Glu Asn  Ser Ile Asp
    1085                1090                1095

Tyr Lys  Arg Glu Ile Leu Arg  Cys Ala Gly Arg Pro  Lys Asn Tyr
    1100                1105                1110

Lys Gly  Gly Ile Ile Arg Gln  Arg Lys Asp Ser Leu  Met Ala Glu
    1115                1120                1125

Glu Leu  Lys Val His Arg Leu  Pro Leu Tyr Asp Asn  Phe Asp Ile
    1130                1135                1140

Pro Asp  Ser Ala Tyr Lys Ala  Asn Asp His Cys Arg  Lys Ser Ala
    1145                1150                1155

Thr Cys  Ser Thr Ser Arg Gly  Cys Arg Glu Arg Phe  Thr Cys Gly
    1160                1165                1170

Ile Lys  Val Arg Asp Lys Asn  Arg Val Phe Leu Asn  Ala Ala Asn
    1175                1180                1185

Asn Asn  Arg Gln Tyr Leu Asn  Asn Ile Lys Lys Ser  Asn His Asp
    1190                1195                1200

Leu Tyr  Leu Gln Tyr Leu Lys  Gly Glu Lys Lys Ile  Arg Phe Asn
    1205                1210                1215

Ser Lys  Val Ile Thr Gly Ser  Glu Arg Ser Pro Ile  Asp Val Ile
    1220                1225                1230

Ala Glu  Leu Asn Glu Arg Gly  Arg Gln Thr Gly Phe  Ile Lys Leu
    1235                1240                1245

Ser Gly  Leu Asn Asn Ser Asn  Lys Ser Gln Gly Asn  Thr Gly Thr
    1250                1255                1260

Thr Phe  Asn Ser Gly Trp Asp  Arg Phe Glu Leu Asn  Ile Leu Leu
    1265                1270                1275

Asp Asp  Leu Glu Thr Arg Pro  Ser Lys Ser Asp Tyr  Pro Arg Pro
    1280                1285                1290

Arg Leu  Leu Phe Thr Lys Asp  Gln Tyr Glu Tyr Asn  Ile Thr Lys
    1295                1300                1305

Arg Cys  Glu Arg Val Phe Glu  Ile Asp Lys Gly Asn  Lys Thr Gly
    1310                1315                1320

Tyr Pro  Val Asp Asp Gln Ile  Lys Lys Asn Tyr Glu  Asp Ile Leu
```

```
    1325                1330                1335

Asp Ser  Tyr Asp Gly Ile Lys  Asp Gln Glu Val Ala  Glu Arg Phe
    1340                1345                1350

Asp Thr  Phe Thr Arg Gly Ser  Lys Leu Lys Val Gly  Asp Leu Val
    1355                1360                1365

Tyr Phe  His Ile Asp Gly Asp  Asn Lys Ile Asp Ser  Leu Ile Pro
    1370                1375                1380

Val Arg  Ile Ser Arg Lys Cys  Ala Ser Lys Thr Leu  Gly Gly Lys
    1385                1390                1395

Leu Asp  Lys Ala Leu His Pro  Cys Thr Gly Leu Ser  Asp Gly Leu
    1400                1405                1410

Cys Pro  Gly Cys His Leu Phe  Gly Thr Thr Asp Tyr  Lys Gly Arg
    1415                1420                1425

Val Lys  Phe Gly Phe Ala Lys  Tyr Glu Asn Gly Pro  Glu Trp Leu
    1430                1435                1440

Ile Thr  Arg Gly Asn Asn Pro  Glu Arg Ser Leu Thr  Leu Gly Val
    1445                1450                1455

Leu Glu  Ser Pro Arg Pro Ala  Phe Ser Ile Pro Asp  Asp Glu Ser
    1460                1465                1470

Glu Ile  Pro Gly Arg Lys Phe  Tyr Leu His His Asn  Gly Trp Arg
    1475                1480                1485

Ile Ile  Arg Gln Lys Gln Leu  Glu Ile Arg Glu Thr  Val Gln Pro
    1490                1495                1500

Glu Arg  Asn Val Thr Thr Glu  Val Met Asp Lys Gly  Asn Val Phe
    1505                1510                1515

Ser Phe  Asp Val Arg Phe Glu  Asn Leu Arg Glu Trp  Glu Leu Gly
    1520                1525                1530

Leu Leu  Leu Gln Ser Leu Asp  Pro Gly Lys Asn Ile  Ala His Lys
    1535                1540                1545

Leu Gly  Lys Gly Lys Pro Tyr  Gly Phe Gly Ser Val  Lys Ile Lys
    1550                1555                1560

Ile Asp  Ser Leu His Thr Phe  Lys Ile Asn Ser Asn  Asn Asp Lys
    1565                1570                1575

Ile Lys  Arg Val Pro Gln Ser  Asp Ile Arg Glu Tyr  Ile Asn Lys
    1580                1585                1590

Gly Tyr  Gln Lys Leu Ile Glu  Trp Ser Gly Asn Asn  Ser Ile Gln
    1595                1600                1605

Lys Gly  Asn Val Leu Pro Gln  Trp His Val Ile Pro  His Ile Asp
    1610                1615                1620

Lys Leu  Tyr Lys Leu Leu Trp  Val Pro Phe Leu Asn  Asp Ser Lys
    1625                1630                1635

Leu Glu  Pro Asp Val Arg Tyr  Pro Val Leu Asn Glu  Glu Ser Lys
    1640                1645                1650

Gly Tyr  Ile Glu Gly Ser Asp  Tyr Thr Tyr Lys Lys  Leu Gly Asp
    1655                1660                1665

Lys Asp  Asn Leu Pro Tyr Lys  Thr Arg Val Lys Gly  Leu Thr Thr
    1670                1675                1680

Pro Trp  Ser Pro Trp Asn Pro  Phe Gln Val Ile Ala  Glu His Glu
    1685                1690                1695

Glu Gln  Glu Val Asn Val Thr  Gly Ser Arg Pro Ser  Val Thr Asp
    1700                1705                1710

Lys Ile  Glu Arg Asp Gly Lys  Met Val
    1715                1720
```

<210> SEQ ID NO 15
<211> LENGTH: 1403
<212> TYPE: PRT
<213> ORGANISM: Deltaproteobacteria bacterium
<220> FEATURE:
<221> NAME/KEY: MOD_RES
<222> LOCATION: (1394)..(1396)
<223> OTHER INFORMATION: Any amino acid

<400> SEQUENCE: 15

```
Met Thr Lys Lys Pro Gly Thr Glu Asp Lys Ala Thr Leu Trp Gly Lys
1               5                   10                  15

Glu Ser Ala Ser Lys Ser Val Lys Thr Ile Leu Glu Glu Ser Ile Gln
            20                  25                  30

Gly Phe Thr Val Glu Gln Lys Arg Ser Phe Phe Ala Asn Leu Ala Asp
        35                  40                  45

Gln Leu Val Ser Arg Ala Gly Glu Gln Gly Ala Lys Ser Val Arg Ser
    50                  55                  60

Gln Gly Leu Ile Ile Gly Arg Lys Glu Asn Tyr Ala Lys Pro Ser Ala
65                  70                  75                  80

Gln Glu Pro Thr Arg His His Leu Tyr Arg Gln Pro Ser Asn Ala Ser
                85                  90                  95

Ala Phe Leu Ala Thr Gly Trp Leu Ile Ala Glu Thr Pro Phe Phe Ile
            100                 105                 110

Gly Ser Gly Thr Glu Gly Gln Lys Gln Thr Asp Asp Gln Ala Glu Ser
        115                 120                 125

Leu His Leu Arg Thr Leu Arg Asp Gly His Gly Arg Phe Arg Ile Pro
    130                 135                 140

Phe Thr Thr Ile Arg Gly Val Met Asp Lys Glu Leu Arg Asp Ile Leu
145                 150                 155                 160

Gln Ala Gly Cys Ala Lys Gly Arg Ser Leu Arg Ala Pro Cys Pro Cys
                165                 170                 175

Gln Val Cys Thr Leu Met Arg Arg Ile Gln Val Arg Asp Ala Ile Ala
            180                 185                 190

Ala Asp Ile Leu Pro Pro Asp Leu Arg Met Arg Thr Arg Ile Asp Pro
        195                 200                 205

Ser His Gly Thr Val Ala His Leu Phe Ser Leu Glu Met Ala Pro Gln
    210                 215                 220

Gly Leu Lys Leu Pro Phe Phe Leu Lys Leu Lys Gly Val Glu Thr Ile
225                 230                 235                 240

Asp Pro Asp Lys Glu Leu Leu Glu Ile Leu Asn Asp Trp Ser Ala Gly
                245                 250                 255

Gln Cys Phe Leu Gly Gly Leu Trp Gly Thr Gly Lys Gly Arg Phe Arg
            260                 265                 270

Leu Asp Asp Leu Gln Trp His Arg Leu Glu Leu Asp Asn Ala Asp Tyr
        275                 280                 285

Tyr Thr Pro Leu Leu Gln Asp Arg Phe Phe Ala Gly Glu Thr Ile Ser
    290                 295                 300

Asp Leu Arg Gln Gly Leu Gln Ser Ile Asn Ile Gln Pro Glu Arg Ile
305                 310                 315                 320

Pro Ala Gln Thr Pro Ser Arg Asn Met Pro Tyr Cys Arg Val Asp Cys
                325                 330                 335

Ile Leu Glu Phe Lys Ser Pro Val Leu Ser Gly Asp Pro Val Ala Ala
            340                 345                 350
```

-continued

```
Leu Phe Glu Ser Asp Ala Pro Asp Asn Val Ala Tyr Lys Lys Pro Val
        355                 360                 365

Val Gln Tyr Asp Glu Thr Gly Arg Leu Arg Thr Thr Asp Pro Gly Pro
    370                 375                 380

Val Glu Met Leu Thr Cys Leu Lys Gly Glu Gly Val Arg Gly Val Val
385                 390                 395                 400

Ala Tyr Leu Ala Gly Lys Ala Tyr Asp Gln His Asp Leu Ser His Asp
                405                 410                 415

Ser Cys Asn Cys Thr Phe Cys Gln Ala Phe Gly Asn Gly Gln Lys Ala
            420                 425                 430

Gly Ser Leu Arg Phe Asp Asp Phe Met Pro Val Gln Phe Glu Ser Asp
        435                 440                 445

Gln Ala Gly Asn Phe Ser Trp Ser Pro His Thr Pro His Ala Met Arg
    450                 455                 460

Ser Asp Arg Val Ala Leu Asp Val Phe Gly Gly Ala Met Pro Glu Ala
465                 470                 475                 480

Lys Phe Asp Asp Arg Pro Leu Ala Ala Ser Pro Gly Lys Pro Leu Asn
                485                 490                 495

Phe Lys Ser Thr Ile Trp Tyr Arg Glu Asp Met Gly Lys Glu Ala Gly
            500                 505                 510

Lys Ala Leu Lys Arg Ala Leu Ile Asp Leu Gln Asn Asn Met Ala Ala
        515                 520                 525

Ile Gly Ser Gly Gly Gly Ile Gly Arg Gly Trp Val Ser Arg Val Cys
    530                 535                 540

Phe Glu Gly Asp Ile Pro Asp Phe Leu Glu Asp Phe Pro Glu Pro Ile
545                 550                 555                 560

Thr Val Thr Glu Pro Glu Gln Asp Ser Gln Leu Leu Lys Asn Gln Ala
                565                 570                 575

Val Ala Asp Glu Thr Ala Val Ser Ala Cys Asp Thr Ala Asp Ala Pro
            580                 585                 590

His Pro Leu Ala Val Thr Leu Glu Pro Gly Ala Arg Tyr Phe Pro Arg
        595                 600                 605

Val Ile Ile Pro Arg Ala Pro Thr Val Lys Arg Asp Glu Cys Val Thr
    610                 615                 620

Gly Gln Arg Tyr His Thr Gly Arg Leu Ser Gly Lys Ile Phe Cys Glu
625                 630                 635                 640

Leu Asn Thr Leu Gly Pro Leu Phe Val Pro Asp Thr Asp Tyr Ser Ala
                645                 650                 655

Gly Val Pro Val Pro Ile Ser Asp Glu Gln Leu Ala Glu Cys Gln Leu
            660                 665                 670

Gln Ala Val Phe Glu Asn Thr Ser Lys Phe Asn Glu Phe Phe Ala Thr
        675                 680                 685

Tyr Pro Glu Glu Thr Val Thr Lys Leu Lys Asp Leu Leu Cys Ala Ala
    690                 695                 700

Asp Asp Lys Trp Ile Leu Ala Val Lys Asp Ile Thr Ala Asp Leu Arg
705                 710                 715                 720

Gln Glu Ile Gly Glu Asp Thr Phe Gln Arg Ile Ile Arg Lys Ala Gly
                725                 730                 735

His Lys Thr Gln Arg Phe His Gln Ile Asn Asp Glu Ile Gly Leu Pro
            740                 745                 750

Gly Ala Ser Leu Arg Gly Met Val Leu Ser Asn Tyr Gln Ile Leu Thr
        755                 760                 765

Asn Ser Cys Tyr Arg Asn Leu Lys Ala Thr Glu Glu Ile Thr Arg Arg
```

```
    770                 775                 780

Met Pro Ala Asp Glu Ala Lys Tyr Arg Lys Ala Gly Arg Val Thr Val
785                 790                 795                 800

Ser Gly Asp Gly Ala Gln Lys Lys Tyr Ser Ile Gln Glu Met Glu Val
                805                 810                 815

Leu Arg Leu Pro Ile Tyr Asp Asn Met Asn Thr Pro Asp Asn Met Pro
            820                 825                 830

Asp Val Ala Lys Gln Ala Thr Thr Ala Lys Arg Cys Asn Asn Leu Met
        835                 840                 845

Asn Glu Ala Ala Lys Thr Ser Arg Val Glu Leu Lys Ala Arg Trp Arg
    850                 855                 860

Glu Gly Gln Ser Lys Ile Lys Tyr Gln Ile Ile Asp Ala Leu Asn Lys
865                 870                 875                 880

Val Asp Pro Ile Ile Gln Val Ile Ser Ser Ser Lys Gln Ile Asn Pro
                885                 890                 895

Asn Asn Gly Lys Thr Gly Trp Gly Tyr Val Lys Tyr Thr Gly Ala Asn
            900                 905                 910

Val Phe Ala Lys Ser Leu Val Ala Pro Ile Asp Cys Leu Arg Lys Lys
        915                 920                 925

Asp Ala Gly His Val Cys Cys Gln Val Asn Leu Asn Pro Ala Trp Glu
    930                 935                 940

Ala Ser Asn Phe Asp Ile Leu Ile Asn Glu Lys Cys Pro Val Glu Arg
945                 950                 955                 960

Gln Ser Gly Pro Arg Pro Thr Leu Arg Cys Lys Gly Gln Asp Ser Ala
                965                 970                 975

Trp Tyr Thr Leu Thr Lys Arg Ser Glu Arg Ile Phe Thr Asp Lys Lys
            980                 985                 990

Pro Val Pro Asp Pro Ile Asn Ile  Pro Pro Arg Glu Val  Lys Arg Tyr
        995                 1000                1005

Asn Glu  Leu Arg Asp Ser Tyr  Lys Lys Asn Thr Ala  His Val Pro
    1010                1015                1020

Lys Pro  Leu Gln Thr Phe Phe  Asn Gln Glu Ser Leu  Ala Asn Gly
    1025                1030                1035

Asp Leu  Val Tyr Phe Glu Val  Asn Gln Phe Gly Glu  Ala Ser Gln
    1040                1045                1050

Leu Thr  Pro Val Ser Ile Ser  Arg Thr Thr Asp Leu  Phe Pro Ile
    1055                1060                1065

Gly Gly  Arg Leu Pro Gln Gly  His Lys Asp Leu Phe  Pro Cys Thr
    1070                1075                1080

Ala Met  Cys Leu Ser Glu Cys  Lys Asn Cys Val Pro  Ala Ser Phe
    1085                1090                1095

Cys Glu  Phe His Ser Arg Ser  His Glu Lys Leu Cys  Pro Ala Cys
    1100                1105                1110

Ser Leu  Ala Gly Thr Thr Gly  Asn Arg Gly Arg Ile  Lys Phe Ser
    1115                1120                1125

Glu Ala  Trp Leu Ser Gly Leu  Pro Lys Trp His Ser  Val Ser Gln
    1130                1135                1140

Asp Asn  Val Gly Arg Gly Leu  Gly Val Thr Met Pro  Arg Leu Glu
    1145                1150                1155

Arg Ser  Arg Arg Thr Trp His  Leu Pro Thr Lys Asp  Ala Tyr Leu
    1160                1165                1170

Leu Gly  Gln Ser Ile Tyr Leu  Asn His Pro Val Pro  Ala Ile Leu
    1175                1180                1185
```

Pro Ser Asp Gln Val Pro Ser Glu Asn Asn Gln Thr Val Glu Pro
1190 1195 1200

Leu Gly Pro Lys Asn Ile Phe Ser Phe Gln Leu Ala Phe Asp Asn
1205 1210 1215

Leu Ser Ile Glu Glu Leu Gly Leu Leu Leu Tyr Ser Leu Glu Leu
1220 1225 1230

Glu Ser Gly Met Ala His Arg Leu Gly Arg Gly Arg Ala Leu Gly
1235 1240 1245

Met Gly Ser Val Gln Ile Ser Val Lys Asp Ile Gln Ile Arg Asp
1250 1255 1260

Asn Lys Ser Phe Leu Phe Ser Ser Asn Ile Ser Lys Lys Ser Glu
1265 1270 1275

Trp Ile Gln Cys Gly Lys Asp Glu Phe Ala Gln Glu Ala Trp Phe
1280 1285 1290

Gly Glu Ser Trp Asp Asn Ile Asp His Ile Gln Arg Leu Arg Gln
1295 1300 1305

Ala Leu Thr Ile Pro Val Lys Gly Asp Val Gly Cys Ile Arg Tyr
1310 1315 1320

Pro Lys Leu Glu Ala Glu Gly Gly Met Pro Asp Tyr Ile Lys Leu
1325 1330 1335

Arg Lys Arg Leu Thr Pro Leu Cys Asp Arg Glu Glu Pro Val Arg
1340 1345 1350

Tyr Arg Ile Asn Pro Val Gln Leu Ala Arg Met Ile Leu Pro Phe
1355 1360 1365

Val Pro Trp His Gly Ala Cys Pro Ala Leu Leu Asn Glu Gln Val
1370 1375 1380

Met Ile Glu Ala Lys Arg Leu Thr Glu Leu Xaa Xaa Xaa Asp Arg
1385 1390 1395

Ala Asn Trp Pro Cys
1400

<210> SEQ ID NO 16
<211> LENGTH: 1601
<212> TYPE: PRT
<213> ORGANISM: Desulfonema ishimotonii

<400> SEQUENCE: 16

Met Thr Thr Thr Met Lys Ile Ser Ile Glu Phe Leu Glu Pro Phe Arg
1 5 10 15

Met Thr Lys Trp Gln Glu Ser Thr Arg Arg Asn Lys Asn Asn Lys Glu
20 25 30

Phe Val Arg Gly Gln Ala Phe Ala Arg Trp His Arg Asn Lys Lys Asp
35 40 45

Asn Thr Lys Gly Arg Pro Tyr Ile Thr Gly Thr Leu Leu Arg Ser Ala
50 55 60

Val Ile Arg Ser Ala Glu Asn Leu Leu Thr Leu Ser Asp Gly Lys Ile
65 70 75 80

Ser Glu Lys Thr Cys Cys Pro Gly Lys Phe Asp Thr Glu Asp Lys Asp
85 90 95

Arg Leu Leu Gln Leu Arg Gln Arg Ser Thr Leu Arg Trp Thr Asp Lys
100 105 110

Asn Pro Cys Pro Asp Asn Ala Glu Thr Tyr Cys Pro Phe Cys Glu Leu
115 120 125

Leu Gly Arg Ser Gly Asn Asp Gly Lys Lys Ala Glu Lys Lys Asp Trp

```
    130                 135                 140

Arg Phe Arg Ile His Phe Gly Asn Leu Ser Leu Pro Gly Lys Pro Asp
145                 150                 155                 160

Phe Asp Gly Pro Lys Ala Ile Gly Ser Gln Arg Val Leu Asn Arg Val
                165                 170                 175

Asp Phe Lys Ser Gly Lys Ala His Asp Phe Phe Lys Ala Tyr Glu Val
            180                 185                 190

Asp His Thr Arg Phe Pro Arg Phe Glu Gly Glu Ile Thr Ile Asp Asn
        195                 200                 205

Lys Val Ser Ala Glu Ala Arg Lys Leu Leu Cys Asp Ser Leu Lys Phe
    210                 215                 220

Thr Asp Arg Leu Cys Gly Ala Leu Cys Val Ile Arg Phe Asp Glu Tyr
225                 230                 235                 240

Thr Pro Ala Ala Asp Ser Gly Lys Gln Thr Glu Asn Val Gln Ala Glu
                245                 250                 255

Pro Asn Ala Asn Leu Ala Glu Lys Thr Ala Glu Gln Ile Ile Ser Ile
            260                 265                 270

Leu Asp Asp Asn Lys Lys Thr Glu Tyr Thr Arg Leu Leu Ala Asp Ala
        275                 280                 285

Ile Arg Ser Leu Arg Arg Ser Ser Lys Leu Val Ala Gly Leu Pro Lys
    290                 295                 300

Asp His Asp Gly Lys Asp Asp His Tyr Leu Trp Asp Ile Gly Lys Lys
305                 310                 315                 320

Lys Lys Asp Glu Asn Ser Val Thr Ile Arg Gln Ile Leu Thr Thr Ser
                325                 330                 335

Ala Asp Thr Lys Glu Leu Lys Asn Ala Gly Lys Trp Arg Glu Phe Cys
            340                 345                 350

Glu Lys Leu Gly Glu Ala Leu Tyr Leu Lys Ser Lys Asp Met Ser Gly
        355                 360                 365

Gly Leu Lys Ile Thr Arg Arg Ile Leu Gly Asp Ala Glu Phe His Gly
    370                 375                 380

Lys Pro Asp Arg Leu Glu Lys Ser Arg Ser Val Ser Ile Gly Ser Val
385                 390                 395                 400

Leu Lys Glu Thr Val Val Cys Gly Glu Leu Val Ala Lys Thr Pro Phe
                405                 410                 415

Phe Phe Gly Ala Ile Asp Glu Asp Ala Lys Gln Thr Asp Leu Gln Val
            420                 425                 430

Leu Leu Thr Pro Asp Asn Lys Tyr Arg Leu Pro Arg Ser Ala Val Arg
        435                 440                 445

Gly Ile Leu Arg Arg Asp Leu Gln Thr Tyr Phe Asp Ser Pro Cys Asn
    450                 455                 460

Ala Glu Leu Gly Gly Arg Pro Cys Met Cys Lys Thr Cys Arg Ile Met
465                 470                 475                 480

Arg Gly Ile Thr Val Met Asp Ala Arg Ser Glu Tyr Asn Ala Pro Pro
                485                 490                 495

Glu Ile Arg His Arg Thr Arg Ile Asn Pro Phe Thr Gly Thr Val Ala
            500                 505                 510

Glu Gly Ala Leu Phe Asn Met Glu Val Ala Pro Glu Gly Ile Val Phe
        515                 520                 525

Pro Phe Gln Leu Arg Tyr Arg Gly Ser Glu Asp Gly Leu Pro Asp Ala
    530                 535                 540

Leu Lys Thr Val Leu Lys Trp Trp Ala Glu Gly Gln Ala Phe Met Ser
545                 550                 555                 560
```

-continued

```
Gly Ala Ala Ser Thr Gly Lys Gly Arg Phe Arg Met Glu Asn Ala Lys
                565                 570                 575

Tyr Glu Thr Leu Asp Leu Ser Asp Glu Asn Gln Arg Asn Asp Tyr Leu
            580                 585                 590

Lys Asn Trp Gly Trp Arg Asp Glu Lys Gly Leu Glu Glu Leu Lys Lys
        595                 600                 605

Arg Leu Asn Ser Gly Leu Pro Glu Pro Gly Asn Tyr Arg Asp Pro Lys
    610                 615                 620

Trp His Glu Ile Asn Val Ser Ile Glu Met Ala Ser Pro Phe Ile Asn
625                 630                 635                 640

Gly Asp Pro Ile Arg Ala Ala Val Asp Lys Arg Gly Thr Asp Val Val
                645                 650                 655

Thr Phe Val Lys Tyr Lys Ala Glu Gly Glu Glu Ala Lys Pro Val Cys
            660                 665                 670

Ala Tyr Lys Ala Glu Ser Phe Arg Gly Val Ile Arg Ser Ala Val Ala
        675                 680                 685

Arg Ile His Met Glu Asp Gly Val Pro Leu Thr Glu Leu Thr His Ser
    690                 695                 700

Asp Cys Glu Cys Leu Leu Cys Gln Ile Phe Gly Ser Glu Tyr Glu Ala
705                 710                 715                 720

Gly Lys Ile Arg Phe Glu Asp Leu Val Phe Glu Ser Asp Pro Glu Pro
                725                 730                 735

Val Thr Phe Asp His Val Ala Ile Asp Arg Phe Thr Gly Gly Ala Ala
            740                 745                 750

Asp Lys Lys Lys Phe Asp Asp Ser Pro Leu Pro Gly Ser Pro Ala Arg
        755                 760                 765

Pro Leu Met Leu Lys Gly Ser Phe Trp Ile Arg Arg Asp Val Leu Glu
    770                 775                 780

Asp Glu Glu Tyr Cys Lys Ala Leu Gly Lys Ala Leu Ala Asp Val Asn
785                 790                 795                 800

Asn Gly Leu Tyr Pro Leu Gly Gly Lys Ser Ala Ile Gly Tyr Gly Gln
                805                 810                 815

Val Lys Ser Leu Gly Ile Lys Gly Asp Asp Lys Arg Ile Ser Arg Leu
            820                 825                 830

Met Asn Pro Ala Phe Asp Glu Thr Asp Val Ala Val Pro Glu Lys Pro
        835                 840                 845

Lys Thr Asp Ala Glu Val Arg Ile Glu Ala Glu Lys Val Tyr Tyr Pro
    850                 855                 860

His Tyr Phe Val Glu Pro His Lys Lys Val Glu Arg Glu Glu Lys Pro
865                 870                 875                 880

Cys Gly His Gln Lys Phe His Glu Gly Arg Leu Thr Gly Lys Ile Arg
                885                 890                 895

Cys Lys Leu Ile Thr Lys Thr Pro Leu Ile Val Pro Asp Thr Ser Asn
            900                 905                 910

Asp Asp Phe Phe Arg Pro Ala Asp Lys Glu Ala Arg Lys Glu Lys Asp
        915                 920                 925

Glu Tyr His Lys Ser Tyr Ala Phe Phe Arg Leu His Lys Gln Ile Met
    930                 935                 940

Ile Pro Gly Ser Glu Leu Arg Gly Met Val Ser Ser Val Tyr Glu Thr
945                 950                 955                 960

Val Thr Asn Ser Cys Phe Arg Ile Phe Asp Glu Thr Lys Arg Leu Ser
                965                 970                 975
```

```
Trp Arg Met Asp Ala Asp His Gln Asn Val Leu Gln Asp Phe Leu Pro
            980                 985                 990

Gly Arg Val Thr Ala Asp Gly Lys  His Ile Gln Lys Phe  Ser Glu Thr
        995                 1000                1005

Ala Arg  Val Pro Phe Tyr Asp  Lys Thr Gln Lys His  Phe Asp Ile
    1010                 1015                 1020

Leu Asp  Glu Gln Glu Ile Ala  Gly Glu Lys Pro Val  Arg Met Trp
    1025                 1030                 1035

Val Lys  Arg Phe Ile Lys Arg  Leu Ser Leu Val Asp  Pro Ala Lys
    1040                 1045                 1050

His Pro  Gln Lys Lys Gln Asp  Asn Lys Trp Lys Arg  Arg Lys Glu
    1055                 1060                 1065

Gly Ile  Ala Thr Phe Ile Glu  Gln Lys Asn Gly Ser  Tyr Tyr Phe
    1070                 1075                 1080

Asn Val  Val Thr Asn Asn Gly  Cys Thr Ser Phe His  Leu Trp His
    1085                 1090                 1095

Lys Pro  Asp Asn Phe Asp Gln  Glu Lys Leu Glu Gly  Ile Gln Asn
    1100                 1105                 1110

Gly Glu  Lys Leu Asp Cys Trp  Val Arg Asp Ser Arg  Tyr Gln Lys
    1115                 1120                 1125

Ala Phe  Gln Glu Ile Pro Glu  Asn Asp Pro Asp Gly  Trp Glu Cys
    1130                 1135                 1140

Lys Glu  Gly Tyr Leu His Val  Val Gly Pro Ser Lys  Val Glu Phe
    1145                 1150                 1155

Ser Asp  Lys Lys Gly Asp Val  Ile Asn Asn Phe Gln  Gly Thr Leu
    1160                 1165                 1170

Pro Ser  Val Pro Asn Asp Trp  Lys Thr Ile Arg Thr  Asn Asp Phe
    1175                 1180                 1185

Lys Asn  Arg Lys Arg Lys Asn  Glu Pro Val Phe Cys  Cys Glu Asp
    1190                 1195                 1200

Asp Lys  Gly Asn Tyr Tyr Thr  Met Ala Lys Tyr Cys  Glu Thr Phe
    1205                 1210                 1215

Phe Phe  Asp Leu Lys Glu Asn  Glu Glu Tyr Glu Ile  Pro Glu Lys
    1220                 1225                 1230

Ala Arg  Ile Lys Tyr Lys Glu  Leu Leu Arg Val Tyr  Asn Asn Asn
    1235                 1240                 1245

Pro Gln  Ala Val Pro Glu Ser  Val Phe Gln Ser Arg  Val Ala Arg
    1250                 1255                 1260

Glu Asn  Val Glu Lys Leu Lys  Ser Gly Asp Leu Val  Tyr Phe Lys
    1265                 1270                 1275

His Asn  Glu Lys Tyr Val Glu  Asp Ile Val Pro Val  Arg Ile Ser
    1280                 1285                 1290

Arg Thr  Val Asp Asp Arg Met  Ile Gly Lys Arg Met  Ser Ala Asp
    1295                 1300                 1305

Leu Arg  Pro Cys His Gly Asp  Trp Val Glu Asp Gly  Asp Leu Ser
    1310                 1315                 1320

Ala Leu  Asn Ala Tyr Pro Glu  Lys Arg Leu Leu Leu  Arg His Pro
    1325                 1330                 1335

Lys Gly  Leu Cys Pro Ala Cys  Arg Leu Phe Gly Thr  Gly Ser Tyr
    1340                 1345                 1350

Lys Gly  Arg Val Arg Phe Gly  Phe Ala Ser Leu Glu  Asn Asp Pro
    1355                 1360                 1365

Glu Trp  Leu Ile Pro Gly Lys  Asn Pro Gly Asp Pro  Phe His Gly
```

```
    1370                1375                1380

Gly Pro  Val Met Leu Ser Leu  Leu Glu Arg Pro Arg  Pro Thr Trp
    1385                1390                1395

Ser Ile  Pro Gly Ser Asp Asn  Lys Phe Lys Val Pro  Gly Arg Lys
    1400                1405                1410

Phe Tyr  Val His His His Ala  Trp Lys Thr Ile Lys  Asp Gly Asn
    1415                1420                1425

His Pro  Thr Thr Gly Lys Ala  Ile Glu Gln Ser Pro  Asn Asn Arg
    1430                1435                1440

Thr Val  Glu Ala Leu Ala Gly  Gly Asn Ser Phe Ser  Phe Glu Ile
    1445                1450                1455

Ala Phe  Glu Asn Leu Lys Glu  Trp Glu Leu Gly Leu  Leu Ile His
    1460                1465                1470

Ser Leu  Gln Leu Glu Lys Gly  Leu Ala His Lys Leu  Gly Met Ala
    1475                1480                1485

Lys Ser  Met Gly Phe Gly Ser  Val Glu Ile Asp Val  Glu Ser Val
    1490                1495                1500

Arg Leu  Arg Lys Asp Trp Lys  Gln Trp Arg Asn Gly  Asn Ser Glu
    1505                1510                1515

Ile Pro  Asn Trp Leu Gly Lys  Gly Phe Ala Lys Leu  Lys Glu Trp
    1520                1525                1530

Phe Arg  Asp Glu Leu Asp Phe  Ile Glu Asn Leu Lys  Lys Leu Leu
    1535                1540                1545

Trp Phe  Pro Glu Gly Asp Gln  Ala Pro Arg Val Cys  Tyr Pro Met
    1550                1555                1560

Leu Arg  Lys Lys Asp Asp Pro  Asn Gly Asn Ser Gly  Tyr Glu Glu
    1565                1570                1575

Leu Lys  Asp Gly Glu Phe Lys  Lys Glu Asp Arg Gln  Lys Lys Leu
    1580                1585                1590

Thr Thr  Pro Trp Thr Pro Trp  Ala
    1595                1600


<210> SEQ ID NO 17
<211> LENGTH: 1575
<212> TYPE: PRT
<213> ORGANISM: Unknown
<220> FEATURE:
<221> NAME/KEY: source
<223> OTHER INFORMATION: /note="Description of Unknown:
      Soil metagenome sequence"

<400> SEQUENCE: 17

Met Arg Leu Lys Ile Asn Ile His Phe Leu Glu Pro Phe Arg Leu Ile
1               5                   10                  15

Glu Trp His Glu Gln Asp Arg Arg Asn Lys Gly Asn Ser Arg Trp Gln
            20                  25                  30

Arg Gly Gln Ser Phe Ala Arg Trp His Arg Arg Lys Asp Asn Asp Gln
        35                  40                  45

Gly Arg Pro Tyr Ile Thr Gly Thr Leu Leu Arg Ser Val Val Ile Arg
    50                  55                  60

Ala Val Glu Glu Glu Leu Ala Arg Pro Asp Thr Ala Trp Gln Ser Cys
65                  70                  75                  80

Gly Gly Leu Phe Ile Thr Pro Asp Gly Gln Thr Lys Pro Gln His Leu
                85                  90                  95

Arg His Arg Ala Thr Val Arg Ala Arg Gln Thr Ala Lys Asp Lys Cys
            100                 105                 110
```

```
Ala Asp Arg Gln Ser Ala Cys Pro Phe Cys Leu Leu Leu Gly Arg Phe
        115                 120                 125

Asp Gln Val Gly Lys Asp Gly Asp Lys Lys Gly Glu Gly Leu Arg Phe
    130                 135                 140

Asp Val Arg Phe Ser Asn Leu Asp Leu Pro Lys Asp Phe Ser Pro Arg
145                 150                 155                 160

Asp Phe Asp Gly Pro Gln Glu Ile Gly Ser Arg Arg Thr Ile Asn Arg
                165                 170                 175

Val Asp Asp Glu Thr Gly Lys Ala His Asp Phe Phe Ser Ile Trp Glu
            180                 185                 190

Val Asp Ala Val Arg Glu Phe Gln Gly Glu Ile Val Leu Ala Ala Asp
        195                 200                 205

Leu Pro Ser Arg Asp Gln Val Glu Ser Leu Leu His His Ala Leu Gly
    210                 215                 220

Phe Val Asp Arg Leu Cys Gly Ala Arg Cys Val Ile Ser Ile Ala Asp
225                 230                 235                 240

Gln Lys Pro Ala Glu Arg Glu Glu Arg Thr Val Ala Ala Gly Asp Glu
                245                 250                 255

Lys Ala Thr Ile Ala Asp Tyr Asp Gln Val Lys Gly Leu Pro Tyr Thr
            260                 265                 270

Arg Leu Arg Pro Leu Ala Asp Ala Val Arg Asn Leu Arg Gln Leu Asp
        275                 280                 285

Leu Ala Glu Leu Asn Lys Pro Asp Gly Lys Phe Leu Pro Pro Gly Arg
    290                 295                 300

Val Asn Lys Asp Gly Arg Arg Val Pro His Tyr Val Trp Asp Ile Pro
305                 310                 315                 320

Leu Gly Lys Gly Asp Thr Leu Arg Lys Arg Leu Glu Phe Leu Ala Ala
                325                 330                 335

Ser Cys Glu Gly Asp Gln Ala Lys Trp Arg Asn Ile Cys Glu Ser Glu
            340                 345                 350

Gly Gln Ala Leu Tyr Glu Lys Ser Lys Lys Leu Lys Asp Ser Pro Ala
        355                 360                 365

Ala Pro Gly Arg His Leu Gly Ala Ala Glu Gln Val Arg Pro Pro Gln
    370                 375                 380

Pro Pro Val Ser Tyr Ser Glu Glu Ser Ile Asn Ser Asp Leu Pro Leu
385                 390                 395                 400

Ala Glu Trp Ile Ile Thr Gly Thr Leu Arg Ala Glu Thr Pro Phe Ala
                405                 410                 415

Ile Gly Met Asp Ala Pro Ile Asp Asp Asp Gln Thr Ser Ser Arg Thr
            420                 425                 430

Leu Val Asp Arg Asp Gly Arg Tyr Arg Leu Pro Arg Ser Thr Leu Arg
        435                 440                 445

Gly Ile Leu Arg Arg Asp Leu Ser Leu Ala Ser Gly Asp Gln Gly Cys
    450                 455                 460

Gln Val Arg Leu Gly Pro Glu Arg Pro Cys Thr Cys Pro Val Cys Leu
465                 470                 475                 480

Ile Leu Arg Gln Val Val Ile Ala Asp Thr Val Ser Glu Thr Thr Val
                485                 490                 495

Pro Ala Asp Ile Arg Gln Arg Ile Arg Arg Asn Pro Ile Thr Gly Thr
            500                 505                 510

Ala Ala Asp Gly Gly Leu Phe Asp Thr Glu Arg Gly Pro Lys Gly Ala
        515                 520                 525
```

```
Gly Phe Pro Phe Ser Leu Arg Tyr Arg Gly His Ala Pro Met Pro Lys
    530                 535                 540

Ala Leu Arg Thr Val Leu Gln Trp Trp Ser Ala Gly Lys Cys Phe Ala
545                 550                 555                 560

Gly Ser Asp Gly Gly Val Gly Cys Gly Arg Phe Ala Leu Asp Asn Leu
                565                 570                 575

Glu Val Tyr Arg Trp Asp Leu Gly Thr Phe Ala Phe Arg Gln Ala Tyr
            580                 585                 590

Ser Glu Asn Asn Gly Leu Arg Ser Pro Glu Glu Glu Phe Asp Leu Ala
        595                 600                 605

Val Ile His Glu Leu Ala Glu Gly Leu Ala Lys Glu Asp Gly Gln Lys
    610                 615                 620

Ile Leu Lys Gly Thr Glu Pro Phe Thr Cys Trp Gln Glu Arg Ser Trp
625                 630                 635                 640

Gln Phe Ser Phe Thr Gly Pro Leu Leu Gln Gly Asp Pro Leu Ala Ala
                645                 650                 655

Leu Asn Ser Asp Thr Ala Asp Ile Ile Ser Phe Arg Arg Thr Val Val
            660                 665                 670

Asp Asn Gly Glu Val Leu Arg Glu Pro Val Leu Arg Gly Glu Gly Leu
        675                 680                 685

Arg Gly Leu Leu Arg Thr Ala Val Gly Arg Val Ala Gly Asp Asp Leu
    690                 695                 700

Leu Thr Arg Ser His Gln Asp Cys Lys Cys Glu Ile Cys Gln Leu Phe
705                 710                 715                 720

Gly Ser Glu His Arg Ala Gly Ile Leu Arg Phe Glu Asp Leu Pro Pro
                725                 730                 735

Val Ser Pro Thr Thr Val Ala Asp Lys Arg Leu Asp His Val Ala Ile
            740                 745                 750

Asp Arg Phe Asp Gln Ser Val Val Glu Lys Tyr Asp Asp Arg Pro Leu
        755                 760                 765

Val Gly Ser Pro Lys Gln Pro Leu Val Phe Lys Gly Cys Phe Trp Val
    770                 775                 780

Gln Thr Ser Gly Met Thr His Gln Leu Thr Glu Leu Leu Ala Gln Ala
785                 790                 795                 800

Trp Arg Asp Ile Ala Ala Gly His Tyr Pro Val Gly Gly Lys Gly Gly
                805                 810                 815

Ile Gly Tyr Gly Trp Ile Asn Ser Leu Val Val Asp Gly Glu Lys Ile
            820                 825                 830

Thr Cys Arg Pro Asp Gly Asp Ser Ile Ser Leu Thr Thr Val Thr Gly
        835                 840                 845

Asp Ile Pro Pro Arg Pro Ala Leu Thr Pro Pro Ala Gly Ala Ile Tyr
    850                 855                 860

Tyr Pro His Tyr Phe Leu Pro Pro Asn Pro Glu His Lys Pro Lys Arg
865                 870                 875                 880

Ser Asp Lys Ile Ile Gly His His Thr Phe Ala Thr Asp Pro Asp Ser
                885                 890                 895

Phe Thr Gly Arg Ile Thr Cys Lys Leu Glu Val Val Thr Pro Leu Ile
            900                 905                 910

Val Pro Asp Thr Glu Gly Glu Gln Pro Lys Asp Gln His Lys Asn Phe
        915                 920                 925

Pro Phe Phe Lys Ile Asn Asp Glu Ile Met Leu Pro Gly Ala Pro Leu
    930                 935                 940

Trp Ala Ala Val Ser Gln Val Tyr Glu Ala Leu Thr Asn Ser Cys Phe
```

-continued

```
945                 950                 955                 960

Arg Val Met Lys Gln Lys Arg Phe Leu Ser Trp Arg Met Glu Ala Glu
                965                 970                 975

Asp Tyr Lys Asp Phe Tyr Pro Gly Arg Val Leu Asp Gly Gly Lys Gln
            980                 985                 990

Ile Lys Lys Met Gly Asp Lys Ala  Ile Arg Met Pro Leu  Tyr Asp Asp
        995                 1000                1005

Ser Thr  Ala Thr Gly Ser Ile  Lys Asp Asp Gln Leu  Ile Ser Asp
    1010                 1015                 1020

Cys Cys  Pro Lys Ser Asp Glu  Lys Leu Gln Lys Ala  Leu Ala Thr
    1025                 1030                 1035

Asn Gln  Lys Ile Ala Leu Ala  Ala Lys His Asn Gln  Glu Tyr Leu
    1040                 1045                 1050

Ala Gln  Leu Ser Pro Asp Glu  Arg Glu Glu Ala Leu  Gln Gly Leu
    1055                 1060                 1065

Lys Lys  Val Ser Phe Trp Thr  Glu Ser Leu Ala Asn  Asn Glu Ala
    1070                 1075                 1080

Pro Pro  Phe Leu Ile Ala Lys  Leu Gly Glu Glu Arg  Gly Lys Pro
    1085                 1090                 1095

Lys Arg  Ala Gly Tyr Leu Lys  Ile Thr Gly Pro Asn  Asn Ala Asn
    1100                 1105                 1110

Ile Ala  Asn Thr Asn Asn Pro  Asp Asp Gly Gly Tyr  Ile Pro Ser
    1115                 1120                 1125

Trp Lys  Asp Gln Phe Asp Tyr  Ser Phe Arg Leu Leu  Gly Pro Pro
    1130                 1135                 1140

Arg Cys  Leu Pro Asn Thr Lys  Gly Asn Arg Glu Tyr  Pro Arg Pro
    1145                 1150                 1155

Gly Phe  Thr Cys Val Ile Asp  Gly Lys Glu Tyr Ser  Leu Thr Lys
    1160                 1165                 1170

Arg Cys  Glu Arg Ile Phe Glu  Asp Ile Ser Gly Gly  Glu Asn Gln
    1175                 1180                 1185

Val Val  Arg Ala Val Thr Glu  Arg Val Arg Glu Gln  Tyr Arg Glu
    1190                 1195                 1200

Ile Leu  Ala Ser Tyr Arg Ala  Asn Ala Ala Gly Ile  Ala Glu Gly
    1205                 1210                 1215

Phe Arg  Thr Arg Met Tyr Asp  Thr Glu Glu Leu Arg  Glu Asn Asp
    1220                 1225                 1230

Leu Val  Tyr Phe Lys Thr Ala  Lys Gln Ala Asp Gly  Lys Glu Arg
    1235                 1240                 1245

Val Val  Ala Ile Ser Pro Val  Cys Ile Ser Arg Glu  Ala Asp Asp
    1250                 1255                 1260

Arg Pro  Leu Gly Lys Arg Leu  Pro Ala Gly Phe Gln  Pro Cys Ser
    1265                 1270                 1275

His Val  Cys Leu Glu Asp Cys  Asn Thr Cys Ser Ala  Lys Asn Cys
    1280                 1285                 1290

Pro Val  Pro Leu Tyr Arg Glu  Gly Trp Pro Val Asn  Gly Leu Cys
    1295                 1300                 1305

Pro Ala  Cys Arg Leu Phe Gly  Ala Gln Met Tyr Lys  Gly Arg Val
    1310                 1315                 1320

Asn Phe  Gly Phe Ala Arg Leu  Pro Asp Asp Lys Gln  Pro Glu Thr
    1325                 1330                 1335

Lys Thr  Leu Thr Leu Pro Leu  Leu Glu Arg Pro Arg  Pro Thr Trp
    1340                 1345                 1350
```

```
Val Leu  Pro Lys Ser Val Lys  Gly Ser Asn Thr Glu  Asp Ala Thr
    1355                 1360                 1365

Ile Pro  Gly Arg Lys Phe Tyr  Leu Arg His Asp Gly  Trp Arg Ile
    1370                 1375                 1380

Val Met  Ala Gly Thr Asn Pro  Ile Thr Gly Glu Ser  Ile Glu Lys
    1385                 1390                 1395

Thr Ala  Asn Asn Ala Thr Val  Glu Ala Ile Met Pro  Gly Ala Thr
    1400                 1405                 1410

Phe Thr  Phe Asp Ile Val Cys  Glu Asn Leu Asp Gln  Gln Glu Leu
    1415                 1420                 1425

Gly Leu  Leu Leu Tyr Ser Leu  Glu Leu Glu Glu Gly  Met Ser His
    1430                 1435                 1440

Thr Leu  Gly Arg Gly Lys Pro  Leu Gly Phe Gly Asn  Val Arg Ile
    1445                 1450                 1455

Lys Val  Glu Lys Ile Glu Lys  Arg Leu Ser Asp Gly  Ser Arg Arg
    1460                 1465                 1470

Glu Met  Ile Pro Pro Lys Gly  Ala Gly Leu Phe Met  Thr Asp Lys
    1475                 1480                 1485

Val Gln  Asp Ala Leu Arg Gly  Leu Thr Glu Gly Gly  Asp Trp His
    1490                 1495                 1500

Gln Arg  Pro His Ile Ser Gly  Leu Arg Arg Leu Leu  Thr Arg Tyr
    1505                 1510                 1515

Pro Glu  Ile Lys Ala Arg Tyr  Pro Lys Leu Ser Gln  Gly Glu Asp
    1520                 1525                 1530

Lys Glu  Pro Gly Tyr Ile Glu  Leu Lys Ser Gln Lys  Asp Glu Asn
    1535                 1540                 1545

Gly Val  Pro Ile Tyr Asn Pro  Asn Arg Glu Leu Arg  Val Ser Glu
    1550                 1555                 1560

Asn Gly  Pro Leu Pro Trp Phe  Leu Leu Ala Lys Lys
    1565                 1570                 1575


<210> SEQ ID NO 18
<211> LENGTH: 1801
<212> TYPE: PRT
<213> ORGANISM: Unknown
<220> FEATURE:
<221> NAME/KEY: source
<223> OTHER INFORMATION: /note="Description of Unknown:
      Dolphin oral metagenome sequence"

<400> SEQUENCE: 18

Met Ile Pro Asp Leu Arg Ser Leu Val Val His Ile Ser Phe Leu Thr
1               5                   10                  15

Pro Tyr Arg Gln Ala Pro Trp Phe Pro Pro Glu Lys Arg Arg Asn Asn
            20                  25                  30

Asn Arg Asp Trp Leu Arg Met Gln Ser Tyr Ala Arg Trp His Lys Val
        35                  40                  45

Ala Pro Glu Glu Gly His Pro Phe Ile Thr Gly Thr Leu Leu Arg Ser
    50                  55                  60

Arg Val Ile Arg Ala Val Glu Glu Glu Leu Cys Leu Ala Asn Gly Ile
65                  70                  75                  80

Trp Arg Gly Val Ala Cys Cys Pro Gly Glu Phe Asn Ser Gln Ala Lys
                85                  90                  95

Lys Lys Pro Lys His Leu Arg Arg Arg Thr Thr Leu Gln Trp Tyr Pro
            100                 105                 110
```

```
Glu Gly Ala Lys Ser Cys Ser Lys Gln Asp Gly Arg Glu Asn Ala Cys
        115                 120                 125

Pro Phe Cys Leu Leu Leu Asp Arg Phe Gly Gly Glu Lys Ser Glu Glu
    130                 135                 140

Gly Arg Lys Lys Asn Asn Asp Tyr Asp Val His Phe Ser Asn Leu Asn
145                 150                 155                 160

Pro Phe Tyr Pro Gly Ser Ser Pro Lys Val Trp Ser Gly Pro Glu Glu
                165                 170                 175

Ile Gly Arg Leu Arg Thr Leu Asn Arg Ile Asp Arg Leu Thr Thr Lys
            180                 185                 190

Ala Gln Asp Phe Phe Arg Ile Tyr Glu Val Asp Gln Val Arg Asp Phe
        195                 200                 205

Phe Gly Thr Ile Thr Leu Ala Gly Asp Leu Pro Arg Lys Val Asp Val
    210                 215                 220

Glu Phe Leu Leu Arg Arg Gly Leu Gly Phe Val Ser Thr Leu Cys Gly
225                 230                 235                 240

Ala Gln Cys Glu Ile Lys Val Val Asp Leu Lys Lys Lys Gln Asn Asn
                245                 250                 255

Lys Glu Asp Ser Ile Leu Pro Val Ser Glu Val Pro Phe Phe Leu Glu
            260                 265                 270

Pro Glu Val Leu Ala Lys Met Cys Gln Asp Val Phe Pro Ser Gly Lys
        275                 280                 285

Leu Arg Met Leu Ala Asp Val Ile Leu Arg Leu Arg Glu Glu Gly Pro
    290                 295                 300

Asp Asn Leu Thr Leu Pro Met Gly Ser Gln Gly Leu Gly Gly Arg Leu
305                 310                 315                 320

Pro His His Leu Trp Asp Val Pro Leu Val Ser Lys Asp Arg Glu Thr
                325                 330                 335

Gln Thr Leu Arg Ser Cys Leu Glu Lys Ile Ala Ala Gln Cys Lys Ser
            340                 345                 350

Glu Gln Thr Gln Phe Arg Leu Phe Cys Gln Lys Leu Gly Ser Ser Leu
        355                 360                 365

Phe Arg Ile Asn Lys Gly Val Tyr Leu Ala Pro Asn Ser Lys Ile Ser
    370                 375                 380

Pro Glu Pro Cys Leu Asp Pro Ser Lys Thr Ile Arg Thr Lys Gly Pro
385                 390                 395                 400

Val Pro Gly Lys Gln Lys His Arg Phe Ser Leu Leu Pro Pro Phe Glu
                405                 410                 415

Trp Ile Ile Thr Gly Thr Leu Lys Ala Gln Thr Pro Phe Phe Ile Pro
            420                 425                 430

Asp Glu Gln Gly Ser His Asp His Thr Ser Arg Lys Ile Leu Leu Thr
        435                 440                 445

Arg Asp Phe Tyr Tyr Arg Leu Pro Arg Ser Leu Leu Arg Gly Ile Ile
    450                 455                 460

Arg Arg Asp Leu His Glu Ala Thr Asp Lys Gly Gly Cys Arg Val Glu
465                 470                 475                 480

Leu Ala Pro Asp Val Pro Cys Thr Cys Gln Val Cys Arg Leu Leu Gly
                485                 490                 495

Arg Met Leu Leu Ala Asp Thr Thr Ser Thr Thr Lys Val Ala Pro Asp
            500                 505                 510

Met Arg His Arg Val Gly Val Asp Arg Ser Cys Gly Ile Val Arg Asp
        515                 520                 525

Gly Ala Leu Phe Asp Thr Glu Tyr Gly Ile Glu Gly Val Cys Phe Pro
```

```
    530                 535                 540

Leu Glu Ile Arg Tyr Arg Gly Asn Lys Asp Leu Glu Gly Pro Ile Arg
545                 550                 555                 560

Gln Leu Leu Ser Trp Trp Gln Gln Gly Leu Leu Phe Leu Gly Gly Asp
                565                 570                 575

Phe Gly Ile Gly Lys Gly Arg Phe Arg Leu Glu Asn Met Lys Ile His
            580                 585                 590

Arg Trp Asp Leu Arg Asp Glu Ser Ala Arg Ala Asp Tyr Val Gln Lys
        595                 600                 605

Cys Gly Leu Arg Arg Gly Val Gly Asp Asp Thr Ala Ile Asn Leu Glu
    610                 615                 620

Lys Asp Leu Ser Leu Asn Leu Pro Glu Ser Gly Tyr Pro Trp Lys Lys
625                 630                 635                 640

His Ala Trp Lys Leu Ser Phe Gln Val Pro Leu Leu Thr Ala Asp Pro
                645                 650                 655

Ile Met Ala Gln Thr Arg His Glu Glu Asp Ser Val Tyr Phe Gln Lys
            660                 665                 670

Arg Ile Phe Thr Ser Asp Gly Arg Val Val Leu Val Pro Ala Leu Arg
        675                 680                 685

Gly Glu Gly Leu Arg Gly Leu Leu Arg Thr Ala Val Ser Arg Ala Tyr
    690                 695                 700

Gly Ile Ser Leu Ile Asn Asp Glu His Glu Asp Cys Asp Cys Pro Leu
705                 710                 715                 720

Cys Lys Ile Phe Gly Asn Glu His His Ala Gly Met Leu Arg Phe Asp
                725                 730                 735

Asp Met Val Pro Val Gly Thr Trp Asn Asp Lys Lys Ile Asp His Val
            740                 745                 750

Ser Cys Ser Arg Phe Asp Ala Ser Val Val Asn Lys Phe Asp Asp Arg
        755                 760                 765

Ser Leu Val Gly Ser Pro Asp Ser Pro Leu His Phe Glu Gly Thr Phe
    770                 775                 780

Trp Leu His Arg Asp Phe Gln Asn Asp Val Glu Ile Lys Thr Ala Leu
785                 790                 795                 800

Gln Asp Phe Ala Asp Gly Leu Tyr Ser Ile Gly Gly Lys Gly Gly Ile
                805                 810                 815

Gly Tyr Gly Trp Leu Phe Asp Met Glu Ile Pro Arg Ser Leu Arg Lys
            820                 825                 830

Leu Asn Ser Gly Phe Arg Glu Ala Ser Ser Ile Gln Asp Ala Leu Leu
        835                 840                 845

Asp Ser Ala Lys Glu Ile Pro Leu Ser Ala Pro Leu Thr Phe Thr Pro
    850                 855                 860

Val Lys Gly Ala Val Tyr Asn Pro Tyr Tyr Tyr Leu Pro Phe Pro Ala
865                 870                 875                 880

Glu Lys Pro Glu Arg Cys Leu Val Pro Pro Ser His Ala Arg Leu Gln
                885                 890                 895

Ser Asp Arg Tyr Thr Gly Cys Leu Thr Cys Glu Leu Glu Thr Val Ser
            900                 905                 910

Pro Leu Leu Leu Pro Asp Thr Cys Arg Glu Lys Asp Gly Asn Tyr Lys
        915                 920                 925

Glu Tyr Pro Ser Phe Arg Leu Asn Asn Thr Pro Met Ile Pro Gly Ala
    930                 935                 940

Gly Leu Arg Ala Ala Val Ser Gln Val Tyr Glu Val Leu Thr Asn Ser
945                 950                 955                 960
```

```
Cys Ile Arg Ile Met Asp Gln Gly Gln Thr Leu Ser Trp Arg Met Ser
                965                 970                 975

Thr Ser Glu His Lys Asp Tyr Gln Pro Gly Lys Ile Thr Asp Asn Gly
            980                 985                 990

Arg Lys Ile Gln Pro Met Gly Lys  Gln Ala Ile Arg Leu  Pro Leu Tyr
        995                 1000                1005

Asp Glu  Val Ile His His Val  Ser Thr Pro Gly Asp  Thr Asp Asp
    1010                1015                1020

Leu Glu  Lys Leu Lys Ala Ile  Val Leu Glu Leu Thr  Arg Pro Trp
    1025                1030                1035

Lys Glu  Leu Pro Glu Glu Gln  Lys Lys Lys Arg Phe  Glu Lys Cys
    1040                1045                1050

Lys Asn  Ile Leu Asp Gly Arg  Met Leu Gln Gln Lys  Glu Leu Arg
    1055                1060                1065

Ala Leu  Glu Asn Ser Gly Phe  Ala Tyr Trp Arg Asp  Lys Thr Ser
    1070                1075                1080

Leu Thr  Phe Asp Ser Phe Leu  Lys Asp Ala Ile Glu  Gln Glu Tyr
    1085                1090                1095

Pro Arg  Tyr Ser Gly Asp Tyr  Gln Arg Ile Lys Ala  Leu Val Val
    1100                1105                1110

Asn Ile  Thr Leu Pro Trp Lys  Leu Leu Lys Lys Glu  Glu Arg His
    1115                1120                1125

Lys Arg  Phe Asp Lys Cys Arg  Arg Ile Leu Lys Gly  Gln Gln Pro
    1130                1135                1140

Leu Thr  Lys Asp Glu Arg Lys  Ala Leu Glu Glu Ser  Gly Phe Ala
    1145                1150                1155

Asn Trp  His Gly Arg Glu Leu  Leu Phe Asp Arg Phe  Leu Lys Asp
    1160                1165                1170

Glu Asn  Ser Cys Leu Ile Lys  Ala Glu Thr Thr Asp  Arg Val Ile
    1175                1180                1185

Ala Ser  Val Ala Lys Asn Asn  Arg Asp Tyr Leu Phe  Glu Ile Lys
    1190                1195                1200

Gln Gln  Asp Phe Ala Arg Tyr  Lys Arg Ile Ile Gln  Gly Leu Glu
    1205                1210                1215

Arg Val  Pro Phe Ser Leu Arg  Ser Leu Ala Lys Ser  Lys Glu Thr
    1220                1225                1230

Ser Phe  Gln Ile Ala Cys Leu  Gly Leu Arg Arg Gly  Arg Phe Leu
    1235                1240                1245

Arg Lys  Gly Tyr Leu Lys Ile  Ser Gly Pro Asn Asn  Ala Asn Val
    1250                1255                1260

Glu Ile  Ser Gly Gly Ser His  Ser Asn Ser Gly Tyr  Ser Asp Ile
    1265                1270                1275

Trp Asp  Asp Pro Leu Asp Phe  Ser Phe Arg Leu Ser  Gly Lys Ser
    1280                1285                1290

Glu Leu  Arg Pro Asn Thr Gln  Lys Thr Arg Glu Tyr  Pro Arg Pro
    1295                1300                1305

Ser Phe  Thr Cys Thr Val Asp  Gly Lys Gln Tyr Thr  Val Asn Lys
    1310                1315                1320

Arg Cys  Glu Arg Val Phe Glu  Asp Ser Ala Ala Pro  Ala Ile Glu
    1325                1330                1335

Leu Pro  Arg Met Val Arg Glu  Gly Tyr Lys Gly Ile  Leu Thr Asp
    1340                1345                1350
```

-continued

```
Tyr Glu  Gln Asn Ala Lys His  Ile Pro Gln Gly Phe  Gln Thr Arg
    1355                 1360                 1365

Phe Ser  Ser Tyr Arg Glu Leu  Asn Asp Gly Asp Leu  Val Tyr Tyr
    1370                 1375                 1380

Lys Thr  Asp Ser Gln Gly Arg  Val Thr Asp Leu Ala  Pro Val Cys
    1385                 1390                 1395

Leu Ser  Arg Leu Ala Asp Asp  Arg Pro Leu Gly Lys  Arg Leu Pro
    1400                 1405                 1410

Glu Glu  Tyr Arg Pro Cys Ala  His Val Cys Leu Glu  Glu Cys Asp
    1415                 1420                 1425

Pro Cys  Thr Gly Lys Asp Cys  Pro Val Pro Ile Tyr  Arg Glu Gly
    1430                 1435                 1440

Tyr Pro  Ala Arg Gly Phe Cys  Pro Ala Cys Gln Leu  Phe Gly Thr
    1445                 1450                 1455

Gln Met  Tyr Lys Gly Arg Val  Arg Phe Ser Phe Gly  Val Pro Val
    1460                 1465                 1470

Asn Ser  Thr Arg Ser Pro Gln  Leu Lys Tyr Val Thr  Leu Pro Ser
    1475                 1480                 1485

Gln Glu  Arg Pro Arg Pro Thr  Trp Val Leu Pro Glu  Ser Cys Lys
    1490                 1495                 1500

Gly Lys  Glu Lys Asp Val Pro  Gly Arg Lys Phe Tyr  Leu Arg His
    1505                 1510                 1515

Asp Gly  Trp Arg Glu Met Trp  Gly Asp Asp Asp Lys  Pro Asp Ser
    1520                 1525                 1530

Arg Pro  Ser Ser Glu Glu Cys  Gln Asp Ile Ile Glu  Gly Ile Gly
    1535                 1540                 1545

Pro Gly  Glu Lys Phe His Phe  Arg Val Ala Phe Glu  Asn Leu Asp
    1550                 1555                 1560

Lys Asn  Glu Leu Gly Arg Leu  Leu Tyr Ser Leu Glu  Leu Asp Ala
    1565                 1570                 1575

Gly Met  Asn His His Leu Gly  Arg Gly Lys Ala Phe  Gly Phe Gly
    1580                 1585                 1590

Gln Val  Lys Ile Arg Val Thr  Lys Leu Glu Arg Arg  Leu Glu Pro
    1595                 1600                 1605

Gly Gln  Trp Arg Ser Glu Lys  Ile Cys Thr Asp Leu  Pro Val Thr
    1610                 1615                 1620

Ser Ser  Glu Leu Val Ile Ser  Ser Leu Lys Lys Val  Glu Glu Arg
    1625                 1630                 1635

Arg Lys  Leu Leu Arg Leu Val  Met Thr Pro Tyr Lys  Gly Leu Thr
    1640                 1645                 1650

Ala Cys  Tyr Pro Gly Leu Glu  Arg Glu Asn Gly Arg  Pro Gly Tyr
    1655                 1660                 1665

Thr Asp  Leu Lys Met Leu Ala  Thr Tyr Asp Pro Tyr  Arg Glu Leu
    1670                 1675                 1680

Val Val  Gln Ile Gly Ser Asn  Gln Pro Leu Arg Pro  Trp Tyr Glu
    1685                 1690                 1695

Pro Gly  Lys Ser Phe Lys Pro  Ser Pro Gly Asn Asp  Cys Thr Gly
    1700                 1705                 1710

Arg Gly  Gly Ser Val Ser Lys  Ser Leu Ile Ser Glu  Pro Lys Val
    1715                 1720                 1725

Val Pro  Ala Ile Ala Pro Phe  Cys Glu Gly Val Val  Lys Trp Phe
    1730                 1735                 1740

Asn Ser  Val Lys Gly Phe Gly  Phe Ile Glu Thr Lys  Glu Gln Arg
```

```
    1745                1750                1755

Asp Ile  Phe Val His Phe Ser  Ala Ile Arg Gly Glu  Gly Tyr Lys
    1760                1765                1770

Ile Leu  Glu Pro Gly Glu Lys  Val Arg Phe Glu Ile  Gly Glu Gly
    1775                1780                1785

Arg Lys  Gly Pro Gln Ala Ile  Asn Val Ile Arg Ile  Arg
    1790                1795                1800


<210> SEQ ID NO 19
<211> LENGTH: 1652
<212> TYPE: PRT
<213> ORGANISM: Unknown
<220> FEATURE:
<221> NAME/KEY: source
<223> OTHER INFORMATION: /note="Description of Unknown:
      Aquatic-marine-hydrothermal vent microbial mat sequence"

<400> SEQUENCE: 19

Met Ile Ile Asn Ile Thr Val Lys Phe Leu Gly Pro Phe Arg Met Leu
1               5                   10                  15

Glu Trp Thr Asp Pro Asp Asn Arg Asn Arg Lys Asn Arg Glu Phe Met
            20                  25                  30

Arg Gly Gln Ala Phe Ala Arg Trp His Asn Ser Asn Pro Gln Lys Gly
        35                  40                  45

Ser Gln Pro Tyr Ile Thr Gly Thr Leu Val Arg Ser Ala Val Ile Arg
    50                  55                  60

Ser Ala Glu Asn Leu Leu Met Leu Ser Glu Gly Lys Val Gly Lys Glu
65                  70                  75                  80

Lys Cys Cys Pro Gly Glu Phe Arg Thr Glu Asn Arg Lys Lys Arg Asp
                85                  90                  95

Ala Met Leu His Leu Arg Gln Arg Ser Thr Leu Gln Trp Lys Thr Asp
            100                 105                 110

Lys Pro Leu Cys Asn Gly Lys Ser Leu Cys Pro Ile Cys Glu Leu Leu
        115                 120                 125

Gly Arg Arg Ile Gly Lys Thr Asp Glu Val Lys Lys Lys Gly Asp Phe
    130                 135                 140

Arg Ile His Phe Gly Asn Leu Thr Pro Leu Asn Arg Tyr Asp Asp Pro
145                 150                 155                 160

Ser Asp Ile Gly Thr Gln Arg Thr Leu Asn Arg Val Asp Tyr Ala Thr
                165                 170                 175

Gly Lys Ala His Asp Phe Phe Lys Val Trp Glu Ile Asp His Ser Leu
            180                 185                 190

Leu Ser Val Phe Gln Gly Lys Ile Ser Ile Ala Asp Asn Ile Gly Asp
        195                 200                 205

Gly Ala Thr Lys Leu Leu Glu Asp Ser Leu Arg Phe Thr Asp Arg Leu
    210                 215                 220

Cys Gly Ala Ile Cys Val Ile Ser Tyr Asp Cys Ile Glu Asn Ser Asp
225                 230                 235                 240

Gly Lys Glu Asn Gly Lys Thr Gly Glu Ala Ala His Ile Met Gly Glu
                245                 250                 255

Ser Asp Ala Gly Lys Thr Asp Ala Glu Asn Ile Ala Asn Ala Ile Ala
            260                 265                 270

Asp Met Met Gly Thr Ala Gly Glu Pro Glu Lys Leu Arg Ile Leu Ala
        275                 280                 285

Asp Ala Val Arg Ala Leu Arg Ile Gly Lys Asn Thr Val Ser Gln Leu
    290                 295                 300
```

```
Pro Leu Asp His Glu Gly Lys Glu Asn His His Leu Trp Asp Ile Gly
305                 310                 315                 320

Glu Gly Lys Ser Ile Arg Glu Leu Leu Leu Glu Lys Ala Glu Ser Leu
                325                 330                 335

Pro Ser Asp Gln Trp Arg Lys Phe Cys Glu Asp Val Gly Glu Ile Leu
            340                 345                 350

Tyr Leu Lys Ser Lys Asp Pro Thr Gly Gly Leu Thr Val Ser Gln Arg
        355                 360                 365

Ile Leu Gly Asp Glu Ala Phe Trp Ser Lys Ala Asp Arg Gln Leu Asn
    370                 375                 380

Pro Ser Ala Val Ser Ile Pro Val Thr Thr Glu Thr Leu Ile Cys Gly
385                 390                 395                 400

Lys Leu Ile Ser Glu Thr Pro Phe Phe Phe Gly Thr Glu Ile Glu Asp
                405                 410                 415

Ala Lys His Thr Asn Leu Lys Val Leu Leu Asp Arg Gln Asn Arg Tyr
            420                 425                 430

Arg Leu Pro Arg Ser Ala Ile Arg Gly Val Leu Arg Arg Asp Leu Arg
        435                 440                 445

Thr Ala Phe Gly Gly Lys Gly Cys Asn Val Glu Leu Gly Gly Arg Pro
    450                 455                 460

Cys Leu Cys Asp Val Cys Arg Ile Met Arg Gly Ile Thr Ile Met Asp
465                 470                 475                 480

Ala Arg Ser Glu Tyr Ala Glu Pro Pro Glu Ile Arg His Arg Ile Arg
                485                 490                 495

Leu Asn Pro Tyr Thr Gly Thr Val Ala Glu Gly Ala Leu Phe Asp Met
            500                 505                 510

Glu Leu Gly Pro Gln Gly Leu Ser Phe Asp Phe Ile Leu Arg Tyr Arg
        515                 520                 525

Gly Lys Gly Lys Ser Ile Pro Lys Ala Leu Arg Asn Val Leu Lys Trp
    530                 535                 540

Trp Thr Lys Gly Gln Ala Phe Leu Ser Gly Ala Ala Ser Thr Gly Lys
545                 550                 555                 560

Gly Ile Phe Arg Leu Asp Asp Leu Lys Tyr Ile Ser Phe Asp Leu Ser
                565                 570                 575

Asp Lys Asp Lys Arg Lys Asp Tyr Leu Asp Asn Tyr Gly Trp Arg Asn
            580                 585                 590

Arg Ile Glu Ala Leu Ser Leu Glu Lys Met Pro Leu Asp Arg Met Asn
        595                 600                 605

Asp Tyr Ala Glu Pro Leu Trp Gln Lys Val Ser Val Glu Ile Glu Ile
    610                 615                 620

Gly Ser Pro Phe Leu Asn Gly Asp Pro Ile Arg Ala Leu Ile Glu Lys
625                 630                 635                 640

Asp Gly Ser Asp Ile Val Ser Phe Arg Lys Tyr Ala Asp Asp Ser Gly
                645                 650                 655

Lys Glu Val Tyr Ala Tyr Lys Ala Glu Ser Phe Arg Gly Val Val Arg
            660                 665                 670

Ala Ala Leu Ala Arg Gln His Phe Asp Lys Glu Gly Lys Pro Leu Asp
        675                 680                 685

Lys Glu Gly Lys Pro Leu Leu Thr Leu Ile His Gln Asp Cys Glu Cys
    690                 695                 700

Leu Ile Cys Arg Leu Phe Gly Ser Glu His Glu Thr Gly Arg Leu Arg
705                 710                 715                 720
```

```
Phe Glu Asp Leu Leu Phe Asp Pro Gln Pro Glu Pro Met Ile Phe Asp
                725                 730                 735

His Val Ala Ile Asp Arg Phe Thr Gly Gly Ala Val Asp Lys Lys Lys
            740                 745                 750

Phe Asp Asp Cys Ser Leu Pro Gly Thr Pro Gly His Pro Leu Thr Leu
        755                 760                 765

Lys Gly Cys Phe Trp Ile Arg Lys Glu Leu Glu Lys Pro Asp Glu Asp
    770                 775                 780

Lys Ser Glu Arg Glu Ala Leu Ser Lys Ala Leu Ala Asp Ile His Asn
785                 790                 795                 800

Gly Leu Tyr Pro Leu Gly Gly Lys Gly Ala Ile Gly Tyr Gly Gln Val
                805                 810                 815

Met Asn Leu Lys Ile Lys Gly Ala Gly Asp Val Ile Lys Ala Ala Leu
            820                 825                 830

Gln Ser Glu Ser Ser Arg Met Ser Ala Ser Glu Pro Glu His Lys Lys
        835                 840                 845

Pro Asp Ser Gly Leu Lys Leu Ser Phe Asp Asp Lys Lys Ala Val Tyr
    850                 855                 860

Tyr Pro His Tyr Phe Leu Lys Pro Ala Ala Glu Glu Val Asn Arg Lys
865                 870                 875                 880

Pro Ile Pro Thr Gly His Glu Thr Leu Asn Ser Gly Leu Leu Thr Gly
                885                 890                 895

Lys Ile Arg Cys Arg Leu Thr Thr Arg Thr Pro Leu Ile Val Pro Asp
            900                 905                 910

Thr Ser Asn Asp Asp Phe Phe Gln Thr Gly Val Glu Gly His Glu Ser
        915                 920                 925

Tyr Ala Phe Phe Ser Val Asn Gly Asp Ile Met Leu Pro Gly Ser Glu
    930                 935                 940

Ile Arg Gly Met Leu Ser Ser Val Tyr Glu Ala Leu Thr Asn Ser Cys
945                 950                 955                 960

Phe Arg Val Phe Asp Glu Gly Tyr Arg Leu Ser Trp Arg Met Glu Ala
                965                 970                 975

Asp Arg Asn Val Leu Met Gln Phe Lys Pro Gly Arg Val Thr Asp Asn
            980                 985                 990

Gly Leu Arg Ile Glu Glu Met Lys  Glu Tyr Arg Tyr Pro  Phe Tyr Asp
        995                 1000                1005

Arg Asp  Cys Ser Asp Lys Lys  Ser Gln Glu Ala Tyr  Phe Asp Glu
    1010                1015                1020

Trp Glu  Arg Ser Ile Thr Leu  Thr Asp Asp Ser Leu  Glu Lys Met
    1025                1030                1035

Ala Glu  Arg Lys Gly Asp Ile  Ser Pro Lys Asp Leu  Lys Val Leu
    1040                1045                1050

Lys Ser  Leu Lys Gly Lys Asn  Tyr Lys Ser Thr Glu  Gly Leu Leu
    1055                1060                1065

Ala Ala  Phe Lys Asp Lys Gly  Gly Asp Thr Gly Gly  Asn Ile Leu
    1070                1075                1080

Gly Leu  Ile Phe Lys Tyr Ala  Glu Arg Ile Gly Asp  Val Pro Arg
    1085                1090                1095

Tyr Glu  His Pro Thr Asp Thr  Asp Arg Met Met Leu  Ser Leu Ser
    1100                1105                1110

Glu Tyr  Asn Arg Asn Gln Lys  Ser Asp Gly Lys Arg  Ala Tyr Lys
    1115                1120                1125

Ile Ile  Lys Pro Ala Ser Lys  Leu Gly Lys Gly Ala  Tyr Phe Met
```

```
    1130                1135                1140

Phe Ala  Gly Thr Ser Val Glu  Asn Lys Arg Ile Cys  Asn Pro Ala
    1145                1150                1155

Cys Thr  Asp Lys Ala Asn Lys  Ser Val Lys Gly Tyr  Leu Lys Ile
    1160                1165                1170

Ser Gly  Pro Asn Lys Leu Glu  Lys Tyr Asn Ile Ser  Glu Pro Glu
    1175                1180                1185

Leu Asp  Gly Val Pro Glu Asp  Arg Asn Cys Gln Ile  Ile His Asn
    1190                1195                1200

Arg Ile  Tyr Leu Arg Lys Ile  Phe Val Ala Asn Ala  Lys Lys Arg
    1205                1210                1215

Lys Glu  Arg Asp Arg Leu Val  Gly Glu Phe Ala Cys  Tyr Asp Pro
    1220                1225                1230

Glu Lys  Lys Val Thr Tyr Ser  Met Thr Lys Arg Cys  Glu Arg Ile
    1235                1240                1245

Phe Ile  Lys Asp Arg Gly Arg  Thr Leu Pro Ile Thr  His Glu Ala
    1250                1255                1260

Ser Glu  Leu Phe Glu Ile Leu  Val Gln Glu Tyr Arg  Glu Asn Ala
    1265                1270                1275

Lys Arg  Gln Asp Thr Pro Glu  Val Phe Gln Thr Leu  Leu Pro Asp
    1280                1285                1290

Asn Gly  Arg Leu Asn Pro Gly  Asp Leu Val Tyr Phe  Arg Glu Glu
    1295                1300                1305

Lys Gly  Lys Thr Val Glu Ile  Ile Pro Val Arg Ile  Ser Arg Lys
    1310                1315                1320

Ile Asp  Asp Ser Pro Ile Gly  Lys Arg Leu Arg Glu  Asp Leu Arg
    1325                1330                1335

Pro Cys  His Gly Glu Trp Ile  Glu Gly Asp Asp Leu  Ser Gln Leu
    1340                1345                1350

Ser Glu  Tyr Pro Glu Lys Lys  Leu Phe Thr Arg Asn  Thr Glu Gly
    1355                1360                1365

Leu Cys  Pro Ala Cys Arg Leu  Phe Gly Thr Gly Ala  Tyr Lys Gly
    1370                1375                1380

Arg Leu  Arg Phe Gly Phe Ala  Lys Leu Glu Asn Asp  Pro Lys Trp
    1385                1390                1395

Leu Met  Lys Asn Ser Asp Gly  Pro Ser His Gly Gly  Pro Leu Thr
    1400                1405                1410

Leu Pro  Leu Leu Glu Arg Pro  Arg Pro Thr Trp Ser  Met Pro Asp
    1415                1420                1425

Asp Thr  Leu Asn Arg Leu Lys  Lys Asp Gly Lys Gln  Glu Pro Lys
    1430                1435                1440

Lys Gln  Lys Gly Lys Lys Gly  Pro Gln Val Pro Gly  Arg Lys Phe
    1445                1450                1455

Tyr Val  His His Asp Gly Trp  Lys Glu Ile Asn Cys  Gly Cys His
    1460                1465                1470

Pro Thr  Thr Lys Glu Asn Ile  Val Gln Asn Gln Asn  Asn Arg Thr
    1475                1480                1485

Val Glu  Pro Leu Asp Lys Gly  Asn Thr Phe Ser Phe  Glu Ile Cys
    1490                1495                1500

Phe Glu  Asn Leu Glu Pro Tyr  Glu Leu Gly Leu Leu  Leu Tyr Thr
    1505                1510                1515

Leu Glu  Leu Glu Lys Gly Leu  Ala His Lys Leu Gly  Met Ala Lys
    1520                1525                1530
```

```
Pro Met  Gly Phe Gly Ser Ile  Asp Ile Glu Val Glu  Asn Val Ser
    1535                 1540                 1545

Leu Arg  Thr Asp Ser Gly Gln  Trp Lys Asp Ala Asn  Glu Gln Ile
    1550                 1555                 1560

Ser Glu  Trp Thr Asp Lys Gly  Lys Lys Asp Ala Gly  Lys Trp Phe
    1565                 1570                 1575

Lys Thr  Asp Trp Glu Ala Ala  Glu His Ile Lys Asn  Leu Lys Lys
    1580                 1585                 1590

Leu Leu  Phe Leu Pro Gly Glu  Glu Gln Asn Pro Arg  Val Ile Tyr
    1595                 1600                 1605

Pro Ala  Leu Lys Gln Lys Asp  Ile Pro Asn Ser Arg  Leu Pro Gly
    1610                 1615                 1620

Tyr Glu  Glu Leu Lys Lys Asn  Leu Asn Met Glu Lys  Arg Lys Glu
    1625                 1630                 1635

Met Leu  Thr Thr Pro Trp Ala  Pro Trp His Pro Ile  Lys Lys
    1640                 1645                 1650


<210> SEQ ID NO 20
<211> LENGTH: 1806
<212> TYPE: PRT
<213> ORGANISM: Unknown
<220> FEATURE:
<221> NAME/KEY: source
<223> OTHER INFORMATION: /note="Description of Unknown:
      Aquatic-marine-deep subsurface sequence"

<400> SEQUENCE: 20

Met Ser Asp Asn Arg Ile Asp Tyr Asp Ile Lys Leu Thr Phe Phe Glu
1               5                   10                  15

Pro Phe Arg Met Ser Pro Trp Val Lys Ser His Ala Arg Ala Lys Ser
            20                  25                  30

Lys Thr Phe Phe Arg Thr Leu Ser Phe Val Arg Trp Leu Glu Thr Ser
        35                  40                  45

Pro Glu Thr Lys Glu Gly Lys Glu Gly Asp Ser Ile Gly Val Pro Phe
    50                  55                  60

Ile Pro Gly Thr Leu Leu Arg Ser Ala Leu Leu Lys Glu Val Glu Phe
65                  70                  75                  80

Leu Ile Thr Leu Lys Asn Lys Tyr Asp Cys Cys Cys Gly Glu Phe Glu
                85                  90                  95

Thr Pro Arg Gln Lys Arg Asp Glu Lys Lys Glu Gln Gly Arg Arg Phe
            100                 105                 110

Phe Gly Arg Lys Arg Pro Thr Tyr Glu Phe Gly Asn Ser Gln Pro Cys
        115                 120                 125

Thr Asp Phe Glu Asn Ala Cys Pro Phe Cys Ser Ile Leu Ser Arg Ser
    130                 135                 140

Phe Asn Asn Asp Asp Trp Phe Asp Asp Arg Gly Asn Pro Ile Val Gly
145                 150                 155                 160

Lys Val Pro Val His Phe Ser Asn Leu Asp Val Thr Asp Ser Lys Leu
                165                 170                 175

Lys Arg Ile Arg Leu Ser Ala Ile Ala Asn Gln Arg Ile Val Asn Arg
            180                 185                 190

Val Asp Phe Arg Ser Gly Lys Ala Gln Asp Tyr Phe Lys Ile Trp Glu
        195                 200                 205

Val Asp Asn Arg Leu Cys Pro Ser Phe Cys Gly Lys Ile Thr Ile Arg
    210                 215                 220
```

```
Gln Asp Ile Asn Gln Val Asp Asp Leu Thr Cys Leu Leu Ala Ala Gly
225                 230                 235                 240

Leu Ala Lys Ile Lys Thr Leu Ala Gly Ala Leu Cys Arg Val Asp Ile
                245                 250                 255

Ile Arg Asp Lys Thr Ile Asp Phe His Gln Arg Leu Ile Gln Lys Tyr
            260                 265                 270

Val Gly Pro Pro Gly Pro Pro His Asn Pro Thr Ala His Pro Thr Leu
        275                 280                 285

Pro Ser Gln Pro Thr Leu Ser Val Asp Val His Gly Leu Ala Arg Thr
    290                 295                 300

Ile Ala Gly Thr Leu Thr Gly Ser Asp Lys Glu Ala Tyr Leu Arg Arg
305                 310                 315                 320

Ile Ala Asp Ala Val Arg Glu Met Arg Asn Arg Lys Cys Ser Ile Leu
                325                 330                 335

His Glu Pro Pro Phe Thr Lys Thr Gly Asp Lys Glu Pro Val Trp Thr
            340                 345                 350

Ile Pro Ala Val Gln Lys Ala Leu Lys Glu Thr Thr Ala Cys Val Ala
        355                 360                 365

Arg Glu Ser Trp Arg Leu Phe Cys Glu Glu Leu Gly Glu Ala Leu Tyr
    370                 375                 380

Lys Lys Ala Lys Glu Leu Lys Lys Lys Asp Glu Ala Ile Pro Arg Leu
385                 390                 395                 400

Leu Gly Asp Thr Glu Tyr Tyr Gly Gln Gln Ala Glu Ala Pro Val Gly
                405                 410                 415

Thr Asp Tyr Arg Leu Thr Ala Ser Ala Leu Pro Lys Tyr Glu Trp Ile
            420                 425                 430

Ile Asn Gly Trp Leu Glu Ala Arg Thr Pro Phe Phe Phe Gly Val Glu
        435                 440                 445

Ser Ala Ser Glu Gln Thr Ser Leu Ala Ile Leu Leu Thr Arg Asp His
    450                 455                 460

Arg Tyr Arg Leu Pro Arg Ser Val Leu Arg Gly Ala Leu Arg Arg Asp
465                 470                 475                 480

Leu Arg Thr Val Ile Gly Ser Gly Cys Asn Val Glu Leu Gly Val Asp
                485                 490                 495

Thr Pro Cys Asp Cys Asp Val Cys Arg Ile Met Ser Arg Val Ile Val
            500                 505                 510

Met Asp Ser Leu Ser Asp Tyr Gln Glu Pro Pro Asp Ile Arg His Arg
        515                 520                 525

Ile Arg Ile Asn Gln His Ser Gly Thr Val Asp Glu Gly Ala Leu Phe
    530                 535                 540

Asp Met Glu Leu Gly Pro Glu Gly Leu Arg Phe Pro Phe Arg Met Tyr
545                 550                 555                 560

Phe Ser Ala Thr Cys Pro Thr Ala Asp Val Pro Leu Ala Lys Val Leu
                565                 570                 575

Lys Met Trp Gln Asp Arg Pro Ala Phe Leu Gly Gly Asp Ala Gly Thr
            580                 585                 590

Gly Asn Gly Arg Phe Arg Leu Ile Lys Ala Lys Thr Arg Ser Glu Pro
        595                 600                 605

Phe Asp Trp Asp Gly Pro Lys Ser Ser Leu Asn Leu Leu Met Ala Arg
    610                 615                 620

Ser Tyr Ile Asp Leu Glu Asp His Asp Thr Leu Leu Asp Ser Lys Leu
625                 630                 635                 640

Glu Cys Ala Lys Ala Trp Lys Val Lys Asp Glu Leu Thr Ser Val Trp
```

```
                645                 650                 655

Thr Asp Tyr Gln Tyr Glu Ile Asp Leu His Ser Pro Ile Leu Ser Asn
            660                 665                 670

Asp Pro Ile Ala Ala Leu Leu Asp Pro Asp Trp Arg Asp Ala Val Pro
        675                 680                 685

Val Lys Lys Arg Val Leu Gln Asp Gly Gly Leu Val Pro Thr Glu Lys
    690                 695                 700

Tyr Tyr Ile Lys Gly Ser Gly Ile Arg Gly Ile Leu Arg Thr Ala Val
705                 710                 715                 720

Gly Arg Asn Cys Val Asn Glu Asp Gly Ile His Leu His Asn Leu Pro
                725                 730                 735

His Asp Asp Cys Pro Cys Val Leu Cys Gln Leu Phe Gly Ser Glu His
            740                 745                 750

His Gln Gly Met Leu Arg Phe Glu Asp Ala His Phe Glu Asn Asp Pro
        755                 760                 765

Met Pro Glu Thr Leu Asp His Val Ala Ile Asp Arg Phe Thr Gly Arg
    770                 775                 780

Ala Arg Asp Lys Phe Lys Phe Glu Asp Ala Pro Leu Ile Ala Thr Pro
785                 790                 795                 800

Asp Gln Pro Ile Lys Leu Lys Gly Thr Phe Trp Leu Lys Arg Glu Leu
                805                 810                 815

His Glu Ala Ser Gln Glu Val Phe Gly Lys Ile Asp Asp Phe Glu Cys
            820                 825                 830

Lys Pro Lys Glu Asp Ser Asp Ser Leu Leu Gly Ala Ala Arg Ala Leu
        835                 840                 845

Trp Cys Ala Phe Leu Asp Leu Lys His Gly Leu Phe Pro Ile Gly Ser
    850                 855                 860

Asn Gly Gly Ile Gly Tyr Gly Trp Val Ser Gly Leu Ser Val Ser Glu
865                 870                 875                 880

Pro Asp Lys Asn Lys Lys Ile Pro Leu Gly Gln Leu Cys Arg Asn Glu
                885                 890                 895

Gly Ala Gln Glu Thr Ala Ser Thr Ser Gly Glu Lys Gly Glu Tyr Asn
            900                 905                 910

Pro Ser Asp Ala Pro Asn Ser Leu Arg Gln Glu Gly His Val Phe Asn
        915                 920                 925

Pro His Tyr Phe Leu Arg Ser Tyr Arg Tyr Glu Asp Lys Asn Gly Lys
    930                 935                 940

Ile Ala Thr His Val Glu Arg Ile Asp Leu Pro Val Thr His Glu Ala
945                 950                 955                 960

Tyr Gln Asp Lys Leu Thr Gly Lys Ile Thr Cys Lys Leu Asn Thr Arg
                965                 970                 975

Gly Pro Val Phe Val Ala Asp Pro Ser Asp Leu Val Val Tyr Phe Thr
            980                 985                 990

Ala Lys Glu Tyr Glu Asp Phe Val  Lys Arg Trp Pro Lys  Ser Ala Glu
        995                 1000                1005

Leu Leu  Gln Ser Leu Val His  Glu Lys Asp Gly Met  Lys Leu Ile
    1010                1015                1020

Pro Val  Lys Gln Ile Pro Lys  Asp Ser Pro Glu Asp  Gly Ala Leu
    1025                1030                1035

Lys Glu  Ile Ser Glu His Gln  Gly His Lys Gly Tyr  Lys Phe Phe
    1040                1045                1050

Arg Leu  Asn Gly Ser Val Met  Ile Pro Gly Ser Glu  Ile Arg Gly
    1055                1060                1065
```

```
Met Val  Ser Ser Val Tyr Glu  Ala Leu Thr Asn Ser  Cys Phe Arg
    1070                 1075                 1080

Val Phe  Asp Gln Arg Arg Ile  Leu Ser Lys Arg Met  Glu Ala Asp
    1085                 1090                 1095

Phe Arg  Thr Val Leu Thr His  Phe Lys Ala Ala Arg  Val Val Pro
    1100                 1105                 1110

Asp Asn  Asn Ser Gly Ser Gly  Leu Ser Val Lys Glu  Phe Thr Asn
    1115                 1120                 1125

Met Val  Arg Val Pro Val Tyr  Asn Cys Pro Gln Thr  Phe Phe Asp
    1130                 1135                 1140

Gly Leu  Thr Gln Gly Gln Ile  Ser Gly Lys Glu Glu  Thr Lys Leu
    1145                 1150                 1155

Trp Val  Lys Asn Tyr Glu Trp  Arg Ile Ser Leu Cys  Asn Pro Trp
    1160                 1165                 1170

Thr His  His Ser Arg Lys Ser  Lys Lys Glu Trp Glu  Lys Asn Ile
    1175                 1180                 1185

Pro Gly  Arg Ile Leu Asn Asn  Gln Gly Asp Lys Ile  Val Leu Asn
    1190                 1195                 1200

Ile Ser  Tyr Lys Gln Glu Glu  Arg Lys Ile Thr Leu  Ile Leu Asp
    1205                 1210                 1215

Asp Lys  Asp Arg Val Val Leu  Asp Gly Ile Thr Pro  Lys Gln Leu
    1220                 1225                 1230

Gly Gly  Lys Glu Glu Ile Arg  Leu Trp Leu Arg Ile  Ser Gln Tyr
    1235                 1240                 1245

Gln Lys  Ala Phe Arg Lys Lys  Pro Asp Asn Asn Gly  Gly Trp Lys
    1250                 1255                 1260

Met Gln  Thr Gly Tyr Leu His  Ile Met Gly Pro Asn  Lys Val Glu
    1265                 1270                 1275

Ile Asp  Ser Ser Gly Thr Ser  Arg Glu Gly Leu Gln  Asp Leu Pro
    1280                 1285                 1290

Glu Thr  Trp Lys Asp Ala Gln  Cys Asn Ser Pro Asp  Gly Lys Ile
    1295                 1300                 1305

Phe Ser  Gly Lys Asp Gly Asn  Ala Val Tyr Thr Met  Asn Lys Tyr
    1310                 1315                 1320

Cys Glu  Met Phe Phe Tyr Asn  Glu Gln Lys Lys Ser  Tyr Arg Val
    1325                 1330                 1335

Pro Gln  Ala Val Leu Asn Gln  Tyr Arg Gln Met Ile  Glu Glu Ser
    1340                 1345                 1350

Met Ser  Asn Pro Gln Ala Pro  Pro Ala Ile Phe Arg  Ser Lys Pro
    1355                 1360                 1365

Ile Arg  Glu Lys Asp Thr Ala  Leu Lys Ala Gly Asp  Leu Val Tyr
    1370                 1375                 1380

Phe Arg  Lys Asn Glu Asn Arg  Glu Gly Glu Val Asp  Ala Val Ile
    1385                 1390                 1395

Pro Val  Arg Ile Tyr Arg Glu  Ser His Arg Lys Pro  Leu Gly Lys
    1400                 1405                 1410

Arg Phe  Pro Asp Gly Leu His  Asp Leu Arg Pro Cys  Thr Phe Glu
    1415                 1420                 1425

Cys Leu  Asp Asp Cys Asp Lys  Cys Pro Asp Arg Cys  Asn Glu Leu
    1430                 1435                 1440

Lys Glu  Phe Phe Asn Pro His  Pro Lys Gly Leu Cys  Pro Ala Cys
    1445                 1450                 1455
```

```
Arg Leu Phe Gly Thr Thr Ser Tyr Lys Ser Arg Val Ser Phe Gly
    1460                1465                1470

Phe Ala Arg Leu Cys Ser Glu Asp Lys Lys Ala Lys Trp Tyr Gly
    1475                1480                1485

Val Glu Glu Asp Ala Glu Gln Gly Lys Pro Leu Thr Leu Pro Leu
    1490                1495                1500

Leu Glu Arg Pro Arg Pro Thr Trp Ser Met Pro Asp Lys Asp Ala
    1505                1510                1515

Lys Ile Pro Gly Arg Lys Phe Tyr Val His His Pro His Ser Val
    1520                1525                1530

Asp Ser Ser Ile Arg Asp Met Gln Phe Asp Pro Glu Leu Ser Asp
    1535                1540                1545

Lys Glu Asn Gln Gly Lys Ile Arg Pro Asn Lys Asn Asn Arg Thr
    1550                1555                1560

Val Glu Pro Leu Asp Lys Gly Asn Glu Phe Thr Phe Asp Ile Arg
    1565                1570                1575

Phe Met Asn Leu Lys Glu Trp Glu Leu Gly Leu Leu Leu Tyr Ser
    1580                1585                1590

Leu Gln Leu Glu Thr Gly Leu Ala His Lys Leu Gly Met Gly Lys
    1595                1600                1605

Ala Gln Gly Phe Gly Ser Val Glu Ile Asp Val Glu Lys Val Glu
    1610                1615                1620

Ile Arg Asn Gly Pro Gly Asp Trp Lys Ser Lys Thr Ser His Lys
    1625                1630                1635

Ile Thr Glu Trp Ile Thr Lys Gly Lys Asp Lys Leu Glu Lys Trp
    1640                1645                1650

Phe Lys Thr Asp Asp Trp Asn Asn Val Asp His Ile Ala Asp Leu
    1655                1660                1665

Lys Lys Phe Leu Tyr Phe Leu Asp Pro Gln Glu Ile Lys Pro Lys
    1670                1675                1680

Val Arg Tyr Pro Ser Leu Ser Arg Asp Asp Asp Lys Lys Asp His
    1685                1690                1695

Phe Pro Gly Tyr Val Asp Leu Lys Arg Lys Pro Ser Lys Glu Lys
    1700                1705                1710

Pro Asn Pro Tyr Tyr Val Pro Glu Asp Lys Arg Arg Ala Leu Leu
    1715                1720                1725

Thr Arg Pro Trp Glu Pro Trp Tyr Val Met Pro Lys Ser Ser Met
    1730                1735                1740

Gly Thr Val Lys Trp Phe Asn Glu Glu Lys Asn Tyr Gly Phe Ile
    1745                1750                1755

Leu Arg Asp Asn Gly Glu Asp Ile Phe Val His Arg Ser Asp Ile
    1760                1765                1770

Asn Gly Ser Leu Gly Thr Leu Thr Glu Gly Gln Lys Val Ile Phe
    1775                1780                1785

Glu Val Lys Gln Gly Pro Lys Gly Leu Gln Ala Thr Asn Val Lys
    1790                1795                1800

Val Ile Ser
    1805
```

<210> SEQ ID NO 21
<211> LENGTH: 1559
<212> TYPE: PRT
<213> ORGANISM: Unknown
<220> FEATURE:
<221> NAME/KEY: source
<223> OTHER INFORMATION: /note="Description of Unknown:
      Aquatic-freshwater-groundwater sequence"

<400> SEQUENCE: 21

```
Met Glu Tyr Thr Leu Thr Leu Asn Phe Ile Glu Pro Phe Arg Leu Ile
1               5                   10                  15

Glu Trp His Asp Ala Pro Asp Arg Glu Asn Leu Arg Leu Arg Gly Phe
            20                  25                  30

Ser Phe Ala Arg Trp His Lys Asp Arg Glu Phe Gly Leu Gly Arg Pro
        35                  40                  45

Tyr Ile Thr Gly Thr Leu Ile Arg Ser Ala Val Ile Arg Ala Val Glu
    50                  55                  60

Glu Phe Leu Trp Leu Asn Asn Gly Lys Thr Gly Asp Val His Cys Cys
65                  70                  75                  80

Gln Gly Glu Phe Thr Lys Ala Arg Phe Tyr Arg Glu Leu Thr Glu Lys
                85                  90                  95

Arg Leu Arg Arg Arg Gln Thr Leu Val Trp Asp Asn Asn Gly Val Cys
            100                 105                 110

Asn Gln Asp Gln Pro Cys Pro Phe Cys Leu Leu Leu Gly Arg Tyr Trp
        115                 120                 125

Gln Pro Gly Pro Gly Tyr Ser Glu Asn Asn Asp Val Asn Phe Gly Asn
    130                 135                 140

Phe Ser Ile Pro Gln Lys Lys Lys Val Leu Leu Asn Leu Glu Asp Ile
145                 150                 155                 160

Ala Glu Pro Arg Ile Ile Asn Arg Val Asp Gln Gln Ser Gly Lys Ala
                165                 170                 175

Glu Asp Phe Phe Glu Ile Arg Glu Ile Asp His Arg Ser Cys Ala Leu
            180                 185                 190

Phe Glu Gly Lys Ile Ser Leu Ser Glu Arg Ala Ala Glu Asn Lys Ala
        195                 200                 205

Leu Ile Ser Leu Leu Asn Ala Ala Leu Pro Leu Val Asn Arg Ile Ser
    210                 215                 220

Gly Ala Leu Cys Tyr Leu Thr Met Glu Glu Val Lys Val Met Asp Lys
225                 230                 235                 240

Ser Val Asn Gly Gly Ser Asp Asn Leu Ser Gly Glu Ala Met Glu Leu
                245                 250                 255

Lys Lys Ser Asp Arg Pro Gly Glu Gly Ser His Phe Ala Arg His Pro
            260                 265                 270

Ile Gly Ala Glu His Ala Ser Tyr Glu Lys Ile Lys Thr Ser Ala Gly
        275                 280                 285

Glu Val Val Asn Ala Phe Glu Glu Ser Asn Lys Leu Val His Leu Arg
    290                 295                 300

Val Phe Ser Asp Val Ile Arg Glu Leu Arg Arg His Asp Pro Arg Lys
305                 310                 315                 320

Leu Asn Leu Pro Gly Gly His Glu Asp Arg Ser Gly Lys Ile Thr Asp
                325                 330                 335

His Phe Leu Trp Asp Met Lys Val Glu Ser Lys Pro Leu Arg Asn Trp
            340                 345                 350

Leu Pro Asp Lys Phe Asn Glu Phe Asn Glu Lys His Lys Leu Pro Trp
        355                 360                 365

Arg Ile Phe Cys Glu Ser Leu Gly Gln Ala Leu Phe Leu Glu Ala Lys
    370                 375                 380

Asp Lys Ala Pro Glu Gln Phe Thr Ser Ala Arg Pro Leu Gly Ala Met
385                 390                 395                 400
```

```
Val Ser Thr Leu Glu Ser Lys Glu Pro Glu Phe Leu Pro Gly Arg Ser
                405                 410                 415

Arg Gln Gly Pro Arg Tyr Glu Trp Leu Met Arg Gly Gln Leu Val Ala
            420                 425                 430

Glu Val Pro Phe Phe Phe Gly Trp Ser Val Asp Lys Asn Asp Thr Asp
        435                 440                 445

His Ile Ser Met Arg Leu Leu Ser Ala Arg Asp Gly Arg Leu Arg Leu
    450                 455                 460

Pro Arg Ser Ala Leu Arg Gly Ile Leu Arg Arg Asp Leu Asn Leu Ala
465                 470                 475                 480

Phe Gly Thr Asn Gly Cys Arg Ala Lys Leu Gly Leu Arg Arg Pro Cys
                485                 490                 495

Pro Cys Pro Val Cys Asn Leu Leu Lys Asn Ile Thr Ile Arg Asp Ser
            500                 505                 510

Leu Ser Asp Tyr Lys Arg Pro Pro Gln Ile Arg His Arg Ile Arg Leu
        515                 520                 525

Asp His Arg Ser Gly Thr Val Ala Lys Gly Ala Leu Phe Asp Met Glu
    530                 535                 540

Val Gly Pro Thr Gly Ala Ile Phe Pro Phe Glu Leu Arg Leu Arg Ser
545                 550                 555                 560

Thr Ser Asp Lys Phe Ser Lys Glu Leu Glu Gln Val Leu Leu Trp Trp
                565                 570                 575

Lys Gln Gly Leu Ala Phe Leu Ser Gly Ala Gly Gly Thr Gly Lys Gly
            580                 585                 590

Arg Phe Arg Leu Lys Glu Leu Lys Cys Ile Phe Trp Asp Leu Gln Asn
        595                 600                 605

Asp Ala Gly Phe Ala His Tyr Lys Glu Thr Tyr Gly Gly Arg Lys Lys
    610                 615                 620

Arg Ile Ser Asp Asp Glu Leu Ile Pro Trp Gln Val Thr Ser Gly Asp
625                 630                 635                 640

Pro Val Ser Glu Pro Pro Trp Thr Ala Trp Glu Ile Asn Phe Leu Val
                645                 650                 655

Cys Ser Pro Phe Leu Thr Lys Asp Pro Val Glu Ser Leu Leu Asp Pro
            660                 665                 670

Gly Gly Thr Asp Ala Val Cys Tyr Arg Ala Val Tyr Leu Gly Glu Asn
        675                 680                 685

Gly Gly Ile Lys Lys Arg Tyr Leu Leu Lys Gly Glu Ser Phe Arg Gly
    690                 695                 700

Ile Leu Arg Thr Ala Val Gly Arg Arg Glu Asn Ser Leu Leu Lys Glu
705                 710                 715                 720

His Glu Glu Cys Asp Cys Val Leu Cys Arg Leu Phe Gly Asn Glu His
                725                 730                 735

Glu Ala Gly Lys Ile Arg Val Glu Asp Leu Leu Ile Gln Asp Glu Pro
            740                 745                 750

Lys Glu Lys Asn Leu Asp Arg Val Ala Ile Asp Arg Phe Thr Gly Gly
        755                 760                 765

Ala Arg Asp Lys His Lys Phe Asp Gln Lys Pro Leu Thr Gly Thr Pro
    770                 775                 780

Ala Phe Pro Leu Val Leu Met Gly Lys Ile Trp Ile Lys Asn Asp Leu
785                 790                 795                 800

Thr Asp Asp Asp Lys Ala Ile Leu Lys Gln Ala Leu Glu Asp Ile Arg
                805                 810                 815
```

```
Cys Gly Leu Tyr Pro Phe Gly Gly Leu Gly Asn Val Gly Phe Gly Trp
            820                 825                 830

Val Asn Tyr Leu Thr Cys Asn Ser Asp Phe Glu Gln Asn Phe Asp Ser
        835                 840                 845

Met Asn Leu Cys Phe Ser Asp Lys Val Lys Val Glu Asn Glu Pro Asp
    850                 855                 860

Lys Ile Tyr Trp Pro His Tyr Phe Ile Pro Phe Gly Pro Lys Val Val
865                 870                 875                 880

Arg Glu Asn Lys Pro Pro Gly His Ala Tyr Pro Lys Thr Glu Phe His
                885                 890                 895

Ser Gly Arg Leu Ile Cys Ser Leu Lys Thr Leu Thr Pro Leu Ile Ile
            900                 905                 910

Pro Asp Gly Gln Pro Ala Ser Gln Glu Ala Asn Gly His Lys Ser Tyr
        915                 920                 925

Asn Phe Phe Glu Leu Ser Gly Glu Leu Cys Ile Pro Gly Ser Glu Ile
    930                 935                 940

Lys Gly Met Ile Ser Ser Val Tyr Glu Ala Leu Thr Asn Ser Cys Met
945                 950                 955                 960

Arg Ile Phe Glu Glu Lys Lys Arg Leu Ser Trp Arg Met Lys Ala Glu
                965                 970                 975

Asn Leu Asp Gln Trp Ser Pro Gly Arg Ile Thr Glu Glu Ala Asp Glu
            980                 985                 990

Leu Phe Val Glu Glu Met Glu Glu  Ile Arg Leu Pro Leu  Tyr Asp Asn
        995                 1000                1005

Pro Asp  Leu Leu Pro Asn Ile  Lys Lys Glu Gly Glu  Lys Gly Phe
    1010                1015                1020

Tyr Arg  Thr Lys Lys Ile Arg  Asp Ser Asn Gly Arg  Glu Arg Leu
    1025                1030                1035

Lys Lys  Gly Gln Pro Thr Gly  Thr Asp Ser Leu Ile  Asn Ile His
    1040                1045                1050

Ser Ala  Glu Ile Arg Glu Phe  Leu Lys Glu Asn Lys  His Leu Ser
    1055                1060                1065

Ser Gly  Gln Ile Pro Thr Lys  Trp Phe Arg Cys Phe  Pro His Pro
    1070                1075                1080

Gly Lys  Arg Gly Phe Asp Gly  Leu Ala Leu Leu Lys  Ile Pro Lys
    1085                1090                1095

Glu Trp  His Asn Lys Asn Thr  Ser Gly Trp Ile Ala  Glu Gly Tyr
    1100                1105                1110

Val Asn  Leu Thr Gly Thr Asn  Lys Val Glu Thr Arg  Arg Ser Gly
    1115                1120                1125

Lys Gly  Ile Ser Ile Arg Glu  Thr Ser Lys Asp Glu  Gln Ile Asn
    1130                1135                1140

Ile Ile  His Asn Glu Val Thr  Leu Glu Glu Lys Pro  Val Asn Ser
    1145                1150                1155

Ser Lys  Leu Gly Gln Val Leu  Arg Lys Arg Ala Ile  Pro Lys Tyr
    1160                1165                1170

Val Thr  Tyr Lys Asn Gly Tyr  Glu Tyr Thr Met Thr  Lys Arg Cys
    1175                1180                1185

Glu Arg  Ile Phe Ile Pro Leu  Gln Lys Pro Thr Lys  His Ile Val
    1190                1195                1200

Ser Arg  Asn Val Glu Asn Lys  Phe Leu Gln Leu Cys  Glu Glu Tyr
    1205                1210                1215

Lys Gln  Asn Ala Glu Lys Ile  Pro Lys Val Phe Arg  Thr Arg Met
```

```
    1220                1225                1230

Pro Lys  Asn Tyr Lys Leu Asn  Asp Gly Asp Leu Ile  Tyr Phe Arg
    1235                1240                1245

Gln Glu  Leu Gly Glu Val Val  Glu Ile Ile Pro Val  Arg Ile Ser
    1250                1255                1260

Arg Ala  Val Asp Asp Glu Val  Leu Gly Glu Lys Phe  Val Asn Asp
    1265                1270                1275

Asp Phe  Arg Pro Cys Val Arg  Glu Ile Leu Asn Arg  Glu Thr Glu
    1280                1285                1290

Lys Lys  Ile Thr Ser Ala Gly  Phe Lys Glu Val Phe  His His His
    1295                1300                1305

Pro Lys  Gly Leu Cys Pro Ala  Cys Ala Ile Phe Gly  Thr Thr Phe
    1310                1315                1320

Tyr Lys  Gly Arg Val Ser Phe  Gly Phe Ala Tyr Leu  Lys Asn Asn
    1325                1330                1335

Glu Thr  Lys Leu Val Glu Asn  Gly Ala Tyr Ile Thr  Leu Pro Leu
    1340                1345                1350

Leu Glu  Arg Pro Arg Pro Thr  Trp Ala Met Pro Thr  Lys Asp Ser
    1355                1360                1365

Lys Val  Pro Gly Arg Lys Phe  Tyr Val His His Gln  Gly Trp Lys
    1370                1375                1380

Asn Ile  Val Glu Asp Ser Lys  Asn Glu Ser Thr Glu  Lys Asn Glu
    1385                1390                1395

Asn Asn  Arg Ser Val Gln Ala  Ile Asp Arg Asn Gln  Val Phe Leu
    1400                1405                1410

Phe Glu  Val Arg Phe Glu Asn  Leu Arg Pro Trp Glu  Leu Gly Leu
    1415                1420                1425

Leu Ile  Tyr Ser Leu Gln Leu  Glu Pro Lys Leu Ala  His Lys Leu
    1430                1435                1440

Gly Met  Gly Lys Pro Leu Gly  Phe Gly Ser Val Lys  Ile Lys Val
    1445                1450                1455

Glu Asn  Val Thr Ser Ser Arg  Gln Lys Asp Val Asn  Asp Asn Thr
    1460                1465                1470

Leu Pro  Glu Ala Val Glu Lys  Glu Leu Lys Glu Ile  Trp Gly Lys
    1475                1480                1485

Glu Thr  Glu Pro Asp Phe Thr  Arg Ser Leu Glu Gly  Leu Tyr Lys
    1490                1495                1500

Ala Leu  His Tyr Glu Ser Lys  Asn Gly Ile Gln Val  Arg Tyr Pro
    1505                1510                1515

Lys Leu  Glu Lys Glu Lys Lys  Asp Asp Pro Gly Glu  Lys Pro Gly
    1520                1525                1530

Tyr Leu  Glu Leu Ala Asp Gly  Pro Phe Ser Thr Glu  Asn Arg Lys
    1535                1540                1545

Glu Lys  Leu Lys Glu Ile Trp  Gly Asn Trp Ala
    1550                1555
```

<210> SEQ ID NO 22
<211> LENGTH: 1549
<212> TYPE: PRT
<213> ORGANISM: Unknown
<220> FEATURE:
<221> NAME/KEY: source
<223> OTHER INFORMATION: /note="Description of Unknown:
      Bioremediation-terephthalate-wastewater bioreactor sequence"

<400> SEQUENCE: 22

```
Met Asn Arg Tyr Lys Val Ser Leu Glu Phe Leu Glu Pro Trp Arg Ile
1               5                   10                  15

Asn His Leu Gly Asp Asp Arg Gly Ala Ala Trp Ala Arg Trp Val Gln
            20                  25                  30

Thr Arg Glu Gly Tyr Gln Arg Pro Glu Ile Thr Gly Thr Leu Val Arg
        35                  40                  45

Ser Ala Val Ile Arg Ala Ala Glu Glu Leu Leu Ala Leu Thr Gly Gly
    50                  55                  60

Val Trp Ala Gly Gln Lys Cys Cys Pro Gly Glu Phe Cys Thr Pro Gly
65                  70                  75                  80

Gly Ser Lys Pro Thr Phe Arg Arg Gln Arg Ala Thr Arg Trp Trp Gly
                85                  90                  95

Glu Asp Ser Leu Cys Thr Pro Asp Ser Pro Cys Pro Phe Cys Gln Leu
            100                 105                 110

Leu Gly Arg His Asp Leu Ala Gly Lys Gln Ala Arg Arg Gly Gly Gly
        115                 120                 125

Phe His Val His Phe Gly Asn Leu Tyr Pro Val Ala Arg Glu Gly Tyr
    130                 135                 140

Gly Ser Leu Ala Glu Ile Thr Arg Gln Arg Thr Ser Asn Arg Leu Asp
145                 150                 155                 160

Trp Leu Thr Gly Lys Ala Gln Asp Ile Leu Thr Ile Cys Glu Val Glu
                165                 170                 175

Glu Leu Arg Arg Phe Ser Gly Leu Ile Thr Val Ala Pro Glu Leu Ala
            180                 185                 190

Asn Gly Glu Ala Val Ser Ser Leu Leu Thr Ala Ala Ala Ala Leu Val
        195                 200                 205

Asp Arg Leu Ser Gly Ala Ala Cys Arg Leu Lys Leu Gln Pro Val Glu
    210                 215                 220

Glu Leu Trp Ser Gly Thr Ala Val Ser Leu Thr Arg Ala Ala Val Pro
225                 230                 235                 240

Glu Thr Ala Tyr Arg Gln Gln Leu Glu Glu Asp Ile Asp Asn Tyr Phe
                245                 250                 255

Gln Glu Leu Ile Gly Asp Gly Ser Gln Leu Gly Pro Glu Arg Leu Arg
            260                 265                 270

Leu Leu Ala Asp Ala Ile Arg Glu Leu Arg Tyr Leu Pro Pro Glu Gln
        275                 280                 285

Thr Leu Pro Asp Trp Leu Gln Ser Leu Pro Gln Gly Lys Asp Gly Lys
    290                 295                 300

Ala His Arg Leu Trp Asp Ala Leu Thr Ala Gln Arg Arg Pro Leu Arg
305                 310                 315                 320

Asn Met Leu Gln Glu Val Ala Ala Ala Tyr Ala Ala Pro Ala Thr Trp
                325                 330                 335

Arg Asp Val Val Gln Gly Leu Gly Gln Ala Leu Tyr Ala His Tyr Lys
            340                 345                 350

Lys Leu Trp Pro Gln Ala Met Pro Val Arg Pro Val Gly Glu Ala Glu
        355                 360                 365

Tyr Trp Gln Thr Lys Phe Arg Asp Arg Gln Pro Ser Arg Gln Arg Gly
    370                 375                 380

Thr Trp Ser His Glu Trp Ile Ile Thr Gly Ala Leu Gln Thr Leu Thr
385                 390                 395                 400

Pro Leu Tyr Leu Gly Thr Gln Val Glu Ala Ala Arg Gln Thr Ser Leu
                405                 410                 415
```

```
Thr Val Leu Leu Thr Ala Glu Gly Arg Tyr Arg Leu Pro Arg Thr Ala
            420                 425                 430

Leu Arg Gly Ala Leu Arg Gln Asp Leu Gln Leu Ala Ser Arg Gly Gln
        435                 440                 445

Gly Cys Leu Met Glu Leu Asn Pro Glu Arg Pro Cys Ser Cys Pro Ile
    450                 455                 460

Cys Gln Ile Met Arg Arg Leu Thr Val Arg Asp Val Thr Ser Ser Ile
465                 470                 475                 480

Ala Leu Pro Pro Pro Leu Val Arg Gln Arg Val Arg Arg Asn Pro Trp
                485                 490                 495

Thr Gly Ile Val Asp Glu Gly Ala Leu Phe Asp Gln Glu Val Ala Pro
            500                 505                 510

Glu Gly Leu Arg Phe Pro Phe Ile Leu Arg Tyr Arg Gly Phe Gly Gly
        515                 520                 525

Leu Asp Ala Trp Leu Gln Thr Val Leu Ser Trp Trp Gln Glu Gly Arg
    530                 535                 540

Leu Phe Leu Gly Gly Ala Gly Gly Thr Gly Lys Gly Arg Leu Arg Leu
545                 550                 555                 560

Thr Asp Leu Arg Ile Trp Arg Trp Ala Leu Asp Glu Thr Gly Leu Pro
                565                 570                 575

Thr Tyr Val Ala His Leu Gly Tyr Arg Gly Arg Glu Glu Glu Leu Ala
            580                 585                 590

Asn Ser Ala Ser Leu Pro Ala Gly Val Glu Ala Val Thr Cys Ser Asp
        595                 600                 605

Pro Ala Thr Val Pro Ser Pro Trp Gln Glu Val Asp Trp Glu Phe Arg
    610                 615                 620

Phe His Gly Pro Val Leu Ala Asn His Pro Leu Thr Ala Leu Leu Arg
625                 630                 635                 640

Gly Glu Ala Asp Ala Val Phe Thr Trp Lys Val Gln Leu Glu Ala Asp
                645                 650                 655

Gln Gln His Tyr Arg Glu Val Cys Thr Leu Lys Gly Glu Thr Val Arg
            660                 665                 670

Gly Leu Val Arg Gly Leu Phe Gly Lys Ser Gln Gly Leu Leu Thr Lys
        675                 680                 685

Ala His Ala Asp Cys Thr Cys Leu Leu Cys Arg Val Phe Gly Asn Glu
    690                 695                 700

His Gln Arg Gly Lys Val Arg Phe Glu Asp Leu Thr Leu Ala Gly Glu
705                 710                 715                 720

Thr Val Pro Lys Lys Arg Leu Asp His Val Ala Ile Asp Arg Ile Ser
                725                 730                 735

Gly Gly Ala Ala Glu Gln Leu Lys Phe Asp Thr Gln Pro Leu Tyr Gly
            740                 745                 750

Thr Pro Glu Asn Pro Leu Val Phe Ala Gly Lys Phe Trp Val His Thr
        755                 760                 765

Glu Leu Asp Glu Glu Glu Gln Lys Ala Leu Arg Ala Ala Leu Thr Ala
    770                 775                 780

Leu Arg Asp Gly Leu Ala Thr Val Gly Ala Lys Gly Ser Val Gly Tyr
785                 790                 795                 800

Gly Trp Leu Asn Gly Leu Arg Leu His Ser Gly Pro Ala Trp Leu Thr
                805                 810                 815

Asp Asn Trp Gln Glu Thr Ala Ala Ala Pro Ser Asp Thr Asn Thr Pro
            820                 825                 830

Pro Glu Phe Ser Trp Pro Gln Leu Pro Asp Leu Thr Leu Asp Ser Arg
```

```
        835                 840                 845

Lys Ile Tyr Tyr Pro His Tyr Phe Leu Pro Pro Asp Leu Gln Val Pro
    850                 855                 860

Arg Leu Ser Gln Pro His Thr His Ser Leu Phe Asp Pro Gln Lys Tyr
865                 870                 875                 880

Thr Gly Trp Leu Thr Cys Arg Leu Thr Thr Leu Thr Pro Leu Ile Ile
                885                 890                 895

Pro Asp Thr Ser Ser Asp Gln Thr Leu Thr Thr Gly Gly Pro Phe Pro
            900                 905                 910

Ala Gly His Gln Ala Phe Gln Phe Phe Arg Leu Gly Asp Gln Pro Leu
        915                 920                 925

Ile Pro Gly Ala Glu Leu Arg Gly Met Ile Ser Ser Val Phe Glu Ala
    930                 935                 940

Ile Thr Asn Ser Cys Phe Arg Val Ile Arg Pro Arg Glu Arg Leu Ser
945                 950                 955                 960

Trp Arg Met Pro Ala Ala Leu Ala Pro Gln Phe Arg Ser Gly Arg Val
                965                 970                 975

Glu Ile Val Asn Asn Gln Tyr Tyr Ile Arg Gln Met Asp Met Gly Arg
            980                 985                 990

Leu Pro Leu Tyr Asp Asp Pro Ala  Thr Arg Arg Leu Phe  Thr Pro Leu
        995                 1000                1005

Ser Leu  Thr Ser Gly His Thr  Leu Asp Phe Val Asp  Asp Asn Arg
    1010                1015                1020

Thr Leu  Leu Gln Ser Asn Pro  Gly Ile Arg Glu Gly  Ala Ile Arg
    1025                1030                1035

Thr Asp  Leu Cys Phe Leu Asn  Arg Phe Trp Leu Leu  Arg Pro Pro
    1040                1045                1050

Ser Ala  Ala Arg Cys Pro Arg  Gly Asn Phe Ser Leu  Thr Ser Gly
    1055                1060                1065

Tyr Val  Lys Phe Thr Gly Pro  Asn Lys Val Glu Val  Ser Arg Ala
    1070                1075                1080

Gly Ala  Gly Ala Gly Gly Leu  Pro Ala Pro Pro Ala  Asp Trp Thr
    1085                1090                1095

Gly Val  Arg Leu Asn Gln Val  Ala Gly Asn Val Pro  Phe Tyr Gln
    1100                1105                1110

Ala Glu  Gln Ser Gly Val Ile  Phe Thr Val Asn Lys  Arg Arg Glu
    1115                1120                1125

Arg Phe  Phe Ile Ser Arg Gly  Asn Ala Arg Ser Tyr  Pro Val Pro
    1130                1135                1140

Leu Ala  Thr Leu Lys Arg Tyr  Glu Gln Val Leu Lys  Glu Tyr Arg
    1145                1150                1155

His Phe  Ala Gln Arg Gly Glu  Val Pro Ala Val Phe  Arg Thr Val
    1160                1165                1170

Leu Pro  Asp Val Arg His Gly  Ala Ser Gly Tyr Asn  Arg Leu Asn
    1175                1180                1185

Asn Gly  Asp Leu Val Tyr Phe  Arg Val Lys Asp Asp  Arg Trp Asn
    1190                1195                1200

Asp Gln  Asn Ala Pro Val Glu  His Ile Ile Pro Val  Ser Ile Ser
    1205                1210                1215

Arg Leu  Val Asp Gln Lys Phe  Leu Gly Glu Arg Val  Pro Glu Pro
    1220                1225                1230

Leu Arg  Pro Cys Ala His Val  Cys Leu Glu Glu Cys  Glu Ala Cys
    1235                1240                1245
```

Leu Lys Gln Glu Ser Cys Pro Ser Ser Phe Tyr Arg Glu Gly Thr
1250 1255 1260

Pro Ser Arg Gly Leu Cys Pro Ala Cys His Leu Phe Gly Thr Thr
1265 1270 1275

Gly Tyr Gln Gly Arg Val Arg Phe Gly Phe Ala Arg Leu Glu Arg
1280 1285 1290

Glu Pro Ala Trp Arg Gln Asn Asp Ala Gly Ser Thr Ala Ile Thr
1295 1300 1305

Leu Pro Leu Leu Glu Gln Pro Arg Leu Thr Trp Ser Met Leu Trp
1310 1315 1320

Glu Arg Arg Asn Ala Glu Gly Thr Val Glu Glu Arg Gln Pro Val
1325 1330 1335

Asn Trp Val Pro Gly Arg Lys Phe Tyr Val His His Gln Gly Trp
1340 1345 1350

Arg Thr Ile Val Ala Gln Gly Ile Asn Pro Ile Asp Gly Gln Arg
1355 1360 1365

Leu Glu Arg Asn Glu Asn Asn Arg Thr Val Glu Val Leu Asp Thr
1370 1375 1380

Gly Arg Thr Phe Thr Phe Gln Val Phe Phe Glu Asn Leu Asp Ala
1385 1390 1395

Trp Glu Leu Gly Leu Leu Leu Tyr Ser Leu Glu Leu Glu Pro Gly
1400 1405 1410

Leu Ala His Lys Leu Gly Met Ala Lys Ala Trp Gly Phe Gly Ser
1415 1420 1425

Val Gln Ile Asp Val Ala Ser Leu Arg Arg Tyr Gln Ala Pro Gly
1430 1435 1440

Ser Met Thr Asp Ile Thr Cys Glu Lys Asp Thr Leu Leu Gln Ala
1445 1450 1455

Gly Phe Ala Trp Leu Lys Glu Gln Ala Asn Ser Ser Ser Trp Asp
1460 1465 1470

Glu Ile Pro Arg Leu Arg Gln Leu Arg Gln Leu Leu Arg Tyr Gln
1475 1480 1485

Glu Asp Gly Thr Leu Thr Val Arg Tyr Pro Ile Leu Lys Gln Glu
1490 1495 1500

Asn Ala Ala Ser Gly Gln Val Pro Gly Tyr Val Glu Leu Arg Asp
1505 1510 1515

Gln Gly Tyr Arg Pro Glu Glu Gln Leu Arg Ile Pro Trp Ser Pro
1520 1525 1530

Trp Tyr Ser Pro Pro Leu Glu Pro Pro Pro Ala Ala Thr Ala Ala
1535 1540 1545

Ala

<210> SEQ ID NO 23
<211> LENGTH: 1668
<212> TYPE: PRT
<213> ORGANISM: Unknown
<220> FEATURE:
<221> NAME/KEY: source
<223> OTHER INFORMATION: /note="Description of Unknown: Aquatic-freshwater-freshwater lake sediment sequence"

<400> SEQUENCE: 23

Met Thr Thr Leu Thr Ile His Leu His Phe Leu Glu Pro Phe Arg Met
1 5 10 15

Ala Pro Trp Phe Ser Val Glu Lys Arg Lys Lys Asn Asn Pro Asp Trp

```
            20                  25                  30

Gln Arg Val Gln Thr Tyr Ala Arg Trp His Lys Asn Thr Ala Gly Asp
        35                  40                  45

Gly Arg Gly Arg Pro Phe Ile Thr Gly Tyr Leu Leu Arg Ser Ala Leu
    50                  55                  60

Ile Gln Ala Val Glu Glu Glu Leu Val Phe Ser Arg Gly Val Trp Ser
65                  70                  75                  80

Gly Ile Ser Cys Cys Pro Gly Leu Phe Phe Thr Glu Pro Asp Lys Asp
                85                  90                  95

Lys Glu Lys Pro Leu Asn Glu Arg Arg Arg Ala Thr Leu Gly Trp Thr
            100                 105                 110

Glu Asn Lys Ala Ile Cys Gln Glu Glu Glu Gly Arg Glu Lys Ala Cys
        115                 120                 125

Pro Leu Cys Leu Leu Ile Asn Arg Phe Lys Glu Asn Gly Glu Asp Asn
    130                 135                 140

Val His Phe Gly Asn Leu Ser Leu Pro Gly Ser Glu Asn Glu Arg Pro
145                 150                 155                 160

Val Trp Asp Gln Pro Glu Gln Ile Ala Lys Leu Arg Thr Leu Asn Arg
                165                 170                 175

Val Asp Arg Ala Thr Thr Lys Ala His Asp His Phe Lys Val Tyr Glu
            180                 185                 190

Val Glu Asp Leu Thr Asp Phe Tyr Gly Thr Ile Thr Phe Ala Asp Asp
        195                 200                 205

Leu Pro Gln Arg Glu Val Ile Glu Ser Leu Ile Arg Arg Gly Leu Gly
    210                 215                 220

Phe Ile Ser Asp Leu Cys Gly Ala Leu Cys Glu Ile Arg Val Glu Lys
225                 230                 235                 240

Gln Lys Pro Leu Pro Thr Glu Pro Lys Gly Ile Thr Gln Ser Lys Ala
                245                 250                 255

Ser Tyr Val Ser Gly Leu Ala Glu Met Cys Trp Glu Lys Met Ala Glu
            260                 265                 270

Thr Glu Leu Arg Ser Leu Ala Gly Ala Val Leu Gln Leu Arg Cys Ser
        275                 280                 285

Asp Pro Lys Lys Phe Thr Leu Pro Lys Gly Arg Ile Asp Arg Asn Gly
    290                 295                 300

Asn Arg Leu Pro His His Ile Trp Asp Ile Glu Leu Glu Gly Asn Gly
305                 310                 315                 320

Asp Lys Lys Thr Leu Arg Lys His Leu Lys Glu Thr Ala Glu Lys Met
                325                 330                 335

Ala Glu Gly Gly Thr Ala Phe Arg Leu Phe Cys Glu Asp Val Gly Asn
            340                 345                 350

Arg Leu Phe Arg Leu Ser Lys Gly Ile Pro Gln Glu Thr Pro Asn Arg
        355                 360                 365

Gln Asp Ala Phe Ser Asp Pro Ser Gln Val Phe Asn Leu Gly Arg Pro
    370                 375                 380

Val Tyr Gly Gln Glu Asn His Arg Asp Pro Met Ile Pro Ser Cys Glu
385                 390                 395                 400

Trp Ile Ile Thr Gly Thr Leu Thr Ala Ala Ser Pro Phe Phe Ile Ala
                405                 410                 415

Asp Glu Leu Ile Asp Asp Asp His Ile Ser Arg Lys Leu Leu Thr Thr
            420                 425                 430

Gln Asp Phe His Tyr Arg Leu Pro Arg Ser Leu Leu Arg Gly Ile Leu
        435                 440                 445
```

```
Arg Arg Asp Leu His Glu Ala Ser Gly Gly Lys Gly Cys Arg Ala Glu
    450                 455                 460

Leu Gly Pro Glu Ser Ser Cys Ile Cys Pro Val Cys Arg Ile Leu Asn
465                 470                 475                 480

Gln Val Lys Ile Arg Asp Ala Arg Ser Asp Ser Phe Val Pro Pro Asp
                485                 490                 495

Ile Arg Gln Arg Val Lys Gln Ser His His His Arg Ile Val Gln Asp
            500                 505                 510

Gly Ala Leu Phe Asp Thr Glu Tyr Gly Leu Glu Gly Val Val Phe Pro
        515                 520                 525

Phe Glu Leu Arg Phe Lys Gly Glu Lys Thr Ile Asp Lys Glu Leu Arg
    530                 535                 540

Thr Val Met Gly Trp Trp Glu Glu Gly Leu Leu Phe Leu Gly Gly Asp
545                 550                 555                 560

Phe Gly Thr Gly Lys Gly Ala Phe Lys Leu Gly Ile Lys Gln Ile His
                565                 570                 575

Arg Trp Asp Leu Ser Thr Pro Gly Ala Arg Glu Glu Tyr Glu Gln Thr
            580                 585                 590

Cys Gly Phe Arg Ala Gly Val Pro Leu Asp Ala Asn Cys Gln Gly Leu
        595                 600                 605

Ser Pro Val Ser Asn Ile Asp Phe Pro Lys Val Asp Tyr Pro Trp Gln
    610                 615                 620

Lys Val Pro Trp Glu Leu Ala Phe Glu Ser Pro Leu Leu Thr Ala Asp
625                 630                 635                 640

Pro Ile Ala Ala Ile Thr Gln Asp Glu Ala Asp Thr Ile Tyr Phe Gln
                645                 650                 655

Lys Arg Arg Leu Lys Ser Asp Gly Ser Val Glu Tyr Ile Pro Ala Leu
            660                 665                 670

Arg Gly Glu Gly Leu Arg Gly Leu Ile Arg Thr Ala Thr Ala Arg Ala
        675                 680                 685

Ser Gly Ser Asp His Leu Thr Val Glu His Glu Asp Cys Thr Cys Val
    690                 695                 700

Leu Cys Lys Thr Phe Gly Asn Glu His Arg Ser Gly Leu Leu Arg Phe
705                 710                 715                 720

Asp Asp Leu Glu Pro Lys Asn Trp Lys Asp Lys Arg Ile Asp His Val
                725                 730                 735

Ser Ile Asp Arg Phe Asp Ala Ser Val Val Glu Lys Phe Asp Asp Arg
            740                 745                 750

Pro Leu Ile Gly Ser Pro Asp Lys Pro Leu Val Phe Ala Gly Ala Phe
        755                 760                 765

Trp Ile His Arg Asp Phe Thr Glu Asn Lys Ala Leu Ser Asn Gly Phe
    770                 775                 780

Gln Asp Leu Lys Ser Gly Leu Tyr Pro Leu Gly Gly Lys Val Gly Ile
785                 790                 795                 800

Gly Tyr Gly Arg Leu Ser Lys Leu Glu Leu Pro Ser Asp Trp Leu Pro
                805                 810                 815

Asn Ser Ala Glu Asn Glu Ser Ile Ser Val Ser Gly Leu Leu Glu Gly
            820                 825                 830

Ser Pro Glu Thr Ser Gly Ile Pro Glu Lys Pro Thr Trp Lys Pro Glu
        835                 840                 845

Pro Asp Ala Ile Tyr Asn Pro Tyr Tyr Tyr Leu Ser Arg Pro Gly Asp
    850                 855                 860
```

```
Gly Pro Lys Arg Thr Leu Thr Pro Val Ser His Ala Thr Leu Ser Lys
865                 870                 875                 880

Glu Arg Tyr Thr Gly Arg Ile Ala Cys Phe Leu Lys Val Lys Ser Pro
                885                 890                 895

Leu Leu Leu Pro Asp Ser Glu His Asp Pro Val Ala Pro Asp Lys Asn
            900                 905                 910

Gly Thr Met Lys Ala Phe Arg Leu Asn Gly Thr Leu Met Ile Pro Gly
        915                 920                 925

Ser Ala Leu Arg Ser Ala Val Ser Gln Val Tyr Glu Ala Leu Thr Asp
    930                 935                 940

Ser Cys Phe Arg Val Met Asp Gln Lys Arg Val Leu Ser Trp Arg Met
945                 950                 955                 960

Glu Thr Gly Asp His Gly Asn Tyr Lys Pro Gly Arg Ile Ser Glu Ser
                965                 970                 975

Gly Asp Gln Ile Phe Pro Met Gly Glu Lys Ala Leu Arg Leu Pro Leu
            980                 985                 990

Tyr Asp Met Ala Pro Gly Thr His  Ser Ala Lys Tyr Ile  Lys Glu Leu
        995                 1000                1005

Glu Glu  Leu His Lys Lys Ala  Leu Glu Gly Asn Ile  His Arg Leu
    1010                1015                1020

Thr Ile  Ala Pro Trp Glu Glu  Met Pro Glu Lys Thr  Arg Glu Lys
    1025                1030                1035

Lys Phe  Glu Lys Cys Asn Lys  Ile Leu Gly Arg Asn  Leu Thr Glu
    1040                1045                1050

Glu Glu  Lys Lys Asn Leu Thr  Asp Gln Gly Met Ala  Lys Leu Lys
    1055                1060                1065

Ile Ser  Glu Met Glu Leu Lys  Thr Leu Ile Gly Arg  Phe Lys Lys
    1070                1075                1080

Asp Glu  Glu Ser Cys Ile Glu  Lys Ala Gln Lys Thr  Asp Ser Asn
    1085                1090                1095

Ile Ala  Glu Ile Ala Lys His  Asn Arg Asp Ile Leu  Asn Val Leu
    1100                1105                1110

Glu Lys  Glu Thr Arg Gln Arg  Val Leu Ala Gly Lys  Glu Lys Val
    1115                1120                1125

Pro Phe  Leu Thr Glu Arg Leu  Ala Pro Asn Asn Asp  Ile Asn Phe
    1130                1135                1140

Gln Ile  Val Lys Leu Leu Lys  Asn Ser Glu Lys Asn  Lys Lys Asn
    1145                1150                1155

Lys Glu  Ile Arg Trp Gly Tyr  Leu Lys Ile Thr Gly  Pro Asn Asn
    1160                1165                1170

Ala Asn  Asp Ala Val Val Glu  Thr Lys Glu Glu Asp  Asp Lys Tyr
    1175                1180                1185

Lys Leu  Glu Trp Glu Asp Pro  Leu Asp Phe Ser Phe  Cys Leu Thr
    1190                1195                1200

Gly Pro  Pro Lys Asn Gln Pro  Asn Thr Gln Lys Ser  Arg Asp Phe
    1205                1210                1215

Pro Arg  Pro Gly Phe Glu Cys  Ile Lys Asp Asp Lys  Arg Tyr Thr
    1220                1225                1230

Ile Ser  Lys Arg Cys Glu Arg  Leu Phe Glu Ala Asp  Glu Lys Ser
    1235                1240                1245

Lys Pro  Ile Pro Ile Pro Lys  Arg Val Arg Glu Gly  Tyr Lys Gly
    1250                1255                1260

Ile Leu  Glu Asp Tyr Gln Lys  Asn Ala Lys Lys Ile  Pro Lys Ala
```

```
    1265                1270                1275

Phe Gln  Thr Arg Leu Asn Ser  Asp Leu Val Tyr Tyr  Lys Ser Asp
    1280                1285                1290

Tyr Val  Glu Asn Gln Ile Asn  Val Thr Ala Leu Ala  Pro Val Cys
    1295                1300                1305

Ile Ser  Arg Leu Ala Asp Asp  Arg Pro Leu Gly Lys  Arg Leu Pro
    1310                1315                1320

Val Gly  Tyr Gln Pro Cys Ser  His Ile Cys Leu Glu  Asp Cys Glu
    1325                1330                1335

Arg Cys  Thr Gly Lys Ala Cys  Pro Ile Pro Leu Tyr  Arg Glu Gly
    1340                1345                1350

Tyr Pro  Val Asn Gly Leu Cys  Pro Ala Cys Gln Leu  Phe Gly Ala
    1355                1360                1365

Gln Met  Tyr Lys Gly Arg Val  Asn Phe Ser Phe Ala  Thr Leu Thr
    1370                1375                1380

Pro Gly  Lys Asn Leu Glu Leu  Arg Asn Val Thr Leu  Pro Ala Gln
    1385                1390                1395

Glu Arg  Pro Arg Pro Thr Trp  Ile Leu Pro Lys Asn  Val Gln Gly
    1400                1405                1410

Lys Asp  Thr Glu Ile Pro Gly  Ala Lys Phe Tyr Leu  Arg His Gly
    1415                1420                1425

Met Trp  Lys Lys Ile Trp Thr  Asp Arg Lys Asp Pro  Arg Thr Asp
    1430                1435                1440

Lys Pro  Ile Glu Glu Lys Asn  Pro Asn Asn Val Thr  Ile Glu Gly
    1445                1450                1455

Ile Asn  Thr Gly Ala Glu Phe  Arg Phe Asp Val Ser  Phe Glu Asn
    1460                1465                1470

Leu Asp  Glu Asn Glu Leu Gly  Trp Leu Leu Tyr Cys  Leu Glu Leu
    1475                1480                1485

Glu Glu  Asp Met Ser His Met  Leu Gly Arg Gly Lys  Pro Phe Gly
    1490                1495                1500

Phe Gly  Gln Val Glu Ile Lys  Ile Asn Glu Leu Ala  Arg Arg Leu
    1505                1510                1515

Ala Pro  Asn Ala Trp Tyr Thr  Glu Ser Pro Lys Glu  Gly Ser Leu
    1520                1525                1530

Ile His  Ser Lys Leu Ile Val  Lys Ala Leu Ala Gly  Leu Lys Ser
    1535                1540                1545

Leu Asp  Ser Leu Arg Leu Leu  Leu Thr Gln Tyr Asn  Asn Leu Thr
    1550                1555                1560

Ala Tyr  Tyr Pro Glu Leu Glu  Gly Lys Gly Gly Lys  Pro Gly Tyr
    1565                1570                1575

Asp Thr  Leu Lys Asn Ser Ser  Gly Tyr Asn Pro His  Cys Phe Leu
    1580                1585                1590

Thr Leu  Gln Thr Lys Gly Asn  Thr Pro Phe Val Tyr  Pro Trp Phe
    1595                1600                1605

Pro Ile  Pro Ile Ser Lys Pro  Gln Ala Thr Lys Ser  Asp Ile Lys
    1610                1615                1620

Pro Lys  Val Glu Asn His Gly  Ile Thr Gly Asn Gly  Phe Lys Lys
    1625                1630                1635

Leu Val  Glu Gly Asp Lys Val  Thr Phe Glu Ile Glu  Glu Arg Pro
    1640                1645                1650

Lys Gly  Pro Cys Ala Val Asn  Val Arg Lys Val Lys  Asp Ile Pro
    1655                1660                1665
```

<210> SEQ ID NO 24
<211> LENGTH: 1821
<212> TYPE: PRT
<213> ORGANISM: Unknown
<220> FEATURE:
<221> NAME/KEY: source
<223> OTHER INFORMATION: /note="Description of Unknown: Terrestrial-soil sequence"

<400> SEQUENCE: 24

```
Met Thr Thr Gly Asn Thr Ser Ala Ser His Pro Gln Phe Val Thr Leu
1               5                   10                  15

Thr Val Cys Leu Arg Phe Cys Ser Pro Phe Gln Ile Arg Pro Trp Ile
            20                  25                  30

Lys Glu Thr Val Arg Asn Lys Val Lys Met Pro Ser Thr Val Asn Ala
        35                  40                  45

His Ala Glu Thr Ala His Leu Pro Asp Asp Gln Asp Thr Asp Asp Thr
    50                  55                  60

Gln Asp Leu Leu Glu Glu Glu Arg Phe Glu Arg Tyr Ala Thr Ala Ala
65                  70                  75                  80

Asp Trp His Lys Gly Ser Ile Asn Gly Asn Ala Lys Tyr Ser Pro Tyr
                85                  90                  95

Val Arg Gly Asp Leu Val Arg Ser Val Val Asp Arg Glu Leu Gln Glu
            100                 105                 110

His Phe His Cys Tyr Asn Glu Lys Leu Ala Asn Glu Asn Lys Gly Cys
        115                 120                 125

Pro Gly Lys Arg Asp Arg His Ile Asn Ala Gly Gly Lys Ala Ser Gly
    130                 135                 140

Phe Met Ala His Leu Pro Ala Ile Lys Asp Pro Ala Gly Lys Glu Ile
145                 150                 155                 160

Cys Lys Gly Ser Asp Asn Ile Cys Pro Val Cys His Phe Leu Gly Ala
                165                 170                 175

Phe Ala Glu Gly Ile Lys Pro Val Lys Phe Arg Asn Phe Phe Ser Gly
            180                 185                 190

Tyr Tyr Val Ala Lys Thr Glu Asp Leu Ala Lys Gln Arg Gly Arg Asn
        195                 200                 205

Cys Tyr Ser Gly Gln Ser Arg Lys Ser Leu Asp Asn Phe Thr Val Trp
    210                 215                 220

Glu Ala Asp His Thr Ala Cys Pro Val Phe Phe Gly Arg Ile Glu Val
225                 230                 235                 240

Asn Lys Thr Leu Leu Pro Lys Glu Gln Ile Leu Ala Leu Leu Ala Gly
                245                 250                 255

Gly Leu Ala Arg Leu Asp Asn Leu Ala Gly Ser Ala Cys Arg Phe Asp
            260                 265                 270

Ile Ile Asp Lys Tyr Glu Gly Val Phe Glu Asp His Glu Trp Thr Ala
        275                 280                 285

Asn Ile Leu Pro Asn Leu Leu Ile Ala Ala Arg Glu Ala Leu Gly Leu
    290                 295                 300

Pro Asp Asp Glu His Gln Ala Leu Leu Asn Asp Phe Ser Arg Phe Phe
305                 310                 315                 320

Ile Asn Pro Glu Lys Ser Pro Ala Val Tyr Thr Ser Ser Pro Val Ile
                325                 330                 335

Val Pro Val Gln Gly Ala Val Asp Lys Val Val Leu Leu Glu Lys Ala
            340                 345                 350
```

```
Gln Asp Ile Ala Gly Arg Ile Ala Ala Cys Val Ser Asp Asn Pro Arg
        355                 360                 365

His Leu His Arg Leu Ala Ala Ala Ile Arg Thr Leu Gly Trp Pro Gly
    370                 375                 380

Arg Ser Leu Ala Ser Val Met Thr Lys Lys Pro Gly Thr Glu Asp Lys
385                 390                 395                 400

Ala Thr Leu Trp Gly Lys Glu Ser Ala Ser Lys Ser Val Lys Thr Ile
                405                 410                 415

Leu Glu Glu Ser Ile Gln Gly Phe Thr Val Glu Gln Lys Arg Ser Phe
            420                 425                 430

Phe Ala Asn Leu Ala Asp Gln Leu Val Ser Arg Ala Gly Glu Gln Gly
        435                 440                 445

Ala Lys Ser Val Arg Ser Gln Gly Leu Ile Ile Gly Arg Lys Glu Asn
    450                 455                 460

Tyr Ala Lys Pro Ser Ala Gln Glu Pro Thr Arg His His Leu Tyr Arg
465                 470                 475                 480

Gln Pro Ser Asn Ala Ser Ala Phe Leu Ala Thr Gly Trp Leu Ile Ala
                485                 490                 495

Glu Thr Pro Phe Phe Ile Gly Ser Gly Thr Glu Gly Gln Lys Gln Thr
            500                 505                 510

Asp Asp Gln Ala Glu Ser Leu His Leu Arg Thr Leu Arg Asp Gly His
        515                 520                 525

Gly Arg Phe Arg Ile Pro Phe Thr Thr Ile Arg Gly Val Met Asp Lys
    530                 535                 540

Glu Leu Arg Asp Ile Leu Gln Ala Gly Cys Ala Lys Gly Arg Ser Leu
545                 550                 555                 560

Arg Ala Pro Cys Pro Cys Gln Val Cys Thr Leu Met Arg Arg Ile Gln
                565                 570                 575

Val Arg Asp Ala Ile Ala Ala Asp Ile Leu Pro Pro Asp Leu Arg Met
            580                 585                 590

Arg Thr Arg Ile Asp Pro Ser His Gly Thr Val Ala His Leu Phe Ser
        595                 600                 605

Leu Glu Met Ala Pro Gln Gly Leu Lys Leu Pro Phe Phe Leu Lys Leu
    610                 615                 620

Lys Gly Val Glu Thr Ile Asp Pro Asp Lys Glu Leu Leu Glu Ile Leu
625                 630                 635                 640

Asn Asp Trp Ser Ala Gly Gln Cys Phe Leu Gly Gly Leu Trp Gly Thr
                645                 650                 655

Gly Lys Gly Arg Phe Arg Leu Asp Asp Leu Gln Trp His Arg Leu Glu
            660                 665                 670

Leu Asp Asn Ala Asp Tyr Tyr Thr Pro Leu Leu Gln Asp Arg Phe Phe
        675                 680                 685

Ala Gly Glu Thr Ile Ser Asp Leu Arg Gln Gly Leu Gln Ser Ile Asn
    690                 695                 700

Ile Gln Pro Glu Arg Ile Pro Ala Gln Thr Pro Ser Arg Asn Met Pro
705                 710                 715                 720

Tyr Cys Arg Val Asp Cys Ile Leu Glu Phe Lys Ser Pro Val Leu Ser
                725                 730                 735

Gly Asp Pro Val Ala Ala Leu Phe Glu Ser Asp Ala Pro Asp Asn Val
            740                 745                 750

Ala Tyr Lys Lys Pro Val Val Gln Tyr Asp Glu Thr Gly Arg Leu Arg
        755                 760                 765

Thr Thr Asp Pro Gly Pro Val Glu Met Leu Thr Cys Leu Lys Gly Glu
```

```
    770                 775                 780

Gly Val Arg Gly Val Val Ala Tyr Leu Ala Gly Lys Ala Tyr Asp Gln
785                 790                 795                 800

His Asp Leu Ser His Asp Ser Cys Asn Cys Thr Phe Cys Gln Ala Phe
                805                 810                 815

Gly Asn Gly Gln Lys Ala Gly Ser Leu Arg Phe Asp Asp Phe Met Pro
            820                 825                 830

Val Gln Phe Glu Ser Asp Gln Ala Gly Asn Phe Ser Trp Ser Pro His
        835                 840                 845

Thr Pro His Ala Met Arg Ser Asp Arg Val Ala Leu Asp Val Phe Gly
    850                 855                 860

Gly Ala Met Pro Glu Ala Lys Phe Asp Asp Arg Pro Leu Ala Ala Ser
865                 870                 875                 880

Pro Gly Lys Pro Leu Asn Phe Lys Ser Thr Ile Trp Tyr Arg Glu Asp
                885                 890                 895

Met Gly Lys Glu Ala Gly Lys Ala Leu Lys Arg Ala Leu Ile Asp Leu
            900                 905                 910

Gln Asn Asn Met Ala Ala Ile Gly Ser Gly Gly Gly Ile Gly Arg Gly
        915                 920                 925

Trp Val Ser Arg Val Cys Phe Glu Gly Asp Ile Pro Asp Phe Leu Glu
    930                 935                 940

Asp Phe Pro Glu Pro Ile Thr Val Thr Glu Pro Glu Gln Asp Ser Gln
945                 950                 955                 960

Leu Leu Lys Asn Gln Ala Val Ala Asp Glu Thr Ala Val Ser Ala Cys
                965                 970                 975

Asp Thr Ala Asp Ala Pro His Pro Leu Ala Val Thr Leu Glu Pro Gly
            980                 985                 990

Ala Arg Tyr Phe Pro Arg Val Ile  Ile Pro Arg Ala Pro  Thr Val Lys
        995                 1000                1005

Arg Asp  Glu Cys Val Thr Gly  Gln Arg Tyr His Thr  Gly Arg Leu
    1010                1015                1020

Ser Gly  Lys Ile Phe Cys Glu  Leu Asn Thr Leu Gly  Pro Leu Phe
    1025                1030                1035

Val Pro  Asp Thr Asp Tyr Ser  Ala Gly Val Pro Val  Pro Ile Ser
    1040                1045                1050

Asp Glu  Gln Leu Ala Glu Cys  Gln Leu Gln Ala Val  Phe Glu Asn
    1055                1060                1065

Thr Ser  Lys Phe Asn Glu Phe  Phe Ala Thr Tyr Pro  Glu Glu Thr
    1070                1075                1080

Val Thr  Lys Leu Lys Asp Leu  Leu Cys Ala Ala Asp  Asp Lys Trp
    1085                1090                1095

Ile Leu  Ala Val Lys Asp Ile  Thr Ala Asp Leu Arg  Gln Glu Ile
    1100                1105                1110

Gly Glu  Asp Thr Phe Gln Arg  Ile Ile Arg Lys Ala  Gly His Lys
    1115                1120                1125

Thr Gln  Arg Phe His Gln Ile  Asn Asp Glu Ile Gly  Leu Pro Gly
    1130                1135                1140

Ala Ser  Leu Arg Gly Met Val  Leu Ser Asn Tyr Gln  Ile Leu Thr
    1145                1150                1155

Asn Ser  Cys Tyr Arg Asn Leu  Lys Ala Thr Glu Glu  Ile Thr Arg
    1160                1165                1170

Arg Met  Pro Ala Asp Glu Ala  Lys Tyr Arg Lys Ala  Gly Arg Val
    1175                1180                1185
```

```
Thr Val  Ser Gly Asp Gly Ala  Gln Lys Lys Tyr Ser  Ile Gln Glu
    1190                 1195                 1200

Met Glu  Val Leu Arg Leu Pro  Ile Tyr Asp Asn Met  Asn Thr Pro
    1205                 1210                 1215

Asp Asn  Met Pro Asp Val Ala  Lys Gln Ala Thr Thr  Ala Lys Arg
    1220                 1225                 1230

Cys Asn  Asn Leu Met Asn Glu  Ala Ala Lys Thr Ser  Arg Val Glu
    1235                 1240                 1245

Leu Lys  Ala Arg Trp Arg Glu  Gly Gln Ser Lys Ile  Lys Tyr Gln
    1250                 1255                 1260

Ile Ile  Asp Ala Leu Asn Lys  Val Asp Pro Ile Ile  Gln Val Ile
    1265                 1270                 1275

Ser Ser  Ser Lys Gln Ile Asn  Pro Asn Asn Gly Lys  Thr Gly Trp
    1280                 1285                 1290

Gly Tyr  Val Lys Tyr Thr Gly  Ala Asn Val Phe Ala  Lys Ser Leu
    1295                 1300                 1305

Val Ala  Pro Ile Asp Cys Leu  Arg Lys Lys Asp Ala  Gly His Val
    1310                 1315                 1320

Cys Cys  Gln Val Asn Leu Asn  Pro Ala Trp Glu Ala  Ser Asn Phe
    1325                 1330                 1335

Asp Ile  Leu Ile Asn Glu Lys  Cys Pro Val Glu Arg  Gln Ser Gly
    1340                 1345                 1350

Pro Arg  Pro Thr Leu Arg Cys  Lys Gly Gln Asp Ser  Ala Trp Tyr
    1355                 1360                 1365

Thr Leu  Thr Lys Arg Ser Glu  Arg Ile Phe Thr Asp  Lys Lys Pro
    1370                 1375                 1380

Val Pro  Asp Pro Ile Asn Ile  Pro Pro Arg Glu Val  Lys Arg Tyr
    1385                 1390                 1395

Asn Glu  Leu Arg Asp Ser Tyr  Lys Lys Asn Thr Ala  His Val Pro
    1400                 1405                 1410

Lys Pro  Leu Gln Thr Phe Phe  Asn Gln Glu Ser Leu  Ala Asn Gly
    1415                 1420                 1425

Asp Leu  Val Tyr Phe Glu Val  Asn Gln Phe Gly Glu  Ala Ser Gln
    1430                 1435                 1440

Leu Thr  Pro Val Ser Ile Ser  Arg Thr Thr Asp Leu  Phe Pro Ile
    1445                 1450                 1455

Gly Gly  Arg Leu Pro Gln Gly  His Lys Asp Leu Phe  Pro Cys Thr
    1460                 1465                 1470

Ala Met  Cys Leu Ser Glu Cys  Lys Asn Cys Val Pro  Ala Ser Phe
    1475                 1480                 1485

Cys Glu  Phe His Ser Arg Ser  His Glu Lys Leu Cys  Pro Ala Cys
    1490                 1495                 1500

Ser Leu  Ala Gly Thr Thr Gly  Asn Arg Gly Arg Ile  Lys Phe Ser
    1505                 1510                 1515

Glu Ala  Trp Leu Ser Gly Leu  Pro Lys Trp His Ser  Val Ser Gln
    1520                 1525                 1530

Asp Asn  Val Gly Arg Gly Leu  Gly Val Thr Met Pro  Arg Leu Glu
    1535                 1540                 1545

Arg Ser  Arg Arg Thr Trp His  Leu Pro Thr Lys Asp  Ala Tyr Leu
    1550                 1555                 1560

Leu Gly  Gln Ser Ile Tyr Leu  Asn His Pro Val Pro  Ala Ile Leu
    1565                 1570                 1575
```

Pro Ser Asp Gln Val Pro Ser Glu Asn Asn Gln Thr Val Glu Pro
1580 1585 1590

Leu Gly Pro Lys Asn Ile Phe Ser Phe Gln Leu Ala Phe Asp Asn
1595 1600 1605

Leu Ser Ile Glu Glu Leu Gly Leu Leu Leu Tyr Ser Leu Glu Leu
1610 1615 1620

Glu Ser Gly Met Ala His Arg Leu Gly Arg Gly Arg Ala Leu Gly
1625 1630 1635

Met Gly Ser Val Gln Ile Ser Val Lys Asp Ile Gln Ile Arg Asp
1640 1645 1650

Asn Lys Ser Phe Leu Phe Ser Ser Asn Ile Ser Lys Lys Ser Glu
1655 1660 1665

Trp Ile Gln Cys Gly Lys Asp Glu Phe Ala Gln Glu Ala Trp Phe
1670 1675 1680

Gly Glu Ser Trp Asp Asn Ile Asp His Ile Gln Arg Leu Arg Gln
1685 1690 1695

Ala Leu Thr Ile Pro Val Lys Gly Asp Val Gly Cys Ile Arg Tyr
1700 1705 1710

Pro Lys Leu Glu Ala Glu Gly Gly Met Pro Asp Tyr Ile Lys Leu
1715 1720 1725

Arg Lys Arg Leu Thr Pro Leu Cys Asp Arg Glu Glu Pro Val Arg
1730 1735 1740

Tyr Arg Ile Asn Pro Val Gln Leu Ala Arg Met Ile Leu Pro Phe
1745 1750 1755

Val Pro Trp His Gly Ala Cys Pro Ala Leu Leu Asn Glu Gln Val
1760 1765 1770

Met Ile Glu Ala Lys Arg Leu Thr Glu Leu Leu Ala Gln Glu Asn
1775 1780 1785

Leu Asp Met Ile Cys Arg Thr Lys Asn Cys Ala Asn Cys Lys Gln
1790 1795 1800

Glu Thr Lys Lys Asp Cys Leu Ala Phe Arg Tyr Asp Arg Ala Asn
1805 1810 1815

Trp Pro Cys
1820

<210> SEQ ID NO 25
<211> LENGTH: 1940
<212> TYPE: PRT
<213> ORGANISM: Unknown
<220> FEATURE:
<221> NAME/KEY: source
<223> OTHER INFORMATION: /note="Description of Unknown:
Aquatic-marine-marine sediment sequence"

<400> SEQUENCE: 25

Met Lys Val Arg Ile Lys Phe Phe Glu Pro Ile Arg Val Met Pro Trp
1 5 10 15

Val Asn Pro Ser Asp Arg Lys Ile Ser Asn Glu Gln Phe Met Arg Gly
20 25 30

Gln Ser Phe Ala Arg Trp His Arg Tyr Asn Lys Asn Ser Asn Ser Gly
35 40 45

Lys Pro Phe Ile Thr Gly Thr Leu Val Arg Ser Ala Val Ile Arg Ala
50 55 60

Ala Glu Val Leu Leu Ser Leu Ser Asn Gly Ile Ile Glu Asn Lys Ala
65 70 75 80

Cys Cys Pro Gly Met Phe Glu Thr Glu Gly Ala Ala Arg Lys Lys Lys

```
                85                  90                  95

Met His Phe Arg Gln Arg Ser Thr Pro Lys Trp Thr Glu Asn Ser Thr
            100                 105                 110

Cys Asn Lys Asp Asn Gln Cys Pro Phe Cys Glu Leu Leu Gly Arg Phe
        115                 120                 125

Gly Asn Asp Glu Ile Gly Ala Val Ile Glu Lys Glu Asn Asn Thr Lys
    130                 135                 140

Arg Leu Lys Tyr Asn Phe His Phe Ser Asn Phe Gln Pro Ser Gly Asn
145                 150                 155                 160

Asn Ser Tyr Pro Asp His Ile Ile Ile Lys Arg Thr Val Asn Arg Val
                165                 170                 175

Asp Tyr Thr Thr Gly Lys Ala His Asp Phe Phe Thr Ile Ser Glu Ile
            180                 185                 190

Asp Asn Ser Phe Phe Pro Ala Phe Glu Gly His Ile Ser Ile Ser Asp
        195                 200                 205

Arg Val Ser His Glu Ala Lys Lys Leu Leu Ser Asp Ser Leu Lys Phe
    210                 215                 220

Ile Asp Lys Leu Cys Gly Ser Ile Cys Val Phe Glu Phe Asp Asp Ser
225                 230                 235                 240

Thr Trp Asp Asp His Leu His Ile Glu Lys Ser Met Glu Lys Asn Asp
                245                 250                 255

Gly Lys Glu Lys Ser Glu Glu Ile Thr Lys Gln Ile Ile Lys Ile Leu
            260                 265                 270

Glu Ser Asn Ser Lys Leu Asp Tyr Leu Arg Ile Leu Ser Asp Ala Ile
        275                 280                 285

Arg Glu Leu Ala Arg Asp Lys Glu Met Val His Lys Leu Pro Leu Asp
    290                 295                 300

Tyr Lys Gly Lys Lys Lys His Tyr Ile Trp Asp Leu Ala Tyr Asn Lys
305                 310                 315                 320

Ile Ser Ile Arg Glu Ile Leu Cys Asn Gln Ala Asn Lys Asn Ala Lys
                325                 330                 335

Asn Asp Tyr Val Glu Leu Cys Lys Thr Ile Gly Lys Glu Leu Tyr His
            340                 345                 350

Glu Ser Gln Lys Lys Thr Glu Leu Leu Thr Lys Pro His Arg Ile Leu
        355                 360                 365

Gly Ser Lys Ser Phe Tyr Gly Lys Pro Gln Arg Asp Ile Gln Pro Thr
    370                 375                 380

Asp Ala Lys Ile Val Pro Thr Glu Glu Thr Ile Phe Thr Gly Lys Leu
385                 390                 395                 400

Val Ser Glu Thr Pro Phe Phe Phe Gly Leu Glu Asn Glu Asp Lys Gln
                405                 410                 415

Gln Thr Asp Phe Thr Val Leu Leu Asp Ser Gln Asn Arg Phe Arg Ile
            420                 425                 430

Pro Arg Ser Ala Leu Arg Gly Val Leu Arg Arg Asp Ile Arg Met Met
        435                 440                 445

Ser Gly Gly Asn Gly Cys Asp Val Lys Leu Gly Gly Arg Gln Cys Leu
    450                 455                 460

Cys Pro Val Cys Arg Met Met Arg Asn Ile Thr Ile Met Asp Val Arg
465                 470                 475                 480

Ser Asn Lys Asp Ile Ile Pro Asp Ile Arg Gln Arg Ile Arg Ile Asn
                485                 490                 495

Pro Tyr Thr Gly Ser Val Ala Glu Gly Ala Leu Phe Ser Met Glu Leu
            500                 505                 510
```

```
Gly Pro Gln Gly Met Glu Phe Asp Phe Val Leu Arg Phe Arg Gly Asn
        515                 520                 525

Asp Ser Ile Pro Lys Ser Leu Lys Lys Val Leu Leu Cys Trp Ala Lys
    530                 535                 540

Gly Gln Ala Phe Leu Ser Gly Ala Ser Ser Thr Gly Lys Gly Arg Phe
545                 550                 555                 560

Lys Leu Lys Asn Leu Lys Phe Lys Ser Phe Asp Leu Ser Thr Lys Glu
                565                 570                 575

Ile Arg Asn Asp Tyr Leu Asn Gln Arg Gly Trp Arg Asn Arg Glu Asn
            580                 585                 590

Glu Leu Pro Leu Glu Pro Leu Phe Leu Thr Asp Lys Tyr Lys Glu Ile
        595                 600                 605

Asn Thr Thr Leu Trp Asn Lys Val Ser Val Glu Ile Lys Leu Ser Ser
    610                 615                 620

Pro Phe Leu Asn Gly Asp Pro Val Arg Ser Leu Val Gln Gly Gln Gly
625                 630                 635                 640

Ala Asp Ile Val Ser Phe Lys Lys Thr Ser Leu Ile Asp Asp Glu Asp
                645                 650                 655

Ile Tyr Ala Tyr Lys Ala Glu Ser Leu Lys Gly Ile Phe Arg Thr Ala
            660                 665                 670

Leu Ala Arg Arg Phe His Tyr Lys Asp Lys Ile Ser Gln Lys Val Leu
        675                 680                 685

Pro Leu Thr Ala Ile Ser His Lys Asp Cys Asp Cys Pro Leu Cys Arg
    690                 695                 700

Leu Phe Gly Ser Glu Phe Glu Thr Gly Lys Ile Arg Phe Glu Asp Leu
705                 710                 715                 720

Glu Phe Ser Thr Asn Pro Ile Pro Lys Lys Phe Asp His Val Ala Ile
                725                 730                 735

Asp Arg Phe Thr Gly Gly Ala Val Asp Lys Lys Lys Phe Asp Asp Cys
            740                 745                 750

Ala Leu Ser Ala Thr Lys Gln Lys Pro Leu Leu Leu Lys Gly Asn Phe
        755                 760                 765

Trp Leu Arg Pro Asp Met Thr Lys Asp Asp Phe Lys Tyr Phe Glu Lys
    770                 775                 780

Ala Phe Leu Asp Ile Lys Ser Gly Phe Tyr Pro Leu Gly Ala Lys Ser
785                 790                 795                 800

Gly Ile Gly Tyr Gly Gln Ile Glu Asp Ile Ser Ile Ser Ile Ser Asp
                805                 810                 815

Ser Asp Asp Tyr Pro Arg Ala Ile Lys Glu Asn Ile Lys Thr Ile Asn
            820                 825                 830

Asn Lys Ser Tyr Thr Gln Glu Ala Lys Asn Asn Ile Asn Asp Lys Asp
        835                 840                 845

Thr Asp Glu Ser Lys Gln Ser Asp Phe Gln Ile Asp Leu Lys Asp Asp
    850                 855                 860

Ala Ile Tyr Tyr Pro His Tyr Phe Leu Lys Pro Asn Lys Lys Val Asp
865                 870                 875                 880

Arg Lys Thr Ile Pro Ile Asn His Leu Thr Leu His Asp Glu Cys His
                885                 890                 895

Thr Gly Lys Ile Val Cys Thr Leu Thr Thr Lys Thr Pro Leu Ile Ile
            900                 905                 910

Pro Asp Thr Glu Asn Asp Asp Ala Phe Gly Leu Lys Lys Ala Lys Leu
        915                 920                 925
```

```
Ala Glu Asp Gly Glu Lys Tyr His Lys Ser Tyr Ser Phe Phe Ser Val
    930                 935                 940

Asn Asp Glu Ile Met Ile Ser Gly Ser Glu Ile Arg Gly Met Ile Ser
945                 950                 955                 960

Ser Ile Tyr Glu Ala Ile Thr Asn Ser Cys Phe Arg Ile Phe Glu Glu
                965                 970                 975

Lys His Arg Leu Ser Trp Arg Met Glu Ala Val Pro Glu Val Leu Glu
            980                 985                 990

Lys Phe Ile Pro Gly Arg Ile Ile  Lys Ile Asn Gly Glu  Leu Lys Met
        995                 1000                1005

Val Glu  Met Glu Glu Val Arg  Tyr Pro Phe Tyr Asp  Lys Asn Cys
    1010                1015                1020

Pro Asp  Thr Lys Thr Gln Lys  Asp His Phe Ser Ser  Lys Gly Lys
    1025                1030                1035

Gly Lys  Leu Tyr Tyr Glu Gln  Pro Thr Phe Ser Asp  Lys Met Ile
    1040                1045                1050

Leu Ser  Leu Ser Glu Tyr Asn  Arg Lys His Gln Asn  Pro Gly Lys
    1055                1060                1065

Lys Glu  Lys Tyr Lys Ile Ile  Lys Pro Asp Ser Lys  Ser Asn Ala
    1070                1075                1080

Asn Phe  Met Phe Thr Ala Thr  Pro Ala Asn Asn Thr  Glu Gly Tyr
    1085                1090                1095

Asp Met  Asp Cys Val His Lys  His Ser Val Lys Gly  Tyr Leu Lys
    1100                1105                1110

Val Ser  Gly Pro Asn Lys Ile  Glu Lys Glu Arg Thr  Asp Gln Pro
    1115                1120                1125

Ala Ser  Asn Lys Ile Pro Met  Glu Asn Glu Ile Val  Ile His Gln
    1130                1135                1140

Lys Thr  Asn Arg Arg Glu Ile  Thr Val Gln Asn Ala  Lys Lys Asn
    1145                1150                1155

Lys Lys  Arg Tyr Arg Leu Ile  Pro Glu Tyr Ile Cys  Ser Glu Lys
    1160                1165                1170

Asp Thr  Asn Tyr Ile Met Asn  Lys Arg Cys Glu Arg  Val Phe Ile
    1175                1180                1185

Glu Pro  Glu Lys Cys Asn His  Asp Gly Ile Pro Ile  Ser Lys Asn
    1190                1195                1200

Ala Ile  Glu Leu Phe Lys His  Leu Val Asp Glu Tyr  Lys Lys Asn
    1205                1210                1215

Ala Asp  Gln Gln Glu Thr Pro  Lys Val Phe Arg Thr  Lys Leu Pro
    1220                1225                1230

Glu Lys  Gly Glu Leu Lys Glu  Gly Ser Leu Val Tyr  Phe Arg Lys
    1235                1240                1245

Asp Ser  Asn Glu Val Val Glu  Ile Ile Pro Val Lys  Ile Ser Arg
    1250                1255                1260

Lys Ile  Asp Asp Arg Phe Ile  Gly Lys Arg Leu Thr  Lys Asn Leu
    1265                1270                1275

Arg Pro  Cys His Gly Glu Trp  Ile Glu Lys Asp Asp  Leu Ser Ile
    1280                1285                1290

Leu Asp  Gln Tyr Pro Glu Lys  Lys Leu Phe Thr Arg  His Pro Lys
    1295                1300                1305

Gly Leu  Cys Pro Ala Cys Gln  Leu Phe Gly Thr Gly  Ala Tyr Lys
    1310                1315                1320

Gly Arg  Leu Arg Phe Gly Phe  Ala Thr Leu Thr Asn  Lys Pro Glu
```

```
    1325                1330                1335

Trp Leu  Asn Lys Glu Asp Lys  Asp His Lys Leu Thr  Leu Pro Leu
    1340                1345                1350

Leu Glu  Arg Pro Arg Pro Thr  Trp Ala Ile Pro Asp  Ala Thr Gln
    1355                1360                1365

Ala Ser  Lys Val Pro Gly Arg  Lys Phe Phe Ile His  His His Ala
    1370                1375                1380

Trp Thr  Asp Ile Glu Lys Gly  Ile Asp Pro Val Thr  Gly Lys Ala
    1385                1390                1395

Ile Gln  Ile Asp Val Asn Asn  Arg Thr Val Gln Pro  Leu Asp Ser
    1400                1405                1410

Asn Asn  Thr Phe Thr Phe Glu  Ile Asn Phe Glu Asn  Leu Glu Pro
    1415                1420                1425

His Glu  Leu Gly Leu Leu Leu  Tyr Ser Leu Gln Leu  Glu Asn Ser
    1430                1435                1440

Leu Ser  His Lys Leu Gly Met  Gly Lys Ala Phe Gly  Phe Gly Ser
    1445                1450                1455

Ile Asp  Ile Lys Val Glu Asn  Leu Leu Leu Phe Asp  Ser Thr Ile
    1460                1465                1470

Asp Lys  Tyr Lys Asn Lys Thr  Asp Gln Val Lys Arg  Phe Val Asp
    1475                1480                1485

Glu Gly  Lys Asn Asn Leu Leu  Glu Ile Phe Glu Asn  Glu Phe Asp
    1490                1495                1500

Asp Ile  Glu His Ile Lys Asp  Leu Lys Ser Leu Leu  Tyr Phe Pro
    1505                1510                1515

Asn Asp  Lys Asn Ile Arg Val  Gln Tyr Pro Leu Leu  Arg Lys Glu
    1520                1525                1530

Asp Tyr  Pro Asp Lys Asp Leu  Pro Gly Tyr Lys Glu  Leu Lys Asp
    1535                1540                1545

Asn Phe  Ser Asn Gly Ile Gln  Ile Arg His Asn Leu  Leu Thr Ile
    1550                1555                1560

Pro Trp  Ser Pro Trp Ala Tyr  Gln Ser Lys Lys Lys  Leu Glu Asn
    1565                1570                1575

Glu Lys  Thr Ile Tyr Pro Pro  Leu Lys Lys Ile Glu  Ile Asn Asn
    1580                1585                1590

Tyr Tyr  Asp Ile Lys Lys Val  Asn Ile Lys Ile Pro  Asp Asn Ala
    1595                1600                1605

Gln Trp  Val Phe Leu Thr Gly  Asn Asn Ser Ile Gly  Lys Ser Leu
    1610                1615                1620

Phe Leu  Lys Ala Ile Ala Thr  Gly Leu Tyr Gly Lys  Ile Thr Glu
    1625                1630                1635

Asp Asp  Glu Asn Asp Ile Asp  Thr Asn Cys Gly Ile  Arg Val Phe
    1640                1645                1650

Ile Thr  Asn Glu Trp Val Asn  Asp Val Lys Lys Asp  Tyr Phe Asn
    1655                1660                1665

Gln Lys  Leu Ser Tyr Lys Asn  Tyr Ala Thr Tyr Gly  Pro Ser Arg
    1670                1675                1680

Leu Asn  Lys Leu Ala Glu Gly  Lys Lys Thr Lys Phe  Pro Tyr Phe
    1685                1690                1695

Ser Leu  Phe Asn Thr Glu Gly  Val Phe Tyr His Asp  Ile Glu Lys
    1700                1705                1710

Glu Phe  Ile Lys Trp Cys Asp  Arg Asp Ser Ser Lys  Phe Asn Leu
    1715                1720                1725
```

```
Leu Lys  Asn Ile Phe Ile Lys  Leu Leu Pro Thr Ile  Asp Asp Ile
    1730                 1735                 1740

Lys Gly  Ile Gln Thr Lys Thr  Asp Phe Tyr Ile Gly  Tyr Lys Glu
    1745                 1750                 1755

Met Glu  Thr Gly Lys Tyr Glu  Lys Gln Ser Lys Leu  Ala Thr Gly
    1760                 1765                 1770

Asn Ile  Ser Ile Leu Arg Met  Phe Gly Asp Met Phe  Ile Arg Phe
    1775                 1780                 1785

Ser Lys  Glu Gln Pro Asp Thr  Leu Pro Glu Asp Phe  Ser Gly Ile
    1790                 1795                 1800

Val Ile  Ile Asp Glu Leu Asp  Leu His Leu His Pro  Ile Trp Leu
    1805                 1810                 1815

Lys Lys  Ile Pro Gly Leu Val  Ser Lys Leu Phe Pro  Lys Ile Arg
    1820                 1825                 1830

Phe Ile  Ala Ser Thr His Ser  Ala Ile Pro Phe Leu  Gly Ala Pro
    1835                 1840                 1845

Lys Asn  Ser Val Tyr Leu Asn  Val Ile Arg Asp Glu  Asp Asn Asn
    1850                 1855                 1860

Ile His  Val Gln Glu Ile Asp  Ile Asp Leu Thr Asn  Leu Leu Pro
    1865                 1870                 1875

Asn Thr  Ile Leu Thr Ser Pro  Leu Phe Asn Met Glu  Asp Ile Thr
    1880                 1885                 1890

Gln Ile  Asn Leu Pro Asp Ile  Thr Asp Val Arg Thr  Glu Asp Thr
    1895                 1900                 1905

Tyr Lys  Glu Ile Ile Glu Ile  Asp Lys Ile Lys Ala  Arg Leu Lys
    1910                 1915                 1920

Lys Phe  Ala Lys Lys Asp Thr  Leu Phe Pro Asp Lys  Leu Phe Lys
    1925                 1930                 1935

Glu Leu
    1940


<210> SEQ ID NO 26
<211> LENGTH: 1812
<212> TYPE: PRT
<213> ORGANISM: Unknown
<220> FEATURE:
<221> NAME/KEY: source
<223> OTHER INFORMATION: /note="Description of Unknown:
      Anammox bioreactor sequence"

<400> SEQUENCE: 26

Met Ser Lys Lys His Phe Ile His Leu Thr Phe Leu Glu Pro Tyr Arg
1               5                   10                  15

Leu Ala Glu Trp His Ala Lys Ala Asp Arg Lys Lys Asn Lys Arg Tyr
            20                  25                  30

Leu Arg Gly Met Ser Phe Ala Gln Trp His Lys Asp Lys Asp Gly Ile
        35                  40                  45

Gly Lys Pro Tyr Ile Thr Gly Thr Leu Leu Arg Ser Ala Val Leu Asn
    50                  55                  60

Ala Ala Glu Glu Leu Ile Ser Leu Asn Gln Gly Met Trp Ala Lys Glu
65                  70                  75                  80

Pro Cys Cys Asn Gly Lys Phe Glu Thr Glu Lys Asp Lys Pro Ala Val
                85                  90                  95

Leu Arg Lys Arg Pro Thr Ile Gln Trp Lys Thr Gly Arg Pro Ala Ile
            100                 105                 110
```

```
Cys Asp Pro Glu Lys Gln Glu Lys Lys Asp Ala Cys Pro Leu Cys Met
        115                 120                 125

Leu Leu Gly Arg Phe Asp Lys Ala Gly Lys Arg His Arg Asp Asn Lys
    130                 135                 140

Tyr Asp Lys His Asp Tyr Asp Ile His Phe Asp Asn Leu Asn Leu Ile
145                 150                 155                 160

Thr Asp Lys Lys Phe Ser His Pro Asp Asp Ile Ala Ser Glu Arg Ile
                165                 170                 175

Leu Asn Arg Val Asp Tyr Thr Thr Gly Lys Ala His Asp Tyr Phe Lys
            180                 185                 190

Val Trp Glu Val Asp Asp Asp Gln Trp Trp Gln Phe Thr Gly Thr Ile
        195                 200                 205

Thr Met His Asp Asp Cys Ser Lys Ala Lys Gly Leu Leu Leu Ala Ser
    210                 215                 220

Leu Cys Phe Val Asp Lys Leu Cys Gly Ala Leu Cys Arg Ile Glu Val
225                 230                 235                 240

Thr Gly Asn Asn Ser Gln Asp Glu Asn Lys Glu Tyr Ala His Pro Asp
                245                 250                 255

Thr Gly Ile Ile Thr Ser Leu Asn Leu Lys Tyr Gln Asn Asn Ser Thr
            260                 265                 270

Ile His Gln Asp Ala Val Pro Leu Ser Gly Ser Ala His Asp Asn Asp
        275                 280                 285

Glu Pro Pro Val His Asp Asn Asp Ser Ser Leu Asp Asn Asp Thr Ile
    290                 295                 300

Thr Leu Leu Ser Met Lys Ala Lys Glu Ile Val Gly Ala Phe His Glu
305                 310                 315                 320

Ser Gly Lys Ile Glu Lys Ala Arg Thr Leu Ala Asp Val Ile Arg Ala
                325                 330                 335

Met Arg Leu Gln Lys Pro Asp Ile Trp Glu Lys Leu Pro Lys Gly Ile
            340                 345                 350

Asn Asp Lys His His Leu Trp Asp Arg Glu Val Asn Gly Lys Lys Leu
        355                 360                 365

Arg Asn Ile Leu Glu Glu Leu Trp Arg Leu Met Ser Lys Arg Asn Ala
    370                 375                 380

Trp Arg Thr Phe Cys Glu Val Leu Gly Asn Glu Leu Tyr Arg Cys Tyr
385                 390                 395                 400

Lys Glu Lys Thr Gly Gly Ile Val Leu Arg Phe Arg Thr Leu Gly Glu
                405                 410                 415

Thr Glu Tyr Tyr Pro Glu Pro Glu Lys Thr Glu Pro Cys Leu Ile Ser
            420                 425                 430

Asp Asn Ser Ile Pro Ile Thr Pro Leu Gly Gly Val Lys Glu Trp Ile
        435                 440                 445

Ile Ile Gly Arg Leu Lys Ala Glu Thr Pro Phe Tyr Phe Gly Ala Gln
    450                 455                 460

Ser Ser Phe Asp Ser Thr Gln Asp Asp Leu Asp Leu Val Pro Asp Ile
465                 470                 475                 480

Val Asn Thr Asp Glu Lys Leu Glu Ala Asn Glu Gln Thr Ser Phe Arg
                485                 490                 495

Ile Leu Met Asp Lys Lys Gly Arg Tyr Arg Ile Pro Arg Ser Leu Ile
            500                 505                 510

Arg Gly Val Leu Arg Arg Asp Leu Arg Thr Ala Phe Gly Gly Ser Gly
        515                 520                 525

Cys Ile Val Glu Leu Gly Arg Met Ile Pro Cys Asp Cys Lys Val Cys
```

```
    530                 535                 540

Ala Ile Met Arg Lys Ile Thr Val Met Asp Ser Arg Ser Glu Asn Ile
545                 550                 555                 560

Glu Leu Pro Asp Ile Arg Tyr Arg Ile Arg Leu Asn Pro Tyr Thr Ala
                565                 570                 575

Thr Val Asp Glu Gly Ala Leu Phe Asp Met Glu Ile Gly Pro Glu Gly
            580                 585                 590

Ile Thr Phe Pro Phe Val Phe Arg Tyr Arg Gly Glu Asp Ala Leu Pro
        595                 600                 605

Arg Glu Leu Trp Ser Val Ile Arg Tyr Trp Met Asp Gly Met Ala Trp
    610                 615                 620

Leu Gly Gly Ser Gly Ser Thr Gly Lys Gly Arg Phe Ala Leu Ile Asp
625                 630                 635                 640

Ile Lys Val Phe Glu Trp Asp Leu Cys Asn Glu Glu Gly Leu Lys Ala
                645                 650                 655

Tyr Ile Cys Ser Arg Gly Leu Arg Gly Ile Glu Lys Glu Val Leu Leu
            660                 665                 670

Glu Asn Lys Thr Ile Thr Glu Ile Thr Asn Leu Phe Lys Thr Glu Glu
        675                 680                 685

Val Lys Phe Phe Glu Ser Tyr Ser Lys His Ile Lys Gln Leu Cys His
    690                 695                 700

Glu Gly Ile Ile Asn Gln Met Ser Phe Ser Gly Gly Leu Arg Ser Tyr
705                 710                 715                 720

His Glu Tyr Leu Ser Pro Leu Trp Thr Glu Val Lys Tyr Glu Ile Lys
                725                 730                 735

Ile Ala Ser Pro Leu Leu Ser Ser Asp Thr Ile Ser Ala Leu Leu Asn
            740                 745                 750

Lys Asp Asn Ile Asp Cys Ile Ala Tyr Glu Lys Arg Lys Trp Glu Asn
        755                 760                 765

Gly Gly Ile Lys Phe Val Pro Thr Ile Lys Gly Glu Thr Ile Arg Gly
    770                 775                 780

Ile Val Arg Met Ala Val Gly Lys Arg Ser Gly Asp Leu Gly Met Asp
785                 790                 795                 800

Asp His Glu Asp Cys Ser Cys Thr Leu Cys Thr Ile Phe Gly Asn Glu
                805                 810                 815

His Glu Ala Gly Lys Leu Arg Phe Glu Asp Leu Glu Val Val Glu Glu
            820                 825                 830

Lys Leu Pro Ser Glu Gln Asn Ser Asp Ser Asn Lys Ile Pro Phe Gly
        835                 840                 845

Pro Val Gln Asp Gly Asp Gly Asn Arg Glu Lys Glu Cys Val Ala Glu
    850                 855                 860

Val Lys Ile Tyr Lys Lys Lys Leu Ile Asp His Val Ala Ile Asp Arg
865                 870                 875                 880

Phe His Gly Gly Ala Glu Asp Lys Met Lys Phe Asn Thr Leu Pro Leu
                885                 890                 895

Val Gly Ser Pro Glu Arg Pro Ile Ile Leu Lys Gly Arg Phe Trp Ile
            900                 905                 910

Lys Lys Asp Met Val Lys Asp Tyr Arg Lys Lys Ile Glu Asp Ala Met
        915                 920                 925

Val Asp Ile Arg Asp Gly Leu Tyr Pro Ile Gly Gly Lys Thr Gly Ile
    930                 935                 940

Gly Tyr Gly Trp Val Thr Asp Leu Thr Ile Leu Asn Pro Gln Ser Gly
945                 950                 955                 960
```

```
Phe Gln Ile Pro Val Lys Lys Asp Ile Ser Pro Glu Pro Gly Thr Tyr
                965                 970                 975

Leu Thr Tyr Pro Ser Tyr Ser Ala Pro Ser Leu Asn Arg Gly His Ile
            980                 985                 990

Tyr Tyr Pro His Tyr Phe Leu Ala  Pro Ala Asn Thr Val  His Arg Glu
        995                 1000                1005

Gln Glu  Met Ile Gly His Glu  Gln Phe His Lys Glu  Gln Lys Gly
    1010                 1015                 1020

Glu Leu  Leu Val Ser Gly Lys  Ile Val Cys Thr Leu  Lys Thr Val
    1025                 1030                 1035

Thr Pro  Leu Ile Ile Pro Asp  Thr Glu Asn Glu Asp  Ala Phe Gly
    1040                 1045                 1050

Leu Gln  Asn Thr Tyr Ser Gly  His Lys Asn Tyr Gln  Phe Phe His
    1055                 1060                 1065

Ile Asn  Asp Glu Ile Met Val  Pro Gly Ser Glu Ile  Arg Gly Met
    1070                 1075                 1080

Ile Ser  Ser Val Tyr Glu Ala  Ile Thr Asn Ser Cys  Phe Arg Val
    1085                 1090                 1095

Tyr Asp  Glu Thr Lys Tyr Ile  Thr Arg Arg Leu Ser  Ser Glu Lys
    1100                 1105                 1110

Lys Asp  Glu Ser Asn Asp Lys  Asn Lys Ser Gln Asp  Asp Ala Ser
    1115                 1120                 1125

Gln Lys  Ile Arg Lys Gly Leu  Val Lys Lys Thr Asp  Glu Gly Phe
    1130                 1135                 1140

Ser Ile  Ile Glu Val Glu Arg  Tyr Ser Met Lys Thr  Lys Gly Arg
    1145                 1150                 1155

Thr Lys  Leu Val Asp Lys Val  Tyr Arg Leu Pro Leu  Tyr Asp Ser
    1160                 1165                 1170

Glu Ala  Val Ile Ala Ser Ile  Lys Phe Glu Gln Tyr  Gly Glu Lys
    1175                 1180                 1185

Asn Glu  Lys Arg Asn Ala Lys  Ile Leu Ala Ala Ile  Lys Arg Asn
    1190                 1195                 1200

Asn Val  Ile Ala Glu Val Ala  Arg Lys Asn Leu Ile  Phe Leu Arg
    1205                 1210                 1215

Ser Leu  Thr Pro Glu Glu Leu  Lys Lys Val Leu Gln  Gly Glu Ile
    1220                 1225                 1230

Leu Val  Lys Phe Ser Leu Lys  Ser Gly Glu Asn Pro  Asn Asp Tyr
    1235                 1240                 1245

Leu Ala  Glu Leu His Glu Asn  Gly Thr Glu Arg Gly  Leu Ile Lys
    1250                 1255                 1260

Phe Thr  Gly Leu Asn Met Val  Asn Ile Lys Asn Val  Asn Glu Glu
    1265                 1270                 1275

Asp Lys  Asp Phe Asn Asp Thr  Trp Asp Trp Glu Lys  Leu Asn Ile
    1280                 1285                 1290

Phe His  Asn Ala His Glu Lys  Arg Asn Ser Leu Lys  Gln Gly Tyr
    1295                 1300                 1305

Pro Arg  Pro Val Leu Lys Phe  Ile Lys Asp Arg Val  Glu Tyr Thr
    1310                 1315                 1320

Ile Pro  Lys Arg Cys Glu Arg  Ile Phe Cys Ile Pro  Val Lys Asn
    1325                 1330                 1335

Thr Ile  Glu Tyr Lys Val Ser  Ser Lys Val Cys Lys  Gln Tyr Lys
    1340                 1345                 1350
```

```
Asp Val  Leu Ser Asp Tyr Glu  Lys Asn Phe Gly His  Ile Asn Lys
    1355                 1360                 1365

Ile Phe  Thr Thr Lys Ile Gln  Lys Arg Glu Leu Thr  Asp Gly Asp
    1370                 1375                 1380

Leu Val  Tyr Phe Ile Pro Asn  Glu Gly Ala Asp Lys  Thr Val Gln
    1385                 1390                 1395

Ala Ile  Met Pro Val Pro Leu  Ser Arg Ile Thr Asp  Ser Arg Thr
    1400                 1405                 1410

Leu Gly  Glu Arg Leu Pro His  Lys Asn Leu Leu Pro  Cys Val His
    1415                 1420                 1425

Glu Val  Asn Glu Gly Leu Leu  Ser Gly Ile Leu Asp  Ser Leu Asp
    1430                 1435                 1440

Lys Lys  Leu Leu Ser Ile His  Pro Glu Gly Leu Cys  Pro Thr Cys
    1445                 1450                 1455

Arg Leu  Phe Gly Thr Thr Tyr  Tyr Lys Gly Arg Val  Arg Phe Gly
    1460                 1465                 1470

Phe Ala  Asn Leu Ile Asn Lys  Pro Lys Trp Leu Thr  Glu Arg Glu
    1475                 1480                 1485

Asn Gly  Cys Gly Gly Tyr Val  Thr Leu Pro Leu Leu  Glu Arg Pro
    1490                 1495                 1500

Arg Leu  Thr Trp Ser Val Pro  Ser Asp Lys Cys Asp  Val Pro Gly
    1505                 1510                 1515

Arg Lys  Phe Tyr Val His His  Asn Gly Trp Gln Glu  Val Leu Arg
    1520                 1525                 1530

Asn Asn  Asp Ile Thr Pro Lys  Thr Glu Asn Asn Arg  Thr Val Glu
    1535                 1540                 1545

Pro Leu  Ala Ala Asp Asn Arg  Phe Thr Phe Asp Val  Tyr Phe Glu
    1550                 1555                 1560

Asn Leu  Arg Glu Trp Glu Leu  Gly Leu Leu Cys Tyr  Cys Leu Glu
    1565                 1570                 1575

Leu Glu  Pro Gly Met Gly His  Lys Leu Gly Met Gly  Lys Pro Leu
    1580                 1585                 1590

Gly Phe  Gly Ser Val Lys Ile  Ala Ile Glu Arg Leu  Gln Thr Phe
    1595                 1600                 1605

Thr Val  His Gln Asp Asp Ile  Asn Trp Lys Pro Ser  Glu Asn Glu
    1610                 1615                 1620

Ile Gly  Val Tyr Val Gln Arg  Gly Arg Glu Lys Leu  Val Glu Trp
    1625                 1630                 1635

Phe Thr  Pro Ser Asp Ser His  Lys Asn Met Glu Trp  Asn Glu Val
    1640                 1645                 1650

Lys His  Ile Lys Asp Leu Arg  Ser Leu Leu Ser Ile  Pro Asp Asp
    1655                 1660                 1665

Lys Pro  Thr Val Lys Tyr Pro  Ala Leu Asn Lys Gly  Ala Glu Gly
    1670                 1675                 1680

Ala Ile  Ser Asp Tyr Thr Tyr  Glu Arg Leu Ser Asp  Thr Lys Leu
    1685                 1690                 1695

Leu Pro  His Asp Lys Arg Val  Glu Tyr Leu Arg Thr  Pro Trp Gly
    1700                 1705                 1710

Pro Trp  Asn Ala Phe Val Lys  Glu Ala Glu Tyr Ser  Thr Ser Glu
    1715                 1720                 1725

Asn Ser  Asp Glu Lys Gly Arg  Glu Thr Ile Arg Thr  Lys Pro Lys
    1730                 1735                 1740

Ser Leu  Pro Ser Val Lys Ser  Ile Gly Lys Val Lys  Trp Phe Asp
```

```
    1745                1750                1755

Glu Gly  Lys Gly Phe Gly Ile  Leu Ile Met Asp Asp  Gly Lys Glu
    1760                1765                1770

Val Ser  Ile Ser Lys Asn Ser  Ile Arg Gly Asn Asn  Leu Leu Lys
    1775                1780                1785

Lys Asp  Gln Lys Val Thr Phe  His Ile Val Gln Gly  Leu Ile Pro
    1790                1795                1800

Lys Ala  Glu Asp Ile Glu Ile  Ala Lys
    1805                1810
```

<210> SEQ ID NO 27
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 27
gttatgaaac aagagaagga cttaatgtca cggtac 36

<210> SEQ ID NO 28
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 28
gttggtgcat cagcccggaa ttatgatgtt ttggtac 37

<210> SEQ ID NO 29
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 29
ggttggaaag ccggttttct ttgatgtcac ggaac 35

<210> SEQ ID NO 30
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 30
attgccccag ccgataaacc cttaatgtca cggaac 36

<210> SEQ ID NO 31
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 31
atagatatag acagaagctt ttaatgtgat gggac 35

<210> SEQ ID NO 32
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 32
gttggaaaag ccggttttat ttgatgtcac ggaac 35

<210> SEQ ID NO 33
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 33
attgggggga ttagattctg ataatgtcac ggtac 35

<210> SEQ ID NO 34
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 34
ggttggattc agccccagat gttttatgtg acggaac 37

<210> SEQ ID NO 35
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 35
gttaaggaga gacggcattc attgatgtca cggcac 36

<210> SEQ ID NO 36
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 36
gttagcatca ggacaatacc ttcgatgtta cgggac 36

<210> SEQ ID NO 37
<211> LENGTH: 35
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 37
gttccgtgac atcaaaagcc gtccatttct caaac 35

<210> SEQ ID NO 38
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 38
cttgaagact aaaggaagga attgatgtca cggtac 36

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

```
Ala Tyr Leu Val Gly Leu Tyr Thr Leu Thr Pro Thr His Pro Gly Ser
1               5                   10                  15

Gly Thr Glu Leu Gly Val Val Asp Gln Pro Ile Gln Arg Glu Arg His
            20                  25                  30

Thr Gly Phe Pro Val Ile Trp Gly Gln Ser Leu Lys Gly Val Leu Arg
        35                  40                  45

Ser Tyr Leu Lys Leu Val Glu Lys Val Asp Glu Glu Lys Ile Asn Lys
    50                  55                  60

Ile Phe Gly Pro Pro Thr Glu Lys Ala His Glu Gln Ala Gly Leu Ile
65                  70                  75                  80

Ser Val Gly Asp Ala Lys Ile Leu Phe Phe Pro Val Arg Ser Leu Lys
                85                  90                  95

Gly Val Tyr Ala Tyr Val Thr Ser Pro Leu Val Leu Asn Arg Phe Lys
            100                 105                 110

Arg Asp Leu Glu Leu Ala Gly Val
        115                 120
```

<210> SEQ ID NO 51
<211> LENGTH: 68
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

```
His His His His Asp Met Leu Asn Ser Leu His Ala Ile Thr Gly Lys
1               5                   10                  15

Phe Lys Thr Gln Ser Arg Leu Val Val Gly Leu Gly Asp Glu Ser Val
            20                  25                  30

Tyr Glu Thr Ser Ile Arg Leu Leu Arg Asn Tyr Gly Val Pro Tyr Ile
        35                  40                  45
```

```
Pro Gly Ser Ala Ile Lys Gly Val Thr Arg His Leu Thr Tyr Tyr Val
    50                  55                  60

Leu Ala Glu Phe
65


<210> SEQ ID NO 52

<400> SEQUENCE: 52

000


<210> SEQ ID NO 53

<400> SEQUENCE: 53

000


<210> SEQ ID NO 54

<400> SEQUENCE: 54

000


<210> SEQ ID NO 55

<400> SEQUENCE: 55

000


<210> SEQ ID NO 56

<400> SEQUENCE: 56

000


<210> SEQ ID NO 57

<400> SEQUENCE: 57

000


<210> SEQ ID NO 58

<400> SEQUENCE: 58

000


<210> SEQ ID NO 59

<400> SEQUENCE: 59

000


<210> SEQ ID NO 60

<400> SEQUENCE: 60

000


<210> SEQ ID NO 61

<400> SEQUENCE: 61

000


<210> SEQ ID NO 62
```

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (4)..(4)
<223> OTHER INFORMATION: a, c, t or g
<220> FEATURE:
<221> NAME/KEY: modified_base
<222> LOCATION: (9)..(9)
<223> OTHER INFORMATION: a, c, t or g

<400> SEQUENCE: 99
tgtnwyggna c 11

<210> SEQ ID NO 100
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (5)..(5)
<223> OTHER INFORMATION: a, c, t or g
<220> FEATURE:
<221> NAME/KEY: modified_base
<222> LOCATION: (7)..(7)
<223> OTHER INFORMATION: a, c, t or g
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (16)..(16)
<223> OTHER INFORMATION: a, c, t or g

<400> SEQUENCE: 100
gttrnrnanm rmcrsnwdyy wttratgtba cggdac 36

<210> SEQ ID NO 101
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 101
accggctttt cca 13

<210> SEQ ID NO 102
<211> LENGTH: 338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 102
ttttccgaat cggatgtggg attgctccgg ccctgcctta ttttcatata agaccggctt 60
atccgactat ctccctaata tgacagggaa aatatcttcc cggacttttc accgggatgg 120
tataagaaca gggaaccaga atcatctgtt ccctgaccac tggaaagttt ttcatatcag 180
tatgttgaat cctgtcaccc ctggggcacg gagggatttc caaatatccg atctgatgtt 240
cgtaatcacc ggcttttcca gccaatggct tgagatgatt taagaaactt gtgactggct 300
ttttctggta aaatggattt ttgtataata tcctgttg 338

<210> SEQ ID NO 103
<211> LENGTH: 791
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 103
agagtcagga caacactctg taccatagtt gtgggataca gaaagccttt gattaccatc 60
ggaaatccca caaacatccc aatgtgtata taatgatttg atctcagcta tgcgttcctg 120
gtataagttt cttttcggtt ttgcctgcat tgtattaacc tcttttcttc ataaataata 180
aaattataaa atactaaacg ttgaaatatt atgcatctcc ttctcgaaaa atcagatcat 240
ataaaatcaa tttcacccct caccataata agacgtacac tgtgggtgaa aagtgacact 300
ctttttaaat atttttaaat tcaaataact gtttatattg agcaaatgga aatgcatcct 360
ttcctcgtgt tatcatcagt gctgtcattt gaattaatcg tatttaatgg agaaaaggtg 420
acaatttttt ataaaaagac ttgtacaaaa aaattaaatt gtactgaact tttttttgtc 480
actttggttt ggtgattaac gactgaatat attagagtat ttttttctct ttttattctt 540
gaaaaaattg ttcttgaata acagtgttta cttaactaaa gtacctctaa taaatatttg 600
ttcacaccaa aaacagtaag gttataaaga agaaatctgt catgaacaat acagaagaaa 660
acattgaccg tatccaggaa ccgaccagag aagacattga tagaaaagaa gcagaacggc 720
ttcttgatga ggcttttaat ccaaggacca aacccgtcga taggaagaag ataattaatt 780
ctgccctgaa g 791

<210> SEQ ID NO 104
<211> LENGTH: 304
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 104
aagttgaaga gtgtatccat tactgaaaag ggtcaacgca catatcctgt agatgcatcc 60
ggtagcagga tagcggaaga ggtcagggat tatacgcaga aaccactaaa cgttgttgtg 120
ctgattatta aatatacata tgaagagtaa cgatatgaac atcactgtag aactcacctt 180
ctttgaaccc taccgtctgg ttgagtggtt tgactgggac gcaagaaaaa agagtcatag 240
cgcaatgaga ggtcaggctt tcgcgcagtg gacgtggaaa ggaaaaggtc gcacagcagg 300
caag 304

<210> SEQ ID NO 105
<211> LENGTH: 680
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 105
agcaccgtta agaagtttgg attcatcagt aaaggtgatg gagaagatat ttttgaaaga 60
atcaaggaaa aatatattaa agcattggaa aacaatatac aattatttga gatctatttg 120
tcggatgaaa aggatactcg gaataaataa cagacaaacg gtttgcgaag aaatacgcga 180
cagggtgatt ggaccgtaac ctcatgatta tatgattgat acacgattta accctgactt 240
gccggttttt gaaaaagttc gcaaaccctg ttttgcttca tgaagtgagt tgggtttgcg 300
aaaaaaggtt attacagcct gatatctaag tagaagagta ccggtattga agaccaaagt 360
tgctgcgtat ggcggtccgg ttgtccttgc tttcgcaagg attccaatac tggaatcctc 420
ccgaaaggga ggtcgcaaaa ggccgttttt cgaaaaccat agtttcatac aaaccggcga 480
tgaggtttgc gaactttttg attgtagtaa gtattattaa aataatggct taatattttt 540
ggtatataca attctcaact ttttcacctt gccggaaatg aggtttgcga aattttagag 600
agccgcatat ctatattatt tacaatcagt tacaaaatgg ccccttctcg ccatatacgt 660
aacctcagag ttgttggagg 680

<210> SEQ ID NO 106
<211> LENGTH: 386
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106
ggtttgattg aatattgatg gttgaaaatc gtctgcccta tgggggaggc aatgtcattg 60
aattaagggc aaaatatgga gtgcatcatc cctgcccgag aatgacacta cagtgtcaac 120
atccctttag gtaggcgtcc acgtcagcct ggcgggaatc cagcaacctc tgctttgaga 180
gtcaattcca ttttagttgt cacctttctg atagaatcct cgactaaatc agtaagatga 240
caactgatac tctacttgaa caatttttaa gcaagtccaa tttcatttct gcctatgagc 300
gtattgcctc aaagaaggct gcaggcggat tggataatgt cacggttgaa tcattcggca 360
accgactgga ccagcatatc agcaaa 386

<210> SEQ ID NO 107

```
<211> LENGTH: 392
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107

gttatccttg gccatttaga ggcttcggtc aaaaaggcgc tcgatgcggt cgaaaacatt     60

gcgtctggcc agccaagtaa tgaggactcg ccagtattac ccacgagccc ggcggaggtg    120

gcggttattc actggagcat aaaccagtga ccacaaattt ccggaaatga tgtccacttc    180

gatagtgtag atggtgcgga cgtatcaccc cttccccaag gcagctcaag gagagcaatg    240

atatgaatca aaatatcgat cgtgcggttg gtgcaattct agcgattgaa acagcgacac    300

cccttaccga atcttcaaca ctcgcgcaac gtgaaaggca tcagaagctg ctgcatgatg    360

aaaccaaaaa gattgagcaa gccttcatag cc                                  392


<210> SEQ ID NO 108
<211> LENGTH: 1348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108

ctgcaaagct gttggatgcg ccaacccggt gccattttta atgatgagta catccgcctt     60

tattatgccg cctctttccg gatactgggt ttcccggaag ttgcgactac aaatatggcg    120

actgcaaccg cccaggagga aatagcatga ctaccggcaa cacttccgct tctcacccgc    180

aatttgtcac gttgacagtc tgtttgcgct tttgcagccc cttccagatc cgaccctgga    240

tcaaggaaac ggtgcgcaac aaggttaaaa tgccatccac tgtcaacgct catgctgaaa    300

ctgctcacct gccggatgac caggataccg acgacacaca agatctattg gaagaagaac    360

gttttgagcg gtatgccact gccgctgatt ggcacaaggg aagtatcaac ggaaacgcga    420

agtattcacc ctatgtgagg ggcgatctgg tccgcagcgt ggtggacagg gaattgcagg    480

agcatttcca ctgttataat gaaaagcttg ccaatgagaa taaggggtgc cctggaaaac    540

gggaccgcca tattaacgcc ggcggcaagg cgtccggttt tatggcacac ctgcccgcga    600

tcaaggaccc ggccggcaag gagatctgca agggcagcga taacatctgc ccggtctgcc    660

atttcctcgg ggcgtttgcg gaaggaataa agccggttaa gttcaggaat cggaagatct    720

ggccaagcag cgcggccgga actgttacag cgggcaaagc cggaaatccc ttgataattt    780

tactgtctgg gaagcggatc ataccgcctg ccctgttttc ttcggcagaa tcgaggtgaa    840

caaaactctt ttgccgaaag aacaaatcct cgccctgctg gctggcggcc ttgctcggct    900

tgacaatttg gcgggtgcgg cgagggaggc acttgggcta ccagacgacg agcaccaggc    960

actcctcaac gatttttcaa gatttttcat taatcccgag aaatcgcctg ctgtttatac   1020

ttcctccccg gttattgtcc ctgtccaggg agctgttgat aaggttgtgc tcttggaaaa   1080

agcccaagat atcgccggca gaattgccgc gtgtgtctcc gacaatcccc gccacctcca   1140

tcggctggct gcggctatcc ggaccctggg ctggccgggc cggtctcttg cttcggttat   1200

gactaaaaaa ccgggtaccg aagacaaggc caccctctgg ggaaaagaat cagcgagtaa   1260

atcggtcaag acgattctgg aagaatcaat ccaaggcttc actgtagaac aaaagcgaag   1320
```

```
cttttttgcc aaccttgccg accagctc                                        1348


<210> SEQ ID NO 109
<211> LENGTH: 340
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109

cgtatcaatc cggtacaact cgcccgaatg attttaccat ttgtaccttg gcatggtgca     60

tgtcctgctt tgctgaacga acaggtaatg atagaggcca aacgattgac tgagttagac    120

cgcgccaatt ggccatgttg aatgccagca caaccagcta atatatcgaa atcgctggca    180

aagttagctt ttattgtaaa attagatgat taggaacgat ccggcaggtt atttaaatga    240

agtaaagtct ggggtcgtag cataatcgca aaaaaaatta tttaacagaa acaaacaaat    300

agacagcata aagttgaatt gagtattata gaaagcaggg                          340


<210> SEQ ID NO 110
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110

tttttctgta actattcagc acaccatatt ttagcataac aactgagtag tcattggggc     60

atcataaatt gaggccattt cccttcaaat aataagcgca                          100


<210> SEQ ID NO 111
<211> LENGTH: 841
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 111

gagacaaaag agcaacggga tatttttgtt cattttagcg ctattcgggg tgagggttat     60

aaaatcctgg aaccgggcga aaaagtacgt tttgaaatag gtgaggggag aaaaggtccc    120

caggccatca atgttattcg tataagatga caaaattact ccagtctcta ttctttttgt    180

aattacttgt tcgctgtttt gtgaagatta tattaagcta tggagctttc aggtaaaaaa    240

gcgtaaagta cgcgaatatt ctgcgtaaaa ctattccggc tatgaaagat gatgttcata    300

gccggaatag ttttttatcg agtttggtgg ggtattcatt ttgggagatg gttgatgaaa    360

gtttcaaggc agggtttcat ttattggcga tggtttaaat atctctttat tctttcttca    420

acaatctgat attattgttt ttttatctaa agatactctg tttttattta tcgtaaaata    480

ttcgacatac atatgaaacc tttgaaaagg caggagtttg gcgaagatgt agtgattgtg    540

gctaaaatta cggaaaaatt ttttttgtaa aattaaggtg atatgaatat agtttttctg    600

gtgcggtcgc caatttcctt ttttgaaatt aggaaactgg tttggcgaat tttttgacag    660

tatcttttta taataaatac gaatagttgt gattagacag gtgttaattt agtagtattt    720
```

```
ccccttttaac tgaagaatga ttggcgtaat atttaataac atgagagaac tccttggtat    780

aatagagatt attaagtata gtgtcagaat gcagcttttg tttgttcttt gattctaaag    840

g                                                                      841
```

<210> SEQ ID NO 112
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 112

```
tctcaaaata atgttaaaga aattttcatt ttattttgat ggtttaggcc acactgactt     60

tgtggttctc tttataccga tagaaaaatt ttattttttc gaaaaaaaac actcttccat    120

tcgtaaggtt aaataaaggc aattacttaa ccatctagca atggaggatt gatcatgaaa    180

agcacacatt ctctttttta ccgttttgct catgttgata cctttcgctc cgcatatgaa    240

agaatttctc taaaaaattc cagcccggga cttgatagag tttccgtaga agagttcggc    300

aagaaacttg aaaaaaatat ccaa                                           324
```

<210> SEQ ID NO 113
<211> LENGTH: 303
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 113

```
attcaggcaa tcctcaatag attggggcag gaggtaaaag gtcgaggtaa ggctttaaca     60

ttgcaggaaa tgatccatcg gcaggcgcag ttgttgaaaa gctatttgat ggataaatct    120

gtttacaaac catatctggc aaggtggtaa cctatgaata cagtcgaatt acttcaggag    180

gaagaacgct tgaccctgga tttggtcttt ttgccaccag gtagtaagaa taaagagcaa    240

aaaaagaatg ctttggtaga ccttttgttg aaaatagtgg agcatgggga attaacccgt    300

aaa                                                                  303
```

<210> SEQ ID NO 114
<211> LENGTH: 403
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114

```
atcgacaatg atgatacctc cgctgtgctc catagttcat taaaaagatt atttgagcat     60

tacgagaaga aaaatgaaaa aactcgtgca cagcttctct ataattgggc gtctttacgt    120

gttctcgctc ctgccaggga atttagttga aaaaaaatca taaaatttcc gaaaaaatag    180

atgatgtcga acgtaatagg ttttagagca acgaataacc gttgctctaa aacctatact    240

ctgggagaac atcatgaaaa aagagcacgg taaagaaaac tattctatcg aaacagttgt    300

tttcgtcgtt ttgcaggaca tcatgagtat tgttctaata ccgtttgcgg taatcgcctc    360

aatttatctt tcttattttt ttgagttatc tgtatacaaa tct                      403
```

<210> SEQ ID NO 115
<211> LENGTH: 584
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115
ccccgcgtta tttatccggc cctgaagcag aaggatattc ctaacagcag gcttcccggg 60
tatgaggagt tgaagaagaa cctcaatatg gagaaacgga aagagatgct gacgacccct 120
tgggccccct ggcatcccat caaaaaataa gatgcctgcg aattcccgga aatatgacag 180
cggatttaaa ggattgaacg gatatcattt tcccaaaaaa tgacagcgga tttaaaggat 240
tgagcggata tccgtttcat cctttgatcc gttgtcatat ttcctacaaa tatgtcgccc 300
ctacggggct ttaatccttt cctcttcttt gtgtcctttg tggctttgtg tgagaaaaac 360
aaaaaatttt tgtcacattt tcagcacaga acacgactaa gtatgcagag aagggaaacg 420
ccctcctttt ctttgtgtcc tttgtggctt tgtgtgagaa aaacaaaaaa tttttgtcac 480
attttcagca cgacatacga ctaagtttgc agaaagggaa aaaacatatc tttttactca 540
taaaggaggt tgccatgaaa aaaacattta tcgtctttgt tctg 584

<210> SEQ ID NO 116
<211> LENGTH: 602
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116
aagcgctggg caactgatga tctgctccgt atggtcgggg atcagatcac tgtgatgagg 60
gggttgctgg aaaagggaga ggattatcgg ccggtggttt acaacagccg gtattccagc 120
gggaagagcg gcctgaaaaa aaagacttga aaaggtcttg acatgggccg ggaaaggggc 180
tatgttcttc tgattataat atcagatcag agggaatatg gcccttatcc cgggaatatc 240
ctgtatttca ggggatcggg cctgttttcc gaatcggatg tgggattgct ccggccctgc 300
cttattttca tataagaccg gcttatccga ctatctccct aatatgacag ggaaaatatc 360
ttcccggact tttcaccggg atggtataag aacagggaac cagaatcatc tgttccctga 420
ccactggaaa gtttttcata tcagtatgtt gaatcctgtc acccctgggg cacggaggga 480
tttccaaata tccgatctga tgttcgtaat caccggcttt tccagccaat ggcttgagat 540
gatttaagaa acttgtgact ggctttttct ggtaaaatgg atttttgtat aatatcctgt 600
tg 602

<210> SEQ ID NO 117
<211> LENGTH: 843
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 117

```
cagctgggtc tcggcctggg cgccaaaatc cgccacgctc tgaccatccc aaccgccggc     60

cgctttttttg gcggctaccc gctgccaggc ggcggacaga ttttccatgg cggtgatggc    120

ggccagttga cgataggtgg tggtagacat cgggacggtg cctcctgcaa ggttctatcc    180

tgttggtcgt cgacgcaagg cctcaggtga ccccctctcc gttattctgc caattttttc    240

ctagggaccg gcctgggcac cgtctgcggc ggggggctgc cgttcaaccc cggccagggc    300

catggaccag attttctttg atttatcatc aggttggctc ctctttcgca aatgctccgg    360

cgccgcgagc ggccaaacca tttgcgaact tggccgatag gcgattattt tatggcaaat    420

caataagata agtgcttttg aggccctttg gcccctcggc ggcgaggggc caaaaagttc    480

gcaaatgccc ctttgggggc cgggcgcccc accatttgcg aaaaaacccg cccggcagcg    540

gccgaggctt ctgccggctg attatatctt atcgatataa ttgaatatta tttttcccca    600

agaccgggtc gaaggcctat tttcgcaaat gcccgccgcg ggccgggggga gccaacgtgt    660

tgcgaaaatc cggttctaag caaatcaagg agttaggcca aaaaaagtga tttttggcaa    720

tccggccaag cgccctttgg gggcatttgc gaaaaaaatcc ggccggcaaa aacttcttga    780

cattaccggg cattttccat tagagtattg cgtagcagta catatctagc tgatttctcc    840

gtt                                                                   843
```

```
<210> SEQ ID NO 118
<211> LENGTH: 462
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118

tatgcgacgg ccttgggcca gcaggatgct ggccctacgg ggttgagcag aggcggcagg     60

ccttgaggac acgtttttga gggcgtttaa cggcaggcgc aggagacggg acgcgaagtg    120

gggttaggga aattaccgcc aggctggaga atagctggcg gtttttgttt ggggggccgg    180

aaaaattttc tgctcctgtc acctcgacgg ttccaagaga gactaatttg ttagaccagg    240

ctccagactg gaagtatttt tgggcgcggc cgcggtgacg gctgtccagc aagcggttgg    300

gacggtttaa acatgactgc aggacattac cagacgattt tggaggccca gattgagctg    360

gccttctgcc tgccggaaga ggcgcataat gtgctgtatg cgcgggatga ggcgtgccgt    420

gagctggtcc aagcctgccg caatcaccgg ggtagcctgc gt                        462
```

```
<210> SEQ ID NO 119
<211> LENGTH: 315
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 119

gcagagaacg gaggcgcctg gttctatgaa cttttatggc aatggcacag ggatgaaata     60

ggacatctta gcaacataag gaatacgttt gaaagaatga aaagatttga taaatttgcc    120

ccctggaggt ccgtgggatt gggttggtga aaaaaagagg agtggatgtc tgcgcctgaa    180

tatgagatcg atctggataa cgatgaccac cctaccataa ttttaacaga catggatgaa    240

tgttatcata tatgccttaa agcggcagga aacgatccta gctgtgctcg atgcaagata    300
```

tttatggcag atttc 315

<210> SEQ ID NO 120
<211> LENGTH: 850
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 120
ttttaattga cccgcatttt ttgttatatc gaataaccat gaagaaaggc gtccttccca 60
ctccatctca aatctatcag gatttgtttc atagatatgt ttgagacgct ttcggcgctt 120
tgctttatct cttttggcgg cctttcccat tagtcctcct tcttagttca ataatggttt 180
tatccattga tttttcgacc tgatcagagg atctaaactc tgttgggccg gtacctaatt 240
tgatttaatc gaaagaacgt tgtacttttt atctcctcta attcttttgt ttcggatcgt 300
ctggatagtc gtgataaatc tcttacatgt tacagggaat cgtaattttt ctatctgaaa 360
tctcacaagc gctatttcga tagtcggggc taagtaaaaa aatgtgacat gaattgctgg 420
gccaccagaa gaaatttttc actaaccact atagtcttct ggaatgtgaa aaagtgacag 480
aaaaaatatg aggctaaaat gtcacatttt aaataaagcc ccgactataa ttatacggat 540
atatctatag acaacccctt ttgatgaaac cttacaccaa taatcggatg ttaaagttat 600
tgacattaca agatttaatg tgttatttat ttaggctcaa cttttctcaa accatccaga 660
ctatttcaaa atatctgtaa agataataag ggggaatgtt atgtattccg actttcctgc 720
acttaggtta cctgaattat ctgttgatca aaaaaaatta tttaagatct ccgggaccaa 780
cccacagctc atatacatct taatgaacga atttgatgga gagggggatg agcccttctt 840
taccggactt 850

<210> SEQ ID NO 121
<211> LENGTH: 308
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 121
gttttaaatc ttttattcat gaaagaaggt ctttttgatc atttttttga gcaacaaaga 60
gaatggtgga aagaagagta tgaacatacc gattcgaaca cagctctcta tgattgcttg 120
tgttttcgaa tgtatcggtg ttatttttag gaaaatatat gccctcatac ccttgcttga 180
aatggaatgg cgattgtagc agatgtcctg attcggcaac atgcagaatc gcacagaaag 240
gtttgggaaa ggtatttacg gttttttca agaaatatct ggcgcgttac tattcttcga 300
aatccgaa 308

<210> SEQ ID NO 122
<211> LENGTH: 367
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 122
atgatgaggc ggtttttctt tgataccagt gcgcttatca aactctatca tgaagaaact 60
ggtacagaaa aactggattc tctgatcgag gccgaaaatc cagttatcat taatgatatg 120
aaattgcctg gcgttatgag ctaatcctta tattaaatgc ttcaggcatc tgaaccttgc 180
aacatatcag gatggtatat aaaccacagg aggaatgatg gaatataccc ttaccctaaa 240
tttcattgaa ccgtttcgct tgattgaatg gcacgatgcg ccagatcggg aaaaccttcg 300
attgaggggg ttttcttttg ccagatggca taaggacagg gaattcggac tgggaaggcc 360
atatatt 367

<210> SEQ ID NO 123
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 123
aatggaatcc aggtccgtta tccaaaattg gaaaaagaaa aaaaagatga cccaggtgaa 60
aagccgggct atcttgagct ggcagatggc cctttcagca cggaaaatcg caaggaaaaa 120
ttaaaggaga tttggggtaa ttgggcctga ttaaccaaat atcgaataat caccaaatac 180
atagcctatt ttcaatgata ttcaatagtt ataataccta tttaataatt caatatttat 240
agaatccaag gattatgcat cgccaaaaat acatccataa acgatttaac aatatgaatt 300
tacaaaatga atttatacca ttgggtttta agaatctttt ataataagca aacatagggg 360
ggg 363

<210> SEQ ID NO 124
<211> LENGTH: 439
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 124
gatgttccgc caggcacggc agcgattctc cttgggcttt gtagagacgt ggacagattg 60
agggccgcca ttgattcaat tgtttcgggc aagaagacgc gggatgatac gatattctgg 120
atactatacc acaccgtgcc ggagaaatag ggcctgtcgc caaatccact cgggccttcc 180
actacaaaaa ggcttaactc gatagtatat gggtttcctt tttttgagtc cgccggaggc 240
ggacgttgta taaaatcgcg aagtgatttt atgtactgga gaggatatca tggtcacgcc 300
acaagcttct aagaaccccg cagtagatga aatcctgaaa cagctcacac cctatgacat 360
ggagactgag aacgcaaagg ctatcgagac aaggaagtct tgtattgagt gcctgaaagg 420
catttgcgaa agggctcaa 439

<210> SEQ ID NO 125
<211> LENGTH: 365
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 125
atattgcgcg ataacgggga agatatattt gtccatcgga gcgatattaa tggtagcctt 60
ggcaccctga cagaagggca aaaagtaatc tttgaggtga agcagggtcc aaagggactc 120
caggccacaa atgtgaaggt aatttcataa tcacttggcc gtattgcacc ttaccacaat 180
atctttttga gaatttcata agagctcatt tcaaagtgaa tattcaatcc acggctgttg 240
aaaaaaagcg aaacgccctt gctctttttg tgcgccttct cctttcatcg cctctcaagg 300
actacgtcgc caagataatc ctgtttggaa gtgtgagaaa aggaaaagct aattcagaga 360
gtgat 365

<210> SEQ ID NO 126
<211> LENGTH: 344
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 126
tgcttgaaat ggcgtgggca tttgcttttg gccccggctg atatctactc ggcaaagcca 60
caccatacaa taatggaggc tgattcaatg tgacataaaa ttttggggta gcgtctacat 120
gcaaaaatct cggtggtgat tcgtttatac ttatagagtg gatcattttc tgagccgaca 180
cccgagattg agctatgact gccacaatat ttgacaaatt tgcaagcttt gaaaacttct 240
gggccgcctt ccaaaaagtt gctgcaaaga attcagcggg cggcatagac ggcacaaccg 300
ttgagaccta ccaaaagcga gccaagcaac gaatcaatgc cctc 344

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 7
<212> TYPE: PRT
<213> ORGANISM: Simian virus 40

<400> SEQUENCE: 300

Pro Lys Lys Lys Arg Lys Val
1               5

```
<210> SEQ ID NO 301
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 301

Lys Arg Pro Ala Ala Thr Lys Lys Ala Gly Gln Ala Lys Lys Lys Lys
1               5                   10                  15


<210> SEQ ID NO 302
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 302

Pro Ala Ala Lys Arg Val Lys Leu Asp
1               5


<210> SEQ ID NO 303
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 303

Arg Gln Arg Arg Asn Glu Leu Lys Arg Ser Pro
1               5                   10


<210> SEQ ID NO 304
<211> LENGTH: 38
<212> TYPE: PRT
<213> ORGANISM: Homo sapiens

<400> SEQUENCE: 304

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35


<210> SEQ ID NO 305
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 305

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30
```

```
Asp Glu Gln Ile Leu Lys Arg Arg Asn Val
        35                  40
```

<210> SEQ ID NO 306
<211> LENGTH: 8
<212> TYPE: PRT
<213> ORGANISM: Unknown
<220> FEATURE:
<221> NAME/KEY: source
<223> OTHER INFORMATION: /note="Description of Unknown: Myoma T protein sequence"

<400> SEQUENCE: 306

```
Val Ser Arg Lys Arg Pro Arg Pro
1               5
```

<210> SEQ ID NO 307
<211> LENGTH: 8
<212> TYPE: PRT
<213> ORGANISM: Unknown
<220> FEATURE:
<221> NAME/KEY: source
<223> OTHER INFORMATION: /note="Description of Unknown: Myoma T protein sequence"

<400> SEQUENCE: 307

```
Pro Pro Lys Lys Ala Arg Glu Asp
1               5
```

<210> SEQ ID NO 308
<211> LENGTH: 8
<212> TYPE: PRT
<213> ORGANISM: Homo sapiens

<400> SEQUENCE: 308

```
Pro Gln Pro Lys Lys Lys Pro Leu
1               5
```

<210> SEQ ID NO 309
<211> LENGTH: 12
<212> TYPE: PRT
<213> ORGANISM: Mus musculus

<400> SEQUENCE: 309

```
Ser Ala Leu Ile Lys Lys Lys Lys Lys Met Ala Pro
1               5                   10
```

<210> SEQ ID NO 310
<211> LENGTH: 5
<212> TYPE: PRT
<213> ORGANISM: Influenza virus

<400> SEQUENCE: 310

```
Asp Arg Leu Arg Arg
1               5
```

<210> SEQ ID NO 311
<211> LENGTH: 7
<212> TYPE: PRT
<213> ORGANISM: Influenza virus

<400> SEQUENCE: 311

```
Pro Lys Gln Lys Lys Arg Lys
1               5
```

<210> SEQ ID NO 312

```
<211> LENGTH: 10
<212> TYPE: PRT
<213> ORGANISM: Hepatitis delta virus

<400> SEQUENCE: 312

Arg Lys Leu Lys Lys Lys Ile Lys Lys Leu
1               5                   10


<210> SEQ ID NO 313
<211> LENGTH: 10
<212> TYPE: PRT
<213> ORGANISM: Mus musculus

<400> SEQUENCE: 313

Arg Glu Lys Lys Lys Phe Leu Lys Arg Arg
1               5                   10


<210> SEQ ID NO 314
<211> LENGTH: 20
<212> TYPE: PRT
<213> ORGANISM: Homo sapiens

<400> SEQUENCE: 314

Lys Arg Lys Gly Asp Glu Val Asp Gly Val Asp Glu Val Ala Lys Lys
1               5                   10                  15

Lys Ser Lys Lys
            20


<210> SEQ ID NO 315
<211> LENGTH: 17
<212> TYPE: PRT
<213> ORGANISM: Homo sapiens

<400> SEQUENCE: 315

Arg Lys Cys Leu Gln Ala Gly Met Asn Leu Glu Ala Arg Lys Thr Lys
1               5                   10                  15

Lys
```

CRISPR-ASSOCIATED SYSTEMS AND COMPONENTS

CROSS REFERENCE TO RELATED APPLICATIONS

This application claims the benefit of priority of U.S. Application No. 62/672,489, filed on May 16, 2018. The content of the foregoing application is hereby incorporated by reference in its entirety.

FIELD OF THE INVENTION

The present disclosure relates to novel CRISPR systems and components, and methods and compositions for the use of CRISPR systems in, for example, nucleic acid detection.

BACKGROUND

Recent application of advances in genome sequencing technologies and analysis have yielded significant insights into the genetic underpinning of biological activities in many diverse areas of nature, ranging from prokaryotic biosynthetic pathways to human pathologies. To fully understand and evaluate the vast quantities of information produced by genetic sequencing technologies, equivalent increases in the scale, efficacy, and ease of technologies for genome and epigenome manipulation are needed. These novel genome and epigenome engineering technologies will accelerate the development of novel applications in numerous areas, including biotechnology, agriculture, and human therapeutics.

Clustered Regularly Interspaced Short Palindromic Repeats (CRISPR) and the CRISPR-associated (Cas) genes, collectively known as the CRISPR-Cas or CRISPR/Cas systems, are currently understood to provide immunity to bacteria and archaea against phage infection. The CRISPR-Cas systems of prokaryotic adaptive immunity are an extremely diverse group of proteins effectors, non-coding elements, as well as loci architectures, some examples of which have been engineered and adapted to produce important biotechnologies.

The components of the system involved in host defense include one or more effector proteins capable of modifying DNA or RNA and an RNA guide element that is responsible to targeting these protein activities to a specific sequence on the phage DNA or RNA. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

Citation or identification of any document in this application is not an admission that such document is available as prior art to the present invention.

SUMMARY

The present disclosure provides methods for computational identification of new CRISPR-Cas systems from genomic databases, together with the development of the natural loci into engineered systems, and experimental validation and application translation.

In one aspect, the present disclosure relates to non-naturally occurring Clustered Regularly Interspaced Short Palindromic Repeat (CRISPR)-Cas systems of CLUST.019911 (Type III-E) including a Type III-E RNA guide or a nucleic acid encoding the Type III-ERNA guide, where the Type III-E RNA guide includes a direct repeat sequence and a spacer sequence capable of hybridizing to a target nucleic acid; and at least one Type III-E CRISPR-Cas effector protein or a nucleic acid encoding the effector protein, where the effector protein includes an amino acid sequence that is at least 80% (e.g., 85, 90, 91, 92, 93, 94, 95, 96, 97, 98, 99, or 100%) identical to an amino acid sequence provided in Table 2 or Table 3; where the Type III-E CRISPR-Cas effector protein is capable of binding to the Type III-E RNA guide and of targeting the target nucleic acid sequence complementary to the spacer sequence.

In some embodiments, the Type III-E CRISPR-Cas system also includes two or more Type III-E RNA guides. In some embodiments, the Type III-E RNA guide includes a direct repeat sequence, a spacer sequence, and a second direct repeat sequence, arranged in order within Type III-E the RNA guide. In some embodiments, the Type III-E CRISPR-Cas system includes at least one Repeat Associated Mysterious Protein (RAMP) domain. In certain embodiments, the Type III-E CRISPR-Cas effector protein also includes two or more Repeat Associated Mysterious Protein (RAMP) domains. In some of these embodiments, the RAMP-domain includes at least about 1400 amino acids or least about 1550 amino acids.

In some embodiments, the RAMP-domain includes an amino acid sequence that is homologous to CRISPR Cmr4, CRISPR Cmr6, or CRISPR Cas7. In certain embodiments, the RAMP-domain does not include an amino acid sequence that is homologous to CRISPR Cas10 or CRISPR Cas 5.

In some embodiments, the Type III-E CRISPR-Cas effector also includes a protease domain. In some of these embodiments, the protease domain is activated when the system binds to the target nucleic acid, thereby exhibiting protease activity. In certain embodiments, the protease activity is a peptidase activity, e.g., an endopeptidase or exopeptidase activitye, e.g., the protease domain can be a caspase domain. In some embodiments, the caspase domain is a Caspase HetF Associated with Tprs (CHAT) domain.

In some embodiments, the target nucleic acid is a transcriptionally active site.

In certain embodiments, the direct repeat sequence includes a nucleotide sequence that is at least 80% (e.g., 85%, 90%, 91%, 92%, 93%, 94%, 95%, 96%, 97%, 98%, 99%, or 100%) identical to a nucleotide sequence provided in Table 4.

In some embodiments, the target nucleic acid is a DNA or a RNA.

In another aspect, the targeting of the target nucleic acid by the Type III-E CRISPR-Cas effector protein and Type III-E RNA guide results in a modification in the target nucleic acid. For example, the modification of the target nucleic acid can be a cleavage event, such as a double-stranded cleavage event or a single-stranded cleavage event. In some embodiments, the modification of the target nucleic acid is a deletion or an insertion event.

In some embodiments, the system inserts a nucleic acid sequence into a DNA via reverse transcription from an RNA template.

In another aspect, the Type III-E CRISPR-Cas effector protein has non-specific protease activity or non-specific nuclease activity. For example, the non-specific activity can be reduced after targeting the target nucleic acid sequence. In some embodiments, the modification results in cell toxicity.

In another aspect, the Type III-E CRISPR-Cas system is present within a cell. For example the cell can be a eukaryotic cell, such as a prokaryotic cell or a eukaryotic cell.

In other aspects, the Type III-E CRISPR-Cas system includes a tracrRNA.

In yet another aspect, the present disclosure relates to methods of targeting and editing a target nucleic acid. The methods include contacting the target nucleic acid with a Type III-E CRISPR-Cas system described herein.

In another aspect, the present disclosure relates to methods of detecting a target nucleic acid in a sample, wherein the methods include contacting the sample with a Type III-E CRISPR-Cas system described herein and a labeled reporter nucleic acid, where hybridization of the Type III-E guide RNA to the target nucleic acid causes cleavage of the labeled reporter nucleic acid; and measuring a detectable signal produced by cleavage of the labeled reporter nucleic acid, thereby detecting the presence of the target nucleic acid in the sample.

In some embodiments, the methods further include comparing a level of the detectable signal with a reference signal level, and determining an amount of target nucleic acid in the sample based on the level of the detectable signal.

In some embodiments, the measuring is performed using gold nanoparticle detection, fluorescence polarization, colloid phase transition/dispersion, electrochemical detection, or semiconductor based-sensing.

In certain embodiments, the labeled reporter nucleic acid includes a fluorescence-emitting dye pair, a fluorescence resonance energy transfer (FRET) pair, or a quencher/fluorophore pair, where cleavage of the labeled reporter nucleic acid by the effector protein results in an increase or a decrease of the amount of signal produced by the labeled reporter nucleic acid.

In another aspect, the present disclosure relates to methods of detecting a target nucleic acid in a sample, wherein the methods include contacting the sample with a Type III-E CRISPR-Cas system described herein and a labeled reporter peptide, where hybridization of the Type III-E guide RNA to the target nucleic acid causes cleavage of the labeled reporter peptide; and measuring a detectable signal produced by cleavage of the labeled reporter peptide, thereby detecting the presence of the target nucleic acid in the sample.

In yet another aspect, the present disclosure relates to methods of specifically editing a double-stranded nucleic acid, wherein the methods include contacting, under sufficient conditions and for a sufficient amount of time, a Type III-E CRISPR-Cas effector protein and one other enzyme with sequence-specific nicking activity, and a crRNA that guides the Type III-E CRISPR-Cas effector protein to nick the opposing strand relative to the activity of the other sequence-specific nickase; and the double-stranded nucleic acid, where the method results in the formation of a double-stranded break.

In another aspect, the present disclosure relates to methods of editing a double-stranded nucleic acid. The methods include contacting, under sufficient conditions and for a sufficient amount of time, a fusion protein including a the Type III-E CRISPR-Cas effector and a protein domain with DNA modifying activity and a Type III-E RNA guide targeting the double-stranded nucleic acid; and the double-stranded nucleic acid, where the Type III-E CRISPR-Cas effector of the fusion protein is modified to nick a non-target strand of the double-stranded nucleic acid.

In yet another aspect, the present disclosure relates to methods of inducing genotype-specific or transcriptional-state-specific cell death or dormancy in a cell, wherein the methods include contacting a cell with a Type III-E CRISPR-Cas system described herein, where the RNA guide hybridizing to the target DNA causes a collateral DNase activity-mediated cell death or dormancy.

In some embodiments of these methods, the cell is a prokaryotic cell such as an infectious cell or a cell infected with an infectious agent, or a eukaryotic cell such as a mammalian cell. For example, the cell can be a cancer cell. In some embodiments, the cell is a cell infected with a virus, a cell infected with a prion, a fungal cell, a protozoan, or a parasite cell.

In another aspect, the present disclosure relates to methods of treating a condition or disease in a subject in need thereof, e.g., in a human or animal subject. The methods include administering to the subject a Type III-E CRISPR-Cas system described herein, where the spacer sequence is complementary to at least 12 nucleotides of a target nucleic acid associated with the condition or disease; where the Type III-E CRISPR-Cas effector protein associates with the Type III-E RNA guide to form a complex; where the complex binds to a target nucleic acid sequence that is complementary to the at least 12 nucleotides of the spacer sequence; and where upon binding of the complex to the target nucleic acid sequence the Type III-E CRISPR-Cas effector protein cleaves the target nucleic acid, thereby treating the condition or disease in the subject.

In some embodiments, the condition or disease is a cancer or an infectious disease. For example, the cancer can be selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In some embodiments, the Type III-E CRISPR-Cas system described herein is for use as a medicament.

In some embodiments, the Type III-E CRISPR-Cas system described herein is for use in the treatment or prevention of a cancer or an infectious disease.

The term "cleavage event," as used herein, refers to a DNA break in a target nucleic acid created by a nuclease of a CRISPR system described herein. In some embodiments, the cleavage event is a double-stranded DNA break. In some embodiments, the cleavage event is a single-stranded DNA break.

The term "CRISPR-Cas system" as used herein refers to nucleic acids and/or proteins involved in the expression of, or directing the activity of, CRISPR-Cas effectors, including sequences encoding CRISPR-Cas effectors, RNA guides, and other sequences and transcripts from a CRISPR locus.

The term "CRISPR array" as used herein refers to the nucleic acid (e.g., DNA) segment that includes CRISPR repeats and spacers, starting with the first nucleotide of the first CRISPR repeat and ending with the last nucleotide of the last (terminal) CRISPR repeat. Typically, each spacer in a CRISPR array is located between two repeats. The term "CRISPR repeat," or "CRISPR direct repeat," or "direct repeat," as used herein, refers to multiple short direct repeating sequences, which show very little or no sequence variation within a CRISPR array.

The term "CRISPR RNA" or "crRNA" as used herein refers to an RNA molecule comprising a guide sequence used by a CRISPR effector to specifically target a nucleic acid sequence. In some embodiments, the crRNA contains a sequence that mediates target recognition and a sequence that forms a duplex with a tracrRNA. The crRNA: tracrRNA duplex binds to a CRISPR effector.

The term "donor template nucleic acid," as used herein refers to a nucleic acid molecule that can be used by one or more cellular proteins to alter the structure of a target nucleic acid after a CRISPR enzyme described herein has altered a target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

The term "CRISPR-Cas effector," "CRISPR effector," "effector," "CRISPR-associated protein," "CRISPR enzyme," "Type III-E CRISPR-Cas effector protein," "Type III-E CRISPR-Cas effector," or "Type III-E effector" as used herein refers to a protein that carries out an enzymatic activity or that binds to a target site on a nucleic acid specified by an RNA guide.

In some embodiments, a Type III-E CRISPR-Cas effector protein has nuclease activity, peptidase activity, or protease activity.

The term "RNA guide" as used herein refers to any RNA molecule that facilitates the targeting of a protein described herein to a target nucleic acid. Exemplary "RNA guides" include, but are not limited to, crRNAs, as well as crRNAs fused to tracrRNAs. In some embodiments, an RNA guide includes both a crRNA and a tracrRNA, either as separate RNAs (dual guide) or fused into a single RNA.

As used herein, the term "targeting" refers to the ability of a complex including a CRISPR-associated protein and an RNA guide, such as a crRNA, to preferentially or specifically bind to, e.g., hybridize to, a specific target nucleic acid compared to other nucleic acids that do not have the same or similar sequence as the target nucleic acid.

The terms "trans-activating crRNA" or "tracrRNA" as used herein refer to an RNA including an anti-repeat region complementary to all or part of the direct repeat sequence of a CRISPR RNA (crRNA). A CRISPR effector bound to the crRNA and tracrRNA (RNA guide) form a functional complex capable of binding to a target nucleic acid.

A "transcriptionally-active site" as used herein refers to a site in a nucleic acid sequence comprising promoter regions at which transcription is initiated and actively occurring.

The term "collateral nuclease activity," "collateral DNase activity," or "collateral RNase activity" as used herein in reference to a CRISPR enzyme, refers to non-specific nuclease activity of a CRISPR enzyme after the enzyme has specifically targeted a nucleic acid.

The term "collateral peptidase activity" or "collateral protease activity" as used herein in reference to a CRISPR enzyme, refers to non-specific peptidase or protease activity of a CRISPR. enzyme after the enzyme has specifically targeted a nucleic acid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF FIGURE DESCRIPTION

The figures are a series of schematics and nucleic acid and amino acid sequences that represent the results of locus analysis of various protein clusters.

FIG. 5 is a schematic representation of PFAM domain mapping results for Type III-E (CLUST.019911) Effector A proteins; a schematic of HHpred domain predictions of an exemplary CLUST.019911 Effector A is depicted below, with a C-terminal match to the CHAT domain, and an N-terminal match to the TPR domain.

Figure 7A:
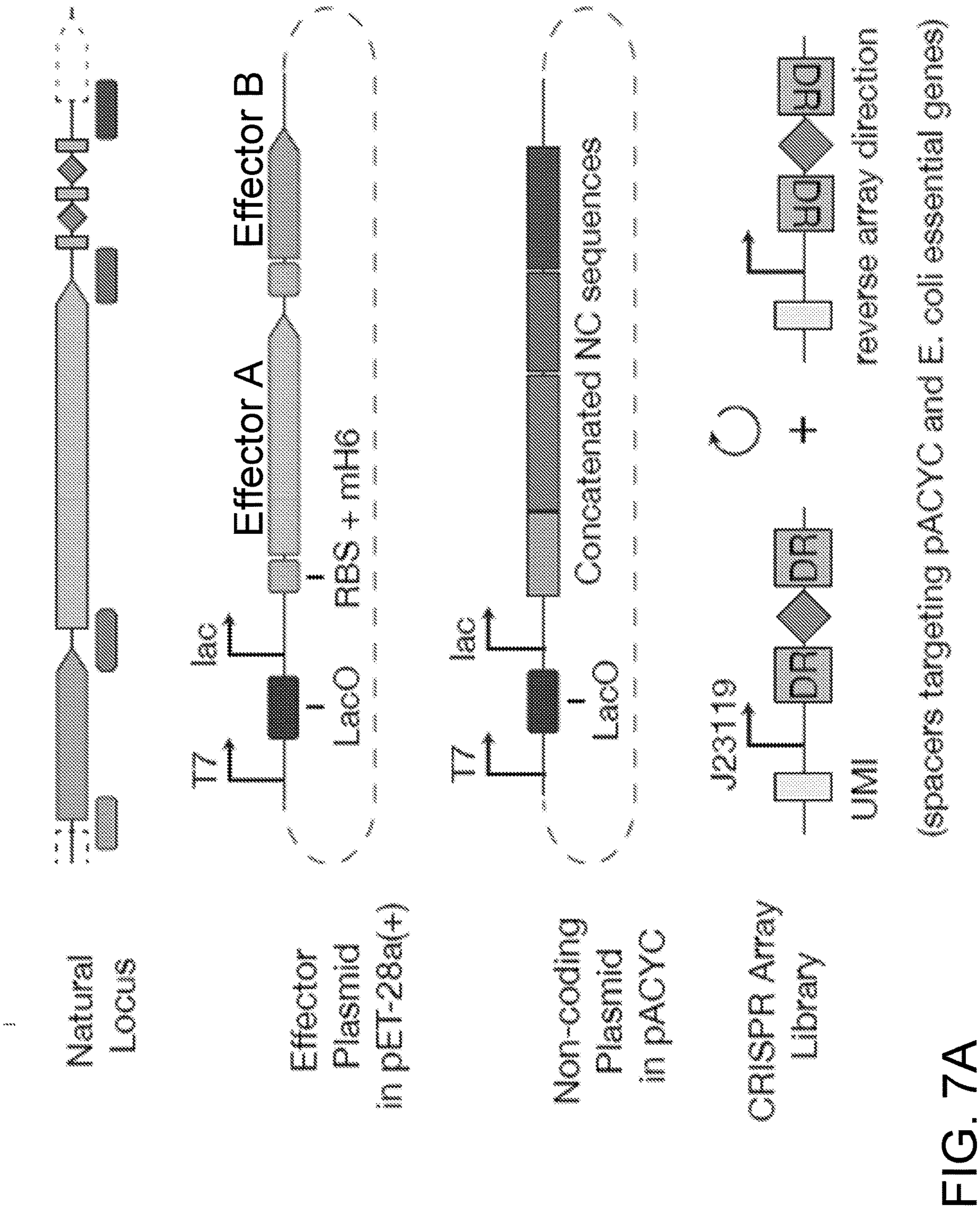
FIG. 7A is a schematic representation of the design of in vivo screen Effector and Non-coding Plasmids. CRISPR array libraries were designed including non-repetitive spacers uniformly sampled from both strands of pACYC184 or *E. coli* essential genes flanked by two DRs and expressed by J23119.
Figure 7B:
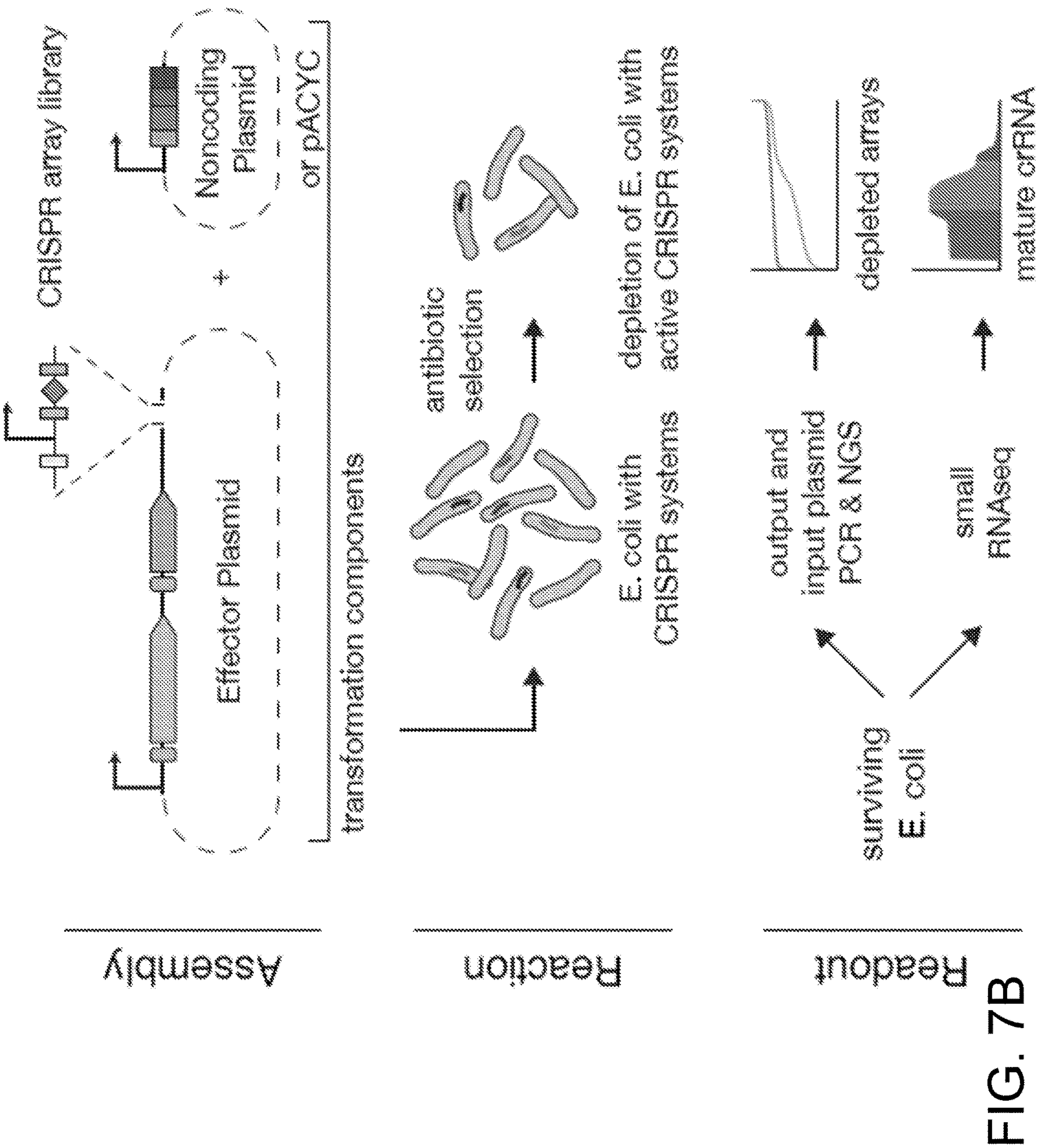

FIG. 7B is a schematic representation of the negative selection screening workflow; 1) CRISPR array libraries were cloned into the Effector Plasmid, 2) the Effector Plasmid and, when present, the Non-coding Plasmid were transformed into *E. coli* followed by outgrowth for negative selection of CRISPR arrays conferring interference against DNA or RNA transcripts from pACYC184 or *E. coli* essential genes, and 3) Targeted sequencing of the Effector Plasmid was used to identify depleted CRISPR arrays and small RNA sequencing was used to identify mature crRNAs and tracrRNAs.

Figure 8:
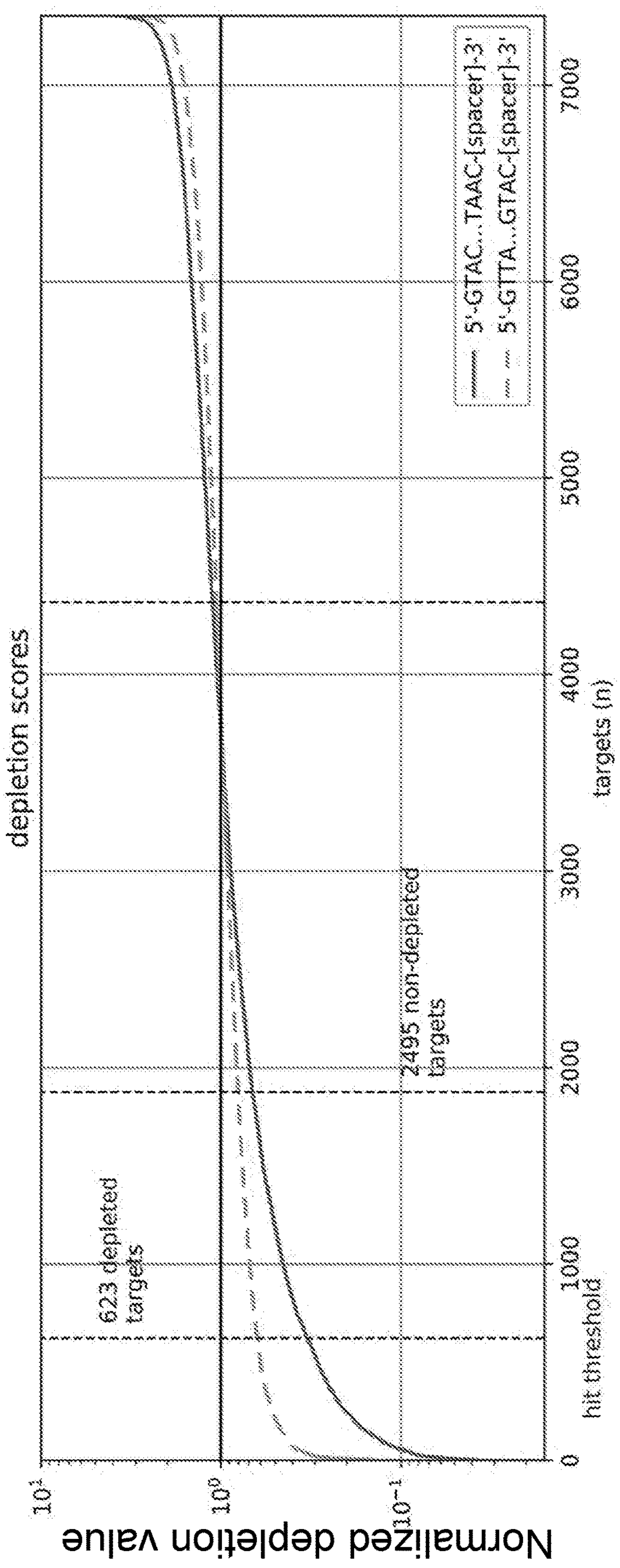

FIG. 8 is a graph that shows depletion values for crRNAs targeting pACYC and *E. coli* essential genes. To quantify depletion, a fold-depletion ratio was calculated as $R_{treated}$/

$R_{input}$ for each direct repeat and spacer. The normalized input read count is computed as:

$R_{input}$=#reads containing crRNA/total reads without expressing the Type III-E system and RNA guide. The treated read count is computed as:

$R_{treated}$=(1+#reads containing crRNA)/total reads with expression of the Type III-E system and RNA guide. A strongly depleted target has a fold depletion greater than 3, which is marked by the vertical line "hit threshold."

Figure 9:
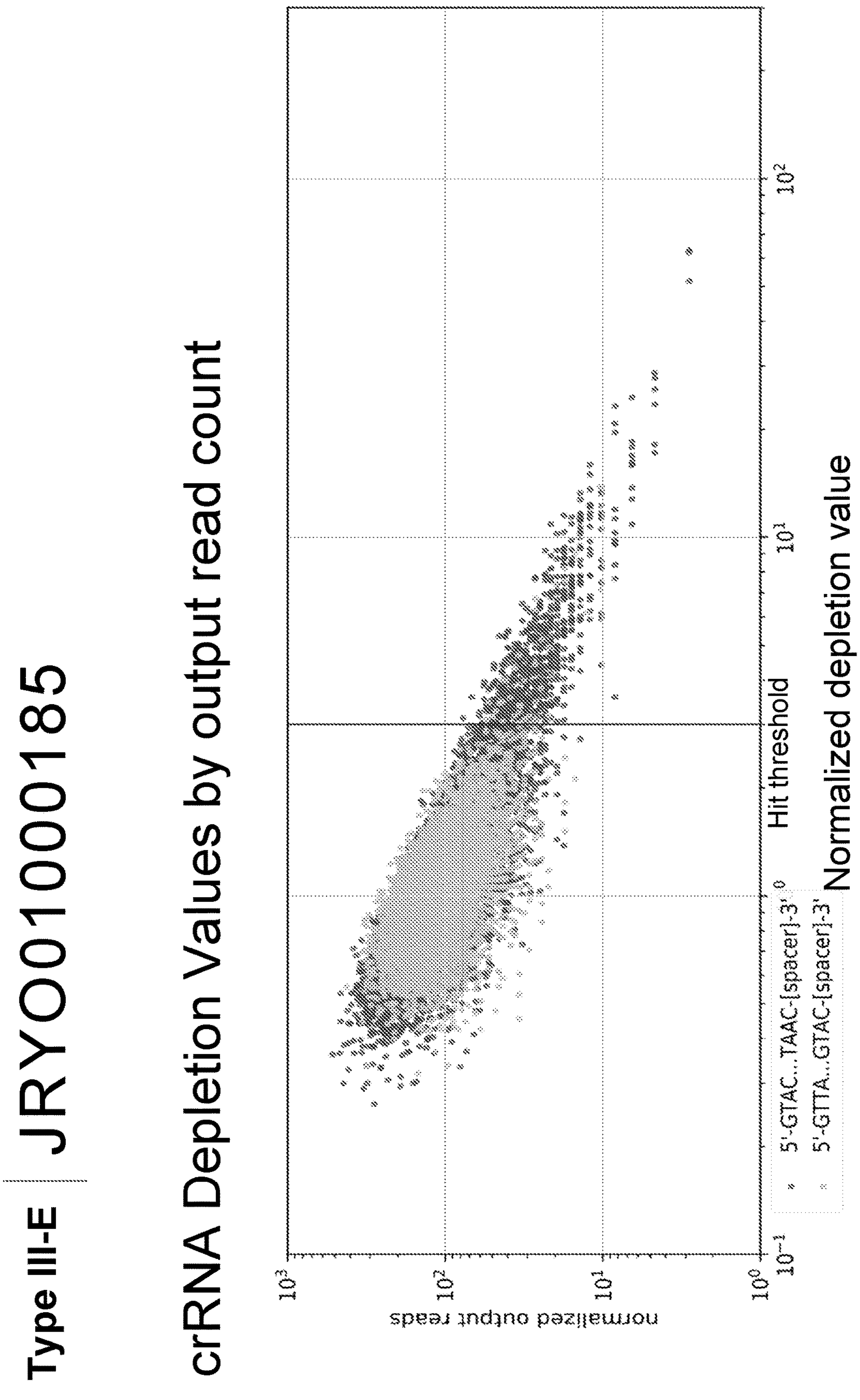

FIG. 9 is a scatter plot where the depletion value and output read count is depicted for each Type III-E system and crRNA tested. Notably, many of the points with high depletion value fall in the range where normalized output read counts are high.

Figure 10:
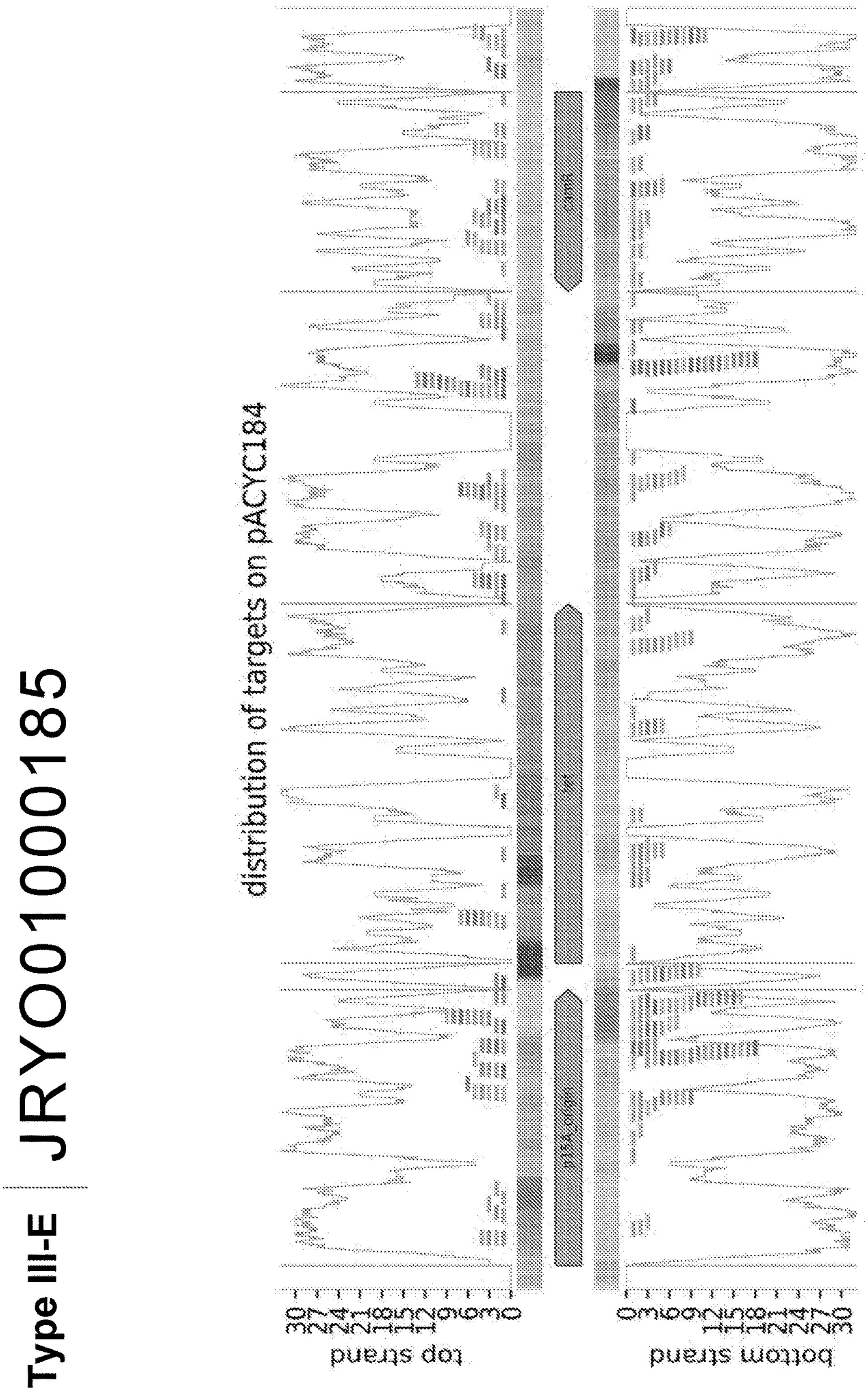

FIG. 10 is a graphic representation of the location of depleted and non-depleted crRNAs for the Type III-E system JRYO01000185 targeting the pACYC184 plasmid. Targets on the top strand and bottom strand are shown separately, and in relation to the orientation of the annotated genes.

Figure 11:
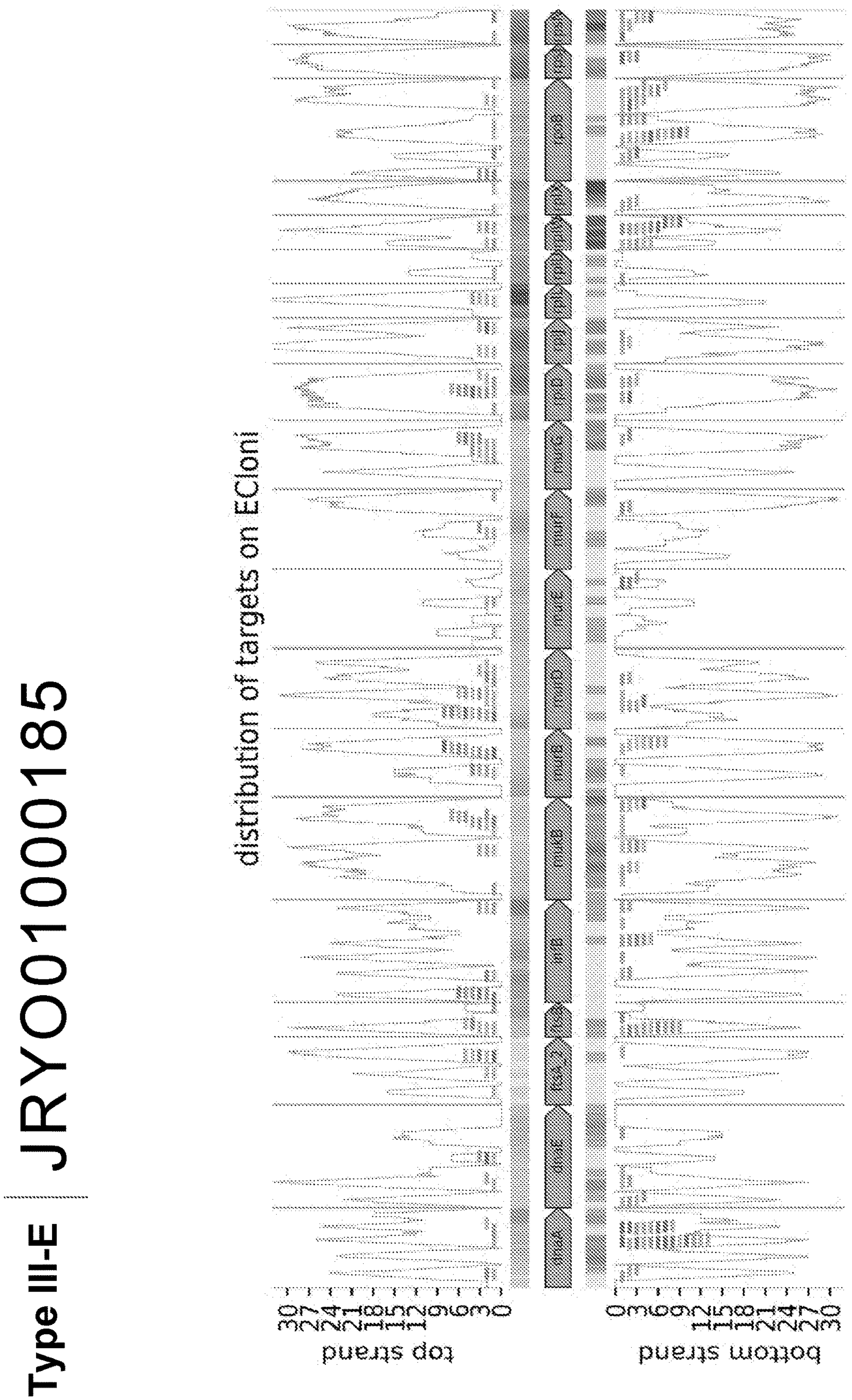

FIG. 11 is a graphic representation of the location of depleted and non-depleted crRNAs for the Type III-E system JRYO01000185 targeting *E. coli* essential genes (strain E. Cloni). Targets on the top strand and bottom strand are shown separately, and in relation to the orientation of the annotated genes.

Figure 12:
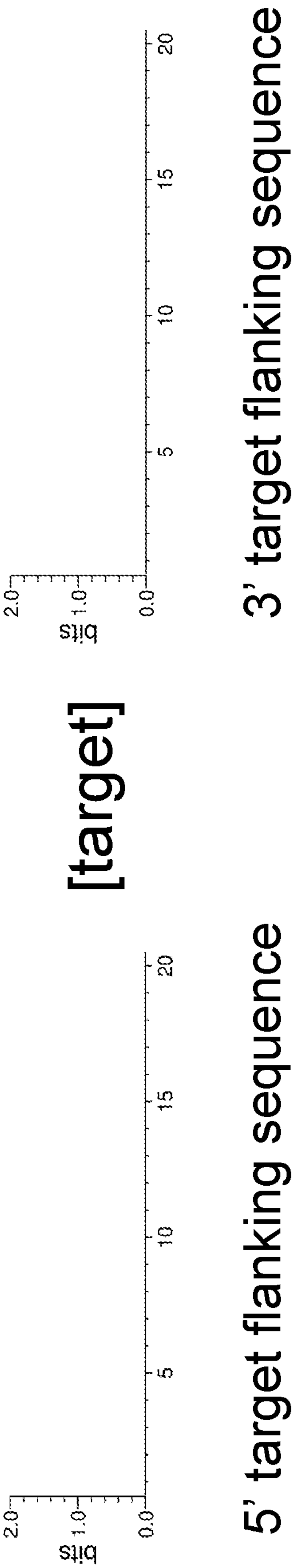

FIG. 12 is a weblogo of the sequences flanking depleted targets for the Type III-E system JRYO01000185, indicating there is no prominent motif adjacent to depleted targets (PAM).

DETAILED DESCRIPTION

The broad natural diversity of CRISPR-Cas defense systems contains a wide range of activity mechanisms and functional elements that can be harnessed for programmable biotechnologies. In a natural system, these mechanisms and parameters enable efficient defense against foreign DNA and viruses while providing self vs. non-self discrimination to avoid self-targeting. In an engineered system, the same mechanisms and parameters also provide a diverse toolbox of molecular technologies and define the boundaries of the targeting space. For instance, systems Cas9 and Cas13a have canonical DNA and RNA endonuclease activity and their targeting spaces are defined by the protospacer adjacent motif (PAM) on targeted DNA and protospacer flanking sites (PFS) on targeted RNA, respectively.

The methods described herein have been used to discover additional mechanisms and parameters within single subunit Class 2 effector systems that can expand the capabilities of RNA-programmable nucleic acid manipulation.

In one aspect, the disclosure relates to the use of computational methods and algorithms to search for and identify novel protein families that exhibit a strong co-occurrence pattern with certain other features within naturally occurring genome sequences. In certain embodiments, these computational methods are directed to identifying protein families that co-occur in close proximity to CRISPR arrays. However, the methods disclosed herein are useful in identifying proteins that naturally occur within close proximity to other features, both non-coding and protein-coding (e.g., fragments of phage sequences in non-coding areas of bacterial loci; or CRISPR Cas1 proteins). It is understood that the methods and calculations described herein may be performed on one or more computing devices.

In some embodiments, a set of genomic sequences is obtained from genomic or metagenomic databases. The databases comprise short reads, or contig level data, or assembled scaffolds, or complete genomic sequences of organisms. Likewise, the database may comprise genomic sequence data from prokaryotic organisms, or eukaryotic organisms, or may include data from metagenomic environmental samples. Examples of database repositories include the National Center for Biotechnology Information (NCBI) RefSeq, NCBI GenBank, NCBI Whole Genome Shotgun (WGS), and the Joint Genome Institute (JGI) Integrated Microbial Genomes (IMG).

In some embodiments, a minimum size requirement is imposed to select genome sequence data of a specified minimum length. In certain exemplary embodiments, the minimum contig length may be 100 nucleotides, 500 nt, 1 kb, 1.5 kb, 2 kb, 3 kb, 4 kb, 5 kb, 10 kb, 20 kb, 40 kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments, CRISPR arrays are identified from the genome sequence data. In some embodiments, PILER-CR is used to identify CRISPR arrays. In some embodiments, CRISPR Recognition Tool (CRT) is used to identify CRISPR arrays. In some embodiments, CRISPR arrays are identified by a heuristic that identifies nucleotide motifs repeated a minimum number of times (e.g. 2, 3, or 4 times), where the spacing between consecutive occurrences of a repeated motif does not exceed a specified length (e.g. 50, 100, or 150 nucleotides). In some embodiments, multiple CRISPR array identification tools may be used over the same set of sequence data with the resulting set of CRISPR arrays de-duplicated.

In some embodiments, proteins in close proximity to CRISPR arrays are identified. In some embodiments, proximity is defined as a nucleotide distance, and may be within 20 kb, 15 kb, or 5 kb. In some embodiments, proximity is defined as the number of open reading frames (ORFs) between a protein and a CRISPR array, and certain exemplary distances may be 10, 5, 4, 3, 2, 1, or 0 ORFs. The proteins identified as being within close proximity to a CRISPR array are then grouped into clusters of homologous proteins. In some embodiments, blastclust is used to form protein clusters. In certain other embodiments, mmseqs2 is used to form protein clusters.

To establish a pattern of strong co-occurrence between the members of a protein cluster with CRISPR arrays, a BLAST search of each member of the protein family may be performed over the complete set of known and predicted proteins previously compiled. In some embodiments, UBLAST or mmseqs2 may be used to search for similar proteins. In some embodiments, a search may be performed only for a representative subset of proteins in the family.

In some embodiments, the clusters of proteins within close proximity to CRISPR arrays are ranked or filtered by a metric to determine co-occurrence. One exemplary metric is the ratio of the number of elements in a protein cluster against the number of BLAST matches up to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the number of elements of the CRISPR associated cluster against the number of elements of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review, and may contain information including pairwise sequence similarity, phylogenetic tree, source organisms/environments, predicted functional domains, and a graphical depiction of locus structures. In some embodiments, the graphical depiction of locus structures may filter for nearby protein families that have a high representation.

In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array, or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

Pooled-Screening

To efficiently validate the activity of the engineered novel CRISPR-Cas systems and simultaneously evaluate in an unbiased manner different activity mechanisms and functional parameters, we developed a new pooled-screening approach in *E. coli.*

First, from the computational identification of the conserved protein and noncoding elements of the novel CRISPR-Cas system, DNA synthesis and molecular cloning was used to assemble the separate components into a single artificial expression vector, which in one embodiment is based on a pET-28a+ backbone. In a second embodiment, the effectors and noncoding elements are transcribed on a single mRNA transcript, and different ribosomal binding sites are used to translate individual effectors.

Second, the natural crRNA and targeting spacers were replaced with a library of unprocessed crRNAs containing non-natural spacers targeting a second plasmid, pACYC184. This crRNA library was cloned into the vector backbone containing the protein effectors and noncoding elements (e.g. pET-28a+), and then subsequently transformed the library into *E. coli* along with the pACYC184 plasmid target. Consequently, each resulting *E. coli* cell contains no more than one targeting spacer. In an alternate embodiment, the library of unprocessed crRNAs containing non-natural spacers additionally target *E. coli* essential genes, drawn from resources such as those described in Baba et al. (2006) Mol. Syst. Biol. 2:2006.0008; and Gerdes et al. (2003) J. Bacteriol. 185 (19): 5673-84, the entire contents of each of which are incorporated herein by reference. In this embodiment, positive, targeted activity of the novel CRISPR-Cas systems that disrupts essential gene function results in cell death or growth arrest. In some embodiments, the essential gene targeting spacers can be combined with the pACYC184 targets to add another dimension to the assay.

Third, the *E. coli* were grown under antibiotic selection. In one embodiment, triple antibiotic selection is used: kanamycin for ensuring successful transformation of the pET-28a+ vector containing the engineered CRISPR-Cas effector system, and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library.

Examining the population of surviving cells at a later time point compared to an earlier time point results in a depleted signal compared to the inactive crRNAs. In some embodiments, double antibiotic selection is used. For example, withdrawal of either chloramphenicol or tetracycline to remove selective pressure can provide novel information about the targeting substrate, sequence specificity, and potency. In some embodiments, only kanamycin is used to ensure successful transformation of the pET-28a+ vector containing the engineered CRISPR-Cas effector system. This embodiment is suitable for libraries containing spacers targeting *E. coli* essential genes, as no additional selection beyond kanamycin is needed to observe growth alterations. In this embodiment, chloramphenicol and tetracycline dependence is removed, and their targets (if any) in the library provides an additional source of negative or positive information about the targeting substrate, sequence specificity, and potency.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters in a broad, hypothesis-agnostic manner. In this way, the features required for reconstituting the novel CRISPR-Cas system in a heterologous prokaryotic species can be more comprehensively tested and studied.

The key advantages of the in vivo pooled-screen described herein include:

(1) Versatility-Plasmid design allows multiple effectors and/or noncoding elements to be expressed; library cloning strategy enables both transcriptional directions of the computationally predicted crRNA to be expressed;

(2) Comprehensive tests of activity mechanisms & functional parameters-Evaluates diverse interference mechanisms, including DNA or RNA cleavage; examines co-occurrence of features such as transcription, plasmid DNA replication; and flanking sequences for crRNA library can be used to reliably determine PAMs with complexity equivalence of 4N's;

(3) Sensitivity-pACYC184 is a low copy plasmid, enabling high sensitivity for CRISPR-Cas activity since even modest interference rates can eliminate the antibiotic resistance encoded by the plasmid; and (4) Efficiency-Optimized molecular biology steps to enable greater speed and throughput RNA-sequencing and protein expression samples can be directly harvested from the surviving cells in the screen.

The novel CRISPR-Cas families described herein were evaluated using this in vivo pooled-screen to evaluate their operational elements, mechanisms and parameters, as well as their ability to be active and reprogrammed in an engineered system outside of their natural cellular environment.

Type III-E CRISPR-Cas System

In one aspect, this disclosure provides the Type III-E CRISPR-Cas system, wherein a Type III-E effector protein may include a Repeat Associated Mysterious Protein (RAMP) domain (see e.g., Makarova and Koonin (2018) *Methods Mol Biol.,* 1311:47-75). In some embodiments, the RAMP-domain containing protein is a single large protein. In some embodiments, the RAMP-domain containing single protein is at least approximately 1400 amino acids. In some embodiments, the RAMP-domain containing single protein is at least approximately 1550 amino acids. In some embodiments, the RAMP-domain containing single protein contains multiple RAMP domains. In some embodiments, the RAMP-domain containing single protein contains domains with homology to CRISPR Cmr4 (e.g., AYLVGLYTLTPTHPGSGTELGVVDQPIQRERHTGFPVIWGQSLKGVLRSYLKLVEKVDE EKINKIFGPPTEKAHEQAGLISVGDAKILFFPVRSLKGVYAYVTSPLVLNRFKRDLELAG V (SEQ ID NO: 50)). In some embodiments, the RAMP-domain containing single protein contains domains with homology to CRISPR Cmr6 (e.g., HHHHDMLNSLHAITGKFKTQSR LVVGLGDESVYETSIRLLRNYGVPYIPGSAIKGVTRHLTYYVLAEF (SEQ ID NO: 51)). In some embodiments, the RAMP-domain containing single protein contains domains with homology to CRISPR Cas7. In some embodiments, the RAMP-domain containing single protein does not contain a domain with homology to CRISPR Cas10. In some embodiments, the RAMP-domain containing single protein does not contain a domain with homology to CRISPR Cas5.

In one aspect, this disclosure provides the Type III-E CRISPR-Cas system, wherein a Type III-E effector protein includes a protease domain. In some embodiments, a complex formed by a CRISPR-associated protein having a protease domain and an RNA guide is activated upon binding to a target nucleic acid, and exhibits protease activity. In some embodiments, the protease activity of the activated complex may induce programmed cell death (e.g., apoptosis). In some embodiments, the protease domain is a caspase domain. In some embodiments, the caspase domain is a Caspase HetF Associated with Tprs (CHAT) domain (see, e.g., Aravind and Koonin (2002) *Proteins* 46 (4): 355-67). In some embodiments, a first CRISPR-associated protein comprising a CHAT domain interacts with a second effector protein comprising a RAMP domain to form a complex, whereby the second effector protein targets the complex to a target nucleic acid (e.g., as mediated by an RNA guide). In some embodiments, a protease activity of the CRISPR-associated protein comprising a CHAT domain is activated upon binding of the complex to a target nucleic acid (e.g., as mediated by an RNA guide and/or the CRISPR-associated protein comprising a RAMP domain). In some embodiments, a CRISPR-associated protein described herein exhibits a peptidase activity (e.g., endopeptidase or exopeptidase activity).

In some embodiments, the Type III-E CRISPR-Cas system provided herein is specific to a transcriptionally active site (see e.g., Estrella et al., (2019) *Genes & Dev* 30:460-470). In some embodiments, the Type III-E CRISPR-Cas system provided herein is specific to a site of DNA replication. In some embodiments, the Type III-E CRISPR-Cas system depends on endogenous bacterial host factors (Chou-Zheng and Hatoum-Aslan (2019) eLife 8: e45393).

CRISPR Enzyme Modifications

Deactivated/Inactivated CRISPR Enzymes

Where the CRISPR enzymes described herein have nuclease activity, the CRISPR enzymes can be modified to have diminished nuclease activity, e.g., nuclease inactivation of at least 50%, at least 60%, at least 70%, at least 80%, at least 90%, at least 95%, at least 97%, or 100% as compared with the wild type CRISPR enzymes. The nuclease activity can be diminished by several methods known in the art, e.g., introducing mutations into the nuclease domains of the proteins. In some embodiments, catalytic residues for the nuclease activities are identified, and these amino acid residues can be substituted by different amino acid residues (e.g., glycine or alanine) to diminish the nuclease activity.

The inactivated CRISPR enzymes can comprise or be associated with one or more functional domains (e.g., via fusion protein, linker peptides, "GS" linkers, etc.). These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, and switch activity (e.g., light inducible). In some embodiments, the functional domains are Krüppel associated box (KRAB), VP64, VP16, Fok1, P65, HSF1, MyoD1, and biotin-APEX.

The positioning of the one or more functional domains on the inactivated CRISPR enzymes allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fok1) is positioned to cleave or partially cleave the target. In some embodiments, the functional domain is positioned at the N-terminus of the CRISPR enzyme. In some embodiments, the functional domain is positioned at the C-terminus of the CRISPR enzyme. In some embodiments, the inactivated CRISPR enzyme is modified to comprise a first functional domain at the N-terminus and a second functional domain at the C-terminus.

Split Enzymes

The present disclosure also provides a split version of the CRISPR enzymes described herein. The split version of the CRISPR enzymes may be advantageous for delivery. In some embodiments, the CRISPR enzymes are split to two parts of the enzymes, which together substantially comprises a functioning CRISPR enzyme.

The split can be done in a way that the catalytic domain(s) are unaffected. The CRISPR enzymes may function as a nuclease or may be inactivated enzymes, which are essentially RNA-binding proteins with very little or no catalytic activity (e.g., due to mutation(s) in its catalytic domains).

In some embodiments, the nuclease lobe and α-helical lobe are expressed as separate polypeptides. Although the lobes do not interact on their own, the guide RNA recruits them into a ternary complex that recapitulates the activity of full-length CRISPR enzymes and catalyzes site-specific DNA cleavage. The use of a modified guide RNA abrogates split-enzyme activity by preventing dimerization, allowing for the development of an inducible dimerization system. The split enzyme is described, e.g., in Wright, Addison V., et al. "Rational design of a split-Cas9 enzyme complex," Proc. Nat'l. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR enzyme for temporal control of CRISPR enzyme activity. The CRISPR enzymes can thus be rendered chemically inducible by being split into two fragments and rapamycin-sensitive dimerization domains can be used for controlled reassembly of the CRISPR enzymes.

The split point is typically designed in silico and cloned into the constructs. During this process, mutations can be introduced to the split enzyme and non-functional domains can be removed. In some embodiments, the two parts or fragments of the split CRISPR enzyme (i.e., the N-terminal and C-terminal fragments), can form a full CRISPR enzyme, comprising, e.g., at least 70%, at least 80%, at least 90%, at least 95%, or at least 99% of the sequence of the wild-type CRISPR enzyme.

Self-Activating or Inactivating Enzymes

The CRISPR enzymes described herein can be designed to be self-activating or self-inactivating. In some embodiments, the CRISPR enzymes are self-inactivating. For example, the target sequence can be introduced into the CRISPR enzyme coding constructs. Thus, the CRISPR enzymes can cleave the target sequence, as well as the construct encoding the enzyme thereby self-inactivating their expression. Methods of constructing a self-inactivating CRISPR system is described, e.g., in Epstein, Benjamin E., and David V. Schaffer. "Engineering a Self-Inactivating CRISPR System for AAV Vectors," Mol. Ther., 24 (2016): S50, which is incorporated herein by reference in its entirety.

In some other embodiments, an additional guide RNA, expressed under the control of a weak promoter (e.g., 7SK promoter), can target the nucleic acid sequence encoding the CRISPR enzyme to prevent and/or block its expression (e.g., by preventing the transcription and/or translation of the nucleic acid). The transfection of cells with vectors expressing the CRISPR enzyme, guide RNAs, and guide RNAs that target the nucleic acid encoding the CRISPR enzyme can lead to efficient disruption of the nucleic acid encoding the CRISPR enzyme and decrease the levels of CRISPR enzyme, thereby limiting the genome editing activity.

In some embodiments, the genome editing activity of the CRISPR enzymes can be modulated through endogenous RNA signatures (e.g., miRNA) in mammalian cells. The CRISPR enzyme switch can be made by using a miRNA-complementary sequence in the 5'-UTR of mRNA encoding the CRISPR enzyme. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa, Moe et al. "Cell-type-specific genome editing with a microRNA-responsive CRISPR-Cas9 switch," Nucl. Acids Res., 2017 Jul. 27; 45 (13): e118).

Inducible CRISPR Enzymes

The CRISPR enzymes can be inducible, e.g., light inducible or chemically inducible. This mechanism allows for activation of the functional domain in the CRISPR enzymes. Light inducibility can be achieved by various methods known in the art, e.g., by designing a fusion complex wherein CRY2 PHR/CIBN pairing is used in split CRISPR Enzymes (see, e.g., Konermann et al. "Optical control of mammalian endogenous transcription and epigenetic states," *Nature,* 500.7463 (2013): 472). Chemical inducibility can be achieved, e.g., by designing a fusion complex wherein FKBP/FRB (FK506 binding protein/FKBP rapamycin binding domain) pairing is used in split CRISPR Enzymes. Rapamycin is required for forming the fusion complex, thereby activating the CRISPR enzymes (see, e.g., Zetsche, Volz, and Zhang, "A split-Cas9 architecture for inducible genome editing and transcription modulation," *Nature Biotech.,* 33.2 (2015): 139-142).

Furthermore, expression of the CRISPR enzymes can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless, Stephen J. et al. "Direct and specific chemical control of eukaryotic translation with a synthetic RNA-protein interaction," *Nucl. Acids Res.,* 40.9 (2012): e64-e64).

Various embodiments of inducible CRISPR enzymes and inducible CRISPR systems are described, e.g., in U.S. Pat. No. 8,871,445, US20160208243, and WO2016205764, each of which is incorporated herein by reference in its entirety.

Functional Mutations

Various mutations or modifications can be introduced into CRISPR enzymes as described herein to improve specificity and/or robustness. In some embodiments, the amino acid residues that recognize the Protospacer Adjacent Motif (PAM) are identified. The CRISPR enzymes described herein can be modified further to recognize different PAMs, e.g., by substituting the amino acid residues that recognize PAM with other amino acid residues.

In some embodiments, the CRISPR-associated proteins include at least one (e.g., 1, 2, 3, 4, 5, 6, 7, 8, 9, or 10) Nuclear Localization Signal (NLS) attached to the N-terminal or C-terminal of the protein. Non-limiting examples of NLSs include an NLS sequence derived from: the NLS of the SV40 virus large T-antigen, having the amino acid sequence PKKKRKV (SEQ ID NO: 300); the NLS from nucleoplasmin (e.g., the nucleoplasmin bipartite NLS with the sequence KRPAATKKAGQAKKKK (SEQ ID NO: 301)); the c-myc NLS having the amino acid sequence PAAKRVKLD (SEQ ID NO: 302) or RQRRNELKRSP (SEQ ID NO: 303); the hRNPA1 M9 NLS having the sequence NQSSNFGPMKGGNFGGRSSGPYGGGGQYFAKPRNQGGY (SEQ ID NO: 304); the sequence RMRIZFKNKGKDTAELRRRRVEVSVELRKAKKDEQILKRRNV (SEQ ID NO: 305) of the IBB domain from importin-alpha; the sequences VSRKRPRP (SEQ ID NO: 306) and PPKKARED (SEQ ID NO: 307) of the myoma T protein; the sequence PQPKKKPL (SEQ ID NO: 308) of human p53; the sequence SALIKKKKKMAP (SEQ ID NO: 309) of mouse c-abl IV; the sequences DRLRR (SEQ ID NO: 310) and PKQKKRK (SEQ ID NO: 311) of the influenza virus NS1; the sequence RKLKKKIKKL (SEQ ID NO: 312) of the Hepatitis virus delta antigen; the sequence REKKKFLKRR (SEQ ID NO: 313) of the mouse Mx1 protein; the sequence KRKGDEVDGVDEVAKKKSKK (SEQ ID NO: 314) of the human poly (ADP-ribose) polymerase; and the sequence RKCLQAGMNLEARKTKK (SEQ ID NO: 315) of the human glucocorticoid receptor. In some embodiments, the CRISPR-associated protein includes at least one (e.g., 1, 2, 3, 4, 5, 6, 7, 8, 9, or 10) Nuclear Export Signal (NES) attached the N-terminal or C-terminal of the protein. In a preferred embodiment, a C-terminal and/or N-terminal NLS or NES is attached for optimal expression and nuclear targeting in eukaryotic cells, e.g., human cells.

In some embodiments, the CRISPR enzymes described herein are mutated at one or more amino acid residues to alter one or more functional activities. For example, in some embodiments, the CRISPR enzyme is mutated at one or more amino acid residues to alter its peptidase or protease activity. In some embodiments, the CRISPR enzyme is mutated at one or more amino acid residues to alter its nuclease activity (e.g., endonuclease activity or exonuclease activity). In some embodiments, the CRISPR enzyme is mutated at one or more amino acid residues to alter its ability to functionally associate with a RNA guide. In some embodiments, the CRISPR enzyme is mutated at one or more amino acid residues to alter its ability to functionally associate with a target nucleic acid.

In some embodiments, the CRISPR enzymes described herein are capable of cleaving a target nucleic acid molecule. In some embodiments, the CRISPR enzyme cleaves both strands of the target nucleic acid molecule. However, in some embodiments, the CRISPR enzyme is mutated at one or more amino acid residues to alter its cleaving activity. For example, in some embodiments, the CRISPR enzyme may comprise one or more mutations that render the enzyme incapable of cleaving a target nucleic acid. In other embodiments, the CRISPR enzyme may comprise one or more mutations such that the enzyme is capable of cleaving a single strand of the target nucleic acid (i.e., nickase activity). In some embodiments, the CRISPR enzyme is capable of cleaving the strand of the target nucleic acid that is complementary to the strand to which the RNA guide hybridizes. In some embodiments, the CRISPR enzyme is capable of cleaving the strand of the target nucleic acid to which the RNA guide hybridizes.

In some embodiments, a CRISPR enzyme described herein may be engineered to comprise a deletion in one or more amino acid residues to reduce the size of the enzyme while retaining one or more desired functional activities (e.g., nuclease activity and the ability to interact functionally with a RNA guide). The truncated CRISPR enzyme may be advantageously used in combination with delivery systems having load limitations.

In one aspect, the present disclosure provides nucleic acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the nucleic sequences described herein. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the amino acid sequences described herein.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments is at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blosum 62 scoring matrix with a gap penalty of 12, a gap extend penalty of 4, and a frameshift gap penalty of 5.

Beyond the biochemical and diagnostic applications described herein, programmable Type III-E CRISPR-Cas systems described herein have important applications in eukaryotic cells such as genotype-gated cell death or therapeutic modification of the genome, with examples of applications including, but not limited to: targeted, sequence-based destruction of specific cell population, such as for treatment of neoplasms by specific targeting of mutated tumor cells, treatment of infections by destroying cells infected with bacteria or virus, preserving a cell lineage surveiling the genome and destroying mutated cells; additionally, in prokaryotic cellular environments, defense against transformants or infections, as well as defense against spontaneous mutations.

In some embodiments, the CRISPR-associated proteins and accessory proteins described herein can be fused to one or more peptide tags, including a His-tag, GST-tag, FLAG-tag, or myc-tag. In some embodiments, the CRISPR-associated proteins or accessory proteins described herein can be fused to a detectable moiety such as a fluorescent protein (e.g., green fluorescent protein or yellow fluorescent protein). In other embodiments, CRISPR-associated proteins or accessory proteins described herein are fused to a peptide or non-peptide moiety that allows these proteins to enter or localize to a tissue, a cell, or a region of a cell. For instance, a CRISPR-associated protein or accessory protein of this disclosure may comprise a nuclear localization sequence (NLS) such as an SV40 (simian virus 40) NLS, c-Myc NLS, or other suitable monopartite NLS. The NLS may be fused to an N-terminal and/or a C-terminal of the CRISPR-associated protein or accessory protein, and may be fused singly (i.e., a single NLS) or concatenated (e.g., a chain of 2, 3, 4, etc. NLS).

In those embodiments where a tag is fused to a CRISPR-associated protein, such tag may facilitate affinity-based or charge-based purification of the CRISPR-associated protein, e.g., by liquid chromatography or bead separation utilizing an immobilized affinity or ion-exchange reagent. As a non-limiting example, a recombinant CRISPR-associated protein of this disclosure comprises a polyhistidine (His) tag, and for purification is loaded onto a chromatography column comprising an immobilized metal ion (e.g. a $Zn^{2+}$, $Ni^{2+}$, $Cu^{2+}$ ion chelated by a chelating ligand immobilized on the resin, which resin may be an individually prepared resin or a commercially available resin or ready to use column such as the HisTrap FF column commercialized by GE Healthcare Life Sciences, Marlborough, Massachusetts). Following the loading step, the column is optionally rinsed, e.g., using one or more suitable buffer solutions, and the His-tagged protein is then eluted using a suitable elution buffer. Alternatively or additionally, if the recombinant CRISPR-associated protein of this disclosure utilizes a FLAG-tag, such protein may be purified using immunoprecipitation methods known in the industry. Other suitable purification methods for tagged CRISPR-associated proteins or accessory proteins of this disclosure will be evident to those of skill in the art.

The proteins described herein (e.g., CRISPR-associated proteins or accessory proteins) can be delivered or used as either nucleic acid molecules or polypeptides. When nucleic acid molecules are used, the nucleic acid molecule encoding the CRISPR-associated proteins can be codon-optimized, as discussed in further detail below. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" available at kazusa.orjp/codon/and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA).

In some instances, nucleic acids of this disclosure which encode CRISPR-associated proteins or accessory proteins for expression in eukaryotic (e.g., human, or other mammalian cells) cells include one or more introns, i.e., one or more non-coding sequences comprising, at a first end (e.g., a 5' end), a splice-donor sequence and, at second end (e.g., the 3' end) a splice acceptor sequence. Any suitable splice donor/splice acceptor can be used in the various embodiments of this disclosure, including without limitation simian virus 40 (SV40) intron, beta-globin intron, and synthetic introns. Alternatively or additionally, nucleic acids of this disclosure encoding CRISPR-associated proteins or accessory proteins may include, at a 3' end of a DNA coding sequence, a transcription stop signal such as a polyadenylation (polyA) signal. In some instances, the polyA signal is located in close proximity to, or adjacent to, an intron such as the SV40 intron.

RNA Guides

In some embodiments, the CRISPR systems described herein include at least one Type III-E RNA guide. The architecture of many RNA guides is known in the art (see, e.g., International Publication Nos. WO 2014/093622 and WO 2015/070083, the entire contents of each of which are incorporated herein by reference). In some embodiments, the CRISPR systems described herein include multiple RNA guides (e.g., two, three, four, five, six, seven, eight, or more RNA guides).

In some embodiments, the CRISPR systems described herein include at least one Type III-ERNA guide or a nucleic acid encoding at least one Type III-E RNA guide. In some embodiments, the RNA guide includes a crRNA. Generally, the crRNAs described herein include a direct repeat sequence and a spacer sequence. In certain embodiments, the crRNA includes, consists essentially of, or consists of a direct repeat sequence linked to a guide sequence or spacer sequence. In some embodiments, the crRNA includes a direct repeat sequence, a spacer sequence, and a direct repeat sequence (DR-spacer-DR), which is typical of precursor crRNA (pre-crRNA) configurations in other CRISPR systems. In some embodiments, the crRNA includes a truncated direct repeat sequence and a spacer sequence, which is typical of processed or mature crRNA. In some embodiments, the CRISPR-Cas effector protein forms a complex with the RNA guide, and the spacer sequence directs the complex to a sequence-specific binding with the target nucleic acid that is complementary to the spacer sequence.

Guide RNA Modifications

Spacer Lengths

The spacer length of guide RNAs can range from about 15 to 50 nucleotides. In some embodiments, the spacer length of a guide RNA is at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer. In some embodiments, the direct repeat length of the guide RNA is at least 16 nucleotides, or is from 16 to 20 nucleotides (e.g., 16, 17, 18, 19, or 20 nucleotides). In some embodiments, the direct repeat length of the guide RNA is 19 nucleotides.

The guide RNA sequences can be modified in a manner that allows for formation of the CRISPR complex and successful binding to the target, while at the same time not allowing for successful nuclease activity (i.e., without nuclease activity/without causing indels). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50%, shorter than respective guide RNAs that have nuclease activity. Dead guide sequences of guide RNAs can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CRISPR enzyme as described herein, and a guide RNA (gRNA) wherein the gRNA comprises a dead guide sequence whereby the gRNA is capable of hybridizing to a target sequence such that the CRISPR system is directed to a genomic locus of interest in a cell without detectable cleavage activity.

A detailed description of dead guides is described, e.g., in WO 2016094872, which is incorporated herein by reference in its entirety.

Inducible Guides

Guide RNAs can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of guide RNA can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, both of which are incorporated herein by reference in the entirety.

Chemical Modifications

Chemical modifications can be applied to the guide RNA's phosphate backbone, sugar, and/or base. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.,* 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2 '-modified oligonucleotide duplexes with improved in vitro potency and stability compared to unmodified small interfering RNA," *J. Med. Chem.,* 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," *Front. Genet.,* 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized guide RNA molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the guide RNA includes one or more phosphorothioate modifications. In some embodiments, the guide RNA includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biotechnol.* 2016 Sep. 10; 233:74-83; WO 2016205764; and U.S. Pat. No. 8,795,965 B2; each which is incorporated by reference in its entirety.

Sequence Modifications

The sequences and the lengths of the guide RNAs, tracrRNAs, and crRNAs described herein can be optimized. In some embodiments, the optimized length of guide RNA can be determined by identifying the processed form of tracrRNA and/or crRNA, or by empirical length studies for guide RNAs, tracrRNAs, crRNAs, and the tracrRNA tetraloops.

The guide RNAs can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the guide RNA has two or more aptamer sequences that are specific to the same adaptor proteins. In some embodiments, the two or more aptamer sequences are specific to different adaptor proteins. The adaptor proteins can include, e.g., MS2, PP7, QB, F2, GA, fr, JP501, M12, R17, BZ13, JP34, JP500, KUI, M11, MX1, TW18, VK, SP, FI, ID2, NL95, TW19, AP205, ϕCb5, ϕCb8r, ϕCb12r, ϕCb23r, 7s, and PRR1. Accordingly, in some embodiments, the aptamer is selected from binding proteins specifically binding any one of the adaptor proteins as described herein. In some embodiments, the aptamer sequence is a MS2 loop. A detailed description of aptamers can be found, e.g., in Nowak et al., "Guide RNA engineering for versatile Cas9 functionality," *Nucl. Acid. Res.,* 2016 Nov. 16; 44 (20): 9555-9564; and WO 2016205764, which are incorporated herein by reference in their entirety.

Guide: Target Sequence Matching Requirements

In classic CRISPR systems, the degree of complementarity between a guide sequence and its corresponding target sequence can be about 50%, 60%, 75%, 80%, 85%, 90%, 95%, 97.5%, 99%, or 100%. In some embodiments, the degree of complementarity is 100%. The guide RNAs can be about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length.

To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required, provided there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Methods of Using CRISPR Systems

The CRISPR systems described herein have a wide variety of utilities including modifying (e.g., deleting, inserting, translocating, inactivating, or activating) a target polynucleotide in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), detecting circulating tumor DNA, preparing next generation library, drug screening, disease diagnosis and prognosis, and treating various genetic disorders.

DNA/RNA Detection

In one aspect, the CRISPR systems described herein can be used in DNA/RNA detection.

While many CRISPR enzymes target DNA, single effector RNA-guided RNases can be reprogrammed with CRISPR RNAs (crRNAs) to provide a platform for specific RNA sensing. Upon recognition of its RNA target, activated single effector RNA-guided RNases engage in "collateral" cleavage of nearby non-targeted RNAs. This crRNA-programmed collateral cleavage activity allows the CRISPR systems to detect the presence of a specific RNA by triggering programmed cell death or by nonspecific degradation of labeled RNA.

The SHERLOCK method (Specific High Sensitivity Enzymatic Reporter UnLOCKing) provides an in vitro nucleic acid detection platform with attomolar sensitivity based on nucleic acid amplification and collateral cleavage of a reporter RNA, allowing for real-time detection of the target. To achieve signal detection, the detection can be combined with different isothermal amplification steps. For example, recombinase polymerase amplification (RPA) can be coupled with T7 transcription to convert amplified DNA to RNA for subsequent detection. The combination of amplification by RPA, T7 RNA polymerase transcription of amplified DNA to RNA, and detection of target RNA by collateral RNA cleavage-mediated release of reporter signal is referred as SHERLOCK. Methods of using CRISPR in SHERLOCK are described in detail, e.g., in Gootenberg, et al. "Nucleic acid detection with CRISPR-Cas13a/C2c2," *Science,* 2017 Apr. 28; 356 (6336): 438-442, which is incorporated herein by reference in its entirety.

The RNA targeting effector proteins can further be used in Northern blot assays, which use electrophoresis to separate RNA samples by size. The RNA targeting effector proteins can be used to specifically bind and detect the target RNA sequence. The RNA targeting effector proteins can also be fused to a fluorescent protein (e.g., GFP) and used to track RNA localization in living cells. More particularly, the RNA targeting effector proteins can be inactivated in that they no longer cleave RNAs. Thus, RNA targeting effector proteins can be used to determine the localization of the RNA or specific splice variants, the level of mRNA transcripts, up- or down-regulation of transcripts and disease-specific diagnosis. The RNA targeting effector proteins can be used for visualization of RNA in (living) cells using, for example, fluorescent microscopy or flow cytometry, such as fluorescence-activated cell sorting (FACS), which allows for high-throughput screening of cells and recovery of living cells following cell sorting. A detailed description regarding how to detect DNA and RNA can be found, e.g., in WO 2017070605, which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," *Science,* 2015 Apr. 24; 348 (6233): aaa6090, which is incorporated herein by reference herein in its entirety.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The RNA targeting effector proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965, WO 2016205764, and WO 2017070605; each of which is incorporated herein by reference herein in its entirety.

RNA Isolation, Purification, Enrichment, and/or Depletion

The CRISPR systems (e.g., RNA targeting effector proteins) described herein can be used to isolate and/or purify the RNA. The RNA targeting effector proteins can be fused to an affinity tag that can be used to isolate and/or purify the RNA-RNA targeting effector protein complex. These applications are useful, e.g., for the analysis of gene expression profiles in cells.

In some embodiments, the RNA targeting effector proteins can be used to target a specific noncoding RNA (ncRNA) thereby blocking its activity. In some embodiments, the effector protein as described herein can be used to specifically enrich a particular RNA (including but not limited to increasing stability, etc.), or alternatively, to specifically deplete a particular RNA (e.g., particular splice variants, isoforms, etc.).

These methods are described, e.g., in U.S. Pat. No. 8,795,965, WO 2016205764, and WO 2017070605; each of which is incorporated herein by reference herein in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR enzyme transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," *BMC Genomics,* 15.1 (2014): 1002, which is incorporated herein by reference in its entirety.

Engineered Microorganisms

Microorganisms (e.g., *E. coli*, yeast, and microalgae) are widely used for synthetic biology. The development of synthetic biology has a wide utility, including various clinical applications. For example, the programmable CRISPR systems can be used to split proteins of toxic domains for targeted cell death, e.g., using cancer-linked RNA as target transcript. Further, pathways involving protein-protein interactions can be influenced in synthetic biological systems with e.g. fusion complexes with the appropriate effectors such as kinases or enzymes.

In some embodiments, guide RNA sequences that target phage sequences can be introduced into the microorganism. Thus, the disclosure also provides methods of vaccinating a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of Saccharomyces cerevisiae," *Yeast,* 2017 Sep. 8. doi: 10.1002/yea.3278; and Hlavova et al., "Improving microalgae for biotechnology—from genetics to synthetic biology," *Biotechnol. Adv.,* 2015 November 1; 33:1194-203, both of which are incorporated herein by reference in the entirety.

Application in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome), or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.,* 2011 June; 11 (3): 222-8, and WO 2016205764 A1; both of which are incorporated herein by reference in the entirety.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae,*" *Nat. Biotechnol.,* 2016 January; 34 (1): 78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of guide RNA (gRNA)-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.,* 2017 March; 14 (3): 297-301, which is incorporated herein by reference in its entirety.

Saturation Mutagenesis ("Bashing")

The CRISPR systems described herein can be used for in situ saturating mutagenesis. In some embodiments, a pooled guide RNA library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature,* 2015 Nov. 12; 527 (7577): 192-7, which is incorporated herein by reference in its entirety.

RNA-Related Applications

The CRISPR systems described herein can have various RNA-related applications, e.g., modulating gene expression, inhibiting RNA expression, screening RNA or RNA products, determining functions of lincRNA or non-coding RNA, inducing cell dormancy, inducing cell cycle arrest, reducing cell growth and/or cell proliferation, inducing cell anergy, inducing cell apoptosis, inducing cell necrosis, inducing cell death, and/or inducing programmed cell death. A detailed description of these applications can be found, e.g., in WO 2016205764 A1, which is incorporated herein by reference in its entirety.

Modulating Gene Expression

The CRISPR systems described herein can be used to modulate gene expression. The CRISPR systems can be used, together with suitable guide RNAs, to target gene expression, via control of RNA processing. The control of RNA processing can include, e.g., RNA processing reactions such as RNA splicing (e.g., alternative splicing), viral replication, and tRNA biosynthesis. The RNA targeting proteins in combination with suitable guide RNAs can also be used to control RNA activation (RNAa). RNA activation is a small RNA-guided and Argonaute (Ago)-dependent gene regulation phenomenon in which promoter-targeted short double-stranded RNAs (dsRNAs) induce target gene expression at the transcriptional/epigenetic level. RNAa leads to the promotion of gene expression, so control of gene expression may be achieved that way through disruption or reduction of RNAa. In some embodiments, the methods include the use of the RNA targeting CRISPR as substitutes for e.g., interfering ribonucleic acids (such as siRNAs, shRNAs, or dsRNAs). The methods of modulating gene expression are described, e.g., in WO 2016205764, which is incorporated herein by reference in its entirety.

Controlling RNA Interference

Control over interfering RNAs or microRNAs (miRNA) can help reduce off-target effects by reducing the longevity of the interfering RNAs or miRNAs in vivo or in vitro. In some embodiments, the target RNAs can include interfering RNAs, i.e., RNAs involved in the RNA interference pathway, such as small hairpin RNAs (shRNAs), small interfering (siRNAs), etc. In some embodiments, the target RNAs include, e.g., miRNAs or double stranded RNAs (dsRNA).

In some embodiments, if the RNA targeting protein and suitable guide RNAs are selectively expressed (for example spatially or temporally under the control of a regulated promoter, for example a tissue- or cell cycle-specific promoter and/or enhancer), this can be used to protect the cells or systems (in vivo or in vitro) from RNA interference (RNAi) in those cells. This may be useful in neighboring tissues or cells where RNAi is not required or for the purposes of comparison of the cells or tissues where the effector proteins and suitable guide RNAs are and are not expressed (i.e., where the RNAi is not controlled and where it is, respectively). The RNA targeting proteins can be used to control or bind to molecules comprising or consisting of RNAs, such as ribozymes, ribosomes, or riboswitches. In some embodiments, the guide RNAs can recruit the RNA targeting proteins to these molecules so that the RNA targeting proteins are able to bind to them. These methods are described, e.g., in WO 2016205764 and WO 2017070605, both of which are incorporated herein by reference in the entirety.

Modifying Riboswitches and Controlling Metabolic Regulations

Riboswitches are regulatory segments of messenger RNAs that bind small molecules and in turn regulate gene expression. This mechanism allows the cell to sense the intracellular concentration of these small molecules. A specific riboswitch typically regulates its adjacent gene by altering the transcription, the translation or the splicing of this gene. Thus, in some embodiments, the riboswitch activity can be controlled by the use of the RNA targeting proteins in combination with suitable guide RNAs to target the riboswitches. This may be achieved through cleavage of, or binding to, the riboswitch. Methods of using CRISPR systems to control riboswitches are described, e.g., in WO 2016205764 and WO 2017070605, both of which are incorporated herein by reference in their entireties.

Therapeutic Applications

The CRISPR systems described herein can have various therapeutic applications. In some embodiments, the new CRISPR systems can be used to treat various diseases and disorders, e.g., genetic disorders (e.g., monogenetic diseases), diseases that can be treated by nuclease activity (e.g., Pcsk9 targeting, Duchenne Muscular Dystrophy (DMD), BCL11a targeting), and various cancers, etc.

In some embodiments, the CRISPR systems described herein can be used to edit a target nucleic acid to modify the target nucleic acid (e.g., by inserting, deleting, or mutating one or more amino acid residues). For example, in some embodiments the CRISPR systems described herein comprise an exogenous donor template nucleic acid (e.g., a DNA molecule or an RNA molecule), which comprises a desirable nucleic acid sequence. Upon resolution of a cleavage event induced with the CRISPR system described herein, the molecular machinery of the cell will utilize the exogenous donor template nucleic acid in repairing and/or resolving the cleavage event. Alternatively, the molecular machinery of the cell can utilize an endogenous template in repairing and/or resolving the cleavage event. In some embodiments, the CRISPR systems described herein may be used to alter a target nucleic acid resulting in an insertion, a deletion, and/or a point mutation). In some embodiments, the insertion is a scarless insertion (i.e., the insertion of an intended nucleic acid sequence into a target nucleic acid resulting in no additional unintended nucleic acid sequence upon resolution of the cleavage event). Donor template nucleic acids may be double stranded or single stranded nucleic acid molecules (e.g., DNA or RNA). Methods of designing exogenous donor template nucleic acids are described, for example, in PCT Publication No. WO 2016094874 A1, the entire contents of which are expressly incorporated herein by reference.

In one aspect, the CRISPR systems described herein can be used for treating a disease caused by overexpression of RNAs, toxic RNAs and/or mutated RNAs (e.g., splicing defects or truncations). For example, expression of the toxic RNAs may be associated with the formation of nuclear inclusions and late-onset degenerative changes in brain, heart, or skeletal muscle. In some embodiments, the disorder is myotonic dystrophy. In myotonic dystrophy, the main pathogenic effect of the toxic RNAs is to sequester binding proteins and compromise the regulation of alternative splicing (see, e.g., Osborne et al., "RNA-dominant diseases," *Hum. Mol. Genet.,* 2009 Apr. 15; 18 (8): 1471-81). Myotonic dystrophy (dystrophia myotonica (DM)) is of particular interest to geneticists because it produces an extremely wide range of clinical features. The classical form of DM, which is now called DM type 1 (DM1), is caused by an expansion of CTG repeats in the 3'-untranslated region (UTR) of DMPK, a gene encoding a cytosolic protein kinase. The CRISPR systems as described herein can target overexpressed RNA or toxic RNA, e.g., the DMPK gene or any of the mis-regulated alternative splicing in DM1 skeletal muscle, heart, or brain.

The CRISPR systems described herein can also target trans-acting mutations affecting RNA-dependent functions that cause various diseases such as, e.g., Prader Willi syndrome, Spinal muscular atrophy (SMA), and Dyskeratosis congenita. A list of diseases that can be treated using the CRISPR systems described herein is summarized in Cooper et al., "RNA and disease," *Cell,* 136.4 (2009): 777-793, and WO 2016205764 A1, both of which are incorporated herein by reference in the entirety. Those of skill in this field will understand how to use the new CRISPR systems to treat these diseases.

The CRISPR systems described herein can also be used in the treatment of various tauopathies, including, e.g., primary and secondary tauopathies, such as primary age-related tauopathy (PART)/Neurofibrillary tangle (NFT)-predominant senile dementia (with NFTs similar to those seen in Alzheimer Disease (AD), but without plaques), dementia pugilistica (chronic traumatic encephalopathy), and progressive supranuclear palsy. A useful list of tauopathies and methods of treating these diseases are described, e.g., in WO 2016205764, which is incorporated herein by reference in its entirety.

The CRISPR systems described herein can also be used to target mutations disrupting the cis-acting splicing codes that can cause splicing defects and diseases. These diseases include, e.g., motor neuron degenerative disease that results from deletion of the SMN1 gene (e.g., spinal muscular atrophy), Duchenne Muscular Dystrophy (DMD), frontotemporal dementia, and Parkinsonism linked to chromosome 17 (FTDP-17), and cystic fibrosis.

The CRISPR systems described herein can also be used in methods of treating a condition or disease in a subject in need thereof. The methods include administering to the subject a CRISPR system as described herein, wherein the spacer sequence is complementary to at least 12 (e.g., 12, 13, 14, 15, 16, 17, 18, 19, 20, 21, or more) nucleotides of a target nucleic acid associated with the condition or disease; wherein the Type III-E CRISPR-Cas effector protein associates with the Type III-E RNA guide to form a complex; wherein the complex binds to a target nucleic acid sequence that is complementary to the at least 12 (e.g., 12-21 or more) nucleotides of the spacer sequence; and wherein upon binding of the complex to the target nucleic acid sequence the Type III-E CRISPR-Cas effector protein cleaves the target nucleic acid, thereby treating the condition or disease in the subject.

For example, the condition or disease can be a cancer or an infectious disease. For example, the condition or disease can be a cancer selected from the group including or consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

The CRISPR systems described herein can further be used for antiviral activity, in particular against RNA viruses. The effector proteins can target the viral RNAs using suitable guide RNAs selected to target viral RNA sequences.

Furthermore, in vitro RNA sensing assays can be used to detect specific RNA substrates. The RNA targeting effector proteins can be used for RNA-based sensing in living cells. Examples of applications are diagnostics by sensing of, for examples, disease-specific RNAs.

A detailed description of therapeutic applications of the CRISPR systems described herein can be found, e.g., in U.S. Pat. No. 8,795,965, EP 3009511, WO 2016205764, and WO 2017070605; each of which is incorporated herein by reference in its entirety.

Delivery of CRISPR Systems

Through this disclosure and the knowledge in the art, the CRISPR systems described herein, or components thereof, nucleic acid molecules thereof, or nucleic acid molecules encoding or providing components thereof, can be delivered by various delivery systems such as vectors, e.g., plasmids, viral delivery vectors. The new CRISPR enzymes and/or any of the RNAs (e.g., guide RNAs) can be delivered using suitable vectors, e.g., plasmids or viral vectors, such as adeno-associated viruses (AAV), lentiviruses, adenoviruses, and other viral vectors, or combinations thereof. The proteins and one or more guide RNAs can be packaged into one or more vectors, e.g., plasmids or viral vectors.

In some embodiments, the vectors, e.g., plasmids or viral vectors, are delivered to the tissue of interest by, e.g., intramuscular injection, intravenous administration, transdermal administration, intranasal administration, oral administration, or mucosal administration. Such delivery may be either via a single dose, or multiple doses. One skilled in the art understands that the actual dosage to be delivered herein may vary greatly depending upon a variety of factors, such as the vector choices, the target cells, organisms, tissues, the general conditions of the subject to be treated, the degrees of transformation/modification sought, the administration routes, the administration modes, the types of transformation/modification sought, etc.

In certain embodiments, the delivery is via adenoviruses, which can be at a single dose containing at least $1\times10^5$ particles (also referred to as particle units, pu) of adenoviruses. In some embodiments, the dose preferably is at least about $1\times10^6$ particles, at least about $1\times10^7$ particles, at least about $1\times10^8$ particles, and at least about $1\times10^9$ particles of the adenoviruses. The delivery methods and the doses are described, e.g., in WO 2016205764 A1 and U.S. Pat. No. 8,454,972 B2, both of which are incorporated herein by reference in the entirety.

In some embodiments, the delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR enzymes, operably linked to the promoter; (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, the delivery is via liposomes or lipofectin formulations and the like, and can be prepared by methods known to those skilled in the art. Such methods are described, for example, in WO 2016205764 and U.S. Pat. Nos. 5,593,972; 5,589,466; and 5,580,859; each of which is incorporated herein by reference in its entirety.

In some embodiments, the delivery is via nanoparticles or exosomes. For example, exosomes have been shown to be particularly useful in delivery RNA.

Further means of introducing one or more components of the new CRISPR systems to the cell is by using cell penetrating peptides (CPP). In some embodiments, a cell penetrating peptide is linked to the CRISPR enzymes. In some embodiments, the CRISPR enzymes and/or guide RNAs are coupled to one or more CPPs to effectively transport them inside cells (e.g., plant protoplasts). In some embodiments, the CRISPR enzymes and/or guide RNA(s) are encoded by one or more circular or non-circular DNA molecules that are coupled to one or more CPPs for cell delivery.

CPPs are short peptides of fewer than 35 amino acids either derived from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin β3 signal peptide sequence, polyarginine peptide Args sequence, Guanine rich-molecular transporters, and sweet arrow peptide. CPPs and methods of using them are described, e.g., in Hällbrink et al., "Prediction of cell-penetrating peptides," *Methods Mol. Biol.,* 2015; 1324:39-58; Ramakrishna et al., "Gene disruption by cell-penetrating peptide-mediated delivery of Cas9 protein and guide RNA," *Genome Res.,* 2014 June; 24 (6): 1020-7; and WO 2016205764 A1; each of which is incorporated herein by reference in its entirety.

Various delivery methods for the CRISPR systems described herein are also described, e.g., in U.S. Pat. No. 8,795,965, EP 3009511, WO 2016205764, and WO 2017070605; each of which is incorporated herein by reference in its entirety.

EXAMPLES

The invention is further described in the following examples, which do not limit the scope of the invention described in the claims.

Example 1—Identification of Minimal Components for Type III-E (CLUST.019911) CRISPR-Cas System (FIGS. 1-6)

Figure 1:
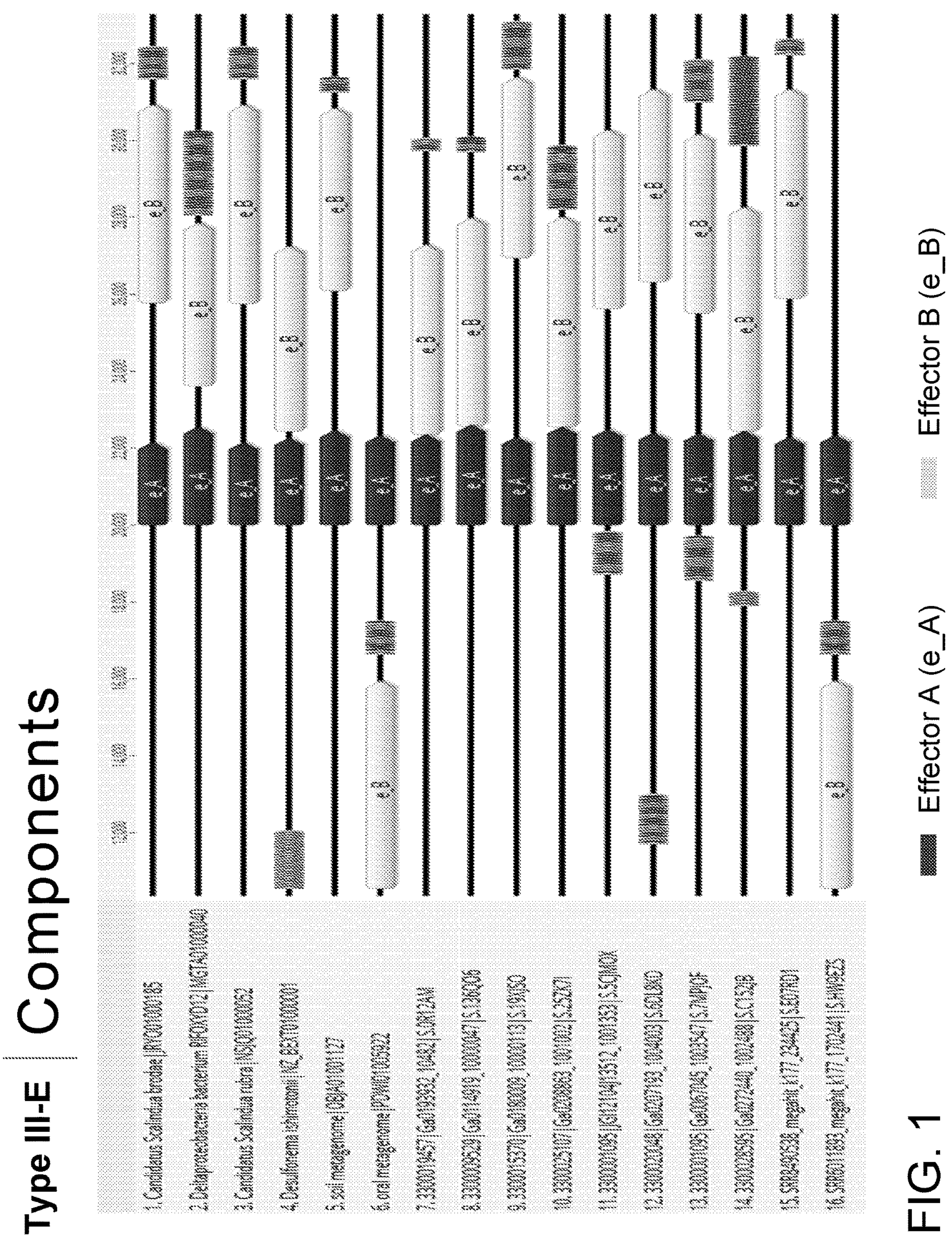
FIG. 1 is a schematic that shows conserved Effector A (e_A), Effector B (e_B), and CRISPR array elements by bacterial genome accession and species for representative Type III-E (CLUST.019911) loci.
Figure 2:
FIG. 2 is a schematic of a consensus sequence (SEQ ID NO:100) and a multiple sequence alignment under the consensus sequence that are examples of Type III-E direct repeat elements described herein (SEQ ID NOs: 27-38).
Figure 3A:
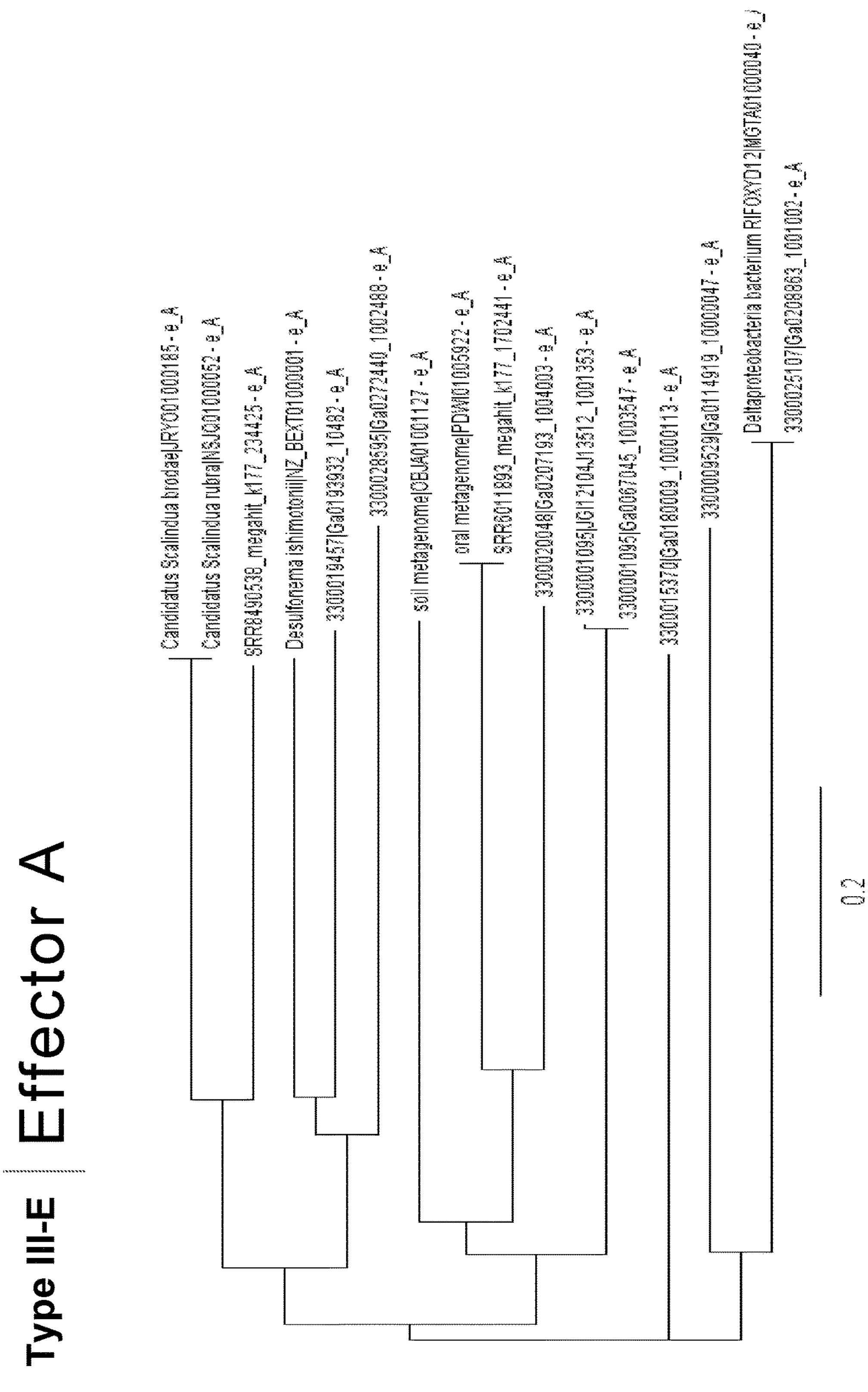
FIG. 3A is a phylogenetic tree of Type III-E (CLUST.019911) Effector A proteins.
Figure 3B:
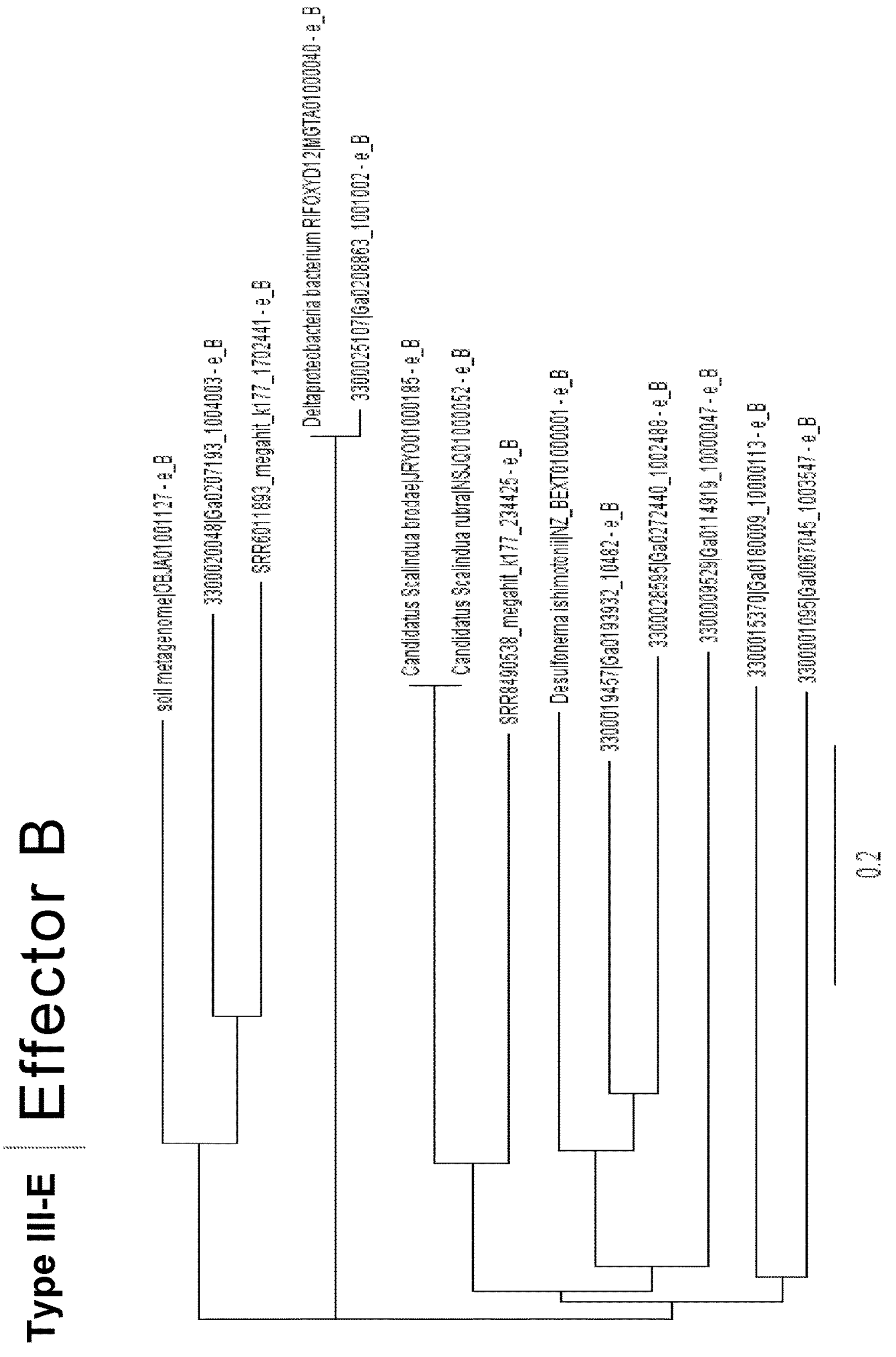
FIG. 3B is a phylogenetic tree of Type III-E (CLUST.019911) Effector B proteins.

This protein family describes a CRISPR system found in organisms including, but not limited to, *Deltaproteobacteria, Candidatus scalindua*, and uncultured metagenomic sequences collected from aquatic freshwater and marine environments (FIGS. 3A-3B). Exemplary naturally occurring loci containing this effector complex are depicted in FIG. 1, indicating that the effector protein Effector A (~800 amino acids) has a high co-occurrence with the effector protein Effector B (~1700 aa). Type III-E CRISPR-Cas systems include the exemplary effectors detailed in TABLES 1-3 and crRNAs containing exemplary sequences detailed in TABLE 4.

Type III-E CRISPR-Cas direct repeat sequences (consensus sequence being GTTRNRNANMRMCRSNWDYYWTTRATGTBACGGDAC (SEQ ID NO: 100)) show a conserved TGTNWYGGNAC (SEQ ID NO: 99) at the 3' end (see FIG. 2), wherein the various letters used in these consensus sequences (other than A, G, C, and T) have the following standard meanings:

| | | |
|---|---|---|
| R | A or G | puRine |
| Y | C, T or U | pYrimidines |
| K | G, T or U | bases which are Ketones |
| M | A or C | bases with aMino groups |
| S | C or G | Strong interaction |
| W | A, T or U | Weak interaction |
| B | not A (i.e. C, G, T or U) | B comes after A |
| D | not C (i.e. A, G, T or U) | D comes after C |
| H | not G (i.e., A, C, T or U) | H comes after G |
| V | neither T nor U (i.e. A, C or G) | V comes after U |
| N | A C G T U | Nucleic acid |
| — | gap of indeterminate length | |

FIGS. 3A and 3B show phylogenetic trees of Type III-E effector A and effector B proteins, respectively, showing that the both effectors exhibit diversity.

Figure 4:
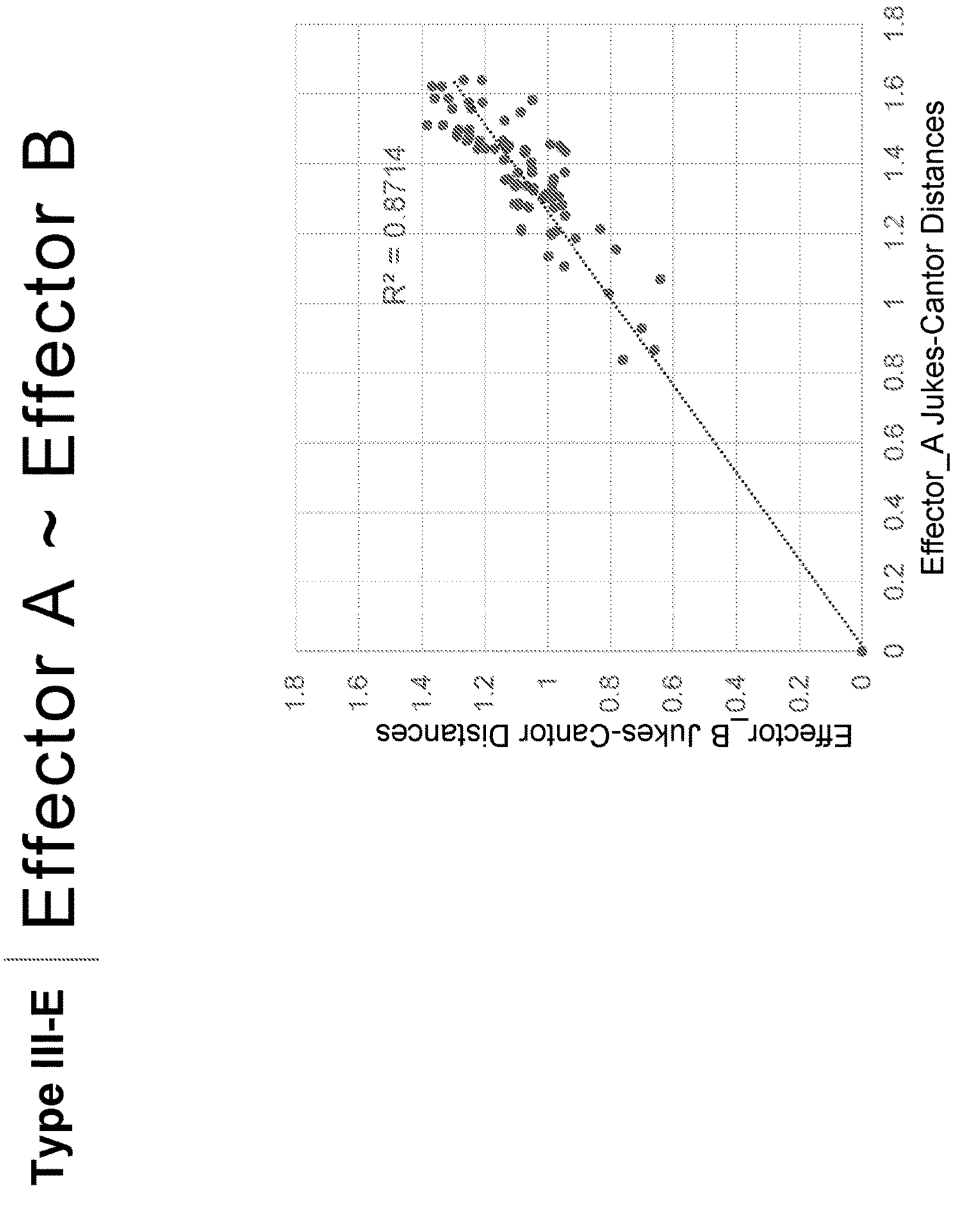
FIG. 4 is a scatter plot that depicts one point for each pair of genomic loci, where the x-value is the pairwise Jukes-Cantor distance of the Type III-E Effector_A proteins from the two loci, and the y-value is the pairwise Jukes_Cantor distance of the Type III-E Effector_B proteins from the two loci.

FIG. 4 shows the pairwise Jukes-Cantor distances for effector A and effector B proteins, indicating that two loci containing similar effector A proteins also contain correspondingly similar effector B proteins, indicative of co-evolution and potential functional association.

Figure 6:
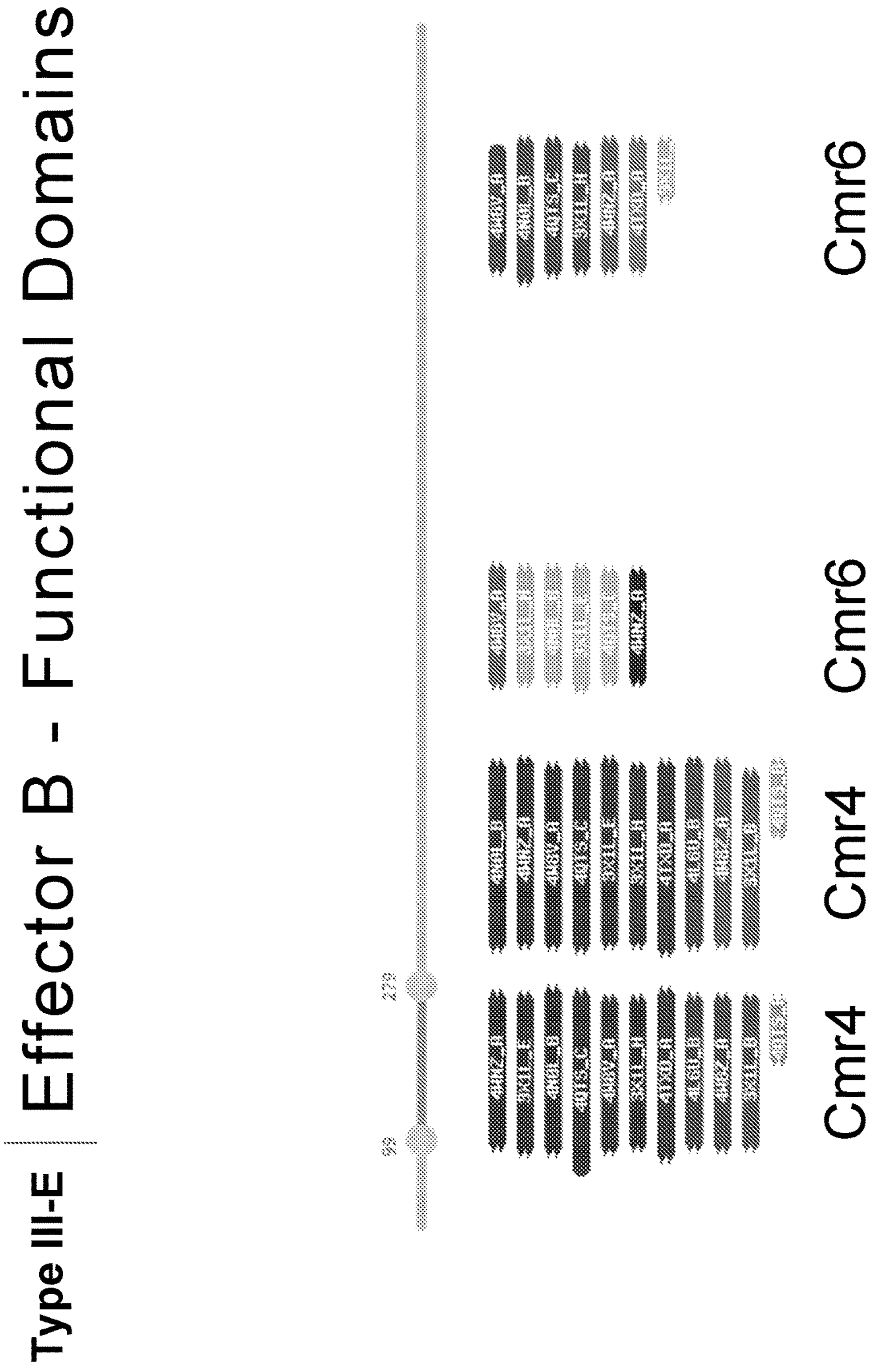
FIG. 6 is a schematic representation of HHpred domain predictions of an example of a Type III-E (CLUST.019911) Effector B, depicting multiple partial matches in different regions of the protein to CRISPR Cmr4 and CRISPR Cmr6.

An HMM profile search of the multiple sequence alignment of Type III-E effector A proteins against the PFAM database indicated the presence of the CHAT domain. HHpred domain predictions of an exemplary Type III-E Effector A are also depicted in FIG. 4, indicating a C-terminal match to the CHAT domain, and an N-terminal match to the TPR domain. HHpred domain predictions of an exemplary Type III-E Effector B are depicted in FIG. 6, which indicates multiple partial matches in different regions of the protein to Cmr4 and Cmr6.

Optionally, the CLUST.019911 CRISPR system includes a transactivating RNA (tracrRNA) with a DR homology as detailed in TABLE 5 and a complete tracrRNA contained in the DR homology loci detailed in TABLE 6. Optionally, the system includes a tracrRNA that is a subset of a non-coding sequence listed in TABLE 7.

Optionally, the system includes a RNA modulator that is a subset of a non-coding sequence listed in TABLE 7.

TABLE 1

Representative Type III-E (CLUST.019911) Effector Proteins

| Source | Effector_A accession | Effector_B accession | # spacers | cas1 | cas2 | Effector_ A size | Effector_ B size |
|---|---|---|---|---|---|---|---|
| Candidatus Scalindua brodae (JRYO01000185) | KHE91663.1 | JRYO01000185_8\|M | 11 | N | N | 716 | 1722 |
| Deltaproteobacteria bacterium RIFOXYD12_FULL_50_9 (MGTA01000040) | OGR07204.1 | OGR07205.1 | 31 | N | N | 849 | 1403 |
| *Desulfonema ishimotonii* (NZ_BEXT01000001) | WP_124327588.1 | WP_124327589.1 | 22 | Y | Y | 751 | 1601 |
| soil metagenome (OBJA01001127) | OBJA01001127_8\|M | OBJA01001127_4\|M | 5 | Y | Y | 816 | 1575 |
| oral metagenome (PDWI01005922) | PDWI01005922_7\|M | PDWI01005922_5\|M | 12 | Y | Y | 769 | 1801 |
| aquatic-marine-hydrothermal vent microbial mat (3300019457\|Ga0193932_10482) | RLC19860.1 | 3300019457\|Ga0193932_ 10482_5\|M | 4 | Y | N | 778 | 1652 |
| aquatic-marine-deep subsurface (3300009529\|Ga0114919_10000047) | 3300009529\|Ga0114919_ 10000047_39\|M | 3300009529\|Ga0114919_ 10000047_40\|M | 5 | Y | Y | 860 | 1806 |
| aquatic-freshwater-groundwater (3300015370\|Ga0180009_10000113) | 3300015370\|Ga0180009_ 10000113_9\|P | 3300015370\|Ga0180009_ 10000113_2\|P | 17 | N | N | 757 | 1559 |
| bioremediation-terephthalate-wastewater bioreactor (3300001095\|JGI12104J13512_1001353) | 3300001095\|JGI12104J13512_ 1001353_7\|M | 3300001095\|JGI12104J13512_ 1001353_10\|M | 15 | Y | Y | 822 | 1549 |
| aquatic-freshwater-freshwater lake sediment (3300020048\|Ga0207193_1004003) | 3300020048\|Ga0207193_ 1004003_10\|P | 3300020048\|Ga0207193_ 1004003_13\|M | 17 | Y | Y | 797 | 1668 |

TABLE 1-continued

| Representative Type III-E (CLUST.019911) Effector Proteins | | | | | | | |
|---|---|---|---|---|---|---|---|
| Source | Effector_A accession | Effector_B accession | # spacers | cas1 | cas2 | Effector_A size | Effector_B size |
| bioremediation-terephthalate-wastewater bioreactor (3300001096\|Ga0067045 1003547) | 3300001096\|Ga0067045_1003547_9\|P | 3300001096\|Ga0067045_1003547_12\|M | 31 | Y | Y | 789 | 1549 |
| terrestrial-soil (3300025107\|Ga0208863_1001002) | OGR07204.1 | 3300025107\|Ga0208863_1001002_11\|M | 23 | N | N | 849 | 1821 |
| aquatic-marine-marine sediment (3300028595\|Ga0272440_1002488) | 3300028595\|Ga0272440_1002488_3\|P | 3300028595\|Ga0272440_1002488_4\|M | 39 | N | N | 809 | 1940 |
| anammox bioreactor (SRR8490538) | SRR8490538_megahit_k177_234425_6\|M | SRR8490538_megahit_k177_234425_10\|M | 5 | N | N | 760 | 1812 |
| dolphin oral metagenome (SRR6011893) | SRR6011893_megahit_k177_1702441_3\|P | SRR6011893_megahit_k177_1702441_5\|M | 12 | Y | Y | 769 | 1801 |

TABLE 2

Amino Acid Sequences of Representative Type III-E (CLUST.019911) Effector_A Proteins >KHE91663.1
[*Candidatus Scalindua brodae*]
MNNTEENIDRIQEPTREDIDRKEAERLLDEAFNPRTKPVDRKKIINSALKILIGLYKEKKDDLTSASFISIARAYYLVSITILP
KGTTIPEKKKEALRKGIEFIDRAINKENGSILDSQRAFRIKSVLSIEFNRIDREKCDNIKLKNLLNEAVDKGCTDFDTYEWDIQ
IAIRLCELGVDMEGHFDNLIKSNKANDLQKAKAYYFIKKDDHKAKEHMDKCTASLKYTPCSHRLWDETVGFIERLKGDSSTLWR
DFAIKTYRSCRVQEKETGTLRLRWYWSRHRVLYDMAFLAVKEQADDEEPDVNVKQAKIKKLAEISDSLKSRFSLRLSDMEKMPK
SDDESNHEFKKFLDKCVTAYQDGYVINRSEDKEGQGENKSTTSKQPEPRPQAKLLELTQVPEGWVVVHFYLNKLEGMGNAIVFD
KCANSWQYKEFQYKELFEVFLTWQANYNLYKENAAEHLVTLCKKIGETMPFLFCDNFIPNGKDVLFVPHDFLHRLPLHGSIENK
TNGKLFLENHSCCYLPAWSFASEKEASTSDEYVLLKNFDQGHFETLQNNQIWGTQSVKDGASSDDLENIRNNPRLLTILCHGEA
NMSNPFRSMLKLANGGITYLEILNSVKGLKGSQVILGACETDLVPPLSDVMDEHYSVATALLLIGAAGVVGTMWKVRSNKTKSL
IEWKLENIEYKLNEWQKETGGAAYKDHPPTFYRSIAFRSIGFPL (SEQ ID NO: 1)

>OGR07204.1
[*Deltaproteobacteria* bacterium RIFOXYD12_FULL_50_9]
MNQNIDRAVGAILAIETATPLTESSTLAQRERHQKLLHDETKKIEQAFIALAQPPQCRAVEIAALSRFLQMTPLAVGPLRKRVI
CRAEPLKDDAHEQEIASHFNGLLLRLAKGLLASALNPAGIPWRRRVLWLEKAAHIAHRFDKEPLADDKERTEAAGVLARCCLHL
ALAHLPKGKDKSAMAERQEDLLQSLMWAQKAIVLAGQDKLSGEEYKLLKALVLIELDNLSPGRFQQQLNYVLYDLAVIWLERDT
ATKPFHPQELFVLWRYLATDFEPDLNMLLFKGSNTSERTAAVQQASPEAERFRPLLPLIHAWSAWKLDPPNNKIAEVILQAVNN
LDEHQVYEQVWKWTVDFLQELRNTGAVDWQLPAIAAWELCNKKEKELPFGFQIRQYWSRLDSLYRLAFDGALELKDCMTAARIV
DSLKSRTPLTWRDMDTLFAKLPKEKADQLREAFYSMEVQARMGFYAEAKEDANKLKKLLAAQVRKIRDIESVPAGWTVVHFHLR
EDQDLGYALACRLTADGMSYWTNHIFPVAGIRRAYDCWLEAYHGMEPGAREKSGYQLVELSEIMGKDLDFLFELAGEDGARGLL
FVPHGFSHLLPLHAAKKDGSYLFEKIPSLTLPAWEFAPDVDQIPVSDGQDFCFISQRANEQDLVGNIERSHTWNGVCNKNAAWT
NVLNTNKEWSKAPPRWLVFWCHGQADPHVAFRSKLLLGTLGVSLFEIQEAALSLTGTKVVLAVCESDLAPPEEYEKTDDHLSLA
APFLLKGARQVLAAIWEGAQLDLLKAMKEMLSNQDKHSWEILRELQSCWMRQPGAIFNDEYIRLYYAASFRILGFPEVATTNMA
TATAQEEIA (SEQ ID NO: 2)

>WP_124327588.1
[*Desulfonema ishimotonii*]
MSNPIRDIQDRLKTAKFDNKDDMMNLASSLYKYEKQLMDSSEATLCQQGLSNRPNSFSQLSQFRDSDIQSKAGGQTGKFWQNEY
EACKNFQTHKERRETLEQIIRFLQNGAEEKDADDLLLKTLARAYFHRGLLYRPKGFSVPARKVEAMKKAIAYCEIILDKNEEES
EALRIWLYAAMELRRCGEEYPENFAEKLFYLANDGFISELYDIRLFLEYTEREEDNNFLDMILQENQDRERLFELCLYKARACF
HLNQLNDVRIYGESAIDNAPGAFADPFWDELVEFIRMLRNKKSELWKEIAIKAWDKCREKEMKVGNNIYLSWYWARQRELYDLA
FMAQDGIEKKTRIADSLKSRTTLRIQELNELRKDAHRKQNRRLEDKLDRIIEQENEARDGAYLRRNPPCFTGGKREEIPFARLP
QNWIAVHFYLNELESHEGGKGGHALIYDPQKAEKDQWQDKSFDYKELHRKFLEWQENYILNEEGSADFLVTLCREIEKAMPFLF
KSEVIPEDRPVLWIPHGFLHRLPLHAAMKSGNNSNIEIFWERHASRYLPAWHLFDPAPYSREESSTLLKNFEEYDFQNLENGEI
EVYAPSSPKKVKEAIRENPAILLLLCHGEADMTNPFRSCLKLKNKDMTIFDLLTVEDVRLSGSRILLGACESDMVPPLEFSVDE
HLSVSGAFLSHKAGEIVAGLWTVDSEKVDECYSYLVEEKDFLRNLQEWQMAETENFRSENDSSLFYKIAPFRIIGFPAE(SEQ
ID NO: 3)

>OBJA01001127_8|M
[soil metagenome]
MEHKTMTEPAGQNPSATDNDFEKFIIDTGCVFFATPQEDPKYQNNKVEWHQGLCRFAQNDSPPTVIGSAIFFLQKLQEPGLFSG
LPVSPELCSKISKDKNEIVAYHQQCILRLCEELLVKGREAKEHRERRQAFDQAIKFLLVLKKGTSSDTPSPNGHIHFQDQVSIL
LAEAYYLRGKIIRPKGFSVPAKKIETLEVAEKILVDLVARDTTGKARRLRAMVHIDLAALRDPADDSGNLQDYRQALEQAVSSI
GDTKTCGRDEIVIILARAEDNAGWTGSDGLSARLEELVNNGAAGPLDQARAYLLLGQNNLAVTQTEKAITRMAATDNPTPFSHE
DWRLLVRLLRDLKHQNTAGIDKLILDTWRKVHQIERQTKNGMHVRWYWSRQRDLYDLAFHAAGNDARLKAQIADSLKARPALHL
GQAADLGLAVEQMEAGLLDRYMPGKMLEQTTDMAAPAAPGSAGWPELPRPWIAVHFYLSNGFGHPEGKQQGHALIQDSSKGDGK
DTWSERTFDYFPIWAAFMTWQENYQRLKKEAAPDLERLCQVMGRQMPFLFAPEDLPLERPVVFVPHDFLHRLPLHAALIDNGEE
SGIPAQSHPITYLPGWWMVTSQAANPNETASKNTPSPVAPVALVHWDNSEDIHDIIKQANGTVVVNASRSDWLKLKHNAVGLKV
LYCHGQAGYTNPFASSLKLDGGGLYLKDVVKGPPLVGRFILAACESDLVLPASTTLDEYFSFSTGLLQKGAAEILGTLWEVNET
DALSLIETVLRAPASGNLSFVLRDWLRDNLRSLTTELFYDIAAFRALGGPYPVDTKEEHR (SEQ ID NO: 4)

TABLE 2-continued

| Amino Acid Sequences of Representative Type III-E (CLUST.019911) Effector_A Proteins |
|---|
| >PDWI01005922_7\|M<br>[oral metagenome]<br>MNTVELLQEEERLTLDLVFLPPGSKNKEQKKNALVDLLLKIVEHGELTRKYSALLTLSRGALRGEVHFGEKLLPSPEACANLAK<br>PEEIKKMIRQHFQYRLDLLEAIVKKAADNTYSHARRRKALRIAIKELEQICEEALDELCFKARLLLAEALFERGRIVRPKGFSE<br>PGKKKELFQKAINCIEGNCSEEALRLRARIYLQWYRFFHDEPPCDLDDIFTKALAVTDDKMLKTELLLLCGERKEPDPYTDDLR<br>ALLNDQNVSPLSRARAAVLLEDWERCNVEIYEAIEDLGKTDFFQQDWELVVTLLKKNYNQFHGWSRACTRLWEITVEKESKDAG<br>HGCVLRWYWSRQRDVYNLAFAAFEECEDKARVVDSLKNRPAHHFSQLEQLAQSSDIIKQWIESEEIINQDSFAHSLRRHEKGAK<br>SHSGGSLRIFPCLPKGWIAVHFFLASWPEPKGYALIHNADTNTWEQRDFKYEQLWATYIAWQEVSLHNKIRESALLLKSLCETL<br>GKEMRWLFDEFLFPKERRRVLFVPHDFLHRLPLHMAIDIESQTVFAAKQPVCYLPAYHLQNNITENKKTSIYALVNLRENKQQK<br>KDEEIFAEKVEKMGAIVRRPALESDLLNLNPVPEKLVLYCHGIGHSANPFASKLCLGDTGVSYRDILALNRSLAGCRVLLFACE<br>TDLVPAQTSSIDEHLSISNALLQKGAFEVLGSLWALPGKTIYGITKTFIDNDDTSAVLHSSLKRLFEHYEKKNEKTRAQLLYNW<br>ASLRVLAPAREFS (SEQ ID NO: 5) |
| >RLC19860.1<br>[aquatic-marine-hydrothermal vent microbial mat]<br>MRYSSRTNCEAIDNLAEALQDQENMPEIARRVLEFEAENAKPENALCQHGLPHTKKAASQIAGVRDKHSEFYDNALLDLVEEWL<br>KTYEEAKKLTHRERRQEMEDKIRVLQPVLQAKGKDADPRFLSLLARIYLYRGMLFRPKGFTTPARKIEALKKAVQLSEKAVEKE<br>KDNPNFLRTWAQAALELEAIPETSFKVSSGLLKDAAVCINRDGIHSLNDLQVILEYAESEGKTSFLQHVLVEKRYWKRPFDLFL<br>LKARAAFALNRMDDVRYFLKSAMDKTPKALSSPFWDHLVDFLKKLRTKEGSDLWKEMAVAAHRLCREKEVKIANNIYLYRHWAR<br>QKSLYNMAFLAQNDLKEKAKIADSLKSRPVLRYQALREMKEHQNIAKLLEQDDQERDGGYHKQQVEMDERTGKRLSEKMEKAGV<br>SYENLPVPWISVHFYLNESENSEDEGSKGYALIFDALTQSWKERRFDYAKLHRKFMTWQEAYISAKKSSFAKDSLVELCREIGN<br>TMPFLFDTACIRDGAPVLWIPHGFLHRLPLHAAIRDEATNEIFLENHASRYLPAWSILNSASARRGKDSYMIKRFRAEDYEKEP<br>FSELEDMEWDNEEHEKLATPDDLKHFMAKNPGVFAVLCHGHGDILNPLKSWLELEGGGVSVLDILRYEKANLSGTRVLLGACEA<br>DMAPPVEYAIDEHVSLSAAFLSHKAQEVIAGLWEINIGEADECYAEILDCSDLSTELKDWQCDWVEKWRDDVEASGDNSTFYHI<br>TPFRIMGFPLKLKENNESEAKQ (SEQ ID NO: 6) |
| >3300009529\|Ga0114919_10000047_39\|M<br>[aquatic-marine-deep subsurface]<br>MVTPQASKNPAVDEILKQLTPYDMETENAKAIETRKSCIECLKGICERAQKQNDWVAFGTALHFLHELSGTTAPVFYGAVKGQS<br>ACGQLHNMQASIKEAVARITKSRAEHLRDKALKPYGIPYLSRHRFLEKAIRMVWELLQSDNGWPDSVWLHREASQFIARCFLDR<br>GRLVLPKGSSIPQKKIEALKKAWHWALKGALKAKEDDADSMKLWLEFREYILQTAKENDADIDSMKLLIEIGLELELYEKSFSP<br>QVNELTRKIASGKLLEDPKSSADWPIIDRGRSIGCFDEKQDEALFKLDLNKKEYKELPTLPLLRAKAGHRLKRDLASAFDEASF<br>FRVVCDAVRKLADVPFSSPIWVETIEFLAQLDPGSEIRNAASVAAWQICKLKEEDLDLGLQVRMWWSRHKMLYDLAFHAALSKD<br>DWALAARIADSPKSRPTIKALAMESVLDGDTLKGYYELEARGVARGYDSTYHRKKKSLEKAEAKKKRASKDTQGLRPLDFEEDI<br>PAGWAAIHLYLDQDKKGHALMRSAGSTKDGWLYKDFEISDIWQKFQAWQAADRYNPKFGGAATELHALCESLGYDDDHLGFLFN<br>KDLPDNLIIIPHDILHLVPIHSVMKNGEILLKQKKCIYLPAWGLPRETDSASTPEGEGLFDNFEDHDPLRQYLQPVLQAWKHSS<br>VSARNIKVPDATANDVRNYLKNTTNPEWMVFLCHGKADPVNPYNSGLLLRGSHLTHAALVELPKKMAGTKVFLGACETDMSPPK<br>QKSVDEHLSVSTAFFQKGASEIAGGLWRVHSAIAKKMVEHISENRKKPLVDVVWEKQKDWWDNGIQYVVDGITVKVSNCFKKLY<br>YLSSYRVVGFPRAIGENTDE (SEQ ID NO: 7) |
| >3300015370\|Ga0180009_10000113_9\|P<br>[aquatic-freshwater-groundwater]<br>MYSDFPALRLPELSVDQKKLFKISGTNPQLIYILMNEFDGEGDEPFFTGLVPDETDLSENKQAPLLKELARHLLKEYEDIGRNR<br>WKHADQRRVLEKAIRLLDKSHQAEENVSLELGKAYLYRARIIRPKGFTVPAKKIEALNNALHFCEDATNHGKAWADHFAGLVAL<br>ELYRCGKTHDNLSELLNKATADAELSEPDRRVEFYQMRVRLEELRQDEGNGSPYFIQNVLTKIFEFQEPGMELEKLKVSLQSPS<br>SSKDKISSSLEDLILVLKEYPFSHPLWEDTVRFARRLYENRLEFWKELALRLWEAAEDESRKISSVHLRWYWSRQRDLYDLSFL<br>AALKQGNPNLAAQVTDSAKSRPALSWQAIERLKHGNEELKDEIENYAQALSGGYIKGLLKPYRKPEVPNEEKPFFEQHLIDNNL<br>IAIQFYLVHLEEFEKVERSRERGYALIYDQESEKKWSFKTFDFAPIWEKYVAWQSVYFDLPPQQRDASGTQLRYLCEALGKALE<br>FLFKSPEKQFSSNEKSKDILFIPHDFLHRVPLHGAMLDNENVLLKTFNCFYLPAISYSAKNQGPQQNKNSVLLYYSGKSEESDD<br>PLFNHLKTKFDTPINFASATDLLDAAQNPPSLLVLYCHGEADATNPYLSRLKLKDDLMLLDFASAAGTFTGSKIFLGACETDLM<br>PPLDAPLDEQISMATIFLIKRSESVIGSMWEAKRMKVLNLLFMKEGLFDHFFEQQREWWKEEYEHTDSNTALYDCLCFRMYRCY<br>F (SEQ ID NO: 8) |
| >3300001095\|JGI12104J13512_1001353_7\|M<br>[bioremediation-terephthalate-wastewater bioreactor]<br>MFGGVEKNCLALSLGRHEKRQIYKSILAAGGLLLAQPADETFLPMITKYYREILAAEVKLAFCLPDEAHNVVYKRDEACRELVQ<br>ACRNQAGGLTEQGYQYLGSALLFLSGGLGEAPGLVALPVLSQELCEALASREADIHAFHARQGLEVAAAIIERAREPQWQHAQR<br>RQALEAVIKDLQQRSAICPPDLQDRLRLLLAQAYLERSRIIRPKGFTISPKKKEALDKALEQLDQVTDTGKTTLDYHRFRGDIF<br>LELGRLEARTGKEIEACLAEAILFLDPRTPANLTPVDCRLIVAYARLARDPSYLPLVLGSSKATALDRAWAAYLSNNASGAAKE<br>INTVLQDLQRRWFSHPDWEGLVDLLVDWARSSQKGWEDLATAAWQVCQKNEQELRYSGCQLRWYWSRHQDLYDLAFQAAPTLEE<br>KARVADSLKSRPLVRLALAEQLAQAQAKKKRGADVDFAQLIEQDARAYANQYIAGGLAAGSASAPVAPLSFTELPDEQWLAVHF<br>YLSSGAAAGLKKNMAYALVYDAKDQKWSCEGPYETTDLWQAYRRWQDNYAAVSQASAPELESLCRQIGTTFPFLWALPSERPVV<br>FIPHGFLHRLPLHMALREDGATLEVWAATHPSTYLPAWSLRPRADAGGSQNVAAVYLPDELHDAEDFQNILAGQSFAAAASWPV<br>FRKQAGQARRLALVCHGLAHAVNPFAARLLLPEEPQLVDFLTDLPALPGSQVFLAACEADMAPAQEAPLDEHLSLATAFLQKGA<br>REVLGGVFEVNKYLANELLSSFGATSAAACYSLLWKWQQARLDNFLDNPDPLNLYWLAPWRVLGLS (SEQ ID NO: 9) |
| >3300020048\|Ga0207193_1004003_10\|P<br>[aquatic-freshwater-freshwater lake sediment]<br>MTETNHLSSDYQKAITLETKLAFLRPTQEQDTIESTRRELAETLSRLVNQKISPETLSAITTLHGMDLQGLGVLSGSLPNKDRC<br>AFAGNKKKFSAAWEFHWLQRIDLMRKIIDKASGQDDKLSHASRRQALGVAINSLEKAIAEIGDTGILVSKARLDLARALFHRGR<br>IVRPKGFSVPGKKKELFLKALDQIRIATNNKDDDQTLFLKAEIYLEWLRFFPMELPEDLDVVFKAAQQKADEPLKTNLILMIGE<br>RGSAKPIELEALQNIEVDEKQEPLTRARAAAISGNWDICAKYLSEAIKKLEIKSFFHQDWEEAVELLKKGRTKISNYQWATICK<br>SLWKLTVQKENRTSNGCHLRWYWSRQREVYDLAFEAAGNDYSKKAKITDSLKGRPALHFAQMETIAEGEDEIKTWIEHQEAGFL<br>NQYISAFESADQGKKPGNLSWPKLPKGWIAVHFYLGLGTCSGEKKGYALIQNGQDWYQRTFDYEVLWVAYLAWQTMYGKCGHLD<br>DILKQQEVLSPVVESLCEQIGKEMPWLFDPGLFPEGQAVVFIPHDFLHRLPLHMALDPKPDPGKAQLFLSLHLVLSLPAWWQAS<br>ETNSPPAPDTVKANEKIFLANFENPSDAFQSLIDAIPKSVKVERVAKKSNLLEANSPSLLVVYCNGEAQPGNPFASRLLFSDSG |

TABLE 2-continued

Amino Acid Sequences of Representative Type III-E (CLUST.019911) Effector_A Proteins LPVSGILGSTINLRRSNIILGACETDLMLALNKTLDEHITLSSAFIQKGAELVSGTLWKIHENDEIDFIKLALVENSSLHEQWL
KWYDTNIKAYENDPKNNPRVFYKAAAIRIVGKPWTIEDIGK (SEQ ID NO: 10)

>3300001096|Ga0067045_1003547_9|P
[bioremediation-terephthalate-wastewater bioreactor]
MAQPADETFLPMITKYYREILAAEVKLAFCLPDEAHNVVYKRDEACRELVQACRNQAGGLTEQGYQYLGSALLFLSGGLGEAPG
LVALPVLSQELCEALASREADIHAFHARQGLEVAAAIIERAREPQWQHAQRRQALEAVIKDLQQRSAICPPDLQDRLRLLLAQA
YLERSRIIRPKGFTISPKKKEALDKALEQLDQVTDTGKTTLDYHRFRGDIFLELGRLEARTGKEIEACLAEAILFLDPRTPANL
TPVDCRLIVAYARLARDPSYLPLVLGSSKATALDRAWAAYLSNNASGAAKEINTVLQDLQRRWFSHPDWEGLVDLLVDWARSSQ
KGWEDLATAAWQVCQKNEQELRYSGCQLRWYWSRHQDLYDLAFQAAPTLEEKARVADSLKSRPLVRLALAEQLAQAQAKKKRGA
DVDFAQLIEQDARAYANQYIAGGLAAGSASAPVAPLSFTELPDEQWLAVHFYLSSGAAAGLKKNMAYALVYDAKDQKWSCEGPY
ETTDLWQAYRRWQDNYAAVSQASAPELESLCRQIGTTFPFLWALPSERPVVFIPHGFLHRLPLHMALREDGATLEVWAATHPST
YLPAWSLRPRADAGGSQNVAAVYLPDELHDAEDFQNILAGQSFAAAASWPVFRKQAGQARRLALVCHGLAHAVNPFAARLLLPE
EPQLVDFLTDLPALPGSQVFLAACEADMAPAQEAPLDEHLSLATAFLQKGAREVLGGVFEVNKYLANELLSSFGATSAAACYSL
LWKWQQARLDNFLDNPDPLNLYWLAPWRVLGLS (SEQ ID NO: 11)

>OGR07204.1
[terrestrial-soil]
MNQNIDRAVGAILAIETATPLTESSTLAQRERHQKLLHDETKKIEQAFIALAQPPQCRAVEIAALSRFLQMTPLAVGPLRKRVI
CRAEPLKDDAHEQEIASHFNGLLLRLAKGLLASALNPAGIPWRRRVLWLEKAAHIAHRFDKEPLADDKERTEAAGVLARCCLHL
ALAHLPKGKDKSAMAERQEDLLQSLMWAQKAIVLAGQDKLSGEEYKLLKALVLIELDNLSPGRFQQQLNYVLYDLAVIWLERDT
ATKPFHPQELFVLWRYLATDFEPDLNMLLFKGSNTSERTAAVQQASPEAERFRPLLPLIHAWSAWKLDPPNNKIAEVILQAVNN
LDEHQVYEQVWKWTVDFLQELRNTGAVDWQLPAIAAWELCNKKEKELPFGFQIRQYWSRLDSLYRLAFDGALELKDCMTAARIV
DSLKSRTPLTWRDMDTLFAKLPKEKADQLREAFYSMEVQARMGFYAEAKEDANKLKKLLAAQVRKIRDIESVPAGWTVVHFHLR
EDQDLGYALACRLTADGMSYWTNHIFPVAGIRRAYDCWLEAYHGMEPGAREKSGYQLVELSEIMGKDLDFLFELAGEDGARGLL
FVPHGFSHLLPLHAAKKDGSYLFEKIPSLTLPAWEFAPDVDQIPVSDGQDFCFISQRANEQDLVGNIERSHTWNGVCNKNAAWT
NVLNTNKEWSKAPPRWLVFWCHGQADPHVAFRSKLLLGTLGVSLFEIQEAALSLTGTKVVLAVCESDLAPPEEYEKTDDHLSLA
APFLLKGARQVLAAIWEGAQLDLLKAMKEMLSNQDKHSWEILRELQSCWMRQPGAIFNDEYIRLYYAASFRILGFPEVATTNMA
TATAQEEIA (SEQ ID NO: 2)

>3300028595|Ga0272440_1002488_3|P
[aquatic-marine-marine sediment]
MVSMQQSACNEIKNLENSIDKDVSELAEALSHFVQANLQPQTALCQRGIPDKNNAVLKIHKAHNTDIVFSTLFNILEKRLVVYE
SEVYDESKSSKKNMNHRQRRQMLEDIIQALIPLKKKVSDSELKLEKLERKESDSVTKLKSDIAQFNYIYAKVYFYRSLLFRPKG
RSIPARKIEAIQEAYSFIKKSLNLSETLSSWRLLGKITLELLSLNEPYLSDDIISSGLHIDENFCLENNSFILRNDIQTLLTFS
EITKDVSFVEKIPTFENINIKKKDKDYLLLLIFARIAFLRNKINESDTLLTKAISNAPEAFANPFWDDLVDFITCLKRNNCHVW
KKAAIDAHKACYKNETEIGNIYLRWYWSRQSDLYDLAFISENKLEEKARIADSLKSRPILGFQALNNMKKNIDILEQILEQENE
ARDNKYLKKIHSKSRKIFKKEKFIDFKLLDNHWMVIHFYLNELEQCGYALIFDCETKNTNIQTFRYNELENTFLSWQETELHEQ
KQKENNEEIFNKDLIQRGKSIHELCCEIGKTMPFIFELPENKSILWVPHGFIHRLPLHAAISIQTNAFLFEKHESRYLAAWHQL
NLKNFGNGEGKHFLRSGGSKFKTITKKCKTDKWEMVKRKANQKHFFESLNKNLKTLVIICHGECDITNSFQSCLEISASSVGES
DSNGLINPLEKKSITILDLLKSENNIKGCRIFLGACESDMASPIEFIVDEHLSLSAVLLSLGAKEVIGGLWKLYDIFVEDCYHQ
LLDSNNLSQSLNEWQLNMAKEWKEDKTDMRYLKLYSFASFRVTGFLPQKKQEP (SEQ ID NO: 12)

>SRR8490538_megahit_k177_234425_6|M
[anammox bioreactor]
MKNRVQIEAIIRNLQGAARDSKTNKLSENIIAYDEYRKIHKSASLYQFGIIPAKESSSVLAENETNHVAYENAIFEMAEKNIEN
FSSEDIHKKRKEMIESALRLLMGLYKDRHEKLQPRTFVLIAKAYLLRSLITRPKGITIPEKKKEALKKGIGFVESAIKKIQSSE
NILSHSSDIDLLEKAWRIKSQLYLEYYRVNKDECDKNTLKEVLENSLISGCDKFDKNIEDVQIAIRYCELESSREYLEQIISSH
LEGIEFEKARAYKLLELENENEDEIRKSMKVVIEEYLSGFSDPLWEDAVEFINKLKSDNKNCWKELSLDMYKVCREQEAETASL
HLRWYWSRQRRLYDLAFIAADKEEEKAKIADSLKSRLSLRWSALEETGKKSKNKREKEEISRILEAEAVAMLGGYIKGARKILK
KRRRPLPDEQRSIPKDWIVIHFYVNQLENKCYALIYNKDENTWKCEFVKEYQRLFHVFLTWQTNYNRCKERAADSLVQLCKEIG
NAMPFLFDECIIPQDKNVLFIPHDFLHRLPLHGAIHEKNNGVFLENHPCCYLPAWSFTAKENNAVVQGSILLKNFPEYSYEELV
SNSTLWTSPVKDPASPDDLKTIIASPEMLVILCHGEADAVNPFNARLKLTGNGISHLEILQSTKMILKGSKIILGACETDLVPP
LSDIMDEHLSIATAFLINGTHEILGTMWQSRPEDIEDIIRLLCDKKTSDTKARGDLWNWQKERIRDYWAGEDAMFYRSVAFRII
GLTI (SEQ ID NO: 13)

>SRR6011893_megahit_k177_1702441_3|P
[dolphin oral metagenome]
MNTVELLQEEERLTLDLVFLPPGSKNKEQKKNALVDLLLKIVEHGELTRKYSALLTLSRGALRGEVHFGEKLLPSPEACANLAK
PEEIKKMIRQHFQYRLDLLEAIVKKAADNTYSHARRRKALRIAIKELEQICEEALDELCFKARLLLAEALFERGRIVRPKGFSE
PGKKKELFQKAINCIEGNCSEEALRLRARIYLQWYRFFHDEPPCDLDDIFTKALAVTDDKMLKTELLLLCGERKEPDPYTDDLR
ALLNDQNVSPLSRARAAVLLEDWERCNVEIYEAIEDLGKTDFFQQDWELVVTLLKKNYNQFHGWSRACTRLWEITVEKESKDAG
HGCVLRWYWSRQRDVYNLAFAAFEECEDKARVVDSLKNRPAHHFSQLEQLAQSSDIIKQWIESEEIINQDSFAHSLRRHEKGAK
SHSGGSLRIFPCLPKGWIAVHFFLASWPEPKGYALIHNADTNTWEQRDFKYEQLWATYIAWQEVSLHNKIRESALLLKSLCETL
GKEMRWLFDEFLFPKERRRVLFVPHDFLHRLPLHMAIDIESQTVFAAKQPVCYLPAYHLQNNITENKKTSIYALVNLRENKQQK
KDEEIFAEKVEKMGAIVRRPALESDLLNLNPVPEKLVLYCHGIGHSANPFASKLCLGDTGVSYRDILALNRSLAGCRVLLFACE
TDLVPAQTSSIDEHLSISNALLQKGAFEVLGSLWALPGKTIYGITKTFIDNDDTSAVLHSSLKRLFEHYEKKNEKTRAQLLYNW
ASLRVLAPAREFS (SEQ ID NO: 5)

TABLE 3

Amino Acid Sequences of Representative Type III-E (CLUST.019911) Effector_B Proteins >JRYO01000185_8|M
[*Candidatus Scalindua brodae*]
MKSNDMNITVELTFFEPYRLVEWFDWDARKKSHSAMRGQAFAQWTWKGKGRTAGKSFITGTLVRSAVIKAVEELLSLNNGKWEG
VPCCNGSFQTDESKGKKPSFLRKRHTLQWQANNKNICDKEEACPFCILLGRFDNAGKVHERNKDYDIHFSNFDLDHKQEKNDLR
LVDIASGRILNRVDFDTGKAKDYFRTWEADYETYGTYTGRITLRNEHAKKLLLASLGFVDKLCGALCRIEVIKKSESPLPSDTK
EQSYTKDDTVEVLSEDHNDELRKQAEVIVEAFKQNDKLEKIRILADAIRTLRLHGEGVIEKDELPDGKEERDKGHHLWDIKVQG
TALRTKLKELWQSNKDIGWRKFTEMLGSNLYLIYKKETGGVSTRFRILGDTEYYSKAHDSEGSDLFIPVTPPEGIETKEWIIVG
RLKAATPFYFGVQQPSDSIPGKEKKSEDSLVINEHTSFNILLDKENRYRIPRSALRGALRRDLRTAFGSGCNVSLGGQILCNCK
VCIEMRRITLKDSVSDFSEPPEIRYRIAKNPGTATVEDGSLFDIEVGPEGLTFPFVLRYRGHKFPEQLSSVIRYWEENDGKNGM
AWLGGLDSTGKGRFALKDIKIFEWDLNQKINEYIKERGMRGKEKELLEMGESSLPDGLIPYKFFEERECLFPYKENLKPQWSEV
QYTIEVGSPLLTADTISALTEPGNRDAIAYKKRVYNDGNNAIEPEPRFAVKSETHRGIFRTAVGRRTGDLGKEDHEDCTCDMCI
IFGNEHESSKIRFEDLELINGNEFEKLEKHIDHVAIDRFTGGALDKAKFDTYPLAGSPKKPLKLKGRFWIKKGFSGDHKLLITT
ALSDIRDGLYPLGSKGGVGYGWVAGISIDDNVPDDFKEMINKTEMPLPEEVEESNNGPINNDYVHPGHQSPKQDHKNKNIYYPH
YFLDSGSKVYREKDIITHEEFTEELLSGKINCKLETLTPLIIPDTSDENGLKLQGNKPGHKNYKFFNINGELMIPGSELRGMLR
THFEALTKSCFAIFGEDSTLSWRMNADEKDYKIDSNSIRKMESQRNPKYRIPDELQKELRNSGNGLFNRLYTSERRFWSDVSNK
FENSIDYKREILRCAGRPKNYKGGIIRQRKDSLMAEELKVHRLPLYDNFDIPDSAYKANDHCRKSATCSTSRGCRERFTCGIKV
RDKNRVFLNAANNNRQYLNNIKKSNHDLYLQYLKGEKKIRFNSKVITGSERSPIDVIAELNERGRQTGFIKLSGLNNSNKSQGN
TGTTFNSGWDRFELNILLDDLETRPSKSDYPRPRLLFTKDQYEYNITKRCERVFEIDKGNKTGYPVDDQIKKNYEDILDSYDGI
KDQEVAERFDTFTRGSKLKVGDLVYFHIDGDNKIDSLIPVRISRKCASKTLGGKLDKALHPCTGLSDGLCPGCHLFGTTDYKGR
VKFGFAKYENGPEWLITRGNNPERSLTLGVLESPRPAFSIPDDESEIPGRKFYLHHNGWRIIRQKQLEIRETVQPERNVTTEVM
DKGNVFSFDVRFENLREWELGLLLQSLDPGKNIAHKLGKGKPYGFGSVKIKIDSLHTFKINSNNDKIKRVPQSDIREYINKGYQ
KLIEWSGNNSIQKGNVLPQWHVIPHIDKLYKLLWVPFLNDSKLEPDVRYPVLNEESKGYIEGSDYTYKKLGDKDNLPYKTRVKG
LTTPWSPWNPFQVIAEHEEQEVNVTGSRPSVTDKIERDGKMV (SEQ ID NO: 14)

>OGR07205.1
[*Deltaproteobacteria* bacterium RIFOXYD12_FULL_50_9]
MTKKPGTEDKATLWGKESASKSVKTILEESIQGFTVEQKRSFFANLADQLVSRAGEQGAKSVRSQGLIIGRKENYAKPSAQEPT
RHHLYRQPSNASAFLATGWLIAETPFFIGSGTEGQKQTDDQAESLHLRTLRDGHGRFRIPFTTIRGVMDKELRDILQAGCAKGR
SLRAPCPCQVCTLMRRIQVRDAIAADILPPDLRMRTRIDPSHGTVAHLFSLEMAPQGLKLPFFLKLKGVETIDPDKELLEILND
WSAGQCFLGGLWGTGKGRFRLDDLQWHRLELDNADYYTPLLQDRFFAGETISDLRQGLQSINIQPERIPAQTPSRNMPYCRVDC
ILEFKSPVLSGDPVAALFESDAPDNVAYKKPVVQYDETGRLRTTDPGPVEMLTCLKGEGVRGVVAYLAGKAYDQHDLSHDSCNC
TFCQAFGNGQKAGSLRFDDFMPVQFESDQAGNFSWSPHTPHAMRSDRVALDVFGGAMPEAKFDDRPLAASPGKPLNFKSTIWYR
EDMGKEAGKALKRALIDLQNNMAAIGSGGGIGRGWVSRVCFEGDIPDFLEDFPEPITVTEPEQDSQLLKNQAVADETAVSACDT
ADAPHPLAVTLEPGARYFPRVIIPRAPTVKRDECVTGQRYHTGRLSGKIFCELNTLGPLFVPDTDYSAGVPVPISDEQLAECQL
QAVFENTSKFNEFFATYPEETVTKLKDLLCAADDKWILAVKDITADLRQEIGEDTFQRIIRKAGHKTQRFHQINDEIGLPGASL
RGMVLSNYQILTNSCYRNLKATEEITRRMPADEAKYRKAGRVTVSGDGAQKKYSIQEMEVLRLPIYDNMNTPDNMPDVAKQATT
AKRCNNLMNEAAKTSRVELKARWREGQSKIKYQIIDALNKVDPIIQVISSSKQINPNNGKTGWGYVKYTGANVFAKSLVAPIDC
LRKKDAGHVCCQVNLNPAWEASNFDILINEKCPVERQSGPRPTLRCKGQDSAWYTLTKRSERIFTDKKPVPDPINIPPREVKRY
NELRDSYKKNTAHVPKPLQTFFNQESLANGDLVYFEVNQFGEASQLTPVSISRTTDLFPIGGRLPQGHKDLFPCTAMCLSECKN
CVPASFCEFHSRSHEKLCPACSLAGTTGNRGRIKFSEAWLSGLPKWHSVSQDNVGRGLGVTMPRLERSRRTWHLPTKDAYLLGQ
SIYLNHPVPAILPSDQVPSENNQTVEPLGPKNIFSFQLAFDNLSIEELGLLLYSLELESGMAHRLGRGRALGMGSVQISVKDIQ
IRDNKSFLFSSNISKKSEWIQCGKDEFAQEAWFGESWDNIDHIQRLRQALTIPVKGDVGCIRYPKLEAEGGMPDYIKLRKRLTP
LCDREEPVRYRINPVQLARMILPFVPWHGACPALLNEQVMIEAKRLTELXXXDRANWPC (SEQ ID NO: 15)

>WP_124327589.1
[*Desulfonema ishimotonii*]
MTTTMKISIEFLEPFRMTKWQESTRRNKNNKEFVRGQAFARWHRNKKDNTKGRPYITGTLLRSAVIRSAENLLTLSDGKISEKT
CCPGKFDTEDKDRLLQLRQRSTLRWTDKNPCPDNAETYCPFCELLGRSGNDGKKAEKKDWRFRIHFGNLSLPGKPDFDGPKAIG
SQRVLNRVDFKSGKAHDFFKAYEVDHTRFPRFEGEITIDNKVSAEARKLLCDSLKFTDRLCGALCVIRFDEYTPAADSGKQTEN
VQAEPNANLAEKTAEQIISILDDNKKTEYTRLLADAIRSLRRSSKLVAGLPKDHDGKDDHYLWDIGKKKKDENSVTIRQILTTS
ADTKELKNAGKWREFCEKLGEALYLKSKDMSGGLKITRRILGDAEFHGKPDRLEKSRSVSIGSVLKETVVCGELVAKTPFFFGA
IDEDAKQTDLQVLLTPDNKYRLPRSAVRGILRRDLQTYFDSPCNAELGGRPCMCKTCRIMRGITVMDARSEYNAPPEIRHRTRI
NPFTGTVAEGALFNMEVAPEGIVFPFQLRYRGSEDGLPDALKTVLKWWAEGQAFMSGAASTGKGRFRMENAKYETLDLSDENQR
NDYLKNWGWRDEKGLEELKKRLNSGLPEPGNYRDPKWHEINVSIEMASPFINGDPIRAAVDKRGTDVVTFVKYKAEGEEAKPVC
AYKAESFRGVIRSAVARIHMEDGVPLTELTHSDCECLLCQIFGSEYEAGKIRFEDLVFESDPEPVTFDHVAIDRFTGGAADKKK
FDDSPLPGSPARPLMLKGSFWIRRDVLEDEEYCKALGKALADVNNGLYPLGGKSAIGYGQVKSLGIKGDDKRISRLMNPAFDET
DVAVPEKPKTDAEVRIEAEKVYYPHYFVEPHKKVEREEKPCGHQKFHEGRLTGKIRCKLITKTPLIVPDTSNDDFFRPADKEAR
KEKDEYHKSYAFFRLHKQIMIPGSELRGMVSSVYETVTNSCFRIFDETKRLSWRMDADHQNVLQDFLPGRVTADGKHIQKFSET
ARVPFYDKTQKHFDILDEQEIAGEKPVRMWVKRFIKRLSLVDPAKHPQKKQDNKWKRRKEGIATFIEQKNGSYYFNVVTNNGCT
SFHLWHKPDNFDQEKLEGIQNGEKLDCWVRDSRYQKAFQEIPENDPDGWECKEGYLHVVGPSKVEFSDKKGDVINNFQGTLPSV
PNDWKTIRTNDFKNRKRKNEPVFCCEDDKGNYYTMAKYCETFFFDLKENEEYEIPEKARIKYKELLRVYNNNPQAVPESVFQSR
VARENVEKLKSGDLVYFKHNEKYVEDIVPVRISRTVDDRMIGKRMSADLRPCHGDWVEDGDLSALNAYPEKRLLLRHPKGLCPA
CRLFGTGSYKGRVRFGFASLENDPEWLIPGKNPGDPFHGGPVMLSLLERPRPTWSIPGSDNKFKVPGRKFYVHHHAWKTIKDGN
HPTTGKAIEQSPNNRTVEALAGGNSFSFEIAFENLKEWELGLLIHSLQLEKGLAHKLGMAKSMGFGSVEIDVESVRLRKDWKQW
RNGNSEIPNWLGKGFAKLKEWFRDELDFIENLKKLLWFPEGDQAPRVCYPMLRKKDDPNGNSGYEELKDGEFKKEDRQKKLTTP
WTPWA (SEQ ID NO: 16)

>OBJA01001127_4|M
[soil metagenome]
MRLKINIHFLEPFRLIEWHEQDRRNKGNSRWQRGQSFARWHRRKDNDQGRPYITGTLLRSVVIRAVEEELARPDTAWQSCGGLF
ITPDGQTKPQHLRHRATVRARQTAKDKCADRQSACPFCLLLGRFDQVGKDGDKKGEGLRFDVRFSNLDLPKDFSPRDFDGPQEI
GSRRTINRVDDETGKAHDFFSIWEVDAVREFQGEIVLAADLPSRDQVESLLHHALGFVDRLCGARCVISIADQKPAEREERTVA
AGDEKATIADYDQVKGLPYTRLRPLADAVRNLRQLDLAELNKPDGKFLPPGRVNKDGRRVPHYVWDIPLGKGDTLRKRLEFLAA
SCEGDQAKWRNICESEGQALYEKSKKLKDSPAAPGRHLGAAEQVRPPQPPVSYSEESINSDLPLAEWIITGTLRAETPFAIGMD
APIDDDQTSSRTLVDRDGRYRLPRSTLRGILRRDLSLASGDQGCQVRLGPERPCTCPVCLILRQVVIADTVSETTVPADIRQRI
RRNPITGTAADGGLFDTERGPKGAGFPFSLRYRGHAPMPKALRTVLQWWSAGKCFAGSDGGVGCGRFALDNLEVYRWDLGTFAF
RQAYSENNGLRSPEEEFDLAVIHELAEGLAKEDGQKILKGTEPFTCWQERSWQFSFTGPLLQGDPLAALNSDTADIISFRRTVV TABLE 3-continued Amino Acid Sequences of Representative Type III-E (CLUST.019911) Effector_B Proteins DNGEVLREPVLRGEGLRGLLRTAVGRVAGDDLLTRSHQDCKCEICQLFGSEHRAGILRFEDLPPVSPTTVADKRLDHVAIDRFD
QSVVEKYDDRPLVGSPKQPLVFKGCFWVQTSGMTHQLTELLAQAWRDIAAGHYPVGGKGGIGYGWINSLVVDGEKITCRPDGDS
ISLTTVTGDIPPRPALTPPAGAIYYPHYFLPPNPEHKPKRSDKIIGHHTFATDPDSFTGRITCKLEVVTPLIVPDTEGEQPKDQ
HKNFPFFKINDEIMLPGAPLWAAVSQVYEALTNSCFRVMKQKRFLSWRMEAEDYKDFYPGRVLDGGKQIKKMGDKAIRMPLYDD
STATGSIKDDQLISDCCPKSDEKLQKALATNQKIALAAKHNQEYLAQLSPDEREEALQGLKKVSFWTESLANNEAPPFLIAKLG
EERGKPKRAGYLKITGPNNANIANTNNPDDGGYIPSWKDQFDYSFRLLGPPRCLPNTKGNREYPRPGFTCVIDGKEYSLTKRCE
RIFEDISGGENQVVRAVTERVREQYREILASYRANAAGIAEGFRTRMYDTEELRENDLVYFKTAKQADGKERVVAISPVCISRE
ADDRPLGKRLPAGFQPCSHVCLEDCNTCSAKNCPVPLYREGWPVNGLCPACRLFGAQMYKGRVNFGFARLPDDKQPETKTLTLP
LLERPRPTWVLPKSVKGSNTEDATIPGRKFYLRHDGWRIVMAGTNPITGESIEKTANNATVEAIMPGATFTFDIVCENLDQQEL
GLLLYSLELEEGMSHTLGRGKPLGFGNVRIKVEKIEKRLSDGSRREMIPPKGAGLFMTDKVQDALRGLTEGGDWHQRPHISGLR
RLLTRYPEIKARYPKLSQGEDKEPGYIELKSQKDENGVPIYNPNRELRVSENGPLPWFLLAKK (SEQ ID NO: 17)

>PDWI01005922_5|M
[oral metagenome]
MIPDLRSLVVHISFLTPYRQAPWFPPEKRRNNNRDWLRMQSYARWHKVAPEEGHPFITGTLLRSRVIRAVEEELCLANGIWRGV
ACCPGEFNSQAKKKPKHLRRRTTLQWYPEGAKSCSKQDGRENACPFCLLLDRFGGEKSEEGRKKNNDYDVHFSNLNPFYPGSSP
KVWSGPEEIGRLRTLNRIDRLTTKAQDFFRIYEVDQVRDFFGTITLAGDLPRKVDVEFLLRRGLGFVSTLCGAQCEIKVVDLKK
KQNNKEDSILPVSEVPFFLEPEVLAKMCQDVFPSGKLRMLADVILRLREEGPDNLTLPMGSQGLGGRLPHHLWDVPLVSKDRET
QTLRSCLEKIAAQCKSEQTQFRLFCQKLGSSLFRINKGVYLAPNSKISPEPCLDPSKTIRTKGPVPGKQKHRFSLLPPFEWIIT
GTLKAQTPFFIPDEQGSHDHTSRKILLTRDFYYRLPRSLLRGIIRRDLHEATDKGGCRVELAPDVPCTCQVCRLLGRMLLADTT
STTKVAPDMRHRVGVDRSCGIVRDGALFDTEYGIEGVCFPLEIRYRGNKDLEGPIRQLLSWWQQGLLFLGGDFGIGKGRFRLEN
MKIHRWDLRDESARADYVQKCGLRRGVGDDTAINLEKDLSLNLPESGYPWKKHAWKLSFQVPLLTADPIMAQTRHEEDSVYFQK
RIFTSDGRVVLVPALRGEGLRGLLRTAVSRAYGISLINDEHEDCDCPLCKIFGNEHHAGMLRFDDMVPVGTWNDKKIDHVSCSR
FDASVVNKFDDRSLVGSPDSPLHFEGTFWLHRDFQNDVEIKTALQDFADGLYSIGGKGGIGYGWLFDMEIPRSLRKLNSGFREA
SSIQDALLDSAKEIPLSAPLTFTPVKGAVYNPYYYLPFPAEKPERCLVPPSHARLQSDRYTGCLTCELETVSPLLLPDTCREKD
GNYKEYPSFRLNNTPMIPGAGLRAAVSQVYEVLTNSCIRIMDQGQTLSWRMSTSEHKDYQPGKITDNGRKIQPMGKQAIRLPLY
DEVIHHVSTPGDTDDLEKLKAIVLELTRPWKELPEEQKKKRFEKCKNILDGRMLQQKELRALENSGFAYWRDKTSLTFDSFLKD
AIEQEYPRYSGDYQRIKALVVNITLPWKLLKKEERHKRFDKCRRILKGQQPLTKDERKALEESGFANWHGRELLFDRFLKDENS
CLIKAETTDRVIASVAKNNRDYLFEIKQQDFARYKRIIQGLERVPFSLRSLAKSKETSFQIACLGLRRGRFLRKGYLKISGPNN
ANVEISGGSHSNSGYSDIWDDPLDFSFRLSGKSELRPNTQKTREYPRPSFTCTVDGKQYTVNKRCERVFEDSAAPAIELPRMVR
EGYKGILTDYEQNAKHIPQGFQTRFSSYRELNDGDLVYYKTDSQGRVTDLAPVCLSRLADDRPLGKRLPEEYRPCAHVCLEECD
PCTGKDCPVPIYREGYPARGFCPACQLFGTQMYKGRVRFSFGVPVNSTRSPQLKYVTLPSQERPRPTWVLPESCKGKEKDVPGR
KFYLRHDGWREMWGDDDKPDSRPSSEECQDIIEGIGPGEKFHFRVAFENLDKNELGRLLYSLELDAGMNHHLGRGKAFGFGQVK
IRVTKLERRLEPGQWRSEKICTDLPVTSSELVISSLKKVEERRKLLRLVMTPYKGLTACYPGLERENGRPGYTDLKMLATYDPY
RELVVQIGSNQPLRPWYEPGKSFKPSPGNDCTGRGGSVSKSLISEPKVVPAIAPFCEGVVKWFNSVKGFGFIETKEQRDIFVHF
SAIRGEGYKILEPGEKVRFEIGEGRKGPQAINVIRIR (SEQ ID NO: 18)

>3300019457|Ga0193932_10482_5|M
[aquatic-marine-hydrothermal vent microbial mat]
MIINITVKFLGPFRMLEWTDPDNRNRKNREFMRGQAFARWHNSNPQKGSQPYITGTLVRSAVIRSAENLLMLSEGKVGKEKCCP
GEFRTENRKKRDAMLHLRQRSTLQWKTDKPLCNGKSLCPICELLGRRIGKTDEVKKKGDFRIHFGNLTPLNRYDDPSDIGTQRT
LNRVDYATGKAHDFFKVWEIDHSLLSVFQGKISIADNIGDGATKLLEDSLRFTDRLCGAICVISYDCIENSDGKENGKTGEAAH
IMGESDAGKTDAENIANAIADMMGTAGEPEKLRILADAVRALRIGKNTVSQLPLDHEGKENHHLWDIGEGKSIRELLLEKAESL
PSDQWRKFCEDVGEILYLKSKDPTGGLTVSQRILGDEAFWSKADRQLNPSAVSIPVTTETLICGKLISETPFFFGTEIEDAKHT
NLKVLLDRQNRYRLPRSAIRGVLRRDLRTAFGGKGCNVELGGRPCLCDVCRIMRGITIMDARSEYAEPPEIRHRIRLNPYTGTV
AEGALFDMELGPQGLSFDFILRYRGKGKSIPKALRNVLKWWTKGQAFLSGAASTGKGIFRLDDLKYISFDLSDKDKRKDYLDNY
GWRNRIEALSLEKMPLDRMNDYAEPLWQKVSVEIEIGSPFLNGDPIRALIEKDGSDIVSFRKYADDSGKEVYAYKAESFRGVVR
AALARQHFDKEGKPLDKEGKPLLTLIHQDCECLICRLFGSEHETGRLRFEDLLFDPQPEPMIFDHVAIDRFTGGAVDKKKFDDC
SLPGTPGHPLTLKGCFWIRKELEKPDEDKSEREALSKALADIHNGLYPLGGKGAIGYGQVMNLKIKGAGDVIKAALQSESSRMS
ASEPEHKKPDSGLKLSFDDKKAVYYPHYFLKPAAEEVNRKPIPTGHETLNSGLLTGKIRCRLTTRTPLIVPDTSNDDFFQTGVE
GHESYAFFSVNGDIMLPGSEIRGMLSSVYEALTNSCFRVFDEGYRLSWRMEADRNVLMQFKPGRVTDNGLRIEEMKEYRYPFYD
RDCSDKKSQEAYFDEWERSITLTDDSLEKMAERKGDISPKDLKVLKSLKGKNYKSTEGLLAAFKDKGGDTGGNILGLIFKYAER
IGDVPRYEHPTDTDRMMLSLSEYNRNQKSDGKRAYKIIKPASKLGKGAYFMFAGTSVENKRICNPACTDKANKSVKGYLKISGP
NKLEKYNISEPELDGVPEDRNCQIIHNRIYLRKIFVANAKKRKERDRLVGEFACYDPEKKVTYSMTKRCERIFIKDRGRTLPIT
HEASELFEILVQEYRENAKRQDTPEVFQTLLPDNGRLNPGDLVYFREEKGKTVEIIPVRISRKIDDSPIGKRLREDLRPCHGEW
IEGDDLSQLSEYPEKKLFTRNTEGLCPACRLFGTGAYKGRLRFGFAKLENDPKWLMKNSDGPSHGGPLTLPLLERPRPTWSMPD
DTLNRLKKDGKQEPKKQKGKKGPQVPGRKFYVHHDGWKEINCGCHPTTKENIVQNQNNRTVEPLDKGNTFSFEICFENLEPYEL
GLLLYTLELEKGLAHKLGMAKPMGFGSIDIEVENVSLRTDSGQWKDANEQISEWTDKGKKDAGKWFKTDWEAAEHIKNLKKLLF
LPGEEQNPRVIYPALKQKDIPNSRLPGYEELKKNLNMEKRKEMLTTPWAPWHPIKK (SEQ ID NO: 19)

>3300009529|Ga0114919_10000047_40|M
[aquatic-marine-deep subsurface]
MSDNRIDYDIKLTFFEPFRMSPWVKSHARAKSKTFFRTLSFVRWLETSPETKEGKEGDSIGVPFIPGTLLRSALLKEVEFLITL
KNKYDCCCGEFETPRQKRDEKKEQGRRFFGRKRPTYEFGNSQPCTDFENACPFCSILSRSFNNDDWFDDRGNPIVGKVPVHFSN
LDVTDSKLKRIRLSAIANQRIVNRVDFRSGKAQDYFKIWEVDNRLCPSFCGKITIRQDINQVDDLTCLLAAGLAKIKTLAGALC
RVDIIRDKTIDFHQRLIQKYVGPPGPPHNPTAHPTLPSQPTLSVDVHGLARTIAGTLTGSDKEAYLRRIADAVREMRNRKCSIL
HEPPFTKTGDKEPVWTIPAVQKALKETTACVARESWRLFCEELGEALYKKAKELKKKDEAIPRLLGDTEYYGQQAEAPVGTDYR
LTASALPKYEWIINGWLEARTPFFFGVESASEQTSLAILLTRDHRYRLPRSVLRGALRRDLRTVIGSGCNVELGVDTPCDCDVC
RIMSRVIVMDSLSDYQEPPDIRHRIRINQHSGTVDEGALFDMELGPEGLRFPFRMYFSATCPTADVPLAKVLKMWQDRPAFLGG
DAGTGNGRFRLIKAKTRSEPFDWDGPKSSLNLLMARSYIDLEDHDTLLDSKLECAKAWKVKDELTSVWTDYQYEIDLHSPILSN
DPIAALLDPDWRDAVPVKKRVLQDGGLVPTEKYYIKGSGIRGILRTAVGRNCVNEDGIHLHNLPHDDCPCVLCQLFGSEHHQGM
LRFEDAHFENDPMPETLDHVAIDRFTGRARDKFKFEDAPLIATPDQPIKLKGTFWLKRELHEASQEVFGKIDDFECKPKEDSDS
LLGAARALWCAFLDLKHGLFPIGSNGGIGYGWVSGLSVSEPDKNKKIPLGQLCRNEGAQETASTSGEKGEYNPSDAPNSLRQEG
HVFNPHYFLRSYRYEDKNGKIATHVERIDLPVTHEAYQDKLTGKITCKLNTRGPVFVADPSDLVVYFTAKEYEDFVKRWPKSAE
LLQSLVHEKDGMKLIPVKQIPKDSPEDGALKEISEHQGHKGYKFFRLNGSVMIPGSEIRGMVSSVYEALTNSCFRVFDQRRILS
KRMEADFRTVLTHFKAARVVPDNNSGSGLSVKEFTNMVRVPVYNCPQTFFDGLTQGQISGKEETKLWVKNYEWRISLCNPWTHH
SRKSKKEWEKNIPGRILNNQGDKIVLNISYKQEERKITLILDDKDRVVLDGITPKQLGGKEEIRLWLRISQYQKAFRKKPDNNG TABLE 3-continued Amino Acid Sequences of Representative Type III-E (CLUST.019911) Effector_B Proteins GWKMQTGYLHIMGPNKVEIDSSGTSREGLQDLPETWKDAQCNSPDGKIFSGKDGNAVYTMNKYCEMFFYNEQKKSYRVPQAVLN
QYRQMIEESMSNPQAPPAIFRSKPIREKDTALKAGDLVYFRKNENREGEVDAVIPVRIYRESHRKPLGKRFPDGLHDLRPCTFE
CLDDCDKCPDRCNELKEFFNPHPKGLCPACRLFGTTSYKSRVSFGFARLCSEDKKAKWYGVEEDAEQGKPLTLPLLERPRPTWS
MPDKDAKIPGRKFYVHHPHSVDSSIRDMQFDPELSDKENQGKIRPNKNNRTVEPLDKGNEFTFDIRFMNLKEWELGLLLYSLQL
ETGLAHKLGMGKAQGFGSVEIDVEKVEIRNGPGDWKSKTSHKITEWITKGKDKLEKWFKTDDWNNVDHIADLKKFLYFLDPQEI
KPKVRYPSLSRDDDKKDHFPGYVDLKRKPSKEKPNPYYVPEDKRRALLTRPWEPWYVMPKSSMGTVKWFNEEKNYGFILRDNGE
DIFVHRSDINGSLGTLTEGQKVIFEVKQGPKGLQATNVKVIS (SEQ ID NO: 20)

>3300015370|Ga0180009_10000113_2|P
[aquatic-freshwater-groundwater]
MEYTLTLNFIEPFRLIEWHDAPDRENLRLRGFSFARWHKDREFGLGRPYITGTLIRSAVIRAVEEFLWLNNGKTGDVHCCQGEF
TKARFYRELTEKRLRRRQTLVWDNNGVCNQDQPCPFCLLLGRYWQPGPGYSENNDVNFGNFSIPQKKKVLLNLEDIAEPRIINR
VDQQSGKAEDFFEIREIDHRSCALFEGKISLSERAAENKALISLLNAALPLVNRISGALCYLTMEEVKVMDKSVNGGSDNLSGE
AMELKKSDRPGEGSHFARHPIGAEHASYEKIKTSAGEVVNAFEESNKLVHLRVFSDVIRELRRHDPRKLNLPGGHEDRSGKITD
HFLWDMKVESKPLRNWLPDKFNEFNEKHKLPWRIFCESLGQALFLEAKDKAPEQFTSARPLGAMVSTLESKEPEFLPGRSRQGP
RYEWLMRGQLVAEVPFFFGWSVDKNDTDHISMRLLSARDGRLRLPRSALRGILRRDLNLAFGINGCRAKLGLRRPCPCPVCNLL
KNITIRDSLSDYKRPPQIRHRIRLDHRSGTVAKGALFDMEVGPTGAIFPFELRLRSTSDKFSKELEQVLLWWKQGLAFLSGAGG
TGKGRFRLKELKCIFWDLQNDAGFAHYKETYGGRKKRISDDELIPWQVTSGDPVSEPPWTAWEINFLVCSPFLTKDPVESLLDP
GGTDAVCYRAVYLGENGGIKKRYLLKGESFRGILRTAVGRRENSLLKEHEECDCVLCRLFGNEHEAGKIRVEDLLIQDEPKEKN
LDRVAIDRFTGGARDKHKFDQKPLTGTPAFPLVLMGKIWIKNDLTDDDKAILKQALEDIRCGLYPFGGLGNVGFGWVNYLTCNS
DFEQNFDSMNLCFSDKVKVENEPDKIYWPHYFIPFGPKVVRENKPPGHAYPKTEFHSGRLICSLKTLTPLIIPDGQPASQEANG
HKSYNFFELSGELCIPGSEIKGMISSVYEALTNSCMRIFEEKKRLSWRMKAENLDQWSPGRITEEADELFVEEMEEIRLPLYDN
PDLLPNIKKEGEKGFYRTKKIRDSNGRERLKKGQPTGTDSLINIHSAEIREFLKENKHLSSGQIPTKWFRCFPHPGKRGFDGLA
LLKIPKEWHNKNTSGWIAEGYVNLTGTNKVETRRSGKGISIRETSKDEQINIIHNEVTLEEKPVNSSKLGQVLRKRAIPKYVTY
KNGYEYTMTKRCERIFIPLQKPTKHIVSRNVENKFLQLCEEYKQNAEKIPKVFRTRMPKNYKLNDGDLIYFRQELGEVVEIIPV
RISRAVDDEVLGEKFVNDDFRPCVREILNRETEKKITSAGFKEVFHHHPKGLCPACAIFGTTFYKGRVSFGFAYLKNNETKLVE
NGAYITLPLLERPRPTWAMPTKDSKVPGRKFYVHHQGWKNIVEDSKNESTEKNENNRSVQAIDRNQVFLFEVRFENLRPWELGL
LIYSLQLEPKLAHKLGMGKPLGFGSVKIKVENVTSSRQKDVNDNTLPEAVEKELKEIWGKETEPDFTRSLEGLYKALHYESKNG
IQVRYPKLEKEKKDDPGEKPGYLELADGPFSTENRKEKLKEIWGNWA (SEQ ID NO: 21)

>3300001095|JGI12104J13512_1001353_10|M
[bioremediation-terephthalate-wastewater bioreactor]
MNRYKVSLEFLEPWRINHLGDDRGAAWARWVQTREGYQRPEITGTLVRSAVIRAAEELLALTGGVWAGQKCCPGEFCTPGGSKP
TFRRQRATRWWGEDSLCTPDSPCPFCQLLGRHDLAGKQARRGGGFHVHFGNLYPVAREGYGSLAEITRQRTSNRLDWLTGKAQD
ILTICEVEELRRESGLITVAPELANGEAVSSLLTAAAALVDRLSGAACRLKLQPVEELWSGTAVSLTRAAVPETAYRQQLEEDI
DNYFQELIGDGSQLGPERLRLLADAIRELRYLPPEQTLPDWLQSLPQGKDGKAHRLWDALTAQRRPLRNMLQEVAAAYAAPATW
RDVVQGLGQALYAHYKKLWPQAMPVRPVGEAEYWQTKFRDRQPSRQRGTWSHEWIITGALQTLTPLYLGTQVEAARQTSLTVLL
TAEGRYRLPRTALRGALRQDLQLASRGQGCLMELNPERPCSCPICQIMRRLTVRDVTSSIALPPPLVRQRVRRNPWTGIVDEGA
LFDQEVAPEGLRFPFILRYRGFGGLDAWLQTVLSWWQEGRLFLGGAGGTGKGRLRLTDLRIWRWALDETGLPTYVAHLGYRGRE
EELANSASLPAGVEAVTCSDPATVPSPWQEVDWEFRFHGPVLANHPLTALLRGEADAVFTWKVQLEADQQHYREVCTLKGETVR
GLVRGLFGKSQGLLTKAHADCTCLLCRVFGNEHQRGKVRFEDLTLAGETVPKKRLDHVAIDRISGGAAEQLKFDTQPLYGTPEN
PLVFAGKFWVHTELDEEEQKALRAALTALRDGLATVGAKGSVGYGWLNGLRLHSGPAWLTDNWQETAAAPSDTNTPPEFSWPQL
PDLTLDSRKIYYPHYFLPPDLQVPRLSQPHTHSLFDPQKYTGWLTCRLTTLTPLIIPDTSSDQTLTTGGPFPAGHQAFQFFRLG
DQPLIPGAELRGMISSVFEAITNSCFRVIRPRERLSWRMPAALAPQFRSGRVEIVNNQYYIRQMDMGRLPLYDDPATRRLFTPL
SLTSGHTLDFVDDNRTLLQSNPGIREGAIRTDLCFLNRFWLLRPPSAARCPRGNFSLTSGYVKFTGPNKVEVSRAGAGAGGLPA
PPADWTGVRLNQVAGNVPFYQAEQSGVIFTVNKRRERFFISRGNARSYPVPLATLKRYEQVLKEYRHFAQRGEVPAVFRTVLPD
VRHGASGYNRLNNGDLVYFRVKDDRWNDQNAPVEHIIPVSISRLVDQKFLGERVPEPLRPCAHVCLEECEACLKQESCPSSFYR
EGTPSRGLCPACHLFGTTGYQGRVRFGFARLEREPAWRQNDAGSTAITLPLLEQPRLTWSMLWERRNAEGTVEERQPVNWVPGR
KFYVHHQGWRTIVAQGINPIDGQRLERNENNRTVEVLDTGRTFTFQVFFENLDAWELGLLLYSLELEPGLAHKLGMAKAWGFGS
VQIDVASLRRYQAPGSMTDITCEKDTLLQAGFAWLKEQANSSSWDEIPRLRQLRQLLRYQEDGTLTVRYPILKQENAASGQVPG
YVELRDQGYRPEEQLRIPWSPWYSPPLEPPPAATAAA (SEQ ID NO: 22)

>3300020048|Ga0207193_1004003_13|M
[aquatic-freshwater-freshwater lake sediment]
MTTLTIHLHFLEPFRMAPWFSVEKRKKNNPDWQRVQTYARWHKNTAGDGRGRPFITGYLLRSALIQAVEEELVFSRGVWSGISC
CPGLFFTEPDKDKEKPLNERRRATLGWTENKAICQEEEGREKACPLCLLINRFKENGEDNVHFGNLSLPGSENERPVWDQPEQI
AKLRTLNRVDRATTKAHDHFKVYEVEDLTDFYGTITFADDLPQREVIESLIRRGLGFISDLCGALCEIRVEKQKPLPTEPKGIT
QSKASYVSGLAEMCWEKMAETELRSLAGAVLQLRCSDPKKFTLPKGRIDRNGNRLPHHIWDIELEGNGDKKTLRKHLKETAEKM
AEGGTAFRLFCEDVGNRLFRLSKGIPQETPNRQDAFSDPSQVFNLGRPVYGQENHRDPMIPSCEWIITGTLTAASPFFIADELI
DDDHISRKLLTTQDFHYRLPRSLLRGILRRDLHEASGGKGCRAELGPESSCICPVCRILNQVKIRDARSDSFVPPDIRQRVKQS
HHHRIVQDGALFDTEYGLEGVVFPFELRFKGEKTIDKELRTVMGWWEEGLLFLGGDFGTGKGAFKLGIKQIHRWDLSTPGAREE
YEQTCGFRAGVPLDANCQGLSPVSNIDFPKVDYPWQKVPWELAFESPLLTADPIAAITQDEADTIYFQKRRLKSDGSVEYIPAL
RGEGLRGLIRTATARASGSDHLTVEHEDCTCVLCKTFGNEHRSGLLRFDDLEPKNWKDKRIDHVSIDRFDASVVEKFDDRPLIG
SPDKPLVFAGAFWIHRDFTENKALSNGFQDLKSGLYPLGGKVGIGYGRLSKLELPSDWLPNSAENESISVSGLLEGSPETSGIP
EKPTWKPEPDAIYNPYYYLSRPGDGPKRTLTPVSHATLSKERYTGRIACFLKVKSPLLLPDSEHDPVAPDKNGTMKAFRLNGTL
MIPGSALRSAVSQVYEALTDSCFRVMDQKRVLSWRMETGDHGNYKPGRISESGDQIFPMGEKALRLPLYDMAPGTHSAKYIKEL
EELHKKALEGNIHRLTIAPWEEMPEKTREKKFEKCNKILGRNLTEEEKKNLTDQGMAKLKISEMELKTLIGRFKKDEESCIEKA
QKTDSNIAEIAKHNRDILNVLEKETRQRVLAGKEKVPFLTERLAPNNDINFQIVKLLKNSEKNKKNKEIRWGYLKITGPNNAND
AVVETKEEDDKYKLEWEDPLDFSFCLTGPPKNQPNTQKSRDFPRPGFECIKDDKRYTISKRCERLFEADEKSKPIPIPKRVREG
YKGILEDYQKNAKKIPKAFQTRLNSDLVYYKSDYVENQINVTALAPVCISRLADDRPLGKRLPVGYQPCSHICLEDCERCTGKA
CPIPLYREGYPVNGLCPACQLFGAQMYKGRVNFSFATLTPGKNLELRNVTLPAQERPRPTWILPKNVQGKDTEIPGAKFYLRHG
MWKKIWTDRKDPRTDKPIEEKNPNNVTIEGINTGAEFRFDVSFENLDENELGWLLYCLELEEDMSHMLGRGKPFGFGQVEIKIN
ELARRLAPNAWYTESPKEGSLIHSKLIVKALAGLKSLDSLRLLLTQYNNLTAYYPELEGKGGKPGYDTLKNSSGYNPHCFLTLQ
TKGNTPFVYPWFPIPISKPQATKSDIKPKVENHGITGNGFKKLVEGDKVTFEIEERPKGPCAVNVRKVKDIP (SEQ ID NO: 23)

TABLE 3-continued

| Amino Acid Sequences of Representative Type III-E (CLUST.019911) Effector_B Proteins |
|---|
| >3300001096\|Ga0067045_1003547_12\|M<br>[bioremediation-terephthalate-wastewater bioreactor]<br>MNRYKVSLEFLEPWRINHLGDDRGAAWARWVQTREGYQRPEITGTLVRSAVIRAAEELLALTGGVWAGQKCCPGEFCTPGGSKP<br>TFRRQRATRWWGEDSLCTPDSPCPFCQLLGRHDLAGKQARRGGGFHVHFGNLYPVAREGYGSLAEITRQRTSNRLDWLTGKAQD<br>ILTICEVEELRRFSGLITVAPELANGEAVSSLLTAAAALVDRLSGAACRLKLQPVEELWSGTAVSLTRAAVPETAYRQQLEEDI<br>DNYFQELIGDGSQLGPERLRLLADAIRELRYLPPEQTLPDWLQSLPQGKDGKAHRLWDALTAQRRPLRNMLQEVAAAYAAPATW<br>RDVVQGLGQALYAHYKKLWPQAMPVRPVGEAEYWQTKFRDRQPSRQRGTWSHEWIITGALQTLTPLYLGTQVEAARQTSLTVLL<br>TAEGRYRLPRTALRGALRQDLQLASRGQGCLMELNPERPCSCPICQIMRRLTVRDVTSSIALPPPLVRQRVRRNPWTGIVDEGA<br>LFDQEVAPEGLRFPFILRYRGFGGLDAWLQTVLSWWQEGRLFLGGAGGTGKGRLRLTDLRIWRWALDETGLPTYVAHLGYRGRE<br>EELANSASLPAGVEAVTCSDPATVPSPWQEVDWEFRFHGPVLANHPLTALLRGEADAVFTWKVQLEADQQHYREVCTLKGETVR<br>GLVRGLFGKSQGLLTKAHADCTCLLCRVFGNEHQRGKVRFEDLTLAGETVPKKRLDHVAIDRISGGAAEQLKFDTQPLYGTPEN<br>PLVFAGKFWVHTELDEEEQKALRAALTALRDGLATVGAKGSVGYGWLNGLRLHSGPAWLTDNWQETAAAPSDTNTPPEFSWPQL<br>PDLTLDSRKIYYPHYFLPPDLQVPRLSQPHTHSLFDPQKYTGWLTCRLTTLTPLIIPDTSSDQTLTTGGPFPAGHQAFQFFRLG<br>DQPLIPGAELRGMISSVFEAITNSCFRVIRPRERLSWRMPAALAPQFRSGRVEIVNNQYYIRQMDMGRLPLYDDPATRRLFTPL<br>SLTSGHTLDFVDDNRTLLQSNPGIREGAIRTDLCFLNRFWLLRPPSAARCPRGNFSLTSGYVKFTGPNKVEVSRAGAGAGGLPA<br>PPADWTGVRLNQVAGNVPFYQAEQSGVIFTVNKRRERFFISRGNARSYPVPLATLKRYEQVLKEYRHFAQRGEVPAVERTVLPD<br>VRHGASGYNRLNNGDLVYFRVKDDRWNDQNAPVEHIIPVSISRLVDQKFLGERVPEPLRPCAHVCLEECEACLKQESCPSSFYR<br>EGTPSRGLCPACHLFGTTGYQGRVRFGFARLEREPAWRQNDAGSTAITLPLLEQPRLTWSMLWERRNAEGTVEERQPVNWVPGR<br>KFYVHHQGWRTIVAQGINPIDGQRLERNENNRTVEVLDTGRTFTFQVFFENLDAWELGLLLYSLELEPGLAHKLGMAKAWGFGS<br>VQIDVASLRRYQAPGSMTDITCEKDTLLQAGFAWLKEQANSSSWDEIPRLRQLRQLLRYQEDGTLTVRYPILKQENAASGQVPG<br>YVELRDQGYRPEEQLRIPWSPWYSPPLEPPPAATAAA (SEQ ID NO: 22) |
| >3300025107\|Ga0208863_1001002_11\|M<br>[terrestrial-soil]<br>MTTGNTSASHPQFVTLTVCLRFCSPFQIRPWIKETVRNKVKMPSTVNAHAETAHLPDDQDTDDTQDLLEEERFERYATAADWHK<br>GSINGNAKYSPYVRGDLVRSVVDRELQEHFHCYNEKLANENKGCPGKRDRHINAGGKASGFMAHLPAIKDPAGKEICKGSDNIC<br>PVCHFLGAFAEGIKPVKFRNFFSGYYVAKTEDLAKQRGRNCYSGQSRKSLDNFTVWEADHTACPVFFGRIEVNKTLLPKEQILA<br>LLAGGLARLDNLAGSACREDIIDKYEGVFEDHEWTANILPNLLIAAREALGLPDDEHQALLNDFSRFFINPEKSPAVYTSSPVI<br>VPVQGAVDKVVLLEKAQDIAGRIAACVSDNPRHLHRLAAAIRTLGWPGRSLASVMTKKPGTEDKATLWGKESASKSVKTILEES<br>IQGFTVEQKRSFFANLADQLVSRAGEQGAKSVRSQGLIIGRKENYAKPSAQEPTRHHLYRQPSNASAFLATGWLIAETPFFIGS<br>GTEGQKQTDDQAESLHLRTLRDGHGRFRIPFTTIRGVMDKELRDILQAGCAKGRSLRAPCPCQVCTLMRRIQVRDAIAADILPP<br>DLRMRTRIDPSHGTVAHLFSLEMAPQGLKLPFFLKLKGVETIDPDKELLEILNDWSAGQCFLGGLWGTGKGRFRLDDLQWHRLE<br>LDNADYYTPLLQDRFFAGETISDLRQGLQSINIQPERIPAQTPSRNMPYCRVDCILEFKSPVLSGDPVAALFESDAPDNVAYKK<br>PVVQYDETGRLRTTDPGPVEMLTCLKGEGVRGVVAYLAGKAYDQHDLSHDSCNCTFCQAFGNGQKAGSLRFDDFMPVQFESDQA<br>GNFSWSPHTPHAMRSDRVALDVFGGAMPEAKFDDRPLAASPGKPLNFKSTIWYREDMGKEAGKALKRALIDLQNNMAAIGSGGG<br>IGRGWVSRVCFEGDIPDFLEDFPEPITVTEPEQDSQLLKNQAVADETAVSACDTADAPHPLAVTLEPGARYFPRVIIPRAPTVK<br>RDECVTGQRYHTGRLSGKIFCELNTLGPLFVPDTDYSAGVPVPISDEQLAECQLQAVFENTSKFNEFFATYPEETVTKLKDLLC<br>AADDKWILAVKDITADLRQEIGEDTFQRIIRKAGHKTQRFHQINDEIGLPGASLRGMVLSNYQIILTNSCYRNLKATEEITRRMP<br>ADEAKYRKAGRVTVSGDGAQKKYSIQEMEVLRLPIYDNMNTPDNMPDVAKQATTAKRCNNLMNEAAKTSRVELKARWREGQSKI<br>KYQIIDALNKVDPIIQVISSSKQINPNNGKTGWGYVKYTGANVFAKSLVAPIDCLRKKDAGHVCCQVNLNPAWEASNFDILINE<br>KCPVERQSGPRPTLRCKGQDSAWYTLTKRSERIFTDKKPVPDPINIPPREVKRYNELRDSYKKNTAHVPKPLQTFFNQESLANG<br>DLVYFEVNQFGEASQLTPVSISRTTDLFPIGGRLPQGHKDLFPCTAMCLSECKNCVPASFCEFHSRSHEKLCPACSLAGTTGNR<br>GRIKFSEAWLSGLPKWHSVSQDNVGRGLGVTMPRLERSRRTWHLPTKDAYLLGQSIYLNHPVPAILPSDQVPSENNQTVEPLGP<br>KNIFSFQLAFDNLSIEELGLLLYSLELESGMAHRLGRGRALGMGSVQISVKDIQIRDNKSFLFSSNISKKSEWIQCGKDEFAQE<br>AWFGESWDNIDHIQRLRQALTIPVKGDVGCIRYPKLEAEGGMPDYIKLRKRLTPLCDREEPVRYRINPVQLARMILPFVPWHGA<br>CPALLNEQVMIEAKRLTELLAQENLDMICRTKNCANCKQETKKDCLAFRYDRANWPC (SEQ ID NO: 24) |
| >3300028595\|Ga0272440_1002488_4\|M<br>[aquatic-marine-marine sediment]<br>MKVRIKFFEPIRVMPWVNPSDRKISNEQFMRGQSFARWHRYNKNSNSGKPFITGTLVRSAVIRAAEVLLSLSNGIIENKACCPG<br>MFETEGAARKKMHFRQRSTPKWTENSTCNKDNQCPFCELLGREGNDEIGAVIEKENNTKRLKYNFHFSNFQPSGNNSYPDHII<br>IKRTVNRVDYTTGKAHDFFTISEIDNSFFPAFEGHISISDRVSHEAKKLLSDSLKFIDKLCGSICVFEFDDSTWDDHLHIEKSM<br>EKNDGKEKSEEITKQIIKILESNSKLDYLRILSDAIRELARDKEMVHKLPLDYKGKKKHYIWDLAYNKISIREILCNQANKNAK<br>NDYVELCKTIGKELYHESQKKTELLTKPHRILGSKSFYGKPQRDIQPTDAKIVPTEETIFTGKLVSETPFFFGLENEDKQQTDF<br>TVLLDSQNRFRIPRSALRGVLRRDIRMMSGGNGCDVKLGGRQCLCPVCRMMRNITIMDVRSNKDIIPDIRQRIRINPYTGSVAE<br>GALFSMELGPQGMEFDFVLRFRGNDSIPKSLKKVLLCWAKGQAFLSGASSTGKGRFKLKNLKFKSFDLSTKEIRNDYLNQRGWR<br>NRENELPLEPLFLTDKYKEINTTLWNKVSVEIKLSSPFLNGDPVRSLVQGQGADIVSFKKTSLIDDEDIYAYKAESLKGIFRTA<br>LARRFHYKDKISQKVLPLTAISHKDCDCPLCRLFGSEFETGKIRFEDLEFSTNPIPKKFDHVAIDRFTGGAVDKKKFDDCALSA<br>TKQKPLLLKGNFWLRPDMTKDDFKYFEKAFLDIKSGFYPLGAKSGIGYGQIEDISISISDSDDYPRAIKENIKTINNKSYTQEA<br>KNNINDKDTDESKQSDFQIDLKDDAIYYPHYFLKPNKKVDRKTIPINHLTLHDECHTGKIVCTLTTKTPLIIPDTENDDAFGLK<br>KAKLAEDGEKYHKSYSFFSVNDEIMISGSEIRGMISSIYEAITNSCFRIFEEKHRLSWRMEAVPEVLEKFIPGRIIKINGELKM<br>VEMEEVRYPFYDKNCPDTKTQKDHFSSKGKGKLYYEQPTFSDKMILSLSEYNRKHQNPGKKEKYKIIKPDSKSNANFMFTATPA<br>NNTEGYDMDCVHKHSVKGYLKVSGPNKIEKERTDQPASNKIPMENEIVIHQKTNRREITVQNAKKNKKRYRLIPEYICSEKDTN<br>YIMNKRCERVFIEPEKCNHDGIPISKNAIELFKHLVDEYKKNADQQETPKVFRTKLPEKGELKEGSLVYFRKDSNEVVEIIPVK<br>ISRKIDDRFIGKRLTKNLRPCHGEWIEKDDLSILDQYPEKKLFTRHPKGLCPACQLFGTGAYKGRLRFGFATLINKPEWLNKED<br>KDHKLTLPLLERPRPTWAIPDATQASKVPGRKFFIHHHAWTDIEKGIDPVTGKAIQIDVNNRTVQPLDSNNTFTFEINFENLEP<br>HELGLLLYSLQLENSLSHKLGMGKAFGFGSIDIKVENLLLFDSTIDKYKNKTDQVKRFVDEGKNNLLEIFENEFDDIEHIKDLK<br>SLLYFPNDKNIRVQYPLLRKEDYPDKDLPGYKELKDNFSNGIQIRHNLLTIPWSPWAYQSKKKLENEKTIYPPLKKIEINNYYD<br>IKKVNIKIPDNAQWVFLTGNNSIGKSLFLKAIATGLYGKITEDDENDIDTNCGIRVFITNEWVNDVKKDYFNQKLSYKNYATYG<br>PSRLNKLAEGKKTKFPYFSLFNTEGVFYHDIEKEFIKWCDRDSSKFNLLKNIFIKLLPTIDDIKGIQTKTDFYIGYKEMETGKY<br>EKQSKLATGNISILRMFGDMFIRFSKEQPDTLPEDFSGIVIIDELDLHLHPIWLKKIPGLVSKLFPKIRFIASTHSAIPFLGAP<br>KNSVYLNVIRDEDNNIHVQEIDIDLTNLLPNTILTSPLENMEDITQINLPDITDVRTEDTYKEIIEIDKIKARLKKFAKKDTLF<br>PDKLFKEL (SEQ ID NO: 25) |

TABLE 3-continued

Amino Acid Sequences of Representative Type III-E (CLUST.019911) Effector_B Proteins >SRR8490538_megahit_k177_234425_10|M
[anammox bioreactor]
MSKKHFIHLTFLEPYRLAEWHAKADRKKNKRYLRGMSFAQWHKDKDGIGKPYITGTLLRSAVLNAAEELISLNQGMWAKEPCCN
GKFETEKDKPAVLRKRPTIQWKTGRPAICDPEKQEKKDACPLCMLLGRFDKAGKRHRDNKYDKHDYDIHFDNLNLITDKKFSHP
DDIASERILNRVDYTTGKAHDYFKVWEVDDDQWQFTGTITMHDDCSKAKGLLLASLCFVDKLCGALCRIEVTGNNSQDENKEY
AHPDTGIITSLNLKYQNNSTIHQDAVPLSGSAHDNDEPPVHDNDSSLDNDTITLLSMKAKEIVGAFHESGKIEKARTLADVIRA
MRLQKPDIWEKLPKGINDKHHLWDREVNGKKLRNILEELWRLMSKRNAWRTFCEVLGNELYRCYKEKTGGIVLRFRTLGETEYY
PEPEKTEPCLISDNSIPITPLGGVKEWIIIGRLKAETPFYFGAQSSFDSTQDDLDLVPDIVNTDEKLEANEQTSFRILMDKKGR
YRIPRSLIRGVLRRDLRTAFGGSGCIVELGRMIPCDCKVCAIMRKITVMDSRSENIELPDIRYRIRLNPYTATVDEGALFDMEI
GPEGITFPFVFRYRGEDALPRELWSVIRYWMDGMAWLGGSGSTGKGRFALIDIKVFEWDLCNEEGLKAYICSRGLRGIEKEVLL
ENKTITEITNLFKTEEVKFFESYSKHIKQLCHEGIINQMSFSGGLRSYHEYLSPLWTEVKYEIKIASPLLSSDTISALLNKDNI
DCIAYEKRKWENGGIKFVPTIKGETIRGIVRMAVGKRSGDLGMDDHEDCSCTLCTIFGNEHEAGKLRFEDLEVVEEKLPSEQNS
DSNKIPFGPVQDGDGNREKECVAEVKIYKKKLIDHVAIDRFHGGAEDKMKFNTLPLVGSPERPIILKGRFWIKKDMVKDYRKKI
EDAMVDIRDGLYPIGGKTGIGYGWVTDLTILNPQSGFQIPVKKDISPEPGTYLTYPSYSAPSLNRGHIYYPHYFLAPANTVHRE
QEMIGHEQFHKEQKGELLVSGKIVCTLKTVTPLIIPDTENEDAFGLQNTYSGHKNYQFFHINDEIMVPGSEIRGMISSVYEAIT
NSCFRVYDETKYITRRLSSEKKDESNDKNKSQDDASQKIRKGLVKKTDEGFSIIEVERYSMKTKGRTKLVDKVYRLPLYDSEAV
IASIKFEQYGEKNEKRNAKILAAIKRNNVIAEVARKNLIFLRSLTPEELKKVLQGEILVKFSLKSGENPNDYLAELHENGTERG
LIKFTGLNMVNIKNVNEEDKDENDTWDWEKLNIFHNAHEKRNSLKQGYPRPVLKFIKDRVEYTIPKRCERIFCIPVKNTIEYKV
SSKVCKQYKDVLSDYEKNFGHINKIFTTKIQKRELTDGDLVYFIPNEGADKTVQAIMPVPLSRITDSRTLGERLPHKNLLPCVH
EVNEGLLSGILDSLDKKLLSIHPEGLCPTCRLFGTTYYKGRVRFGFANLINKPKWLTERENGCGGYVTLPLLERPRLTWSVPSD
KCDVPGRKFYVHHNGWQEVLRNNDITPKTENNRTVEPLAADNRFTFDVYFENLREWELGLLCYCLELEPGMGHKLGMGKPLGFG
SVKIAIERLQTFTVHQDDINWKPSENEIGVYVQRGREKLVEWFTPSDSHKNMEWNEVKHIKDLRSLLSIPDDKPTVKYPALNKG
AEGAISDYTYERLSDTKLLPHDKRVEYLRTPWGPWNAFVKEAEYSTSENSDEKGRETIRTKPKSLPSVKSIGKVKWFDEGKGFG
ILIMDDGKEVSISKNSIRGNNLLKKDQKVTFHIVQGLIPKAEDIEIAK (SEQ ID NO: 26)

>SRR6011893_megahit_k177_1702441_5|M
[dolphin oral metagenome]
MIPDLRSLVVHISFLTPYRQAPWFPPEKRRNNNRDWLRMQSYARWHKVAPEEGHPFITGTLLRSRVIRAVEEELCLANGIWRGV
ACCPGEFNSQAKKKPKHLRRRTTLQWYPEGAKSCSKQDGRENACPFCLLLDRFGGEKSEEGRKKNNDYDVHFSNLNPFYPGSSP
KVWSGPEEIGRLRTLNRIDRLTTKAQDFFRIYEVDQVRDFFGTITLAGDLPRKVDVEFLLRRGLGFVSTLCGAQCEIKVVDLKK
KQNNKEDSILPVSEVPFFLEPEVLAKMCQDVFPSGKLRMLADVILRLREEGPDNLTLPMGSQGLGGRLPHHLWDVPLVSKDRET
QTLRSCLEKIAAQCKSEQTQFRLFCQKLGSSLFRINKGVYLAPNSKISPEPCLDPSKTIRTKGPVPGKQKHRFSLLPPFEWIIT
GTLKAQTPFFIPDEQGSHDHTSRKILLTRDFYYRLPRSLLRGIIRRDLHEATDKGGCRVELAPDVPCTCQVCRLLGRMLLADTT
STTKVAPDMRHRVGVDRSCGIVRDGALFDTEYGIEGVCFPLEIRYRGNKDLEGPIRQLLSWWQQGLLFLGGDFGIGKGRFRLEN
MKIHRWDLRDESARADYVQKCGLRRGVGDDTAINLEKDLSLNLPESGYPWKKHAWKLSFQVPLLTADPIMAQTRHEEDSVYFQK
RIFTSDGRVVLVPALRGEGLRGLLRTAVSRAYGISLINDEHEDCDCPLCKIFGNEHHAGMLRFDDMVPVGTWNDKKIDHVSCSR
FDASVVNKFDDRSLVGSPDSPLHFEGTFWLHRDFQNDVEIKTALQDFADGLYSIGGKGGIGYGWLFDMEIPRSLRKLNSGFREA
SSIQDALLDSAKEIPLSAPLTFTPVKGAVYNPYYYLPFPAEKPERCLVPPSHARLQSDRYTGCLTCELETVSPLLLPDTCREKD
GNYKEYPSFRLNNTPMIPGAGLRAAVSQVYEVLTNSCIRIMDQGQTLSWRMSTSEHKDYQPGKITDNGRKIQPMGKQAIRLPLY
DEVIHHVSTPGDTDDLEKLKAIVLELTRPWKELPEEQKKKRFEKCKNILDGRMLQQKELRALENSGFAYWRDKTSLTFDSFLKD
AIEQEYPRYSGDYQRIKALVVNITLPWKLLKKEERHKRFDKCRRILKGQQPLTKDERKALEESGFANWHGRELLFDRFLKDENS
CLIKAETTDRVIASVAKNNRDYLFEIKQQDFARYKRIIQGLERVPFSLRSLAKSKETSFQIACLGLRRGRFLRKGYLKISGPNN
ANVEISGGSHSNSGYSDIWDDPLDFSFRLSGKSELRPNTQKTREYPRPSFTCTVDGKQYTVNKRCERVFEDSAAPAIELPRMVR
EGYKGILTDYEQNAKHIPQGFQTRFSSYRELNDGDLVYYKTDSQGRVTDLAPVCLSRLADDRPLGKRLPEEYRPCAHVCLEECD
PCTGKDCPVPIYREGYPARGFCPACQLFGTQMYKGRVRFSFGVPVNSTRSPQLKYVTLPSQERPRPTWVLPESCKGKEKDVPGR
KFYLRHDGWREMWGDDDKPDSRPSSEECQDIIEGIGPGEKFHFRVAFENLDKNELGRLLYSLELDAGMNHHLGRGKAFGFGQVK
IRVTKLERRLEPGQWRSEKICTDLPVTSSELVISSLKKVEERRKLLRLVMTPYKGLTACYPGLERENGRPGYTDLKMLATYDPY
RELVVQIGSNQPLRPWYEPGKSFKPSPGNDCTGRGGSVSKSLISEPKVVPAIAPFCEGVVKWFNSVKGFGFIETKEQRDIFVHF
SAIRGEGYKILEPGEKVRFEIGEGRKGPQAINVIRIR (SEQ ID NO: 18)

TABLE 4

Consensus Type III-E (CLUST.019911) Direct Repeat Sequence and Nucleotide Sequences of Representative Type III-E (CLUST.019911) Direct Repeats

<table>
<tr><th>CLUST.019911 Effector_A Protein Accession</th><th>Direct Repeat Nucleotide Sequence</th></tr>
<tr><td>CONSENSUS DIRECT REPEAT SEQUENCE</td><td>GTTRNRNANMRMCRSNWDYYWTTRATGTBACGGDAC (SEQ ID NO: 100)</td></tr>
<tr><td>KHE91663.1 (SEQ ID NO: 1)</td><td>GTTATGAAACAAGAGAAGGACTTAATGTCACGGTAC (SEQ ID NO: 27)</td></tr>
<tr><td>OGR07204.1 (SEQ ID NO: 2)</td><td>GTTGGTGCATCAGCCCGGAATTATGATGTTTTGGTAC (SEQ ID NO: 28)</td></tr>
<tr><td>WP_124327588.1 (SEQ ID NO: 3)</td><td>GGTTGGAAAGCCGGTTTTCTTTGATGTCACGGAAC (SEQ ID NO: 29)</td></tr>
<tr><td>OBJA01001127_8|M (SEQ ID NO: 4)</td><td>ATTGCCCCAGCCGATAAACCCTTAATGTCACGGAAC (SEQ ID NO: 30)</td></tr>
</table>

TABLE 4-continued

Consensus Type III-E (CLUST.019911) Direct Repeat Sequence and Nucleotide Sequences of Representative Type III-E (CLUST.019911) Direct Repeats

| CLUST.019911 Effector_A Protein Accession | Direct Repeat Nucleotide Sequence |
|---|---|
| PDWI01005922_7\|M (SEQ ID NO: 5) | ATAGATATAGACAGAAGCTTTTAATGTGATGGGAC (SEQ ID NO: 31) |
| RLC19860.1 (SEQ ID NO: 6) | GTTGGAAAAGCCGGTTTTATTTGATGTCACGGAAC (SEQ ID NO: 32) |
| 3300009529\|Ga0114919_10000047_39\|M (SEQ ID NO: 7) | ATTGGGGGGATTAGATTCTGATAATGTCACGGTAC (SEQ ID NO: 33) |
| 3300015370\|Ga0180009_10000113_9\|P (SEQ ID NO: 8) | GGTTGGATTCAGCCCCAGATGTTTTATGTGACGGAAC (SEQ ID NO: 34) |
| 3300001095\|JGI12104J13512_1001353_7\|M (SEQ ID NO: 9) | GTTAAGGAGAGACGGCATTCATTGATGTCACGGCAC (SEQ ID NO: 35) |
| 3300020048\|Ga0207193_1004003_10\|P (SEQ ID NO: 10) | GTTAGCATCAGGACAATACCTTCGATGTTACGGGAC (SEQ ID NO: 36) |
| 3300001096\|Ga0067045_1003547_9\|P (SEQ ID NO: 11) | GTTAAGGAGAGACGGCATTCATTGATGTCACGGCAC (SEQ ID NO: 35) |
| OGR07204.1 (SEQ ID NO: 2) | GTTGGTGCATCAGCCCGGAATTATGATGTTTTGGTAC (SEQ ID NO: 28) |
| 3300028595\|Ga0272440_1002488_3\|P (SEQ ID NO: 12) | GTTCCGTGACATCAAAAGCCGTCCATTTCTCAAAC (SEQ ID NO: 37) |
| SRR8490538_megahit_k177_234425_6\|M (SEQ ID NO: 13) | CTTGAAGACTAAAGGAAGGAATTGATGTCACGGTAC (SEQ ID NO: 38) |
| SRR6011893_megahit_k177_1702441_3\|P (SEQ ID NO: 5) | ATAGATATAGACAGAAGCTTTTAATGTGATGGGAC (SEQ ID NO: 31) |

TABLE 5

Direct Repeat Homology-Containing Regions of Representative Type III-E (CLUST.019911) Systems

| family | effector accession | homologous region | start | end | strand |
|---|---|---|---|---|---|
| CLUST.019911 | S.XXMH0-MGM 5 | ACCGGCTTTTCCA (SEQ ID NO: 101) | 29649 | 29662 | BS |

TABLE 6

Direct Repeat Homology-Containing Loci Sequences of Representative Type III-E (CLUST.019911) Systems >CLUST.019911 | S.XXMH0-MGM_5 | 29649 | 29662
TTTTCCGAATCGGATGTGGGATTGCTCCGGCCCTGCCTTATTTTCATATAAGACCGGCTTATCCGACTATCTCCCTAATATGA
CAGGGAAAATATCTTCCCGGACTTTTCACCGGGATGGTATAAGAACAGGGAACCAGAATCATCTGTTCCCTGACCACTGGAAA
GTTTTTCATATCAGTATGTTGAATCCTGTCACCCCTGGGGCACGGAGGGATTTCCAAATATCCGATCTGATGTTCGTAATCAC
CGGCTTTTCCAGCCAATGGCTTGAGATGATTTAAGAAACTTGTGACTGGCTTTTTCTGGTAAAATGGATTTTTGTATAATATC
CTGTTG (SEQ ID NO: 102)

TABLE 7

Non-Coding Flank Sequences of Representative Type III-E (CLUST.019911) Systems

>CLUST.019911 | JRYO01000185_8 | 19509 | 20000
AGAGTCAGGACAACACTCTGTACCATAGTTGTGGGATACAGAAAGCCTTTGATTACCATCGGAAATCCCACAAACATCCCAAT
GTGTATATAATGATTTGATCTCAGCTATGCGTTCCTGGTATAAGTTTCTTTTCGGTTTTGCCTGCATTGTATTAACCTCTTTT
CTTCATAAATAATAAAATTATAAAATACTAAACGTTGAAATATTATGCATCTCCTTCTCGAAAAATCAGATCATATAAAATCA
ATTTCACCCCTCACCATAATAAGACGTACACTGTGGGTGAAAAGTGACACTCTTTTTAAATATTTTTAAATTCAAATAACTGT
TTATATTGAGCAAATGGAAATGCATCCTTTCCTCGTGTTATCATCAGTGCTGTCATTTGAATTAATCGTATTTAATGGAGAAA
AGGTGACAATTTTTTATAAAAAGACTTGTACAAAAAAATTAAATTGTACTGAACTTTTTTTTGTCACTTTGGTTTGGTGATTA

TABLE 7-continued

Non-Coding Flank Sequences of Representative Type III-E (CLUST.019911) Systems

ACGACTGAATATATTAGAGTATTTTTTTCTCTTTTTATTCTTGAAAAAATTGTTCTTGAATAACAGTGTTTACTTAACTAAAG
TACCTCTAATAAATATTTGTTCACACCAAAAACAGTAAGGTTATAAAGAAGAAATCTGTCATGAACAATACAGAAGAAAACAT
TGACCGTATCCAGGAACCGACCAGAGAAGACATTGATAGAAAAGAAGCAGAACGGCTTCTTGATGAGGCTTTTAATCCAAGGA
CCAAACCCGTCGATAGGAAGAAGATAATTAATTCTGCCCTGAAG (SEQ ID NO: 103)

>CLUST.019911 | JRYO01000185_8 | 25772 | 25776
AAGTTGAAGAGTGTATCCATTACTGAAAAGGGTCAACGCACATATCCTGTAGATGCATCCGGTAGCAGGATAGCGGAAGAGGT
CAGGGATTATACGCAGAAACCACTAAACGTTGTTGCTGATTATTAAATATACATATGAAGAGTAACGATATGAACATCACT
GTAGAACTCACCTTCTTTGAACCCTACCGTCTGGTTGAGTGGTTTGACTGGGACGCAAGAAAAAAGAGTCATAGCGCAATGAG
AGGTCAGGCTTTCGCGCAGTGGACGTGGAAAGGAAAAGGTCGCACAGCAGGCAAG (SEQ ID NO: 104)

>CLUST.019911 | JRYO01000185_8 | 31078 | 31608
AGCACCGTTAAGAAGTTTGGATTCATCAGTAAAGGTGATGGAGAAGATATTTTTGAAAGAATCAAGGAAAAATATATTAAAGC
ATTGGAAAACAATATACAATTATTTGAGATCTATTTGTCGGATGAAAAGGATACTCGGAATAAATAACAGACAAACGGTTTGC
GAAGAAATACGCGACAGGGTGATTGGACCGTAACCTCATGATTATATGATTGATACACGATTTAACCCTGACTTGCCGGTTTT
TGAAAAAGTTCGCAAACCCTGTTTTGCTTCATGAAGTGAGTTGGGTTTGCGAAAAAAGGTTATTACAGCCTGATATCTAAGTA
GAAGAGTACCGGTATTGAAGACCAAAGTTGCTGCGTATGGCGGTCCGGTTGTCCTTGCTTTCGCAAGGATTCCAATACTGGAA
TCCTCCCGAAAGGGAGGTCGCAAAAGGCCGTTTTTCGAAAACCATAGTTTCATACAAACCGGCGATGAGGTTTGCGAACTTTT
TGATTGTAGTAAGTATTATTAAAATAATGGCTTAATATTTTTGGTATATACAATTCTCAACTTTTTCACCTTGCCGGAAATGA
GGTTTGCGAAATTTTAGAGAGCCGCATATCTATATTATTTACAATCAGTTACAAAATGGCCCCTTCTCGCCATATACGTAACC
TCAGAGTTGTTGGAGG (SEQ ID NO: 105)

>CLUST.019911 | JRYO01000185_8 | 32437 | 32673
GGTTTGATTGAATATTGATGGTTGAAAATCGTCTGCCCTATGGGGGAGGCAATGTCATTGAATTAAGGGCAAAATATGGAGTG
CATCATCCCTGCCCGAGAATGACACTACAGTGTCAACATCCCTTTAGGTAGGCGTCCACGTCAGCCTGGCGGGAATCCAGCAA
CCTCTGCTTTGAGAGTCAATTCCATTTTAGTTGTCACCTTTCTGATAGAATCCTCGACTAAATCAGTAAGATGACAACTGATA
CTCTACTTGAACAATTTTTAAGCAAGTCCAATTTCATTTCTGCCTATGAGCGTATTGCCTCAAAGAAGGCTGCAGGCGGATTG
GATAATGTCACGGTTGAATCATTCGGCAACCGACTGGACCAGCATATCAGCAAA (SEQ ID NO: 106)

>CLUST.019911 | MGTA01000040_4 | 19908 | 20000
GTTATCCTTGGCCATTTAGAGGCTTCGGTCAAAAAGGCGCTCGATGCGGTCGAAAACATTGCGTCTGGCCAGCCAAGTAATGA
GGACTCGCCAGTATTACCCACGAGCCCGGCGGAGGTGGCGGTTATTCACTGGAGCATAAACCAGTGACCACAAATTTCCGGAA
ATGATGTCCACTTCGATAGTGTAGATGGTGCGGACGTATCACCCCTTCCCCAAGGCAGCTCAAGGAGAGCAATGATATGAATC
AAAATATCGATCGTGCGGTTGGTGCAATTCTAGCGATTGAAACAGCGACACCCCTTACCGAATCTTCAACACTCGCGCAACGT
GAAAGGCATCAGAAGCTGCTGCATGATGAAACCAAAAAGATTGAGCAAGCCTTCATAGCC (SEQ ID NO: 107)

>CLUST.019911 | MGTA01000040_4 | 22550 | 23634
CTGCAAAGCTGTTGGATGCGCCAACCCGGTGCCATTTTTAATGATGAGTACATCCGCCTTTATTATGCCGCCTCTTTCCGGAT
ACTGGGTTTCCCGGAAGTTGCGACTACAAATATGGCGACTGCAACCGCCCAGGAGGAAATAGCATGACTACCGGCAACACTTC
CGCTTCTCACCCGCAATTTGTCACGTTGACAGTCTGTTTGCGCTTTTGCAGCCCCTTCCAGATCCGACCCTGGATCAAGGAAA
CGGTGCGCAACAAGGTTAAAATGCCATCCACTGTCAACGCTCATGCTGAAACTGCTCACCTGCCGGATGACCAGGATACCGAC
GACACACAAGATCTATTGGAAGAAGAACGTTTTGAGCGGTATGCCACTGCCGCTGATTGGCACAAGGGAAGTATCAACGGAAA
CGCGAAGTATTCACCCTATGTGAGGGGCGATCTGGTCCGCAGCGTGGTGGACAGGGAATTGCAGGAGCATTTCCACTGTTATA
ATGAAAAGCTTGCCAATGAGAATAAGGGGTGCCCTGGAAAACGGGACCGCCATATTAACGCCGGCGGCAAGGCGTCCGGTTTT
ATGGCACACCTGCCCGCGATCAAGGACCCGGCCGGCAAGGAGATCTGCAAGGGCAGCGATAACATCTGCCCGGTCTGCCATTT
CCTCGGGGCGTTTGCGGAAGGAATAAAGCCGGTTAAGTTCAGGAATCGGAAGATCTGGCCAAGCAGCGCGGCCGGAACTGTTA
CAGCGGGCAAAGCCGGAAATCCCTTGATAATTTACTGTCTGGGAAGCGGATCATACCGCCTGCCCTGTTTTCTTCGGCAGAA
TCGAGGTGAACAAAACTCTTTTGCCGAAAGAACAAATCCTCGCCCTGCTGGCTGGCGGCCTTGCTCGGCTTGACAATTTGGCG
GGTGCGGCGAGGGAGGCACTTGGGCTACCAGACGACGAGCACCAGGCACTCCTCAACGATTTTTCAAGATTTTTCATTAATCC
CGAGAAATCGCCTGCTGTTTATACTTCCTCCCCGGTTATTGTCCCTGTCCAGGGAGCTGTTGATAAGGTTGTGCTCTTGGAAA
AAGCCCAAGATATCGCCGGCAGAATTGCCGCGTGTGTCTCCGACAATCCCCGCCACCTCCATCGGCTGGCTGCGGCTATCCGG
ACCCTGGGCTGGCCGGGCCGGTCTCTTGCTTCGGTTATGACTAAAAAACCGGGTACCGAAGACAAGGCCACCCTCTGGGGAAA
AGAATCAGCGAGTAAATCGGTCAAGACGATTCTGGAAGAATCAATCCAAGGCTTCACTGTAGAACAAAAGCGAAGCTTTTTG
CCAACCTTGCCGACCAGCTC (SEQ ID NO: 108)

>CLUST.019911 | MGTA01000040_4 | 27846 | 28045
CGTATCAATCCGGTACAACTCGCCCGAATGATTTTACCATTTGTACCTTGGCATGGTGCATGTCCTGCTTTGCTGAACGAACA
GGTAATGATAGAGGCCAAACGATTGACTGAGTTAGACCGCGCCAATTGGCCATGTTGAATGCCAGCACAACCAGCTAATATAT
CGAAATCGCTGGCAAAGTTAGCTTTTATTGTAAAATTAGATGATTAGGAACGATCCGGCAGGTTATTTAAATGAAGTAAAGTC
TGGGGTCGTAGCATAATCGCAAAAAAAATTATTTAACAGAAACAAACAAATAGACAGCATAAAGTTGAATTGAGTATTATAGA
AAGCAGGG (SEQ ID NO: 109)

>CLUST.019911 | MGTA01000040_4 | 30276 | 42550
TTTTTCTGTAACTATTCAGCACACCATATTTAGCATAACAACTGAGTAGTCATTGGGGCATCATAAATTGAGGCCATTTCCC
TTCAAATAATAAGCGCA (SEQ ID NO: 110)

>CLUST.019911 | S.12JQSS-MGM_10 | 15939 | 16630
GAGACAAAAGAGCAACGGGATATTTTTGTTCATTTTAGCGCTATTCGGGGTGAGGGTTATAAAATCCTGGAACCGGGCGAAAA
AGTACGTTTTGAAATAGGTGAGGGGAGAAAAGGTCCCCAGGCCATCAATGTTATTCGTATAAGATGACAAAATTACTCCAGTC
TCTATTCTTTTTGTAATTACTTGTTCGCTGTTTTGTGAAGATTATATTAAGCTATGGAGCTTTCAGGTAAAAAAGCGTAAAGT
ACGCGAATATTCTGCGTAAAACTATTCCGGCTATGAAAGATGATGTTCATAGCCGGAATAGTTTTTTATCGAGTTTGGTGGGG
TATTCATTTTGGGAGATGGTTGATGAAAGTTTCAAGGCAGGGTTTCATTTATTGGCGATGGTTTAAATATCTCTTTATTCTTT
CTTCAACAATCTGATATTATTGTTTTTTTATCTAAAGATACTCTGTTTTTATTTATCGTAAAATATTCGACATACATATGAAA
CCTTTGAAAAGGCAGGAGTTTGGCGAAGATGTAGTGATTGTGGCTAAAATTACGGAAAAATTTTTTTTGTAAAATTAAGGTGA
TATGAATATAGTTTTTCTGGTGCGGTCGCCAATTTCCTTTTTTGAAATTAGGAAACTGGTTTGGCGAATTTTTTGACAGTATC

TABLE 7-continued

Non-Coding Flank Sequences of Representative Type III-E (CLUST.019911) Systems

TTTTTATAATAAATACGAATAGTTGTGATTAGACAGGTGTTAATTTAGTAGTATTTCCCCTTTAACTGAAGAATGATTGGCGT
AATATTTAATAACATGAGAGAACTCCTTGGTATAATAGAGATTATTAAGTATAGTGTCAGAATGCAGCTTTTGTTTGTTCTTT
GATTCTAAAGG (SEQ ID NO: 111)

>CLUST.019911 | S.12JQSS-MGM_10 | 17528 | 17702
TCTCAAAATAATGTTAAAGAAATTTTCATTTTATTTTGATGGTTTAGGCCACACTGACTTTGTGGTTCTCTTTATACCGATAG
AAAAATTTTATTTTTTCGAAAAAAAACACTCTTCCATTCGTAAGGTTAAATAAAGGCAATTACTTAACCATCTAGCAATGGAG
GATTGATCATGAAAAGCACACATTCTCTTTTTTACCGTTTTGCTCATGTTGATACCTTTCGCTCCGCATATGAAAGAATTTCT
CTAAAAAATTCCAGCCCGGGACTTGATAGAGTTTCCGTAGAAGAGTTCGGCAAGAAACTTGAAAAAAATATCCAA (SEQ ID
NO: 112)

>CLUST.019911 | S.12JQSS-MGM_10 | 19997 | 20000
ATTCAGGCAATCCTCAATAGATTGGGGCAGGAGGTAAAAGGTCGAGGTAAGGCTTTAACATTGCAGGAAATGATCCATCGGCA
GGCGCAGTTGTTGAAAAGCTATTTGATGGATAAATCTGTTTACAAACCATATCTGGCAAGGTGGTAACCTATGAATACAGTCG
AATTACTTCAGGAGGAAGAACGCTTGACCCTGGATTTGGTCTTTTTGCCACCAGGTAGTAAGAATAAAGAGCAAAAAAAGAAT
GCTTTGGTAGACCTTTTGTTGAAAATAGTGGAGCATGGGGAATTAACCCGTAAA (SEQ ID NO: 113)

>CLUST.019911 | S.12JQSS-MGM_10 | 22310 | 22413
ATCGACAATGATGATACCTCCGCTGTGCTCCATAGTTCATTAAAAAGATTATTTGAGCATTACGAGAAGAAAAATGAAAAAAC
TCGTGCACAGCTTCTCTATAATTGGGCGTCTTTACGTGTTCTCGCTCCTGCCAGGGAATTTAGTTGAAAAAAAATCATAAAAT
TTCCGAAAAAATAGATGATGTCGAACGTAATAGGTTTTAGAGCAACGAATAACCGTTGCTCTAAAACCTATACTCTGGGAGAA
CATCATGAAAAAAGAGCACGGTAAAGAAAACTATTCTATCGAAACAGTTGTTTTCGTCGTTTTGCAGGACATCATGAGTATTG
TTCTAATACCGTTTGCGGTAATCGCCTCAATTTATCTTTCTTATTTTTTTGAGTTATCTGTATACAAATCT (SEQ ID NO:
114)

>CLUST.019911 | S.XXMH0-MGM_5 | 27292 | 27576
CCCCGCGTTATTTATCCGGCCCTGAAGCAGAAGGATATTCCTAACAGCAGGCTTCCCGGGTATGAGGAGTTGAAGAAGAACCT
CAATATGGAGAAACGGAAAGAGATGCTGACGACCCCTTGGGCCCCCTGGCATCCCATCAAAAAATAAGATGCCTGCGAATTCC
CGGAAATATGACAGCGGATTTAAAGGATTGAACGGATATCATTTTCCCAAAAAATGACAGCGGATTTAAAGGATTGAGCGGAT
ATCCGTTTCATCCTTTGATCCGTTGTCATATTTCCTACAAATATGTCGCCCCTACGGGGCTTTAATCCTTTCCTCTTCTTTGT
GTCCTTTGTGGCTTTGTGTGAGAAAAACAAAAAATTTTGTCACATTTTCAGCACAGAACACGACTAAGTATGCAGAGAAGGG
AAACGCCCTCCTTTTCTTTGTGTCCTTTGTGGCTTTGTGTGAGAAAAACAAAAAATTTTTGTCACATTTTCAGCACGACATAC
GACTAAGTTTGCAGAAAGGGAAAAAACATATCTTTTTACTCATAAAGGAGGTTGCCATGAAAAAAACATTTATCGTCTTTGTT
CTG (SEQ ID NO: 115)

>CLUST.019911 | S.XXMH0-MGM_5 | 29288 | 29740
AAGCGCTGGGCAACTGATGATCTGCTCCGTATGGTCGGGGATCAGATCACTGTGATGAGGGGGTTGCTGGAAAAGGGAGAGGA
TTATCGGCCGGTGGTTTACAACAGCCGGTATTCCAGCGGGAAGAGCGGCCTGAAAAAAAAGACTTGAAAAGGTCTTGACATGG
GCCGGGAAAGGGGCTATGTTCTTCTGATTATAATATCAGATCAGAGGGAATATGGCCCTTATCCCGGGAATATCCTGTATTTC
AGGGGATCGGGCCTGTTTTCCGAATCGGATGTGGGATTGCTCCGGCCCTGCCTTATTTTCATATAAGACCGGCTTATCCGACT
ATCTCCCTAATATGACAGGGAAAATATCTTCCCGGACTTTTCACCGGGATGGTATAAGAACAGGGAACCAGAATCATCTGTTC
CCTGACCACTGGAAAGTTTTTCATATCAGTATGTTGAATCCTGTCACCCCTGGGGCACGGAGGGATTTCCAAATATCCGATCT
GATGTTCGTAATCACCGGCTTTTCCAGCCAATGGCTTGAGATGATTTAAGAAACTTGTGACTGGCTTTTTCTGGTAAAATGGA
TTTTTGTATAATATCCTGTTG (SEQ ID NO: 116)

>CLUST.019911 | S.MJ1HS-PDG_1 | 18611 | 19304
CAGCTGGGTCTCGGCCTGGGCGCCAAAATCCGCCACGCTCTGACCATCCCAACCGCCGGCCGCTTTTTTGGCGGCTACCCGCT
GCCAGGCGGCGGACAGATTTTCCATGGCGGTGATGGCGGCCAGTTGACGATAGGTGGTGGTAGACATCGGGACGGTGCCTCCT
GCAAGGTTCTATCCTGTTGGTCGTCGACGCAAGGCCTCAGGTGACCCCCTCTCCGTTATTCTGCCAATTTTTTCCTAGGGACC
GGCCTGGGCACCGTCTGCGGCGGGGGGCTGCCGTTCAACCCCGGCCAGGGCCATGGACCAGATTTTCTTTGATTTATCATCAG
GTTGGCTCCTCTTTCGCAAATGCTCCGGCGCCGCGAGCGGCCAAACCATTTGCGAACTTGGCCGATAGGCGATTATTTTATGG
CAAATCAATAAGATAAGTGCTTTTGAGGCCCTTTGGCCCCTCGGCGGCGAGGGGCCAAAAAGTTCGCAAATGCCCCTTTGGGG
GCCGGGCGCCCCACCATTTGCGAAAAAACCCGCCCGGCAGCGGCCGAGGCTTCTGCCGGCTGATTATATCTTATCGATATAAT
TGAATATTATTTTTCCCCAAGACCGGGTCGAAGGCCTATTTTCGCAAATGCCCGCCGCGGGCCGGGGGAGCCAACGTGTTGCG
AAAATCCGGTTCTAAGCAAATCAAGGAGTTAGGCCAAAAAAAGTGATTTTTGGCAATCCGGCCAAGCGCCCTTTGGGGGCATT
TGCGAAAAAATCCGGCCGGCAAAAACTTCTTGACATTACCGGGCATTTTCCATTAGAGTATTGCGTAGCAGTACATATCTAGC
TGATTTCTCCGTT (SEQ ID NO: 117)

>CLUST.019911 | S.MJ1HS-PDG_1 | 19688 | 20000
TATGCGACGGCCTTGGGCCAGCAGGATGCTGGCCCTACGGGGTTGAGCAGAGGCGGCAGGCCTTGAGGACACGTTTTTGAGGG
CGTTTAACGGCAGGCGCAGGAGACGGGACGCGAAGTGGGGTTAGGGAAATTACCGCCAGGCTGGAGAATAGCTGGCGGTTTTT
GTTTGGGGGGCCGGAAAAATTTTCTGCTCCTGTCACCTCGACGGTTCCAAGAGAGACTAATTTGTTAGACCAGGCTCCAGACT
GGAAGTATTTTTGGGCGCGGCCGCGGTGACGGCTGTCCAGCAAGCGGTTGGGACGGTTTAAACATGACTGCAGGACATTACCA
GACGATTTTGGAGGCCCAGATTGAGCTGGCCTTCTGCCTGCCGGAAGAGGCGCATAATGTGCTGTATGCGCGGGATGAGGCGT
GCCGTGAGCTGGTCCAAGCCTGCCGCAATCACCGGGGTAGCCTGCGT (SEQ ID NO: 118)

>CLUST.019911 | S.MJ1HS-PDG_1 | 22355 | 22370
GCAGAGAACGGAGGCGCCTGGTTCTATGAACTTTTATGGCAATGGCACAGGGATGAAATAGGACATCTTAGCAACATAAGGAA
TACGTTTGAAAGAATGAAAAGATTTGATAAATTTGCCCCCTGGAGGTCCGTGGGATTGGGTTGGTGAAAAAAAGAGGAGTGGA
TGTCTGCGCCTGAATATGAGATCGATCTGGATAACGATGACCACCCTACCATAATTTTAACAGACATGGATGAATGTTATCAT
ATATGCCTTAAAGCGGCAGGAAACGATCCTAGCTGTGCTCGATGCAAGATATTTATGGCAGATTTC (SEQ ID NO: 119)

>CLUST.019911 | S.TJLN2-PDG_0 | 19450 | 20000
TTTTAATTGACCCGCATTTTTTGTTATATCGAATAACCATGAAGAAAGGCGTCCTTCCCACTCCATCTCAAATCTATCAGGAT
TTGTTTCATAGATATGTTTGAGACGCTTTCGGCGCTTTGCTTTATCTCTTTTGGCGGCCTTTCCCATTAGTCCTCCTTCTTAG
TTCAATAATGGTTTTATCCATTGATTTTTCGACCTGATCAGAGGATCTAAACTCTGTTGGGCCGGTACCTAATTTGATTTAAT
CGAAAGAACGTTGTACTTTTTATCTCCTCTAATTCTTTTGTTTCGGATCGTCTGGATAGTCGTGATAAATCTCTTACATGTTA

TABLE 7-continued

| Non-Coding Flank Sequences of Representative Type III-E (CLUST.019911) Systems |
|---|
| CAGGGAATCGTAATTTTTCTATCTGAAATCTCACAAGCGCTATTTCGATAGTCGGGGCTAAGTAAAAAAATGTGACATGAATT<br>GCTGGGCCACCAGAAGAAATTTTTCACTAACCACTATAGTCTTCTGGAATGTGAAAAAGTGACAGAAAAAATATGAGGCTAAA<br>ATGTCACATTTTAAATAAAGCCCCGACTATAATTATACGGATATATCTATAGACAACCCCTTTTGATGAAACCTTACACCAAT<br>AATCGGATGTTAAAGTTATTGACATTACAAGATTTAATGTGTTATTTATTTAGGCTCAACTTTTCTCAAACCATCCAGACTAT<br>TTCAAAATATCTGTAAAGATAATAAGGGGGAATGTTATGTATTCCGACTTTCCTGCACTTAGGTTACCTGAATTATCTGTTGA<br>TCAAAAAAAATTATTTAAGATCTCCGGGACCAACCCACAGCTCATATACATCTTAATGAACGAATTTGATGGAGAGGGGGATG<br>AGCCCTTCTTTACCGGACTT (SEQ ID NO: 120) |
| >CLUST.019911 \| S.TJLN2-PDG_0 \| 22274 \| 22282<br>GTTTTAAATCTTTTATTCATGAAAGAAGGTCTTTTTGATCATTTTTTTGAGCAACAAAGAGAATGGTGGAAAGAAGAGTATGA<br>ACATACCGATTCGAACACAGCTCTCTATGATTGCTTGTGTTTTCGAATGTATCGGTGTTATTTTTAGGAAAATATATGCCCTC<br>ATACCCTTGCTTGAAATGGAATGGCGATTGTAGCAGATGTCCTGATTCGGCAACATGCAGAATCGCACAGAAAGGTTTGGGAA<br>AGGTATTTACGGTTTTTTTCAAGAAATATCTGGCGCGTTACTATTCTTCGAAATCCGAA (SEQ ID NO: 121) |
| >CLUST.019911 \| S.TJLN2-PDG_0 \| 26892 \| 26965<br>ATGATGAGGCGGTTTTTCTTTGATACCAGTGCGCTTATCAAACTCTATCATGAAGAAACTGGTACAGAAAAACTGGATTCTCT<br>GATCGAGGCCGAAAATCCAGTTATCATTAATGATATGAAATTGCCTGGCGTTATGAGCTAATCCTTATATTAAATGCTTCAGG<br>CATCTGAACCTTGCAACATATCAGGATGGTATATAAACCACAGGAGGAATGATGGAATATACCCTTACCCTAAATTTCATTGA<br>ACCGTTTCGCTTGATTGAATGGCACGATGCGCCAGATCGGGAAAACCTTCGATTGAGGGGGTTTTCTTTTGCCAGATGGCATA<br>AGGACAGGGAATTCGGACTGGGAAGGCCATATATT (SEQ ID NO: 122) |
| >CLUST.019911 \| S.TJLN2-PDG_0 \| 31645 \| 31858<br>AATGGAATCCAGGTCCGTTATCCAAAATTGGAAAAAGAAAAAAAAGATGACCCAGGTGAAAAGCCGGGCTATCTTGAGCTGGC<br>AGATGGCCCTTTCAGCACGGAAAATCGCAAGGAAAAATTAAAGGAGATTTGGGGTAATTGGGCCTGATTAACCAAATATCGAA<br>TAATCACCAAATACATAGCCTATTTTCAATGATATTCAATAGTTATAATACCTATTTAATAATTCAATATTTATAGAATCCAA<br>GGATTATGCATCGCCAAAAATACATCCATAAACGATTTAACAATATGAATTTACAAAATGAATTTATACCATTGGGTTTTAAG<br>AATCTTTTATAATAAGCAAACATAGGGGGGG (SEQ ID NO: 123) |
| >CLUST.019911 \| S.J3DH2-PDG_7 \| 19861 \| 20000<br>GATGTTCCGCCAGGCACGGCAGCGATTCTCCTTGGGCTTTGTAGAGACGTGGACAGATTGAGGGCCGCCATTGATTCAATTGT<br>TTCGGGCAAGAAGACGCGGGATGATACGATATTCTGGATACTATACCACACCGTGCCGGAGAAATAGGGCCTGTCGCCAAATC<br>CACTCGGGCCTTCCACTACAAAAAGGCTTAACTCGATAGTATATGGGTTTCCTTTTTTTGAGTCCGCCGGAGGCGGACGTTGT<br>ATAAAATCGCGAAGTGATTTTATGTACTGGAGAGGATATCATGGTCACGCCACAAGCTTCTAAGAACCCCGCAGTAGATGAAA<br>TCCTGAAACAGCTCACACCCTATGACATGGAGACTGAGAACGCAAAGGCTATCGAGACAAGGAAGTCTTGTATTGAGTGCCTG<br>AAAGGCATTTGCGAAAGGGCTCAA (SEQ ID NO: 124) |
| >CLUST.019911 \| S.J3DH2-PDG_7 \| 27996 \| 28061<br>ATATTGCGCGATAACGGGGAAGATATATTTGTCCATCGGAGCGATATTAATGGTAGCCTTGGCACCCTGACAGAAGGGCAAAA<br>AGTAATCTTTGAGGTGAAGCAGGGTCCAAAGGGACTCCAGGCCACAAATGTGAAGGTAATTTCATAATCACTTGGCCGTATTG<br>CACCTTACCACAATATCTTTTTGAGAATTTCATAAGAGCTCATTTCAAAGTGAATATTCAATCCACGGCTGTTGAAAAAAAGC<br>GAAACGCCCTTGCTCTTTTTGTGCGCCTTCTCCTTTCATCGCCTCTCAAGGACTACGTCGCCAAGATAATCCTGTTTGGAAGT<br>GTGAGAAAAGGAAAAGCTAATTCAGAGAGTGAT (SEQ ID NO: 125) |
| >CLUST.019911 \| S.J3DH2-PDG_7 \| 30118 \| 30312<br>TGCTTGAAATGGCGTGGGCATTTGCTTTTGGCCCCGGCTGATATCTACTCGGCAAAGCCACACCATACAATAATGGAGGCTGA<br>TTCAATGTGACATAAAATTTTGGGGTAGCGTCTACATGCAAAAATCTCGGTGGTGATTCGTTTATACTTATAGAGTGGATCAT<br>TTTCTGAGCCGACACCCGAGATTGAGCTATGACTGCCACAATATTTGACAAATTTGCAAGCTTTGAAAACTTCTGGGCCGCCT<br>TCCAAAAAGTTGCTGCAAAGAATTCAGCGGGCGGCATAGACGGCACAACCGTTGAGACCTACCAAAAGCGAGCCAAGCAACGA<br>ATCAATGCCCTC (SEQ ID NO: 126) |

Example 2: In Vivo Bacterial Validation of Engineered Type III-E (CLUST.019911) CRISPR-Cas Systems (FIGS. 7A-12)

Having identified the minimal components of Type III-E CRISPR-Cas systems, we selected one system for functional validation, from *Candidatus scalindua* brodae (JRYO01000185, SEQ ID NO: 1, SEQ ID NO: 14).

Methods

Gene Synthesis and Oligo Library Cloning

The *E. coli* codon-optimized protein sequences for CRISPR effectors, accessory proteins were cloned into pET-28a (+) (EMD-Millipore) to create the Effector Plasmid. Noncoding sequences flanking Cas genes (including 150 nt of terminal CDS coding sequence) or the CRISPR array were synthesized (Genscript) into pACYC184 (New England Biolabs) to create the Non-coding Plasmid (FIG. 7A). Effector mutants (e.g., D513A or A513D) plasmids were cloned by site directed mutagenesis using the indicated primers in the sequence table: sequence changes were first introduced into PCR fragments, which were then re-assembled into a plasmid using NEBuilder HiFi DNA Assembly Master Mix or NEB Gibson Assembly Master Mix (New England Biolabs) following the manufacturer's instructions.

For the pooled spacer library, we first computationally designed an oligonucleotide library synthesis (OLS) pool (Agilent) to express a minimal CRISPR array of "repeat-spacer-repeat" sequences. The "repeat" elements were derived from the consensus direct repeat sequence found in the CRISPR array associated with the effector, and "spacer" represents ~8,900 sequences targeting the pACYC184 plasmid and *E. coli* essential genes, or negative control non-targeting sequences. The spacer length was determined by the mode of the spacer lengths found in the endogenous CRISPR array. Flanking the minimal CRISPR array were unique PCR priming sites that enabled amplification of a specific library from a larger pool of oligo synthesis.

We next cloned the minimal CRISPR array library into the Effector Plasmid to create an Effector Plasmid library. We appended flanking restriction sites, a unique molecular identifier, and a J23119 promoter for array expression onto the oligo library using PCR (NEBNext High-Fidelity 2×PCR Master Mix), and then used NEB Golden Gate Assembly Master Mix (New England Biolabs) to assemble the full plasmid library of effectors with their targeting arrays. This represented the "input library" for the screen.

In Vivo *E. coli* Screen

We performed the in vivo screen using electrocompetent E. cloni EXPRESS BL21 (DE3) *E. coli* cells (Lucigen), unless otherwise indicated. Competent cells were co-transformed with the Effector Plasmid and/or Non-coding (FIG. 7B). The cells were electroporated with the "input library" according to the manufacturer's protocols using a Gene Pulser Xcell® (Bio-rad) with a 1.0 mm cuvette. The cells were plated onto bioassay plates containing both Chloramphenicol (Fisher) and Kanamycin (Alfa Aesar), and grown for 11 hours, after which we estimated the approximate colony count to ensure sufficient library representation and harvested the cells.

Plasmid DNA fractions were extracted from the harvested cells to create the 'output library' using a QIAprep® Spin Miniprep Kit (Qiagen), while total RNA=17 nt was harvested by lysing the harvested cells in Direct-zol® (Zymo Research), followed by extraction using the Direct-zol RNA miniprep kit (Zymo Research).

The next generation sequencing library for the DNA depletion signal was prepared by performing a PCR on both the input and output libraries, using custom primers flanking the CRISPR array cassette of the Effector Plasmid library and containing barcodes and handles compatible with Illumina sequencing chemistry. This library was then normalized, pooled, and loaded onto a Nextseq 550 (Illumina) to evaluate the activity of the effectors.

Bacterial Screen Sequencing Analysis

Next generation sequencing data for screen input and output libraries were demultiplexed using Illumina bcl2fastq. Reads in resulting fastq files for each sample contained the CRISPR array elements for the screening plasmid library. The direct repeat sequence of the CRISPR array was used to determine the array orientation, and the spacer sequence was mapped to the source (pACYC184 or *E. coli* essential genes) or negative control sequence (GFP) to determine the corresponding target. For each sample, the total number of reads for each unique array element ($r_a$) in a given plasmid library was counted and normalized as follows: ($r_a$+1)/total reads for all library array elements. The depletion score was calculated by dividing normalized output reads for a given array element by normalized input reads.

To identify specific parameters resulting in enzymatic activity and bacterial cell death, we used next generation sequencing (NGS) to quantify and compare the representation of individual CRISPR arrays (i.e., repeat-spacer-repeat) in the PCR product of the input and output plasmid libraries. We defined the fold depletion for each CRISPR array as the normalized input read count divided by the normalized output read count (with 1 added to avoid division by zero). An array was considered to be "strongly depleted" if the fold depletion was greater than 3. When calculating the array fold depletion across biological replicates, we took the maximum fold depletion value for a given CRISPR array across all experiments (i.e. a strongly depleted array must be strongly depleted in all biological replicates).

FIG. 8 shows the degree of interference activity (depletion ratio) of the engineered Type III-E compositions by plotting for a given target the normalized ratio of sequencing reads in the screen output versus the screen input. The results are plotted for each crRNA transcriptional orientation. In the functional screen for each composition, an active effector, or effector and accessory complex, complexed with an active crRNA (expressed as a DR::spacer::DR) will interfere with *E. coli* essential gene function or the ability of the pACYC184 to confer *E. coli* resistance to chloramphenicol and tetracycline, resulting in cell death and depletion of the spacer element within the pool. Comparing the results of deep sequencing the initial DNA library (screen input) versus the surviving transformed *E. coli* (screen output) suggest specific target sequences and DR transcriptional orientation that enable an active, programmable CRISPR system. The screen also indicates that the effector complex is only active with one orientation of the DR.

FIG. 9 depicts the measured interference activity (depletion ratio) against the sequencing read coverage of the screen output. Notably, many of the points with depletion values above the hit threshold fall in the range where normalized output read counts are high (e.g. above 10), indicating the depletion ratio measurement is unlikely to be a technical artifact.

FIGS. 10 and 11 depict the location of strongly depleted targets for the Type III-E CRISPR-Cas system targeting pACYC184 and *E. coli* E. Cloni essential genes. Notably, the location of strongly depleted targets appears dispersed throughout the potential target space.

FIG. 12 depicts a weblogo of the sequences flanking depleted targets, indicating the absence of a prominent PAM.

Together, the interference activity displayed in the *E. coli* screen with the Type III-E CRISPR system suggests a programmable system capable of sequence-specific bacterial cell death or dormancy, which may yield new modalities of programmable CRISPR activities based on the Type III-E effectors.

Example 3—Identification of Transactivating RNA Elements

In addition to an effector protein, a crRNA, and an accessory protein, some CRISPR systems as described herein also include an additional small RNA that activates robust enzymatic activity referred to as a transactivating RNA (tracrRNA). Such tracrRNAs typically include a complementary region that hybridizes to the crRNA. The crRNA-tracrRNA hybrid forms a complex with an enzymatic module formed by an effector and an accessory protein resulting in the activation of programmable enzymatic activity.

TracrRNA sequences are identified as described herein by searching genomic sequences flanking CRISPR arrays for short sequence motifs that are homologous to the direct repeat portion of the crRNA. Search methods include exact or degenerate sequence matching for the complete direct repeat (DR) or DR subsequences. For example, a DR of length n nucleotides can be decomposed into a set of overlapping 6-10 nt kmers. These kmers are aligned to sequences flanking a CRISPR locus, and regions of homology with 1 or more kmer alignments are identified as DR homology regions for experimental validation as tracrRNAs. Alternatively, RNA cofold free energy can be calculated for the complete DR or DR subsequences and short kmer sequences from the genomic sequence flanking the elements of a CRISPR system. Flanking sequence elements with low minimum free energy structures are identified as DR homology regions for experimental validation as tracrRNAs. Notably, tracrRNA elements frequently occur within close proximity to CRISPR associated genes or a CRISPR array. As an alternative to searching for DR homology regions to identify tracrRNA elements, non-coding sequences flanking CRISPR associated proteins or the CRISPR array can be isolated by cloning or gene synthesis for direct experimental validation of tracrRNAs.

Experimental validation of tracrRNA elements is performed using small RNA sequencing of the host organism for a CRISPR system or synthetic sequences expressed heterologously in non-native species. Alignment of small RNA sequences from the originating genomic locus is used to identify expressed RNA products containing DR homology regions and stereotyped processing typical of complete tracrRNA elements.

Complete tracrRNA candidates identified by RNA sequencing are validated in vitro or in vivo by expressing the crRNA and effector in combination with or without the tracrRNA candidate, and monitoring the activation of effector enzymatic activity. Constructs are engineered to have the expression of tracrRNAs can be driven bypromoters including, but not limited to, U6, U1, and H1 promoters for expression in mammalian cells or J23119 promoter for expression in bacteria. In some instances, a tracrRNA can be fused with a crRNA and expressed as a single guide RNA.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An engineered, non-naturally occurring Clustered Regularly Interspaced Short Palindromic Repeat (CRISPR)-Cas system comprising:

an RNA guide or a nucleic acid encoding the RNA guide, wherein the RNA guide comprises a direct repeat sequence and a spacer sequence capable of hybridizing to a target nucleic acid in a eukaryotic cell, wherein the direct repeat comprises a nucleotide sequence according to SEQ ID NO: 99 (TGTNWYGGNAC), wherein N is any nucleotide; W is A, T, or U; and Y is C, T, or U; and at least one CRISPR-Cas effector protein or a nucleic acid encoding the CRISPR-Cas effector protein, wherein the CRISPR-Cas effector protein comprises an amino acid sequence that is at least 93% identical to an amino acid sequence according to SEQ ID NO: 14;

wherein the CRISPR-Cas effector protein is capable of binding to the RNA guide and of targeting the target nucleic acid complementary to the spacer sequence.

2. The system of claim 1, further comprising two or more RNA guides.

3. The system of claim 1, wherein the RNA guide comprises the direct repeat sequence, the spacer sequence, and a second direct repeat sequence, arranged in order within the RNA guide.

4. The system of claim 1, wherein the at least one CRISPR-Cas effector protein comprises four Repeat Associated Mysterious Protein (RAMP) domain-domains.

5. The system of claim 1, further comprising a second CRISPR-Cas effector protein comprising a protease domain.

6. The system of claim 5, wherein the protease domain is activated when the system binds to the target nucleic acid, thereby exhibiting protease activity.

7. The system of claim 6, wherein the protease activity is a peptidase activity.

8. The system of claim 7, wherein the peptidase activity is an endopeptidase or exopeptidase activity.

9. The system of claim 5, wherein the protease domain is a caspase domain.

10. The system of claim 9, wherein the caspase domain is a Caspase HetF Associated with Tprs (CHAT) domain.

11. The system of claim 1, wherein:

i) the target nucleic acid is a transcriptionally active site; or ii) the target nucleic acid is a RNA.

12. The system of claim 1, wherein the targeting of the target nucleic acid by the at least one CRISPR-Cas effector protein and the RNA guide results in a modification in the target nucleic acid.

13. The system of claim 12, wherein the modification in the target nucleic acid is:

a) a deletion or an insertion event;

b) a double stranded cleavage event; or c) a single-stranded cleavage event.

14. The system of claim 12, wherein the modification results in cell toxicity.

15. The system of claim 1, wherein the system is present within a eukaryotic cell.

16. The system of claim 1, wherein the system comprises a tracrRNA.

17. The system of claim 1, wherein the direct repeat sequence comprises a nucleotide sequence that is at least 80% identical to a nucleotide sequence according to SEQ ID NO: 27.

18. The system of claim 1, wherein the at least one CRISPR-Cas effector protein comprises an amino acid sequence that is at least 95% identical to an amino acid sequence according to SEQ ID NO: 14.

* * * * *